United States Patent
Bebernitz et al.

(10) Patent No.: US 9,255,093 B2
(45) Date of Patent: Feb. 9, 2016

(54) POLYCYCLIC HERG ACTIVATORS

(71) Applicants: Gregory Raymond Bebernitz, Stow, MA (US); Emma Cody, Cambridge, MA (US); Tajesh Patel, Medford, MA (US); Ming Qian, Watertown, MA (US); Lewis Whitehead, Swampscott, MA (US); Thomas Zabawa, Boston, MA (US); Frederic Zecri, Brookline, MA (US)

(72) Inventors: Gregory Raymond Bebernitz, Stow, MA (US); Emma Cody, Cambridge, MA (US); Tajesh Patel, Medford, MA (US); Ming Qian, Watertown, MA (US); Lewis Whitehead, Swampscott, MA (US); Thomas Zabawa, Boston, MA (US); Frederic Zecri, Brookline, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/688,397

(22) Filed: Apr. 16, 2015

(65) Prior Publication Data
US 2015/0299181 A1    Oct. 22, 2015

Related U.S. Application Data

(60) Provisional application No. 61/980,932, filed on Apr. 17, 2014.

(51) Int. Cl.
| | |
|---|---|
| *C07D 405/04* | (2006.01) |
| *A61K 31/41* | (2006.01) |
| *C07D 417/12* | (2006.01) |
| *C07D 405/14* | (2006.01) |
| *C07D 307/85* | (2006.01) |
| *A61K 31/343* | (2006.01) |
| *C07D 407/12* | (2006.01) |
| *A61K 31/357* | (2006.01) |
| *A61K 31/443* | (2006.01) |
| *A61K 31/428* | (2006.01) |

(52) U.S. Cl.
CPC ............ *C07D 417/12* (2013.01); *A61K 31/343* (2013.01); *A61K 31/357* (2013.01); *A61K 31/41* (2013.01); *A61K 31/428* (2013.01); *A61K 31/443* (2013.01); *C07D 307/85* (2013.01); *C07D 405/04* (2013.01); *C07D 405/14* (2013.01); *C07D 407/12* (2013.01)

(58) Field of Classification Search
CPC .............................. C07D 405/04; A61K 31/41
See application file for complete search history.

(56) References Cited

U.S. PATENT DOCUMENTS 4,455,427 A  *  6/1984  Johnson ..................... 546/284.1

FOREIGN PATENT DOCUMENTS

EP       1 338 594 A1    8/2003

OTHER PUBLICATIONS

Marella et al., Medicinal Chemistry Research, 22(11):5153-5166 (2013).
Perry et al., The Journal of Physiology, 588(17):3157-3167 (2010).
Zhou et al., Acta Pharmacologica Sinica, 32(6):781-788 (2011).

* cited by examiner

*Primary Examiner* — Robert Havlin
(74) *Attorney, Agent, or Firm* — Joshua Roth

(57) ABSTRACT

The present invention provides a compound of formula I, in which $R^1$, $R^2$, X and $R^3$ are defined in the Summary of the Invention, or a pharmaceutically acceptable salt thereof;

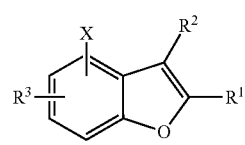

(I)

a method for manufacturing the compounds of the invention, and its therapeutic uses. The present invention further provides a combination of pharmacologically active agents and a pharmaceutical composition.

16 Claims, No Drawings

POLYCYCLIC HERG ACTIVATORS

BACKGROUND OF THE INVENTION

Coordinated cardiac contractility is governed by electrical changes that occur in cardiomyocytes. The cardiac impulse or action potential is determined by successive opening and closing of membrane ion channels that regulate the depolarizing (mainly $Na^+$ and $Ca^{++}$) and repolarizing (mainly $K^+$) currents (Nerbonne and Kass, 2005). Genetic defects resulting in the malfunctioning of these channels and the associated ionic currents can lead to cardiac rhythm disorders generally described as cardiac channelopathies (Webster and Berul, 2013). Inherited mutations in cardiac ion channels resulting in gain or loss of channel function can alter the atrial and ventricular action potential and cause various cardiac arrhythmia syndromes, including long QT syndrome (LQTS), short QT syndrome, Brugada syndrome, and familial atrial fibrillation (Giudicessi and Ackerman, 2012). Prolongation of QT interval caused by abnormal cardiac repolarization is associated with an increased risk of life-threatening tachyarrhythmia. Presently 16 genes associated with LQTS have been identified with differing signs and symptoms, depending on the locus involved. The majority of cases have mutations in the KCNQ1 (LQT1), KCNH2 (LQT2) and SCN5A (LQT3) genes (Schwartz et al. 2013).

Cardiac repolarization is primarily mediated by the slow delayed rectifier current, IKs (KCNQ1) and the rapid delayed rectifier current IKr (KCNH2) conducted by the hERG channels (Sanguinetti and Tristani-Firouzi, 2006). Impairment or loss of $K^+$ channel function delays cardiac repolarization, leads to excessive prolongation of the action potential duration and associated QT interval in the electrocardiogram and predisposes affected individuals to high risk of developing torsades de pointes arrhythmia and sudden cardiac death (Ravens and Cerbai, 2008). Jervell and Lange-Nielsen syndrome (JLN) is a rare cause of LQTS characterized by deafness, severe QT prolongation and lethal arrhythmias (Crotti et al. 2008). Most patients die of this disorder as children before age 10 despite aggressive therapy including behavior modification, beta blockers, defibrillators and sympathectomy. This syndrome is caused by homozygous or compound heterozygous mutations in genes KCNQ1 and KCNE1 that are responsible for the delayed rectifier repolarizing current IKs (Crotti et al. 2008). Acquired LQTS is often observed in the setting of structural or functional cardiac disease such as ischemic or diabetic cardiomyopathy. The altered substrate in coronary disease (ischemia or scar) may lower the threshold for afterdepolarization. Thus, subclinical IKs dysfunction with associated reduction in repolarization reserve may be exacerbated in these conditions.

hERG channel activators described in the literature include NS1643, NS3623, RPR260243, PD-118057, PD307243, ICA105574, A935142 and KB130015 (Zhou et al., 2011). These compounds act by altering channel activation, inactivation or deactivation (Perry et al. 2010). Pharmacological activation of hERG $K^+$ channels is anticipated to normalize the QT interval, functionally mitigate the arrhythmic substrate and consequently reduce cardiac arrhythmia in patients with inherited or acquired LQTS. This approach is likely to be effective in LQTS resulting from mutations in genes other than KCNQ1 since it targets the alteration in QT per se and not specific genetic defects. hERG channel activators may also function as general antiarrhythmics since they reportedly reduce electrical heterogeneity in the myocardium and thereby reduce the possibility of re-entry (Grunnet et al. 2008). Thus, the current invention relates to hERG activators useful as pharmaceuticals for the treatment of genetic or acquired long QT syndromes and as a novel class of agents for the treatment of arrhythmias of other etiologies.

1. Nerbonne J M, Kass R S. Molecular physiology of cardiac repolarization. Physiol Rev. 2005; 85:1205-53.
2. Webster G, Berul C I. An update on channelopathies: from mechanisms to management. Circulation. 2013; 127:126-40.
3. Giudicessi, J. R. & Ackerman, M. J. Potassium-channel mutations and cardiac arrhythmias—diagnosis and therapy. Nat Rev Cardiol. 2012; 9:319-32.
4. Schwartz P J, Ackerman M J, George A L Jr, Wilde A A. Impact of Genetics on the Clinical Management of Channelopathies. J Am Coll Cardiol. 2013 May 15 (Epub ahead of print)
5. Sanguinetti M C, Tristani-Firouzi M. hERG potassium channels and cardiac arrhythmia. Nature. 2006; 440:463-9.
6. Ravens U, Cerbai E. Role of potassium currents in cardiac arrhythmias. Europace. 2008; 10:1133-7.
7. Crotti L, Celano G, Dagradi F, Schwartz P J. Congenital long QT syndrome. Orphanet J Rare Dis. 2008; 3:18.
8. Zhou P Z, Babcock J, Liu L Q, Li M, Gao Z B. Activation of human ether-a-go-go related gene (hERG) potassium channels by small molecules. Acta Pharmacol Sin. 2011; 32:781-8.
9. Perry M, Sanguinetti M, Mitcheson J. Revealing the structural basis of action of hERG potassium channel activators and blockers. J Physiol. 2010; 588(Pt 17):3157-67.
10. Grunnet M, Hansen R S, Olesen S P. hERG1 channel activators: a new anti-arrhythmic principle. Prog Biophys Mol Biol. 2008; 98:347-62.

SUMMARY OF THE INVENTION

There remains a need for new compounds that activate hERG. The invention provides compounds, salts thereof, pharmaceutical formulations thereof and combinations thereof which compounds are hERG activators. The invention further provides methods of treating, preventing, or ameliorating hERG related conditions, comprising administering to a subject in need thereof an effective amount of a hERG modulator (e.g., a compound of the invention).

Various embodiments of the invention are described herein. It will be recognized that features specified in each embodiment may be combined with other specified features to provide further embodiments.

Within certain aspects, hERG modulators provided herein are compounds of Formula I and salts thereof:

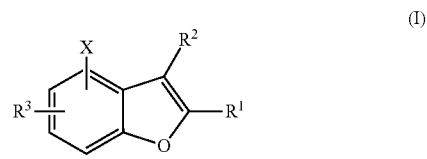

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more therapeutically active ingredients.

One embodiment of the invention is to provide a method for treating, preventing, or ameliorating a hERG related condition, comprising administering to a subject in need thereof an effective amount of a hERG modulator of Formula (I), or a pharmaceutical composition comprising the same.

DETAILED DESCRIPTION OF THE INVENTION

As noted above, the present invention provides compounds that modulate hERG activity. Such compounds may be used in vitro or in vivo to modulate hERG activity in a variety of contexts. In a first embodiment, the invention provides compounds of Formula I and pharmaceutically acceptable salts thereof, which modulate hERG activity. Compounds of Formula I are represented by the structure, or salt thereof, of formula (I):

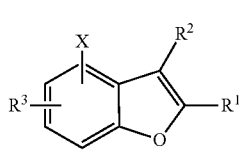
(I)

wherein $R^1$ is selected from: $CO_2H$ or tetrazole and $R^2$ is selected from: H, halo, $(C_1\text{-}C_4)$alkyl or halo-substituted$(C_1\text{-}C_4)$alkyl, or $R^1$ is H and $R^2$ is $CO_2H$ or tetrazole; X is selected from: H, halo, $(C_1\text{-}C_4)$alkyl, $(C_1\text{-}C_4)$alkoxy, $NR^8R^9$, halo-substituted$(C_1\text{-}C_4)$alkyl, phenyl or a 5 to 6 membered heteroaryl containing 1 to 3 heteroatoms each independently selected from O, N, or S, where said phenyl or heteroaryl are optionally substituted with 1 to 2 substituents each independently selected from halo, $(C_1\text{-}C_4)$alkyl, $(C_1\text{-}C_4)$alkoxy, halo-substituted$(C_1\text{-}C_4)$alkyl, hydroxy-substituted$(C_1\text{-}C_4)$alkyl, $(C_1\text{-}C_4)$alkylamino-substituted$(C_1\text{-}C_4)$alkyl, dimethylamino-substituted$(C_1\text{-}C_4)$alkyl; $R^8$ is selected from: H, or $(C_1\text{-}C_4)$alkyl; $R^9$ is selected from: H, or $(C_1\text{-}C_4)$alkyl; $R^3$ is

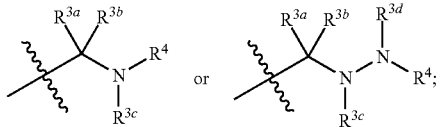

where $R^{3a}$ is selected from: H, $(C_1\text{-}C_4)$alkyl or halo-substituted$(C_1\text{-}C_4)$alkyl; $R^{3b}$ is selected from: H, $(C_1\text{-}C_4)$alkyl or taken together with $R^{3a}$ forms a 3 to 7 membered saturated cycloalkyl or a 3 to 7 membered saturated heterocycle containing 1 to 2 heteroatoms selected from O, S or N; $R^{3a}$ is selected from: H or $CH_3$; $R^{3d}$ is selected from: H or $CH_3$; $R^4$ is selected from:

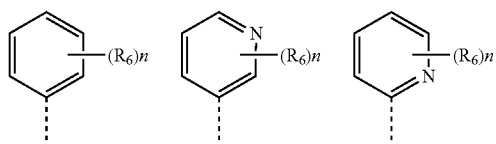

wherein the dotted line indicates the point of attachment; $R^5$ is selected from: H or $CH_3$; $R^6$ is independently selected from: halo, nitrile, $(C_1\text{-}C_4)$alkyl, halo-substituted$(C_1\text{-}C_4)$alkyl, nitrile-substituted$(C_1\text{-}C_4)$alkyl, $(C_1\text{-}C_4)$alkoxy, halo-substituted$(C_1\text{-}C_4)$alkoxy, nitrile-substituted$(C_1\text{-}C_4)$alkoxy, $(C_1\text{-}C_4)$alkylene, N-acetyl, trifluouroacetyl, $(C_1\text{-}C_4)$alkylthio, halo-substituted thio, halo-substituted $(C_1\text{-}C_4)$alkylthio, $(C_3\text{-}C_6)$cycloalkyl, methylamino-substituted$(C_1\text{-}C_4)$alkyl, dimethylamino-substituted$(C_1\text{-}C_4)$alkyl, halo-substituted$(C_1\text{-}C_4)$ hydroxyalkyl, a 4 to 6 membered saturated heterocycle containing 1 to 2 heteroatoms selected from O, S or N, or a 5 to 6 membered heteroaryl containing 1 to 3 heteroatoms each independently selected from O, N, or S, where said heterocycle or heteroaryl are optionally substituted with 1 to 2 substituents each independently selected from $(C_1\text{-}C_4)$alkyl, halo, hydroxyl, amino or $(C_1\text{-}C_4)$alkoxy; $R^7$ is selected from: H or halo; n is 1, 2 or 3; m is 0, 1 or 2; or $R^{3c}$ and $R^4$ taken together with the amine to which $R^{3c}$ and $R^4$ are attached forms a fully saturated 4 to 7 membered heterocycle, where 1 to 2 of the ring carbons are each independently optionally replaced with a N or O, and said heterocycle is optionally substituted with 1 to 2 substituents each independently selected from $(C_1\text{-}C_4)$alkoxy, $(C_1\text{-}C_4)$alkyl, halo-substituted$(C_1\text{-}C_4)$alkyl, hydroxy$(C_1\text{-}C_4)$alkyl, cyclopropyl or oxo or a pharmaceutically acceptable salt thereof.

In a second embodiment, the invention is a compound, or salt thereof, according to the first embodiment, wherein $R^1$ is selected from: $CO_2H$, or tetrazole; $R^2$ is selected from: H, halo, $(C_1-C_4)$alkyl or halo-substituted$(C_1-C_4)$alkyl; X is selected from: H, halo, $(C_1-C_4)$alkyl, $(C_1-C_4)$alkoxy, $NR^8R^9$, halo-substituted$(C_1-C_4)$alkyl, phenyl or a 5 to 6 membered heteroaryl containing 1 to 3 heteroatoms each independently selected from O, N, or S, where said phenyl or heteroaryl are optionally substituted with 1 to 2 substituents each independently selected from halo, $(C_1-C_4)$alkyl, $(C_1-C_4)$alkoxy, halo-substituted$(C_1-C_4)$alkyl, hydroxy-substituted$(C_1-C_4)$alkyl, $(C_1-C_4)$alkylamino-substituted$(C_1-C_4)$alkyl, dimethylamino-substituted$(C_1-C_4)$alkyl; $R^8$ is selected from: H, or $(C_1-C_4)$alkyl; $R^9$ is selected from: H, or $(C_1-C_4)$alkyl; $R^3$ is

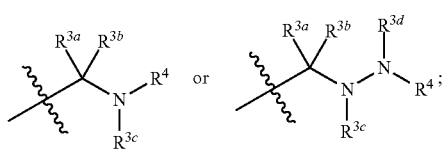

where $R^{3a}$ is selected from: H, $(C_1-C_4)$alkyl or halo-substituted$(C_1-C_4)$alkyl; $R^{3b}$ is selected from: H, $(C_1-C_4)$alkyl or taken together with $R^{3a}$ forms a 3 to 7 membered saturated cycloalkyl or a 3 to 7 membered saturated heterocycle containing 1 to 2 heteroatoms selected from O, S or N; $R^{3c}$ is selected from: H or $CH_3$; $R^{3d}$ is selected from: H or $CH_3$; $R^4$ is selected from:

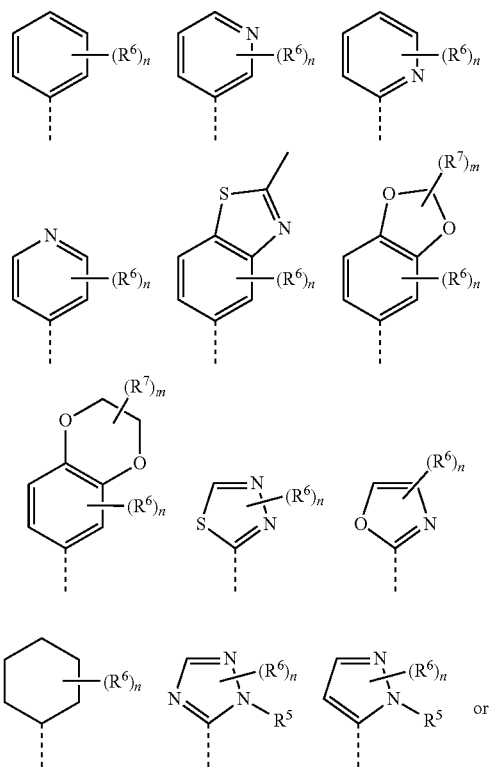

wherein the dotted line indicates the point of attachment; $R^5$ is selected from: H or $CH_3$; $R^6$ is independently selected from: halo, $(C_1-C_4)$alkyl, halo-substituted$(C_1-C_4)$alkyl, $(C_1-C_4)$alkoxy, halo-substituted$(C_1-C_4)$alkoxy, nitrile-substituted$(C_1-C_4)$alkoxy, $(C_1-C_4)$alkylene, N-acetyl, trifluoroacetyl, $(C_1-C_4)$alkylthio, halo-substituted thio, halo-substituted $(C_1-C_4)$alkylthio, $(C_3-C_6)$cycloalkyl, methylamino-substituted$(C_1-C_4)$alkyl, dimethylamino-substituted$(C_1-C_4)$alkyl, halo-substituted$(C_1-C_4)$ hydroxyalkyl, a 4 to 6 membered saturated heterocycle containing 1 to 2 heteroatoms selected from O, S or N, or a 5 to 6 membered heteroaryl containing 1 to 3 heteroatoms each independently selected from O, N, or S, where said heterocycle or heteroaryl are optionally substituted with 1 to 2 substituents each independently selected from $(C_1-C_4)$alkyl, halo, hydroxyl, amino or $(C_1-C_4)$alkoxy; $R^7$ is selected from: H or halo; n is 1, 2 or 3; m is 0, 1 or 2; or $R^{3c}$ and $R^4$ taken together with the amine to which $R^{3c}$ and $R^4$ are attached forms a fully saturated 4 to 7 membered heterocycle, where 1 to 2 of the ring carbons are each independently optionally replaced with a N or O, and said heterocycle is optionally substituted with 1 to 2 substituents each independently selected from $(C_1-C_4)$alkoxy, $(C_1-C_4)$alkyl, halo-substituted$(C_1-C_4)$alkyl, hydroxy$(C_1-C_4)$alkyl, cyclopropyl or oxo or a pharmaceutically acceptable salt thereof.

In one embodiment, the invention is the compound, or pharmaceutically acceptable salt thereof, according any one of the preceding embodiments, wherein $R^1$ is tetrazole.

In another embodiment, the invention is the compound, or pharmaceutically acceptable salt thereof, according any one of the preceding embodiments, wherein $R^2$ is hydrogen.

In a third embodiment, the invention is the compound according to the first or second embodiments, or a salt thereof, wherein the compound is of formula (II):

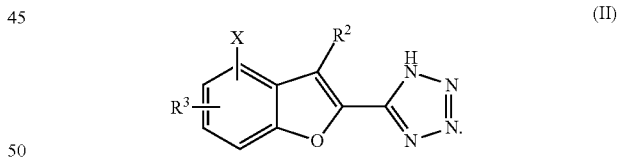

(II)

In a fourth embodiment, the invention is the compound according to any one of the first through third embodiments, or a salt thereof, wherein the compound is of formula (III):

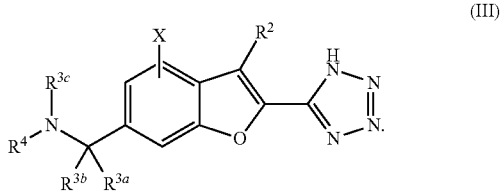

(III)

In a fifth embodiment, the invention is the compound according to any one of the first through third embodiments, or a salt thereof, wherein the compound is of formula (IV):

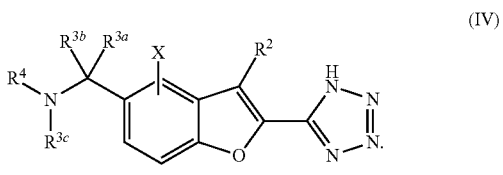
(IV)

In a sixth embodiment, the invention is the compound according any one of the first through fourth embodiments, or a salt thereof, wherein the compound is of formula (V):

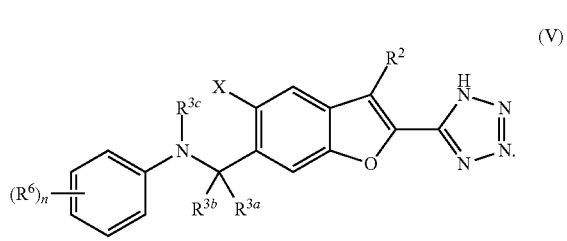
(V)

In a seventh embodiment, the invention is the compound according to any one of the first through fourth or sixth embodiments, or a salt thereof, wherein the compound is of formula (VI):

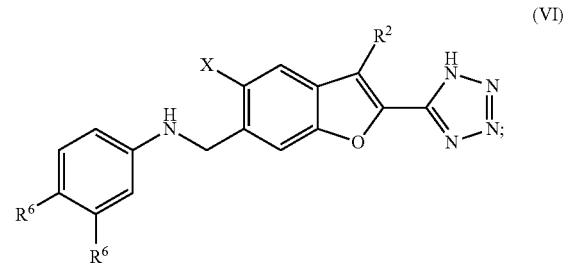
(VI)

wherein, $R^2$ is selected from: H, $CH_3$ or $CF_3$; X is selected from: H, halo, $(C_1-C_4)$alkyl, $(C_1-C_4)$alkoxy, halo-substituted $(C_1-C_4)$alkyl; $R^6$ is independently selected from: halo, $(C_1-C_4)$alkyl, halo-substituted$(C_1-C_4)$alkyl, $(C_1-C_4)$alkoxy, halo-substituted$(C_1-C_4)$alkoxy; or a pharmaceutically acceptable salt thereof In an eighth embodiment, the invention is the compound according to any one of first or second embodiments, or a salt thereof, wherein the compound is of formula (VII):

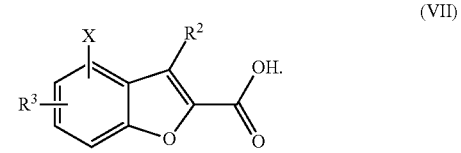
(VII)

In a ninth embodiment, the invention is the compound according to any one of the first, second or eighth embodiments, or a salt thereof, wherein the compound is of formula (VIII):

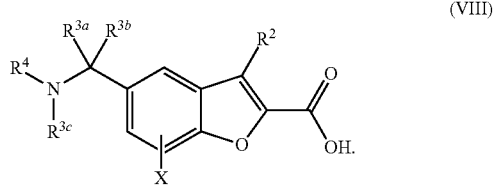
(VIII)

In a tenth embodiment, the invention is the compound according to any one of the first, second or eighth embodiments, or a salt thereof, wherein the compound is of formula (IX):

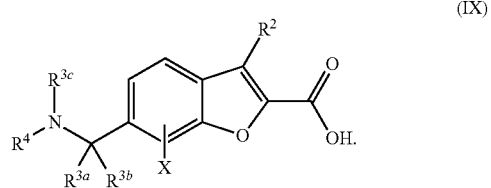
(IX)

In an eleventh embodiment, the invention is the compound, or salt thereof, according to any one of the first through tenth embodiments, wherein X is selected from: H, halo, $(C_1-C_4)$ alkyl, $(C_1-C_1)$alkoxy, halo-substituted$(C_1-C_4)$alkyl; $R^{3b}$ is H; or a pharmaceutically acceptable salt thereof.

In a twelfth embodiment, the invention is the compound according to the first embodiment, or a salt thereof, wherein the compound is selected from:
N-((2-(2H-tetrazol-5-yl)benzofuran-6-yl)methyl)-3-bromo-5-fluoro-4-methoxyaniline;
N-((2-(2H-tetrazol-5-yl)benzofuran-6-yl)methyl)-3-bromo-4-ethoxy-5-fluoroaniline;
N-((2-(2H-tetrazol-5-yl)benzofuran-6-yl)methyl)-3-bromo-4-(trifluoromethyl)aniline;
N-((2-(2H-tetrazol-5-yl)benzofuran-6-yl)methyl)-3,5-dibromo-4-(difluoromethoxy)aniline;
3,5-dichloro-N-((5-chloro-2-(1H-tetrazol-5-yl)benzofuran-6-yl)methyl)-4-ethoxyaniline;
N-((5-chloro-2-(1H-tetrazol-5-yl)benzofuran-6-yl)methyl)-4-(trifluoromethoxy)-3-(trifluoromethyl)aniline;
N-((5-chloro-2-(1H-tetrazol-5-yl)benzofuran-6-yl)methyl)-3-fluoro-4-((trifluoromethyl)thio)aniline;
3-chloro-N-((5-chloro-2-(1H-tetrazol-5-yl)benzofuran-6-yl)methyl)-4-(2,2,2-trifluoroethoxy)aniline;
N-((5-chloro-2-(1H-tetrazol-5-yl)benzofuran-6-yl)methyl)-4-fluoro-3-(trifluoromethoxy)aniline;
N-((5-chloro-2-(1H-tetrazol-5-yl)benzofuran-6-yl)methyl)-4-ethoxy-3-(trifluoromethyl)aniline;
N-((2-(2H-tetrazol-5-yl)benzofuran-6-yl)methyl)-3-(prop-1-en-2-yl)-4-(trifluoromethoxy)aniline;
3-chloro-N-((5-chloro-2-(1H-tetrazol-5-yl)benzofuran-6-yl)methyl)-4-propylaniline;
4-chloro-N-((5-chloro-2-(1H-tetrazol-5-yl)benzofuran-6-yl)methyl)-3-(trifluoromethoxy)aniline;
N-((5-chloro-2-(1H-tetrazol-5-yl)benzofuran-6-yl)methyl)-3,4-bis(trifluoromethyl)aniline;
3,4,5-trichloro-N-((5-chloro-2-(1H-tetrazol-5-yl)benzofuran-6-yl)methyl)aniline;
N-((1H-tetrazol-5-yl)benzofuran-6-yl)methyl)-4-propyl-3-(trifluoromethyl)aniline;
N-((2-(2H-tetrazol-5-yl)benzofuran-6-yl)methyl)-3-chloro-4-(difluoromethoxy)aniline;

N-((5-chloro-2-(1H-tetrazol-5-yl)benzofuran-6-yl)methyl)-4-isopropoxy-3-(trifluoromethyl)aniline;
N-((2-(2H-tetrazol-5-yl)benzofuran-6-yl)methyl)-3,4,5-trichloroaniline;
N-((2-(2H-tetrazol-5-yl)benzofuran-6-yl)methyl)-3-chloro-4-((trifluoromethyl)thio)aniline;
N-((2-(2H-tetrazol-5-yl)benzofuran-6-yl)methyl)-3-methyl-4-(trifluoromethoxy)aniline;
N-((5-chloro-2-(1H-tetrazol-5-yl)benzofuran-6-yl)methyl)-4-(2,2,2-trifluoroethoxy)-3-(trifluoromethyl)aniline;
N-((2-(2H-tetrazol-5-yl)benzofuran-6-yl)methyl)-4-(trifluoromethoxy)-3-(trifluoromethyl)aniline;
3-chloro-N-((5-chloro-2-(1H-tetrazol-5-yl)benzofuran-6-yl)methyl)-4-((trifluoromethyl)thio)aniline;
N-((5-chloro-2-(1H-tetrazol-5-yl)benzofuran-6-yl)methyl)-4-(difluoromethoxy)-3-(trifluoromethyl)aniline;
N-((2-(2H-tetrazol-5-yl)benzofuran-6-yl)methyl)-4-(methylthio)-3-(trifluoromethyl)aniline;
N-((2-(2H-tetrazol-5-yl)benzofuran-6-yl)methyl)-4-(2,2,2-trifluoroethoxy)-3-(trifluoromethyl)aniline;
N-((2-(2H-tetrazol-5-yl)benzofuran-6-yl)methyl)-3-(methylthio)aniline;
2-(4-(((5-chloro-2-(1H-tetrazol-5-yl)benzofuran-6-yl)methyl)amino)-2-(trifluoromethyl)phenoxy)acetonitrile;
1-(4-(((2-(1H-tetrazol-5-yl)benzofuran-6-yl)methyl)amino)phenyl)-2,2,2-trifluoroethanone;
N-((5-chloro-2-(1H-tetrazol-5-yl)benzofuran-6-yl)methyl)-4-propyl-3-(trifluoromethyl)aniline;
3-chloro-N-((5-chloro-2-(1H-tetrazol-5-yl)benzofuran-6-yl)methyl)-4-(trifluoromethoxy)aniline;
N-((2-(2H-tetrazol-5-yl)benzofuran-6-yl)methyl)-4-chloroaniline;
3-bromo-N-((5-chloro-2-(1H-tetrazol-5-yl)benzofuran-6-yl)methyl)-4-propylaniline;
N-((2-(2H-tetrazol-5-yl)benzofuran-6-yl)methyl)-3-bromo-4,5-difluoroaniline;
3-bromo-N-((5-chloro-2-(1H-tetrazol-5-yl)benzofuran-6-yl)methyl)-4-(trifluoromethoxy)aniline;
N-((2-(2H-tetrazol-5-yl)benzofuran-6-yl)methyl)-3-bromo-4-(trifluoromethoxy)aniline;
N-((2-(1H-tetrazol-5-yl)-3-(trifluoromethyl)benzofuran-6-yl)methyl)-4-(trifluoromethoxy)-3-(trifluoromethyl)aniline;
N-((2-(2H-tetrazol-5-yl)benzofuran-6-yl)methyl)-4-bromo-3-(trifluoromethyl)aniline;
N-((2-(2H-tetrazol-5-yl)benzofuran-6-yl)methyl)-2,2-difluorobenzo[d][1,3]dioxol-5-amine;
N-((2-(2H-tetrazol-5-yl)benzofuran-6-yl)methyl)-3,4-bis(trifluoromethoxy)aniline;
N-((2-(1H-tetrazol-5-yl)benzofuran-6-yl)methyl)-3-bromo-4-propylaniline;
N-((2-(2H-tetrazol-5-yl)benzofuran-6-yl)methyl)-3-fluoro-4-(trifluoromethoxy)aniline;
N-((2-(2H-tetrazol-5-yl)benzofuran-6-yl)methyl)-3-chloro-4-(2,2,2-trifluoroethoxyl)aniline;
5-(6-((2-(3,4,5-trichlorophenyl)hydrazinyl)methyl)benzofuran-2-yl)-2H-tetrazole;
N-((2-(2H-tetrazol-5-yl)benzofuran-6-yl)methyl)-3-chloro-4-(trifluoromethoxy)aniline;
N-((2-(1H-tetrazol-5-yl)-3-(trifluoromethyl)benzofuran-6-yl)methyl)-3-bromo-4-(trifluoromethoxy)aniline;
N-((2-(2H-tetrazol-5-yl)benzofuran-6-yl)methyl)-4-bromo-3-(trifluoromethoxy)aniline;
N-((2-(1H-tetrazol-5-yl)-3-(trifluoromethyl)benzofuran-6-yl)methyl)-3,5-dichloro-4-ethoxyaniline;
N-((5-chloro-2-(1H-tetrazol-5-yl)benzofuran-6-yl)methyl)-3-fluoro-4-(trifluoromethoxy)aniline;
N-((3-methyl-2-(1H-tetrazol-5-yl)benzofuran-6-yl)methyl)-4-propyl-3-(trifluoromethyl)aniline;
N-((2-(2H-tetrazol-5-yl)benzofuran-6-yl)methyl)-3,4-bis(trifluoromethyl)aniline;
3-bromo-N-((3-methyl-2-(1H-tetrazol-5-yl)benzofuran-6-yl)methyl)-4-(trifluoromethoxy)aniline;
N-((2-(1H-tetrazol-5-yl)-3-(trifluoromethyl)benzofuran-6-yl)methyl)-3-chloro-4-(trifluoromethoxy)aniline;
N-((2-(1H-tetrazol-5-yl)-3-(trifluoromethyl)benzofuran-6-yl)methyl)-4-propyl-3-(trifluoromethyl)aniline;
N-((2-(1H-tetrazol-5-yl)-3-(trifluoromethyl)benzofuran-6-yl)methyl)-4-ethoxy-3-(trifluoromethyl)aniline;
N-((2-(1H-tetrazol-5-yl)-3-(trifluoromethyl)benzofuran-6-yl)methyl)-4-isopropoxy-3-(trifluoromethyl)aniline;
N-((2-(2H-tetrazol-5-yl)benzofuran-6-yl)methyl)-4-fluoro-3-(2,2,2-trifluoroethyl)aniline;
N-((2-(2H-tetrazol-5-yl)benzofuran-6-yl)methyl)-3-bromoaniline;
N-((2-(1H-tetrazol-5-yl)-3-(trifluoromethyl)benzofuran-6-yl)methyl)-4-(difluoromethoxy)-3-(trifluoromethyl)aniline;
N-((2-(1H-tetrazol-5-yl)-3-(trifluoromethyl)benzofuran-6-yl)methyl)-3-chloro-4-(trifluoromethyl)aniline;
N-((2-(2H-tetrazol-5-yl)benzofuran-6-yl)methyl)-3,4,5-trimethoxyaniline;
N-((2-(2H-tetrazol-5-yl)benzofuran-6-yl)methyl)-4-(trifluoromethoxy)aniline;
N-((2-(1H-tetrazol-5-yl)benzofuran-5-yl)methyl)-3-chloro-4-((trifluoromethyl)thio)aniline;
N-((2-(1H-tetrazol-5-yl)benzofuran-5-yl)methyl)-3-chloro-4-(trifluoromethoxy)aniline;
N-((2-(1H-tetrazol-5-yl)benzofuran-5-yl)methyl)-4-propyl-3-(trifluoromethyl)aniline;
N-((2-(1H-tetrazol-5-yl)benzofuran-5-yl)methyl)-2,2-difluorobenzo[d][1,3]dioxol-5-amine;
N-((2-(1H-tetrazol-5-yl)benzofuran-5-yl)methyl)-4-chloro-3-propylaniline;
N-((2-(1H-tetrazol-5-yl)benzofuran-5-yl)methyl)-3-chloro-5-methyl-4-propylaniline;
3-chloro-N-((3-methyl-2-(1H-tetrazol-5-yl)benzofuran-5-yl)methyl)-4-((trifluoromethyl)thio)aniline;
N-((2-(1H-tetrazol-5-yl)benzofuran-5-yl)methyl)-3-chloro-4-propylaniline;
N-((2-(1H-tetrazol-5-yl)benzofuran-5-yl)methyl)-4-fluoro-3-(trifluoromethoxy)aniline;
N-(1-(2-(1H-tetrazol-5-yl)benzofuran-5-yl)ethyl)-3,4,5-trichloroaniline;
N-(1-(2-(1H-tetrazol-5-yl)benzofuran-5-yl)ethyl)-3-chloro-4-((trifluoromethyl)thio)aniline;
N-((2-(1H-tetrazol-5-yl)benzofuran-5-yl)methyl)-3-chloro-5-(trifluoromethoxy)aniline;
N-((2-(1H-tetrazol-5-yl)benzofuran-5-yl)methyl)-4-propyl-3-(trifluoromethoxy)aniline;
N-(1-(2-(1H-tetrazol-5-yl)benzofuran-5-yl)ethyl)-3-chloro-4-(trifluoromethoxy)aniline;
N-((2-(1H-tetrazol-5-yl)benzofuran-5-yl)methyl)-4-ethyl-3-(trifluoromethyl)aniline;
N-((2-(1H-tetrazol-5-yl)benzofuran-5-yl)methyl)-3-fluoro-4-propylaniline;
N-((2-(1H-tetrazol-5-yl)benzofuran-5-yl)methyl)-3-methyl-4-propylaniline;
N-(1-(2-(1H-tetrazol-5-yl)benzofuran-5-yl)ethyl)-4-propyl-3-(trifluoromethyl)aniline;
N-((3-methyl-2-(1H-tetrazol-5-yl)benzofuran-5-yl)methyl)-4-propyl-3-(trifluoromethyl)aniline;
N-(1-(2-(1H-tetrazol-5-yl)benzofuran-5-yl)ethyl)-2,2-difluorobenzo[d][1,3]dioxol-5-amine;

N-(1-(2-(1H-tetrazol-5-yl)benzofuran-5-yl)ethyl)-3-chloro-4-propylaniline;
6-(((3,4,5-tribromophenyl)amino)methyl)benzofuran-2-carboxylic acid;
6-(((3,4,5-trichlorophenyl)amino)methyl)benzofuran-2-carboxylic acid;
6-(((3-chloro-4-((trifluoromethyl)thio)phenyl)amino)methyl)benzofuran-2-carboxylic acid;
6-(((3-chloro-4-(trifluoromethoxy)phenyl)amino)methyl)benzofuran-2-carboxylic acid;
6-(((2,2-difluorobenzo[d][1,3]dioxol-5-yl)amino)methyl)benzofuran-2-carboxylic acid;
6-(((3-bromo-4-(trifluoromethoxy)phenyl)amino)methyl)benzofuran-2-carboxylic acid;
6-(((3-(trifluoromethyl)-4-((trifluoromethyl)thio)phenyl)amino)methyl)benzofuran-2-carboxylic acid;
6-(((4-(trifluoromethoxy)-3-(trifluoromethyl)phenyl)amino)methyl)benzofuran-2-carboxylic acid;
6-(((3-chloro-4-propylphenyl)amino)methyl)benzofuran-2-carboxylic acid;
6-(((2,2,3,3-tetrafluoro-2,3-dihydrobenzo[b][1,4]dioxin-6-yl)amino)methyl)benzofuran-2-carboxylic acid;
6-(((4-propyl-3-(trifluoromethyl)phenyl)amino)methyl)benzofuran-2-carboxylic acid;
6-(((4-(methylthio)-3-(trifluoromethyl)phenyl)amino)methyl)benzofuran-2-carboxylic acid;
6-(((3-(methylthio)phenyl)amino)methyl)benzofuran-2-carboxylic acid;
6-(((3-bromo-4-morpholinophenyl)amino)methyl)benzofuran-2-carboxylic acid;
6-(((4-(pentafluorothio)phenyl)amino)methyl)benzofuran-2-carboxylic acid;
6-(((4-ethyl-3-(trifluoromethyl)phenyl)amino)methyl)benzofuran-2-carboxylic acid;
6-(((3,4-bis(trifluoromethyl)phenyl)amino)methyl)benzofuran-2-carboxylic acid;
6-(((3-methyl-4-(trifluoromethoxy)phenyl)amino)methyl)benzofuran-2-carboxylic acid;
6-(((4-(2,2,2-trifluoroacetyl)phenyl)amino)methyl)benzofuran-2-carboxylic acid;
6-(((3,4-bis(trifluoromethoxy)phenyl)amino)methyl)benzofuran-2-carboxylic acid;
6-(((2,3-dihydrobenzo[b][1,4]dioxin-6-yl)amino)methyl)benzofuran-2-carboxylic acid;
6-(((3-bromo-4,5-difluorophenyl)amino)methyl)benzofuran-2-carboxylic acid;
6-(((3-bromo-4-(trifluoromethoxy)phenyl)amino)methyl)-3-(trifluoromethyl)benzofuran-2-carboxylic acid;
6-(((3-chloro-4-(2,2,2-trifluoroethoxyl)phenyl)amino)methyl)benzofuran-2-carboxylic acid;
6-(((3-morpholinophenyl)amino)methyl)benzofuran-2-carboxylic acid;
6-(((3-chloro-4-fluoro-5-(trifluoromethyl)phenyl)amino)methyl)benzofuran-2-carboxylic acid;
6-(((4-propyl-3-(trifluoromethyl)phenyl)amino)methyl)-3-(trifluoromethyl)benzofuran-2-carboxylic acid;
6-(((5-(trifluoromethyl)pyridin-2-yl)amino)methyl)benzofuran-2-carboxylic acid;
6-(((4-((trifluoromethyl)thio)phenyl)amino)methyl)benzofuran-2-carboxylic acid;
6-(((2-methylbenzo[d]thiazol-5-yl)amino)methyl)benzofuran-2-carboxylic acid;
6-(((3-chloro-4-methoxyphenyl)amino)methyl)benzofuran-2-carboxylic acid;
6-(((3,5-bis(trifluoromethyl)phenyl)amino)methyl)benzofuran-2-carboxylic acid;
6-(((4-methoxy-3-(trifluoromethyl)phenyl)amino)methyl)benzofuran-2-carboxylic acid;
6-(((4-(2,2,2-trifluoroethoxy)-3-(trifluoromethyl)phenyl)amino)methyl)benzofuran-2-carboxylic acid;
6-(((2,6-dichloropyridin-4-yl)amino)methyl)benzofuran-2-carboxylic acid;
5-(((3,4,5-trichlorophenyl)amino)methyl)benzofuran-2-carboxylic acid;
5-(((3-chloro-4-propylphenyl)amino)methyl)benzofuran-2-carboxylic acid;
5-(((4-propyl-3-(trifluoromethyl)phenyl)amino)methyl)benzofuran-2-carboxylic acid;
5-(((3,4-dichlorophenyl)amino)methyl)benzofuran-2-carboxylic acid;
5-(((4-ethyl-3-(trifluoromethyl)phenyl)amino)methyl)benzofuran-2-carboxylic acid;
5-(((3-propyl-4-(trifluoromethyl)phenyl)amino)methyl)benzofuran-2-carboxylic acid;
5-(((4-chloro-3-propylphenyl)amino)methyl)benzofuran-2-carboxylic acid;
N-((6-fluoro-2-(1H-tetrazol-5-yl)benzofuran-5-yl)methyl)-4-(2,2,2-trifluoroethoxy)-3-(trifluoromethyl)aniline;
N-((6-fluoro-2-(1H-tetrazol-5-yl)benzofuran-5-yl)methyl)-4-propyl-3-(trifluoromethyl)aniline;
3,4-dichloro-N-((6-fluoro-2-(1H-tetrazol-5-yl)benzofuran-5-yl)methyl)aniline;
N-((6-fluoro-2-(1H-tetrazol-5-yl)benzofuran-5-yl)methyl)-4-(trifluoromethoxy)-3-(trifluoromethyl)aniline;
3-bromo-N-((6-fluoro-2-(1H-tetrazol-5-yl)benzofuran-5-yl)methyl)-4-(trifluoromethoxy)aniline;
4-(difluoromethoxy)-N-((6-fluoro-2-(1H-tetrazol-5-yl)benzofuran-5-yl)methyl)-3-(trifluoromethyl)aniline;
4-bromo-N-((6-fluoro-2-(1H-tetrazol-5-yl)benzofuran-5-yl)methyl)-3,5-bis(trifluoromethyl)aniline;
N-((6-chloro-2-(1H-tetrazol-5-yl)benzofuran-5-yl)methyl)-4-(difluoromethoxy)-3-(trifluoromethyl)aniline;
N-((6-chloro-2-(1H-tetrazol-5-yl)benzofuran-5-yl)methyl)-4-(2,2,2-trifluoroethoxy)-3-(trifluoromethyl)aniline;
3-bromo-N-((6-chloro-2-(1H-tetrazol-5-yl)benzofuran-5-yl)methyl)-4-(trifluoromethoxy)aniline;
4-bromo-N-((6-chloro-2-(1H-tetrazol-5-yl)benzofuran-5-yl)methyl)-3,5-bis(trifluoromethyl)aniline;
3-chloro-N-((6-chloro-2-(1H-tetrazol-5-yl)benzofuran-5-yl)methyl)-4-(trifluoromethyl)aniline;
3,4-dichloro-N-((6-chloro-2-(1H-tetrazol-5-yl)benzofuran-5-yl)methyl)aniline;
3-bromo-N-((4-fluoro-2-(1H-tetrazol-5-yl)benzofuran-5-yl)methyl)-4-(trifluoromethoxy)aniline;
4-(difluoromethoxy)-N-((4-fluoro-2-(1H-tetrazol-5-yl)benzofuran-5-yl)methyl)-3-(trifluoromethyl)aniline
N-((4-fluoro-2-(1H-tetrazol-5-yl)benzofuran-5-yl)methyl)-4-(2,2,2-trifluoroethoxy)-3-(trifluoromethyl)aniline;
4-bromo-N-((4-fluoro-2-(1H-tetrazol-5-yl)benzofuran-5-yl)methyl)-3,5-bis(trifluoromethyl)aniline;
N-((4-fluoro-2-(1H-tetrazol-5-yl)benzofuran-5-yl)methyl)-4-(trifluoromethoxy)-3-(trifluoromethyl)aniline;
4-(difluoromethoxy)-N-((7-fluoro-2-(1H-tetrazol-5-yl)benzofuran-5-yl)methyl)-3-(trifluoromethyl)aniline;
N-((7-fluoro-2-(1H-tetrazol-5-yl)benzofuran-5-yl)methyl)-4-(trifluoromethoxy)-3-(trifluoromethyl)aniline;
N-((7-fluoro-2-(1H-tetrazol-5-yl)benzofuran-5-yl)methyl)-4-(2,2,2-trifluoroethoxy)-3-(trifluoromethyl)aniline;
3-bromo-N-((7-fluoro-2-(1H-tetrazol-5-yl)benzofuran-5-yl)methyl)-4-(trifluoromethoxy)aniline;
4-chloro-N-((5-fluoro-2-(1H-tetrazol-5-yl)benzofuran-6-yl)methyl)-3-(trifluoromethyl)aniline;

4-bromo-N-((7-fluoro-2-(1H-tetrazol-5-yl)benzofuran-6-yl)methyl)-3,5-bis(trifluoromethyl)aniline;
4-(difluoromethoxy)-N-((5-fluoro-2-(1H-tetrazol-5-yl)benzofuran-6-yl)methyl)-3-(trifluoromethyl)aniline;
N-((5-methoxy-2-(1H-tetrazol-5-yl)benzofuran-6-yl)methyl)-4-(2,2,2-trifluoroethoxy)-3-(trifluoromethyl)aniline;
N-((7-fluoro-2-(1H-tetrazol-5-yl)benzofuran-6-yl)methyl)-4-(2,2,2-trifluoroethoxy)-3-(trifluoromethyl)aniline;
2-(4-(((5-bromo-2-(1H-tetrazol-5-yl)benzofuran-6-yl)methyl)amino)-2-(trifluoromethyl)phenoxy)acetonitrile;
N-((5-bromo-2-(1H-tetrazol-5-yl)benzofuran-6-yl)methyl)-4-(difluoromethoxy)-3-(trifluoromethyl)aniline;
N-((5-chloro-2-(1H-tetrazol-5-yl)benzofuran-6-yl)methyl)-4-(2,2-difluoroethoxy)-3-(trifluoromethyl)aniline;
N-((5-fluoro-2-(1H-tetrazol-5-yl)benzofuran-6-yl)methyl)-3,4-bis(trifluoromethyl)aniline;
4-bromo-N-((5-fluoro-2-(1H-tetrazol-5-yl)benzofuran-6-yl)methyl)-3,5-bis(trifluoromethyl)aniline;
3-bromo-N-((5-fluoro-2-(1H-tetrazol-5-yl)benzofuran-6-yl)methyl)-4-isopropylaniline;
N-((2-(2H-tetrazol-5-yl)benzofuran-5-yl)methyl)-3-bromo-4-(trifluoromethoxy)aniline;
4-ethoxy-N-((5-fluoro-2-(1H-tetrazol-5-yl)benzofuran-6-yl)methyl)-3-(trifluoromethyl)aniline;
4-(2,2-difluoroethoxy)-N-((5-fluoro-2-(1H-tetrazol-5-yl)benzofuran-6-yl)methyl)-3-(trifluoromethyl)aniline;
N-((5-fluoro-2-(1H-tetrazol-5-yl)benzofuran-6-yl)methyl)-4-isopropoxy-3-(trifluoromethyl)aniline;
N-((5-bromo-2-(1H-tetrazol-5-yl)benzofuran-6-yl)methyl)-4-(2,2,2-trifluoroethoxy)-3-(trifluoromethyl)aniline;
N-((5-bromo-2-(1H-tetrazol-5-yl)benzofuran-6-yl)methyl)-4-(trifluoromethoxy)-3-(trifluoromethyl)aniline;
4-(difluoromethoxy)-N-((5-methoxy-2-(1H-tetrazol-5-yl)benzofuran-6-yl)methyl)-3-(trifluoromethyl)aniline;
4-(difluoromethoxy)-N-((7-fluoro-2-(1H-tetrazol-5-yl)benzofuran-6-yl)methyl)-3-(trifluoromethyl)aniline;
N-((5-fluoro-2-(1H-tetrazol-5-yl)benzofuran-6-yl)methyl)-4-(2,2,2-trifluoroethoxy)-3-(trifluoromethyl)aniline;
N-((7-fluoro-2-(1H-tetrazol-5-yl)benzofuran-6-yl)methyl)-4-(trifluoromethoxy)-3-(trifluoromethyl)aniline;
N-((5-methyl-2-(1H-tetrazol-5-yl)benzofuran-6-yl)methyl)-4-(2,2,2-trifluoroethoxy)-3-(trifluoromethyl)aniline;
N-((7-chloro-2-(1H-tetrazol-5-yl)benzofuran-6-yl)methyl)-4-isopropoxy-3-(trifluoromethyl)aniline;
N-((2-(2H-tetrazol-5-yl)benzofuran-5-yl)methyl)-3-bromo-4-ethoxyaniline;
N-((5-bromo-2-(1H-tetrazol-5-yl)benzofuran-6-yl)methyl)-4-isopropoxy-3-(trifluoromethyl)aniline;
N-((2-(2H-tetrazol-5-yl)benzofuran-5-yl)methyl)-3-bromo-4-methoxyaniline;
N-((5-fluoro-2-(1H-tetrazol-5-yl)benzofuran-6-yl)methyl)-4-(trifluoromethoxy)-3-(trifluoromethyl)aniline;
4-fluoro-N-((5-fluoro-2-(1H-tetrazol-5-yl)benzofuran-6-yl)methyl)-3-(trifluoromethyl)aniline;
3-bromo-N-((5-fluoro-2-(1H-tetrazol-5-yl)benzofuran-6-yl)methyl)-4-(trifluoromethyl)aniline;
N-((5-bromo-2-(1H-tetrazol-5-yl)benzofuran-6-yl)methyl)-4-ethoxy-3-(trifluoromethyl)aniline;
6-chloro-N-((5-chloro-2-(1H-tetrazol-5-yl)benzofuran-6-yl)methyl)-5-(trifluoromethyl)pyridin-3-amine;
3-bromo-4-chloro-N-((5-fluoro-2-(1H-tetrazol-5-yl)benzofuran-6-yl)methyl)aniline;
3-bromo-4-ethyl-N-((5-fluoro-2-(1H-tetrazol-5-yl)benzofuran-6-yl)methyl)aniline;
N-((2-(2H-tetrazol-5-yl)benzofuran-5-yl)methyl)-3-bromo-4-chloroaniline;
3-bromo-N-((5-fluoro-2-(1H-tetrazol-5-yl)benzofuran-6-yl)methyl)-4-(trifluoromethoxy)aniline;
N-((7-chloro-2-(1H-tetrazol-5-yl)benzofuran-6-yl)methyl)-4-(trifluoromethoxy)-3-(trifluoromethyl)aniline;
3,5-dibromo-4-(difluoromethoxy)-N-((5-fluoro-2-(1H-tetrazol-5-yl)benzofuran-6-yl)methyl)aniline;
3-chloro-N-((5-fluoro-2-(1H-tetrazol-5-yl)benzofuran-6-yl)methyl)-4-(trifluoromethoxy)aniline;
N-((7-chloro-2-(1H-tetrazol-5-yl)benzofuran-6-yl)methyl)-4-(2,2,2-trifluoroethoxy)-3-(trifluoromethyl)aniline;
7-chloro-N-((5-chloro-2-(1H-tetrazol-5-yl)benzofuran-6-yl)methyl)-2-methylbenzofuran-5-amine;
4-bromo-N-((5-chloro-2-(1H-tetrazol-5-yl)benzofuran-6-yl)methyl)-3,5-bis(trifluoromethyl)aniline;
3-fluoro-N-((5-fluoro-2-(1H-tetrazol-5-yl)benzofuran-6-yl)methyl)-4-propylaniline;
N-((7-chloro-2-(1H-tetrazol-5-yl)benzofuran-6-yl)methyl)-4-(difluoromethoxy)-3-(trifluoromethyl)aniline;
3-fluoro-N-((5-fluoro-2-(1H-tetrazol-5-yl)benzofuran-6-yl)methyl)-4-(trifluoromethoxy)aniline;
3-bromo-N-((7-fluoro-2-(1H-tetrazol-5-yl)benzofuran-6-yl)methyl)-4-(trifluoromethoxy)aniline;
N-((2-(2H-tetrazol-5-yl)benzofuran-6-yl)methyl)-7-chloro-2-methylbenzofuran-5-amine;
N-((5-fluoro-2-(1H-tetrazol-5-yl)benzofuran-6-yl)methyl)-3-methyl-5-(trifluoromethyl)aniline;
3-chloro-N-((5-fluoro-2-(1H-tetrazol-5-yl)benzofuran-6-yl)methyl)-4-(trifluoromethyl)aniline;
2-(difluoromethoxy)-5-(((5-fluoro-2-(1H-tetrazol-5-yl)benzofuran-6-yl)methyl)amino)benzonitrile;
3-chloro-N-((5-chloro-2-(1H-tetrazol-5-yl)benzofuran-6-yl)methyl)-4-(trifluoromethyl)aniline;
3-chloro-N-((5-chloro-2-(1H-tetrazol-5-yl)benzofuran-6-yl)methyl)-4-(difluoromethoxy)aniline;
5-(((5-bromo-2-(1H-tetrazol-5-yl)benzofuran-6-yl)methyl)amino)-2-(difluoromethoxy)benzonitrile;
3-chloro-N-((5-chloro-2-(1H-tetrazol-5-yl)benzofuran-6-yl)methyl)-4-fluoro-5-(trifluoromethyl)aniline;
5-(((7-chloro-2-(1H-tetrazol-5-yl)benzofuran-6-yl)methyl)amino)-2-(difluoromethoxy)benzonitrile;
3-fluoro-N-((5-fluoro-2-(1H-tetrazol-5-yl)benzofuran-6-yl)methyl)-4-(trifluoromethyl)aniline;
N-((2-(2H-tetrazol-5-yl)benzofuran-6-yl)methyl)-6-chloro-5-(trifluoromethyl)pyridin-3-amine;
3-chloro-N-((5-fluoro-2-(1H-tetrazol-5-yl)benzofuran-6-yl)methyl)-4-(2,2,2-trifluoroethoxy)aniline;
N-((7-chloro-2-(1H-tetrazol-5-yl)benzofuran-6-yl)methyl)-4-ethoxy-3-(trifluoromethyl)aniline;
N-((5-chloro-2-(1H-tetrazol-5-yl)benzofuran-6-yl)methyl)-4-isopropyl-3-(trifluoromethyl)aniline;
3,4-dichloro-N-((5-fluoro-2-(1H-tetrazol-5-yl)benzofuran-6-yl)methyl)aniline;
N-((2-(2H-tetrazol-5-yl)benzofuran-6-yl)methyl)-3-methyl-benzo[d]isothiazol-5-amine;
2-(4-(((7-chloro-2-(1H-tetrazol-5-yl)benzofuran-6-yl)methyl)amino)-2-(trifluoromethyl)phenoxy)acetonitrile;
3-chloro-4-ethoxy-N-((5-fluoro-2-(1H-tetrazol-5-yl)benzofuran-6-yl)methyl)aniline;
3-chloro-N-((5-chloro-2-(1H-tetrazol-5-yl)benzofuran-6-yl)methyl)-5-(trifluoromethoxy)aniline;
N-((5-chloro-2-(1H-tetrazol-5-yl)benzofuran-6-yl)methyl)-3-methyl-5-(trifluoromethyl)aniline;
4-chloro-3-fluoro-N-((5-fluoro-2-(1H-tetrazol-5-yl)benzofuran-6-yl)methyl)aniline;
3-chloro-4-fluoro-N-((5-fluoro-2-(1H-tetrazol-5-yl)benzofuran-6-yl)methyl)aniline;

N-((2-(2H-tetrazol-5-yl)benzofuran-6-yl)methyl)-3-bromo-4-isobutoxyaniline;
3-chloro-N-((5-chloro-2-(1H-tetrazol-5-yl)benzofuran-6-yl)methyl)-4-ethoxyaniline;
N-((2-(2H-tetrazol-5-yl)benzofuran-6-yl)methyl)-2-fluoro-4-(trifluoromethoxy)aniline;
N-((2-(2H-tetrazol-5-yl)benzofuran-6-yl)methyl)-2,2,4,4-tetrafluoro-4H-benzo[d][1,3]dioxin-6-amine;
3-chloro-N-((5-chloro-2-(1H-tetrazol-5-yl)benzofuran-6-yl)methyl)-5-methyl-4-propylaniline;
N-((5-chloro-2-(1H-tetrazol-5-yl)benzofuran-6-yl)methyl)-4-fluoro-3-(2,2,2-trifluoroethyl)aniline;
N,N-bis((2-(2H-tetrazol-5-yl)benzofuran-6-yl)methyl)-3-bromo-4-isobutoxyaniline;
7-(((2-(2H-tetrazol-5-yl)benzofuran-6-yl)methyl)amino)-4-(trifluoromethyl)-2H-chromen-2-one;
5-chloro-6-(((4-(difluoromethoxy)-3-(trifluoromethyl)phenyl)amino)methyl)benzofuran-2-carboxylic acid;
5-chloro-6-(((4-(2,2,2-trifluoroethoxy)-3-(trifluoromethyl)phenyl)amino)methyl)benzofuran-2-carboxylic acid;
6-(((3-chloro-4-(2,2,2-trifluoroethoxyl)phenyl)amino)methyl)-5-fluorobenzofuran-2-carboxylic acid;
6-(((3-chloro-4-(trifluoromethoxy)phenyl)amino)methyl)-5-fluorobenzofuran-2-carboxylic acid;
6-(((3-bromo-4-(trifluoromethoxy)phenyl)amino)methyl)-5-fluorobenzofuran-2-carboxylic acid;
6-(((3-chloro-4-((trifluoromethyl)thio)phenyl)amino)methyl)-5-fluorobenzofuran-2-carboxylic acid;
6-(((4-bromo-3,5-bis(trifluoromethyl)phenyl)amino)methyl)-5-fluorobenzofuran-2-carboxylic acid;
6-(((4-(difluoromethoxy)-3-(trifluoromethyl)phenyl)amino)methyl)-5-fluorobenzofuran-2-carboxylic acid;
5-fluoro-6-(((4-(2,2,2-trifluoroethoxy)-3-(trifluoromethyl)phenyl)amino)methyl)benzofuran-2-carboxylic acid;
5-fluoro-6-(((3,4,5-trichlorophenyl)amino)methyl)benzofuran-2-carboxylic acid; and
N-((3-(2H-tetrazol-5-yl)benzofuran-6-yl)methyl)-3-bromo-4-(trifluoromethoxy)aniline.

In another embodiment, the invention is the compound according to the first or twelfth embodiments, or a salt thereof, wherein the compound is selected from:
N-((2-(2H-tetrazol-5-yl)benzofuran-6-yl)methyl)-3-bromo-5-fluoro-4-methoxyaniline;
N-((2-(2H-tetrazol-5-yl)benzofuran-6-yl)methyl)-3-bromo-4-ethoxy-5-fluoroaniline;
N-((2-(2H-tetrazol-5-yl)benzofuran-6-yl)methyl)-3-bromo-4-(trifluoromethyl)aniline;
N-((2-(2H-tetrazol-5-yl)benzofuran-6-yl)methyl)-3,5-dibromo-4-(difluoromethoxy)aniline;
3,5-dichloro-N-((5-chloro-2-(1H-tetrazol-5-yl)benzofuran-6-yl)methyl)-4-ethoxyaniline;
N-((5-chloro-2-(1H-tetrazol-5-yl)benzofuran-6-yl)methyl)-4-(trifluoromethoxy)-3-(trifluoromethyl)aniline;
N-((5-chloro-2-(1H-tetrazol-5-yl)benzofuran-6-yl)methyl)-3-fluoro-4-((trifluoromethyl)thio)aniline;
3-chloro-N-((5-chloro-2-(1H-tetrazol-5-yl)benzofuran-6-yl)methyl)-4-(2,2,2-trifluoroethoxy)aniline;
N-((5-chloro-2-(1H-tetrazol-5-yl)benzofuran-6-yl)methyl)-4-fluoro-3-(trifluoromethoxy)aniline;
N-((5-chloro-2-(1H-tetrazol-5-yl)benzofuran-6-yl)methyl)-4-ethoxy-3-(trifluoromethyl)aniline;
N-((2-(2H-tetrazol-5-yl)benzofuran-6-yl)methyl)-3-(prop-1-en-2-yl)-4-(trifluoromethoxy)aniline;
3-chloro-N-((5-chloro-2-(1H-tetrazol-5-yl)benzofuran-6-yl)methyl)-4-propylaniline;
4-chloro-N-((5-chloro-2-(1H-tetrazol-5-yl)benzofuran-6-yl)methyl)-3-(trifluoromethoxy)aniline;
N-((5-chloro-2-(1H-tetrazol-5-yl)benzofuran-6-yl)methyl)-3,4-bis(trifluoromethyl)aniline;
3,4,5-trichloro-N-((5-chloro-2-(1H-tetrazol-5-yl)benzofuran-6-yl)methyl)aniline;
N-((2-(1H-tetrazol-5-yl)benzofuran-6-yl)methyl)-4-propyl-3-(trifluoromethyl)aniline;
N-((2-(2H-tetrazol-5-yl)benzofuran-6-yl)methyl)-3-chloro-4-(difluoromethoxy)aniline;
N-((5-chloro-2-(1H-tetrazol-5-yl)benzofuran-6-yl)methyl)-4-isopropoxy-3-(trifluoromethyl)aniline;
N-((2-(2H-tetrazol-5-yl)benzofuran-6-yl)methyl)-3,4,5-trichloroaniline;
N-((2-(2H-tetrazol-5-yl)benzofuran-6-yl)methyl)-3-chloro-4-((trifluoromethyl)thio)aniline;
N-((2-(2H-tetrazol-5-yl)benzofuran-6-yl)methyl)-3-methyl-4-(trifluoromethoxy)aniline;
N-((5-chloro-2-(1H-tetrazol-5-yl)benzofuran-6-yl)methyl)-4-(2,2,2-trifluoroethoxy)-3-(trifluoromethyl)aniline;
N-((2-(2H-tetrazol-5-yl)benzofuran-6-yl)methyl)-4-(trifluoromethoxy)-3-(trifluoromethyl)aniline;
3-chloro-N-((5-chloro-2-(1H-tetrazol-5-yl)benzofuran-6-yl)methyl)-4-((trifluoromethyl)thio)aniline;
N-((5-chloro-2-(1H-tetrazol-5-yl)benzofuran-6-yl)methyl)-4-(difluoromethoxy)-3-(trifluoromethyl)aniline;
N-((2-(2H-tetrazol-5-yl)benzofuran-6-yl)methyl)-4-(methylthio)-3-(trifluoromethyl)aniline;
N-((2-(2H-tetrazol-5-yl)benzofuran-6-yl)methyl)-4-(2,2,2-trifluoroethoxy)-3-(trifluoromethyl)aniline;
N-((2-(2H-tetrazol-5-yl)benzofuran-6-yl)methyl)-3-(methylthio)aniline;
2-(4-(((5-chloro-2-(1H-tetrazol-5-yl)benzofuran-6-yl)methyl)amino)-2-(trifluoromethyl)phenoxy)acetonitrile;
1-(4-(((2-(1H-tetrazol-5-yl)benzofuran-6-yl)methyl)amino)phenyl)-2,2,2-trifluoroethanone;
N-((5-chloro-2-(1H-tetrazol-5-yl)benzofuran-6-yl)methyl)-4-propyl-3-(trifluoromethyl)aniline;
3-chloro-N-((5-chloro-2-(1H-tetrazol-5-yl)benzofuran-6-yl)methyl)-4-(trifluoromethoxy)aniline;
N-((2-(2H-tetrazol-5-yl)benzofuran-6-yl)methyl)-4-chloroaniline;
3-bromo-N-((5-chloro-2-(1H-tetrazol-5-yl)benzofuran-6-yl)methyl)-4-propylaniline;
N-((2-(2H-tetrazol-5-yl)benzofuran-6-yl)methyl)-3-bromo-4,5-difluoroaniline;
3-bromo-N-((5-chloro-2-(1H-tetrazol-5-yl)benzofuran-6-yl)methyl)-4-(trifluoromethoxy)aniline;
N-((2-(2H-tetrazol-5-yl)benzofuran-6-yl)methyl)-3-bromo-4-(trifluoromethoxy)aniline;
N-((2-(1H-tetrazol-5-yl)-3-(trifluoromethyl)benzofuran-6-yl)methyl)-4-(trifluoromethoxy)-3-(trifluoromethyl)aniline;
N-((2-(2H-tetrazol-5-yl)benzofuran-6-yl)methyl)-4-bromo-3-(trifluoromethyl)aniline;
N-((2-(2H-tetrazol-5-yl)benzofuran-6-yl)methyl)-2,2-difluorobenzo[d][1,3]dioxol-5-amine;
N-((2-(2H-tetrazol-5-yl)benzofuran-6-yl)methyl)-3,4-bis(trifluoromethoxy)aniline;
N-((2-(1H-tetrazol-5-yl)benzofuran-6-yl)methyl)-3-bromo-4-propylaniline;
N-((2-(2H-tetrazol-5-yl)benzofuran-6-yl)methyl)-3-fluoro-4-(trifluoromethoxy)aniline;
N-((2-(2H-tetrazol-5-yl)benzofuran-6-yl)methyl)-3-chloro-4-(2,2,2-trifluoroethoxyl)aniline;
5-(6-((2-(3,4,5-trichlorophenyl)hydrazinyl)methyl)benzofuran-2-yl)-2H-tetrazole;
N-((2-(2H-tetrazol-5-yl)benzofuran-6-yl)methyl)-3-chloro-4-(trifluoromethoxy)aniline;

N-((2-(1H-tetrazol-5-yl)-3-(trifluoromethyl)benzofuran-6-yl)methyl)-3-bromo-4-(trifluoromethoxy)aniline;
N-((2-(2H-tetrazol-5-yl)benzofuran-6-yl)methyl)-4-bromo-3-(trifluoromethoxy)aniline;
N-((2-(1H-tetrazol-5-yl)-3-(trifluoromethyl)benzofuran-6-yl)methyl)-3,5-dichloro-4-ethoxyaniline;
N-((5-chloro-2-(1H-tetrazol-5-yl)benzofuran-6-yl)methyl)-3-fluoro-4-(trifluoromethoxy)aniline;
N-((3-methyl-2-(1H-tetrazol-5-yl)benzofuran-6-yl)methyl)-4-propyl-3-(trifluoromethyl)aniline;
N-((2-(2H-tetrazol-5-yl)benzofuran-6-yl)methyl)-3,4-bis(trifluoromethyl)aniline;
3-bromo-N-((3-methyl-2-(1H-tetrazol-5-yl)benzofuran-6-yl)methyl)-4-(trifluoromethoxy)aniline;
N-((2-(1H-tetrazol-5-yl)-3-(trifluoromethyl)benzofuran-6-yl)methyl)-3-chloro-4-(trifluoromethoxy)aniline;
N-((2-(1H-tetrazol-5-yl)-3-(trifluoromethyl)benzofuran-6-yl)methyl)-4-propyl-3-(trifluoromethyl)aniline;
N-((2-(1H-tetrazol-5-yl)-3-(trifluoromethyl)benzofuran-6-yl)methyl)-4-ethoxy-3-(trifluoromethyl)aniline;
N-((2-(1H-tetrazol-5-yl)-3-(trifluoromethyl)benzofuran-6-yl)methyl)-4-isopropoxy-3-(trifluoromethyl)aniline;
N-((2-(2H-tetrazol-5-yl)benzofuran-6-yl)methyl)-4-fluoro-3-(2,2,2-trifluoroethyl)aniline;
N-((2-(2H-tetrazol-5-yl)benzofuran-6-yl)methyl)-3-bromoaniline;
N-((2-(1H-tetrazol-5-yl)-3-(trifluoromethyl)benzofuran-6-yl)methyl)-4-(difluoromethoxy)-3-(trifluoromethyl)aniline;
N-((2-(1H-tetrazol-5-yl)-3-(trifluoromethyl)benzofuran-6-yl)methyl)-3-chloro-4-(trifluoromethyl)aniline;
N-((2-(2H-tetrazol-5-yl)benzofuran-6-yl)methyl)-3,4,5-trimethoxyaniline;
N-((2-(2H-tetrazol-5-yl)benzofuran-6-yl)methyl)-4-(trifluoromethoxy)aniline;
N-((2-(1H-tetrazol-5-yl)benzofuran-5-yl)methyl)-3-chloro-4-((trifluoromethyl)thio)aniline;
N-((2-(1H-tetrazol-5-yl)benzofuran-5-yl)methyl)-3-chloro-4-(trifluoromethoxy)aniline;
N-((2-(1H-tetrazol-5-yl)benzofuran-5-yl)methyl)-4-propyl-3-(trifluoromethyl)aniline;
N-((2-(1H-tetrazol-5-yl)benzofuran-5-yl)methyl)-2,2-difluorobenzo[d][1,3]dioxol-5-amine;
N-((2-(1H-tetrazol-5-yl)benzofuran-5-yl)methyl)-4-chloro-3-propylaniline;
N-((2-(1H-tetrazol-5-yl)benzofuran-5-yl)methyl)-3-chloro-5-methyl-4-propylaniline;
3-chloro-N-((3-methyl-2-(1H-tetrazol-5-yl)benzofuran-5-yl)methyl)-4-((trifluoromethyl)thio)aniline;
N-((2-(1H-tetrazol-5-yl)benzofuran-5-yl)methyl)-3-chloro-4-propylaniline;
N-((2-(1H-tetrazol-5-yl)benzofuran-5-yl)methyl)-4-fluoro-3-(trifluoromethoxy)aniline;
N-(1-(2-(1H-tetrazol-5-yl)benzofuran-5-yl)ethyl)-3,4,5-trichloroaniline;
N-(1-(2-(1H-tetrazol-5-yl)benzofuran-5-yl)ethyl)-3-chloro-4-((trifluoromethyl)thio)aniline;
N-((2-(1H-tetrazol-5-yl)benzofuran-5-yl)methyl)-3-chloro-5-(trifluoromethoxy)aniline;
N-((2-(1H-tetrazol-5-yl)benzofuran-5-yl)methyl)-4-propyl-3-(trifluoromethoxy)aniline;
N-(1-(2-(1H-tetrazol-5-yl)benzofuran-5-yl)ethyl)-3-chloro-4-(trifluoromethoxy)aniline;
N-((2-(1H-tetrazol-5-yl)benzofuran-5-yl)methyl)-4-ethyl-3-(trifluoromethyl)aniline;
N-((2-(1H-tetrazol-5-yl)benzofuran-5-yl)methyl)-3-fluoro-4-propylaniline;
N-((2-(1H-tetrazol-5-yl)benzofuran-5-yl)methyl)-3-methyl-4-propylaniline;
N-(1-(2-(1H-tetrazol-5-yl)benzofuran-5-yl)ethyl)-4-propyl-3-(trifluoromethyl)aniline;
N-((3-methyl-2-(1H-tetrazol-5-yl)benzofuran-5-yl)methyl)-4-propyl-3-(trifluoromethyl)aniline;
N-(1-(2-(1H-tetrazol-5-yl)benzofuran-5-yl)ethyl)-2,2-difluorobenzo[d][1,3]dioxol-5-amine;
N-(1-(2-(1H-tetrazol-5-yl)benzofuran-5-yl)ethyl)-3-chloro-4-propylaniline;
6-(((3,4,5-tribromophenyl)amino)methyl)benzofuran-2-carboxylic acid;
6-(((3,4,5-trichlorophenyl)amino)methyl)benzofuran-2-carboxylic acid;
6-(((3-chloro-4-((trifluoromethyl)thio)phenyl)amino)methyl)benzofuran-2-carboxylic acid;
6-(((3-chloro-4-(trifluoromethoxy)phenyl)amino)methyl)benzofuran-2-carboxylic acid;
6-(((2,2-difluorobenzo[d][1,3]dioxol-5-yl)amino)methyl)benzofuran-2-carboxylic acid;
6-(((3-bromo-4-(trifluoromethoxy)phenyl)amino)methyl)benzofuran-2-carboxylic acid;
6-(((3-(trifluoromethyl)-4-((trifluoromethyl)thio)phenyl)amino)methyl)benzofuran-2-carboxylic acid;
6-(((4-(trifluoromethoxy)-3-(trifluoromethyl)phenyl)amino)methyl)benzofuran-2-carboxylic acid;
6-(((3-chloro-4-propylphenyl)amino)methyl)benzofuran-2-carboxylic acid;
6-(((2,2,3,3-tetrafluoro-2,3-dihydrobenzo[b][1,4]dioxin-6-yl)amino)methyl)benzofuran-2-carboxylic acid;
6-(((4-propyl-3-(trifluoromethyl)phenyl)amino)methyl)benzofuran-2-carboxylic acid;
6-(((4-(methylthio)-3-(trifluoromethyl)phenyl)amino)methyl)benzofuran-2-carboxylic acid;
6-(((3-(methylthio)phenyl)amino)methyl)benzofuran-2-carboxylic acid;
6-(((3-bromo-4-morpholinophenyl)amino)methyl)benzofuran-2-carboxylic acid;
6-(((4-(pentafluorothio)phenyl)amino)methyl)benzofuran-2-carboxylic acid;
6-(((4-ethyl-3-(trifluoromethyl)phenyl)amino)methyl)benzofuran-2-carboxylic acid;
6-(((3,4-bis(trifluoromethyl)phenyl)amino)methyl)benzofuran-2-carboxylic acid;
6-(((3-methyl-4-(trifluoromethoxy)phenyl)amino)methyl)benzofuran-2-carboxylic acid;
6-(((4-(2,2,2-trifluoroacetyl)phenyl)amino)methyl)benzofuran-2-carboxylic acid;
6-(((3,4-bis(trifluoromethoxy)phenyl)amino)methyl)benzofuran-2-carboxylic acid;
6-(((2,3-dihydrobenzo[b][1,4]dioxin-6-yl)amino)methyl)benzofuran-2-carboxylic acid;
6-(((3-bromo-4,5-difluorophenyl)amino)methyl)benzofuran-2-carboxylic acid;
6-(((3-bromo-4-(trifluoromethoxy)phenyl)amino)methyl)-3-(trifluoromethyl)benzofuran-2-carboxylic acid;
6-(((3-chloro-4-(2,2,2-trifluoroethoxyl)phenyl)amino)methyl)benzofuran-2-carboxylic acid;
6-(((3-morpholinophenyl)amino)methyl)benzofuran-2-carboxylic acid;
6-(((3-chloro-4-fluoro-5-(trifluoromethyl)phenyl)amino)methyl)benzofuran-2-carboxylic acid;
6-(((4-propyl-3-(trifluoromethyl)phenyl)amino)methyl)-3-(trifluoromethyl)benzofuran-2-carboxylic acid;
6-(((5-(trifluoromethyl)pyridin-2-yl)amino)methyl)benzofuran-2-carboxylic acid;

6-(((4-((trifluoromethyl)thio)phenyl)amino)methyl)benzofuran-2-carboxylic acid;
6-(((2-methylbenzo[d]thiazol-5-yl)amino)methyl)benzofuran-2-carboxylic acid;
6-(((3-chloro-4-methoxyphenyl)amino)methyl)benzofuran-2-carboxylic acid;
6-(((3,5-bis(trifluoromethyl)phenyl)amino)methyl)benzofuran-2-carboxylic acid;
6-(((4-methoxy-3-(trifluoromethyl)phenyl)amino)methyl)benzofuran-2-carboxylic acid;
6-(((4-(2,2,2-trifluoroethoxy)-3-(trifluoromethyl)phenyl)amino)methyl)benzofuran-2-carboxylic acid;
6-(((2,6-dichloropyridin-4-yl)amino)methyl)benzofuran-2-carboxylic acid;
5-(((3,4,5-trichlorophenyl)amino)methyl)benzofuran-2-carboxylic acid;
5-(((3-chloro-4-propylphenyl)amino)methyl)benzofuran-2-carboxylic acid;
5-(((4-propyl-3-(trifluoromethyl)phenyl)amino)methyl)benzofuran-2-carboxylic acid;
5-(((3,4-dichlorophenyl)amino)methyl)benzofuran-2-carboxylic acid;
5-(((4-ethyl-3-(trifluoromethyl)phenyl)amino)methyl)benzofuran-2-carboxylic acid;
5-(((3-propyl-4-(trifluoromethyl)phenyl)amino)methyl)benzofuran-2-carboxylic acid; and
5-(((4-chloro-3-propylphenyl)amino)methyl)benzofuran-2-carboxylic acid.

In one embodiment, the invention is the compound, or salt thereof: N-((5-fluoro-2-(1H-tetrazol-5-yl)benzofuran-6-yl)methyl)-4-(trifluoromethoxy)-3-(trifluoromethyl)aniline.

In another embodiment, the invention is the compound, or salt thereof: N-((2-(2H-tetrazol-5-yl)benzofuran-6-yl)methyl)-3-bromo-4-(trifluoromethoxy)aniline.

In a thirteenth embodiment, the invention is a pharmaceutical composition comprising a therapeutically effective amount of a compound according to any one of the preceding embodiments, or a pharmaceutically acceptable salt thereof and one or more pharmaceutically acceptable carriers.

In a fourteenth embodiment, the invention is a combination comprising a therapeutically effective amount of a compound according to any one of the preceding embodiments or a pharmaceutically acceptable salt thereof and one or more therapeutically active co-agents.

In a fifteenth embodiment, the invention is a method to treat, prevent or ameliorate a hERG related condition, comprising administering to a subject in need thereof an effective amount of a compound or pharmaceutically acceptable salt thereof of any one of the preceding embodiments.

In a sixteenth embodiment, the invention is the method according to the fifteenth embodiment, wherein the hERG related condition is selected from LQT syndrome, GOF syndrome, Na syndrome, Jervell syndrome and Lange-Nielsen syndrome.

In one embodiment, the invention is a compound according to any one of the preceding embodiments, or a pharmaceutically acceptable salt thereof, for use as a medicament.

In another embodiment, the invention is a compound according to any one of the preceding embodiments, or a pharmaceutically acceptable salt thereof, for use in the treatment of a hERG related condition.

In yet another embodiment, the invention is the compound according to the preceding embodiment, wherein the hERG related condition is selected from LQT syndrome, GOF syndrome, Na syndrome, Jervell syndrome and Lange-Nielsen syndrome.

In another embodiment, the invention is the use of a compound according to any one of the preceding embodiments or a pharmaceutically acceptable salt thereof in the manufacture of a medicament for the treatment of a hERG related condition.

In yet another embodiment, the invention is the use of a compound according to the preceding embodiment, wherein the hERG related condition is selected from LQT syndrome, GOF syndrome, Na syndrome, Jervell syndrome and Lange-Nielsen syndrome.

For purposes of interpreting this specification, the following definitions will apply and whenever appropriate, terms used in the singular will also include the plural and vice versa.

As used herein, the term "$C_{1-4}$alkyl" refers to a fully saturated branched or unbranched hydrocarbon moiety having 1 to 4 carbon atoms. The terms "$C_{1-6}$alkyl" and "$C_{1-10}$alkyl" are to be construed accordingly. Representative examples of $C_{1-10}$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

As used herein, the term "$C_{1-4}$alkylene" refers to divalent alkyl group as defined herein above having 1 to 4 carbon atoms. The terms "$C_{1-6}$alkylene" and "$C_{1-10}$alkylene" are to be construed accordingly. Representative examples of $C_{1-10}$alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

As used herein, the term "halo-substituted($C_1$-$C_4$)alkyl" refers to a $C_{1-4}$alkyl group as defined herein, wherein at least one of the hydrogen atoms is replaced by a halo atom. The halo$C_{1-4}$alkyl group can be monohalo$C_{1-4}$alkyl, dihalo$C_{1-4}$alkyl or polyhalo$C_{1-4}$alkyl including perhalo$C_{1-4}$alkyl. A monohalo$C_{1-4}$alkyl can have one iodo, bromo, chloro or fluoro within the alkyl group. Dihalo$C_{1-4}$alkyl and polyhalo$C_{1-4}$alkyl groups can have two or more of the same halo atoms or a combination of different halo groups within the alkyl. Typically the polyhalo$C_{1-4}$alkyl group contains up to 12, or 10, or 8, or 6, or 4, or 3, or 2 halo groups. Non-limiting examples of halo$C_{1-4}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-4}$alkyl group refers to a $C_{1-4}$alkyl group having all hydrogen atoms replaced with halo atoms.

As used herein, the term "$C_{1-4}$alkylthio" refers to $C_{1-4}$alkyl-S—, wherein $C_{1-4}$alkyl is defined herein above. The terms "$C_{1-6}$alkylthio" and "$C_{1-10}$alkylthio" are to be construed accordingly. Representative examples of $C_{1-4}$alkylthio include, but are not limited to, methylthio, ethylthio, n-propylthio, iso-propylthio, n-butylthio, sec-butylthio, iso-butylthio and tert-butylthio.

As used herein, the term "halo$C_{1-4}$alkylthio" refers to a $C_{1-4}$alkylthio group as defined herein, wherein at least one of the hydrogen atoms is replaced by a halo atom. The halo$C_{1-4}$alkylthio group can be monohalo$C_{1-4}$alkylthio, dihalo$C_{1-4}$alkylthio or polyhalo$C_{1-4}$alkylthio including perhalo$C_{1-4}$alkylthio. A monohalo$C_{1-4}$alkylthio can have one iodo, bromo, chloro or fluoro within the alkylthio group. Dihalo$C_{1-4}$alkylthio and polyhalo$C_{1-4}$alkylthio groups can have two or more of the same halo atoms or a combination of different halo groups within the alkylthio. Typically the polyhalo- $C_{1-4}$alkylthio group contains up to 8, or 6, or 4, or 3, or 2 halo groups. Non-limiting examples of halo$C_{1-10}$alkylthio include fluoromethylthio, difluoromethylthio, trifluoromethylthio, chloromethylthio, dichloromethylthio, trichloromethylthio, pentafluoroethylthio, heptafluoropropylthio, difluorochloromethylthio, dichlorofluoromethylthio, difluoroethylthio, difluoropropylthio, dichloroethylthio and dichloropropylthio. A perhalo$C_{1-4}$alkylthio group refers to a $C_{1-10}$alkylthio group having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

As used herein, the term "$C_{1-4}$alkoxy" or "$C_{1-4}$alkoxyl" refers to $C_{1-4}$alkyl-O—, wherein $C_{1-4}$alkyl is defined herein above. Representative examples of $C_{1-4}$alkoxy include, but are not limited to, methoxy, ethoxy, propoxy, 2-propoxy, butoxy and tert-butoxy.

As used herein, the term "halo-substituted($C_1$-$C_4$)alkoxy" refers to a $C_{1-4}$alkoxy group as defined herein, wherein at least one of the hydrogen atoms is replaced by a halo atom. The halo$C_{1-4}$alkoxy group can be monohalo$C_{1-4}$alkoxy, dihalo$C_{1-4}$alkoxy or polyhalo$C_{1-4}$alkoxy including perhalo$C_{1-4}$alkoxy. A monohalo$C_{1-4}$alkoxy can have one iodo, bromo, chloro or fluoro within the alkoxy group. Dihalo$C_{1-4}$alkoxy and polyhalo$C_{1-4}$alkoxy groups can have two or more of the same halo atoms or a combination of different halo groups within the alkoxy. Typically the polyhalo$C_{1-4}$alkoxy group contains up to 8, or 6, or 4, or 3, or 2 halo groups. Non-limiting examples of halo$C_{1-4}$alkyl include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy. A perhalo$C_{1-4}$alkoxy group refers to a $C_{1-4}$alkoxy group having all hydrogen atoms replaced with halo atoms.

As used herein, the term "heterocyclyl" or "heterocyclo" refers to a saturated or unsaturated non-aromatic ring or ring system, which is a 4-, 5-, 6-, or 7-membered monocyclic ring containing 1, 2 or 3 heteroatoms selected from O, S and N, a 7-, 8-, 9-, 10-, 11-, or 12-membered bicyclic ring system containing 1, 2, 3, 4 or 5 heteroatoms selected from O, S and N, or a 10-, 11-, 12-, 13-, 14- or 15-membered tricyclic ring system and containing 1, 2, 3, 4, 5, 6 or 7 heteroatoms selected from O, S and N, where the N and S can also optionally be oxidized to various oxidation states. The heterocyclic group can be attached via a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane and thiomorpholine.

As used herein, the term "$C_{3-6}$cycloalkyl" refers to saturated or unsaturated monocyclic, bicyclic or tricyclic hydrocarbon groups of 3-6 carbon atoms. The term "$C_{3-6}$cycloalkyl" refers to a fully saturated or unsaturated monocyclic hydrocarbon group of 3-8 carbon atoms. Exemplary monocyclic hydrocarbon groups include, but are not limited to, cyclopropyl, cyclobutyl, cyclopentyl, cyclopentenyl, cyclohexyl and cyclohexenyl.

As used herein, the term "heteroaryl" refers to a 5-, 6-, or 7-membered monocyclic aromatic ring containing 1, 2, 3 or 4 heteroatoms selected from O, S and N, an 8-, 9-, or 10-membered fused bicyclic ring system containing 1, 2, 3, 4 or 5 heteroatoms selected from O, S and N, or an 11-, 12-, 13-, or 14-membered fused tricyclic ring system containing 1, 2, 3, 4, 5 or 6 heteroatoms selected from O, S and N, wherein at least one of the rings of the bicyclic or tricyclic ring systems is fully aromatic. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl, 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl and tetrazole.

As used herein, the term "tetrazole" refers to both 1-tetrazole and 2-tetrazole, i.e.

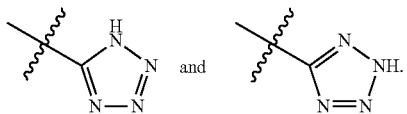 [SMILES: *c1nnn[nH]1 ; *c1nn[nH]n1]

As used herein, the term "halogen" or "halo" refers to fluoro, chloro, bromo, and iodo.

As used herein, the term "isomers" refers to different compounds that have the same molecular formula but differ in arrangement and configuration of the atoms, e.g. 1-tetrazole and 2-tetrazole are inseparable isomers. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts." The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$F, $^{32}$F, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g., $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by hERG; or (2) activating the activity of hERG.

In another non-limiting embodiment, the term "a therapeutically effective amount" refers to the amount of the compound of the present invention that, when administered to a cell, or a tissue, or a non-cellular biological material, or a medium, is effective to at least partially activating the activity of hERG; or at least partially activating the expression of hERG.

The phrases "therapeutically effective amount" and "effective amount" are used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a hERG related condition. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat", "treating" or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
- diluents, e.g., lactose, dextrose, sucrose, mannitol, sorbitol, cellulose and/or glycine;
- lubricants, e.g., silica, talcum, stearic acid, its magnesium or calcium salt and/or polyethyleneglycol; for tablets also
- binders, e.g., magnesium aluminum silicate, starch paste, gelatin, tragacanth, methylcellulose, sodium carboxymethylcellulose and/or polyvinylpyrrolidone; if desired
- disintegrants, e.g., starches, agar, alginic acid or its sodium salt, or effervescent mixtures; and/or
- absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g., as indicated in in vitro tests as provided in the next sections, and are therefore indicated for therapy or for use as research chemicals, e.g., as tool compounds.

Thus, as a further embodiment, the present invention provides the use of a compound of formula (I) or a salt thereof in therapy. In a further embodiment, the therapy is selected from a disease which may be treated by modulating hERG protein production. In another embodiment, the disease is selected from the afore-mentioned list, e.g., LQT syndrome, GOF syndrome, Na syndrome, Jervell syndrome and Lange-Nielsen syndrome.

In another embodiment, the invention provides a method of treating a disease which is treated by modulating hERG protein production comprising administration of a therapeutically acceptable amount of a compound of formula (I) or salt thereof to a patient in need of such therapy. In a further embodiment, the disease is selected from the afore-mentioned list, suitably LQT syndrome, GOF syndrome, Na syndrome, Jervell syndrome and Lange-Nielsen syndrome.

Thus, as a further embodiment, the present invention provides the use of a compound of formula (I) or salt thereof for the manufacture of a medicament. In a further embodiment, the medicament is for treatment of a disease which may be treated by modulation of hERG protein production. In another embodiment, the disease is selected from the afore-mentioned list, suitably LQT syndrome, GOF syndrome, Na syndrome, Jervell syndrome and Lange-Nielsen syndrome.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a spinal muscular atrophy. Products provided as a combined preparation include a composition comprising the compound of formula (I) and the other therapeutic agent(s) together in the same pharmaceutical composition, or the compound of formula (I) and the other therapeutic agent(s) in separate form, e.g., in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g., in the case of a kit comprising the compound of the invention and the other therapeutic agent); (ii) by the physician themselves (or under the guidance of the physician) shortly before administration; (iii) in the patient themselves, e.g., during sequential administration of the compound of the invention and the other therapeutic agent.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Preparations of Compounds

INTERMEDIATES AND EXAMPLES

The following Examples are intended to be illustrative only and not limiting in any way. Unless otherwise noted, the following Intermediates and Examples were purified via silica gel column chromatography using RediSep® Rf columns from Teledyne Isco, Inc. Abbreviations used are those conventional in the art or the following:
AcOH acetic acid
AIBN azobisisobutyronitrile
$AlCl_3$ aluminium chloride
Aq aqueous
Ar aryl
atm atmosphere
BOC tert-Butyl-carbonate
BP boiling point
Br bromine
br.s., bs broad singlet
° C. Celsius
$CaCl_2$ calcium chloride
CC column chromatography
$CD_2Cl_2$ deuterated dichloromethane
$CDCl_3$ deuterated chloroform
$CH_2Cl_2$, DCM dichloromethane
$CH_3CN$, MeCN acetonitrile
CO carbon monoxide
$Cs_2CO_3$ caesium carbonate
CuI copper(I) Iodide
d doublet
DCE 1,2-dichloroethene
dd doublet of doublets
ddd doublet of doublets of doublets
DIPEA N-ethyldiisopropylamine
DME 1,4-dimethoxyethane
DMF N,N-dimethylformamide
DMAP dimethyl aminopyridine
DMSO dimethylsulfoxide
DPPF bis(diphenylphosphino)ferrocene
dq doublet of quartets
dt doublet of triplets
EDC 1-ethyl-3-(3-dimethylaminopropyl)carbodiimide
EtOAc ethyl acetate
EtOH ethanol
FCC flash column chromatography
g gram
h, hr hour
HCl hydrochloric acid
HMPA hexamethylphosphoramide
$H_2O$ water
HPLC high pressure liquid chromatography
HT high throughput
Hz Hertz
IBX 2-Iodoxybenzoic acid
i-PrOH isopropyl alcohol
$H_2O$ water
K kelvin
$K_2CO_3$ potassium carbonate
$K_4Fe(CN)_6$ potassium ferrocyanide
KOH potassium hydroxide
LC liquid chromatography
LCMS liquid chromatography mass spectroscopy
LiOH lithium hydroxide
M molar
m meta
m multiplet
MeOH methanol
$MgSO_4$ magnesium sulfate
mg milligram
MHz mega herz
mL milliliter
mm millimeter
mmol millimole
min. minute
MS mass spectroscopy
mw microwave
N normal
$N_2$ nitrogen
$NaBH_4$ sodium borohydride
NaH sodium hydride
NaHMDS sodium hexamethyldisilazane
NaOEt sodium ethoxide
NaOH sodium hydroxide
$Na_2CO_3$ sodium carbonate
$NaHCO_3$ sodium bicarbonate
$Na_2SO_4$ sodium sulfate
$Na_2S_2O_3$ sodium thiosulfate
NBS N-Bromosuccinimide
$NEt_3$, TEA triethylamine
ng nanogram
$NH_3$ ammonia
NMR nuclear magnetic resonance
quint. quintuplet
Pd/C palladium on carbon
$PdCl_2(PPh_3)_2$ bis(triphenylphosphine)palladium(II) dichloride
$Pd(OAc)_2$ palladium acetate
$PPh_3$ triphenylphosphine
PPT precipitate
q quartet
Rf retardation factor
rt, RT room temperature
Rt Retention time
rxn reaction
s singlet
sat. saturated
SM starting material
$SOCl_2$ thionyl chloride
sxt sextet
t triplet
TFA trifluoroacetic acid
TFAA trifluoroacetic anhydride
TFE 2,2,2-trifluoroethanol
THF tetrahydrofuran
$Ti(OiPr)_4$ titanium(IV) isopropoxide
TLC thin layer chromatography
$TMS-CHN_2$ trimethylsilyldiazomethane
UPLC ultra performance liquid chromatography
wt weight
μg microgram
μL microliter
LC Specificity:
LC method 1: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 98/2 to 2/98 was applied over 1.7 min., then held for 0.24 min. (1.0 mL/min. as solvent flow) at an oven temperature of 50° C.
LC method 2: The retention times (Rt) were obtained on a Waters Acquity SDS system with an Acquity BEH C18 1.7 μm 2.1×50 mm column. A gradient of $H_2O$ (+0.1% formic acid)/$CH_3CN$ (+0.1% formic acid) 98/2 to 2/98 was applied over 1.7 min., then held for 0.3 min. (1.0 mL/min. as solvent flow) at an oven temperature of 50° C.

LC method 3: The retention times (Rt) were obtained on an Agilent 1100 system with an XBridge C18 Column, 3.5 µm, 2.1×50 mm column. A gradient of H₂O (+0.1% formic acid)/CH₃CN (+0.1% formic acid) 95/5 to 5/95 was applied over 1.2 min., then held for 0.5 min. (1.0 mL/min. as solvent flow) at an oven temperature of 50° C.

LC method 4: The retention times (Rt) were obtained on an Agilent 1100 system with an Sunfire C18 Column, 3.5 µm, 3.0×30 mm column. A gradient of H₂O (+0.05% trifluoroacetic acid)/CH₃CN (+0.05% trifluoroacetic acid) 95/5 to 5/95 was applied over 1.7 min., then held for 0.3 min. (2.0 mL/min. as solvent flow) at an oven temperature of 40° C.

LC method 5: The retention times (Rt) were obtained on an Agilent 1100 system with an XBridge C18 Column, 3.5 µm, 3.0×30 mm column. A gradient of H₂O (+0.05% ammonium hydroxide)/CH₃CN (+0.05% ammonium hydroxide) 98/2 to 2/98 was applied over 1.7 min., then held for 0.3 min. (2.0 mL/min. as solvent flow) at an oven temperature of 40° C.

LC method 6: The retention times (Rt) were obtained on a Waters Acquity SDS system with an Acquity CSH 1.7 µm 2.1×50 mm column. A gradient of H₂O (+2% CH₃CN+3.75 mM ammonium acetate)/CH₃CN (+5% water+3.75 mM ammonium acetate) 98/2 to 2/98 was applied over 1.7 min., then held for 0.3 min. (1.0 mL/min. as solvent flow) at an oven temperature of 50° C.

LC method 7: The retention times (Rt) were obtained on a Waters Acquity SDS system with an Acquity CSH 1.7 µm 2.1×50 mm column. A gradient of H₂O (+3.75 mM ammonium acetate+2% CH₃CN)/CH₃CN 98/2 to 2/98 was applied over 1.7 min., then held for 0.3 min. (1.0 mL/min. as solvent flow) at an oven temperature of 50° C.

LC method 8: The retention times (Rt) were obtained on an Agilent 1100 system with an XBridge C18 Column, 3.5 µm, 3.0×30 mm column. A gradient of H₂O (5 mM ammonium formate, 2% CH₃CN)/CH₃CN 95/5 to 5/95 was applied over 1.7 min., then held for 0.3 min. (2.0 mL/min. as solvent flow) at an oven temperature of 40° C.

LC method 9: The retention times (Rt) were obtained on an Agilent 1100 system with an XBridge C18 Column, 3.5 µm, 3.0×30 mm column. A gradient of H₂O (+5 mM ammonium hydroxide)/CH₃CN 95/5 to 5/95 was applied over 1.7 min., then held for 0.3 min. (2.0 mL/min. as solvent flow) at an oven temperature of 40° C.

LC method 10: The retention times (Rt) were obtained on an Agilent 1100 system with an XBridge C18 Column, 3.5 µm, 3.0×30 mm column. A gradient of H₂O (+5 mM ammonium hydroxide)/CH₃CN 95/5 to 5/95 was applied over 1.7 min., then held for 0.3 min. (2.0 mL/min. as solvent flow) at an oven temperature of 40° C.

LC method 11: The retention times (Rt) were obtained on an Agilent 1100 system with an Sunfire C18 Column, 3.5 µm, 3.0×30 mm column. A gradient of H₂O (+0.05% trifluoroacetic acid)/CH₃CN (+0.05% trifluoroacetic acid) 95/5 to 5/95 was applied over 1.7 min., then held for 0.3 min. (2.0 mL/min. as solvent flow) at an oven temperature of 40° C.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following:

N-((2-(2H-tetrazol-5-yl)benzofuran-6-yl)methyl)-3-bromo-4-(trifluoromethoxy)aniline

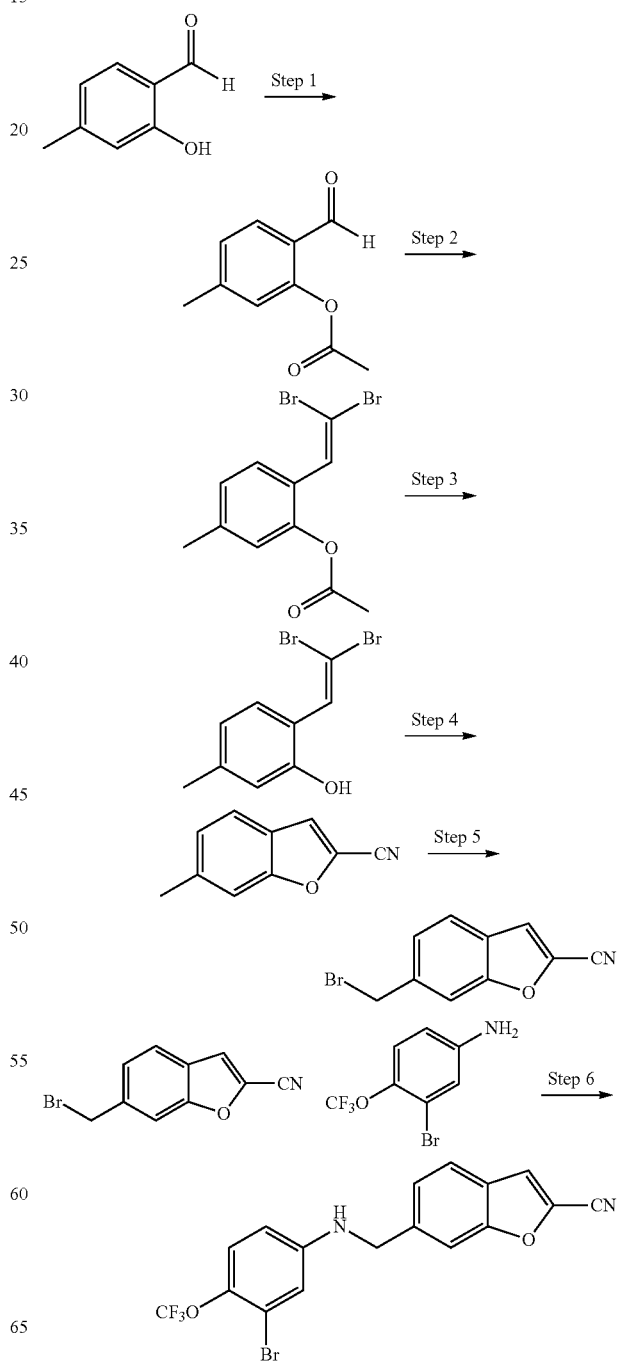

-continued

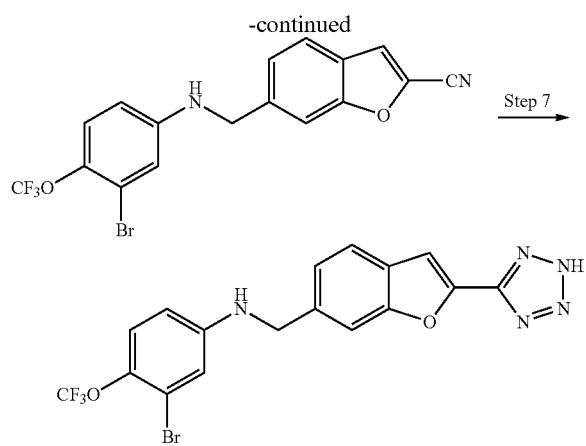

Step 1: Synthesis of 2-formyl-5-methylphenyl acetate

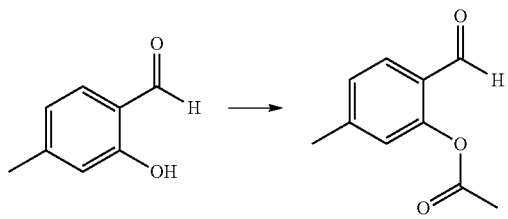

To a 0-5° C. solution of 2-hydroxy-4-methylbenzaldehyde (15 g, 110 mmol) in 250 mL of DCM was added TEA (30.7 ml, 220 mmol) followed by dropwise addition of acetyl chloride (8.65 g, 110 mmol) over 15 min. The reaction was stirred at 0-5° C. for 30 min. The reaction mixture was concentrated under reduced pressure. To this residue 100 mL of 1N HCl was added. The crude mixture was extracted with EtOAc×2. The combined organic layers were washed with brine, dried over MgSO$_4$, filtered, and concentrated under reduced pressure to give a yellow oil, 2-formyl-5-methylphenyl acetate (18 g). $^1$H NMR (400 MHz, DMSO-d$_6$) δ 2.34 (s, 3H), 2.40 (s, 3H), 7.13 (s, 1H), 7.31 (d, J=7.6 Hz, 1H), 7.80 (d, J=7.8 Hz, 1H), 10.01 (s, 1H).

Step 2: Synthesis of 2-(2,2-dibromovinyl)-5-methylphenyl acetate

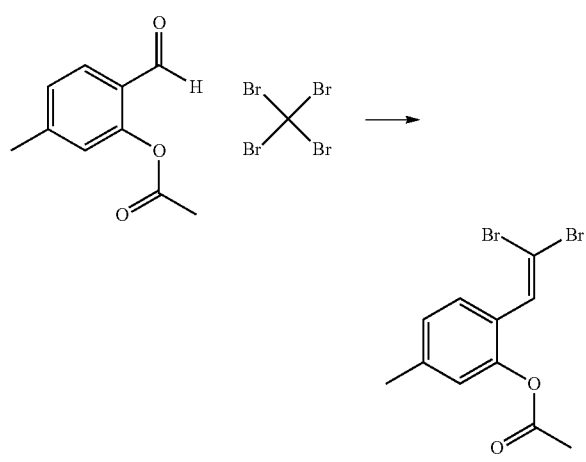

To a stirred mixture of 2-formyl-5-methylphenyl acetate (12.8 g, 71.8 mmol), carbon tetrabromide (47.6 g, 144 mmol), and 150 mL of DCM at 0° C. (translucent clear/yellow solution) under nitrogen was added a solution of triphenylphosphine (75 g, 287 mmol) in 140 mL of DCM dropwise over 15 min. A clear orange solution results initially. After 1 hr a purplish suspension results. The reaction was stirred for 2 hr at RT. After 2 hr 100 mL of heptane was added. The mixture was filtered to remove solids and the collected filtrate was concentrated under reduced pressure to give a dark brown gum. This was dissolved in minimal DCM and filtered through a silica gel plug which was flushed with 70% Heptane/30% EtOAc. The combined washes from the silica plug were concentrated under reduced pressure to give a yellow oil, 2-(2,2-dibromovinyl)-5-methylphenyl acetate (16.7 g). $^1$H NMR (400 MHz, DMSO-d$_6$) δ 2.28 (s, 3H), 2.31 (s, 3H), 7.01 (s, 1H), 7.14 (d, J=8.0 Hz, 1H), 7.48 (s, 1H), 7.54 (d, J=8.0 Hz, 1H).

Step 3: Synthesis of 2-(2,2-dibromovinyl)-5-methylphenol

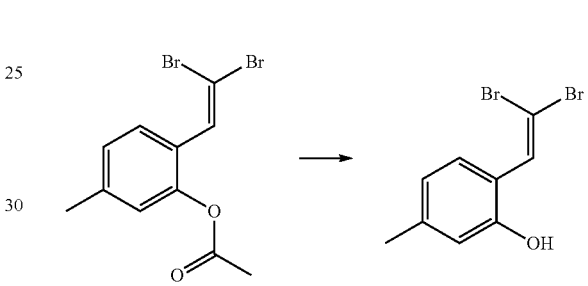

A solution of 2-(2,2-dibromovinyl)-5-methylphenyl acetate (16.5 g, 49.4 mmol) in 100 mL of MeOH was treated with a solution of K$_2$CO$_3$ (10.24 g, 74.1 mmol) dissolved in 5.0 mL of water and stirred at RT. The reaction mixture immediately turned yellow and cloudy. After 30 min the mixture was concentrated under reduced pressure to remove MeOH. The crude material was diluted with water and carefully adjusted to pH~5-6 via addition of 2M HCl. The crude mixture was extracted with EtOAc×2, dried over MgSO$_4$, filtered, and concentrated under reduced pressure to give an orange oil, 2-(2,2-dibromovinyl)-5-methylphenol (13.5 g). $^1$H NMR (400 MHz, DMSO-d$_6$) δ 2.21 (s, 3H), 6.65 (d, J=8.2 Hz, 1H), 6.68 (s, 1H), 7.49 (d, J=7.9 Hz, 1H), 7.57 (s, 1H), 9.83 (s, 1H).

Step 4: Synthesis of 6-methylbenzofuran-2-carbonitrile

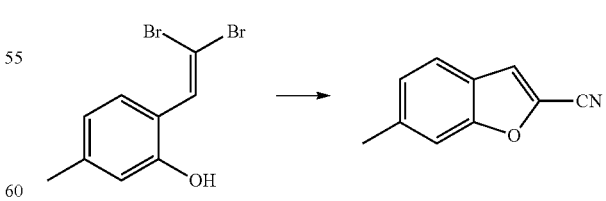

To a 500 mL 3-neck flask was added 2-(2,2-dibromovinyl)-5-methylphenol (17.7 g, 60.6 mmol), CuI (1.16 g, 6.06 mmol), Na$_2$CO$_3$ (12.85 g, 121 mmol) and DMF (120 mL). The reaction was heated to 80° C. for 6 hr. After 6 hr the rxn was cooled to RT and anhydrous K$_4$Fe(CN)$_6$ (4.47 g, 12.12 mmol), Pd(OAc)$_2$ (2.04 g, 3.03 mmol) and PPh$_3$ (0.32 g, 1.21 mmol) were added to the reaction and the reaction was flushed with nitrogen for 10 min. The reaction was then heated to 120° C. for 18 hr. After 18 hr the rxn was cooled to RT and diluted with EtOAc. The reaction mixture was filtered through a silica plug to remove solids and flushed with EtOAc. The collected filtrates were diluted with water and brine and extracted with EtOAc×2. The combined organic layers were washed with brine, dried over Na$_2$SO$_4$, filtered, and concentrated under reduced pressure. The crude mixture was purified via silica gel FCC, 100% Heptane-20% EtOAc/ 80% Heptane to give a yellow solid, 6-methylbenzofuran-2-carbonitrile (5.1 g). $^1$H NMR (400 MHz, DMSO-d$_6$) δ 2.47 (s, 3H), 7.27 (ddd, J=8.2, 1.4, 0.7 Hz, 1H), 7.57 (s, 1H), 7.71 (d, J=8.1 Hz, 1H), 8.05 (d, J=1.0 Hz, 1H).

Step 5: Synthesis of 6-(bromomethyl)benzofuran-2-carbonitrile

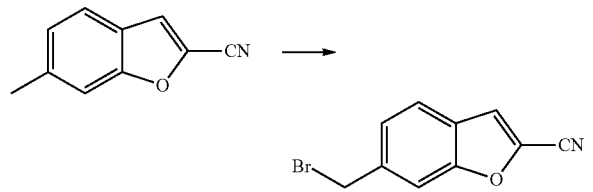

6-methylbenzofuran-2-carbonitrile (12 g, 76 mmol), NBS (13.59 g, 76 mmol), and AIBN (1.25 g, 7.64 mmol) were dissolved in carbon tetrachloride (191 ml). The mixture was heated to reflux overnight. After 18 h the reaction was cooled to RT and concentrated under reduced pressure. The product was then crashed out using MeOH and the slurry was placed in the fridge overnight. The slurry was filtered and the collected PPT was washed with MeOH. The collected PPT was pure 6-(bromomethyl)benzofuran-2-carbonitrile (13.864 g). $^1$H NMR (400 MHz, DMSO-d$_6$) δ 4.87 (s, 2H), 7.52 (dd, J=8.2, 1.4 Hz, 1H), 7.83 (d, J=8.2 Hz, 1H), 7.87 (d, J=1.5 Hz, 1H), 8.11 (d, J=1.0 Hz, 1H).

Step 6: Synthesis of 6-(((3-bromo-4-(trifluoromethoxy)phenyl)amino)methyl)benzofuran-2-carbonitrile

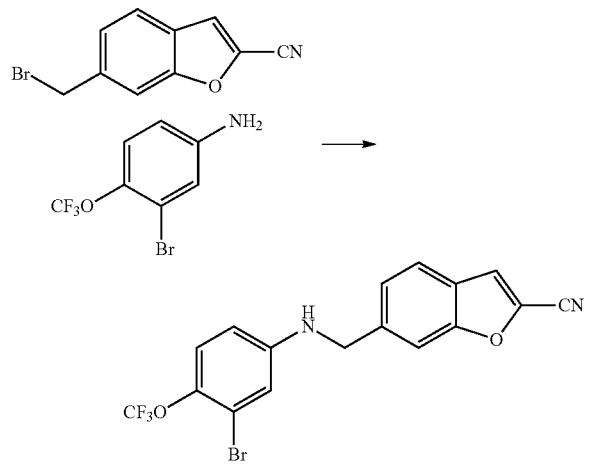

6-(bromomethyl)benzofuran-2-carbonitrile (0.5 g, 2.12 mmol) was dissolved in DMF (21.2 ml). K$_2$CO$_3$ (0.44 g, 3.18 mmol) was added, followed by 3-bromo-4-(trifluoromethoxy)aniline (314 μL, 2.12 mmol), and the mixture was stirred at RT for 18 hr. The reaction was diluted with EtOAc and water. The organic layer was washed with water×6, brine, dried over Na$_2$SO$_4$, filtered, and concentrated under reduced pressure. The crude mixture was diluted with DCM and silica gel was added. The mixture was concentrated under reduced pressure to dry-load material for purification. The crude mixture was purified via silica gel FCC, 100% Heptane-50% EtOAc/50% Heptane to give 6-(((3-bromo-4-(trifluoromethoxy)phenyl)amino)methyl)benzofuran-2-carbonitrile (651 mg). LCMS retention time=1.57 minutes (LC method 1); MS (m+1)=412.1. $^1$H NMR (400 MHz, DMSO-d$_6$) δ 4.46 (d, J=6.0 Hz, 2H), 6.62 (dd, J=9.0, 2.8 Hz, 1H), 6.88-6.95 (m, 2H), 7.17 (dq, J=9.0, 1.3 Hz, 1H), 7.44 (dd, J=8.2, 1.4 Hz, 1H), 7.70 (s, 1H), 7.80 (dd, J=8.1, 0.7 Hz, 1H), 8.08 (d, J=1.0 Hz, 1H).

Step 7: Synthesis of N-((2-(2H-tetrazol-5-yl)benzofuran-6-yl)methyl)-3-bromo-4-(trifluoromethoxy)aniline

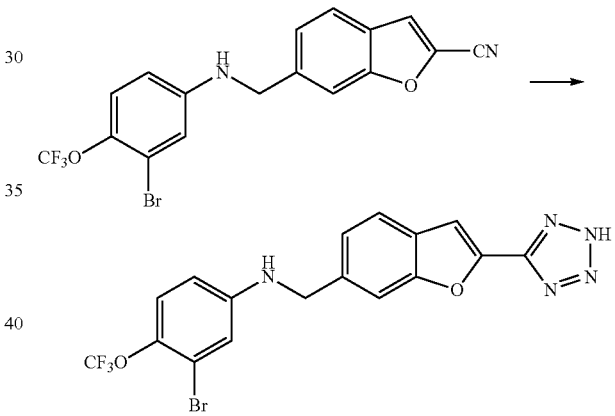

6-(((3-bromo-4-(trifluoromethoxy)phenyl)amino)methyl)benzofuran-2-carbonitrile (651 mg, 1.58 mmol), sodium azide (0.12 g, 1.90 mmol) and ammonium chloride (0.10 g, 1.90 mmol) were dissolved in DMF (15.84 ml). The mixture was stirred at RT for 18 hr. After 18 hr the rxn was not complete and the reaction was heated to 50° C. for 2 hr. The reaction was cooled to RT and diluted with water (pH~1). The crude material was extracted from the diluted aqueous pH=1 layer three times with a 10% MeOH/90% EtOAc mixture. The combined organic layers were washed 5× with pH=1 water to remove DMF and sodium azide, they were then washed with brine, dried over Na$_2$SO$_4$, filtered, and concentrated under reduced pressure. The crude mixture was purified on basic HPLC (ammonium hydroxide modifier) 15-40% MeCN/Water to give N-((2-(2H-tetrazol-5-yl)benzofuran-6-yl)methyl)-3-bromo-4-(trifluoromethoxy)aniline (413 mg). LCMS retention time=1.35 minutes (LC method 1); MS (m+1)=454.2. $^1$H NMR (400 MHz, DMSO-d$_6$) δ 4.39 (d, J=5.8 Hz, 2H), 6.66 (dd, J=9.0, 2.8 Hz, 1H), 6.83 (t, J=5.9 Hz, 1H), 6.93 (d, J=2.7 Hz, 1H), 7.08 (d, J=0.9 Hz, 1H), 7.17 (dd, J=9.2, 1.1 Hz, 1H), 7.25 (dd, J=8.0, 1.3 Hz, 1H), 7.54-7.64 (m, 2H).

6-(((3-bromo-4-(trifluoromethoxy)phenyl)amino)methyl)benzofuran-2-carboxylic acid

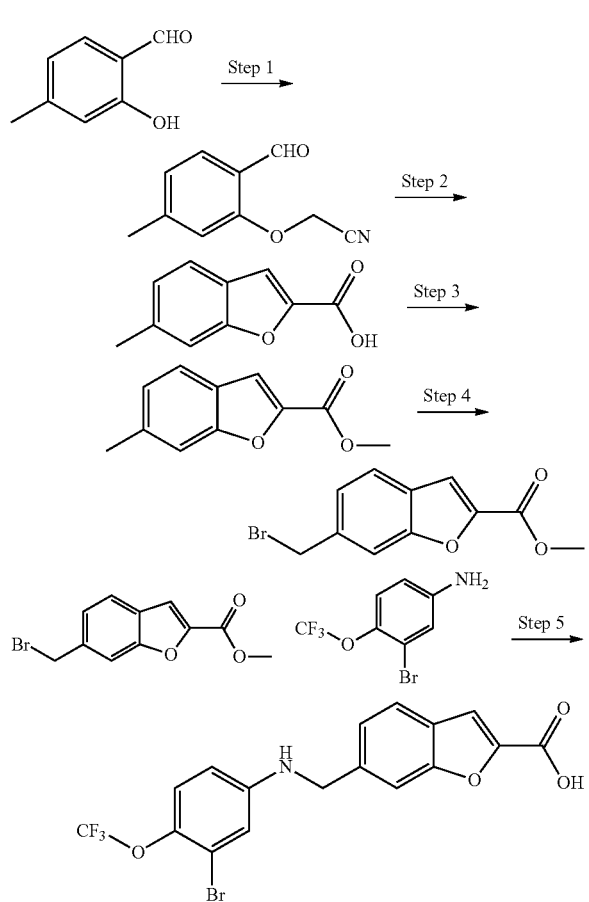

Step 1: Synthesis of 2-(2-formyl-5-methylphenoxy)acetonitrile

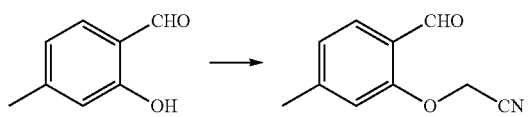

To a solution of 2-hydroxy-4-methylbenzaldehyde (12 g, 88 mmol) in 432 mL of CH$_3$CN was added Cs$_2$CO$_3$ (34.5 g, 106 mmol) followed by 2-bromoacetonitrile (6.75 mL, 97 mmol), After the mixture was stirred at room temperature for 6 hr, the mixture was filtered through Celite to remove solid, washed with DCM, and the filtrate was concentrated under reduced pressure. The resulting residue was purified by silica gel flash chromatography, 100% Heptane-20% Ethyl Acetate/80% Heptane) to give a white solid, 2-(2-formyl-5-methylphenoxy)acetonitrile (14.2 g). LCMS retention time=1.06 minutes (LC method 3); MS (m+1)=175.8. $^1$H NMR (400 MHz, DMSO-d$_6$) δ 2.41 (s, 3H), 5.33 (s, 2H), 7.05 (d, J=7.8 Hz, 1H), 7.20 (s, 1H), 7.68 (s, 1H), 10.26 (d, J=0.8 Hz, 1H).

Step 2: Synthesis of 6-methylbenzofuran-2-carboxylic acid

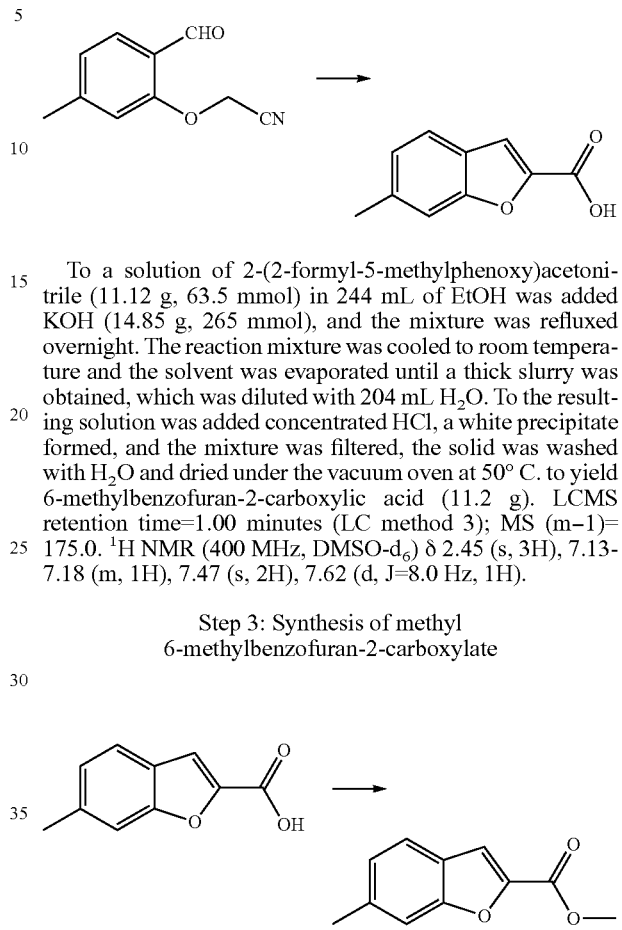

To a solution of 2-(2-formyl-5-methylphenoxy)acetonitrile (11.12 g, 63.5 mmol) in 244 mL of EtOH was added KOH (14.85 g, 265 mmol), and the mixture was refluxed overnight. The reaction mixture was cooled to room temperature and the solvent was evaporated until a thick slurry was obtained, which was diluted with 204 mL H$_2$O. To the resulting solution was added concentrated HCl, a white precipitate formed, and the mixture was filtered, the solid was washed with H$_2$O and dried under the vacuum oven at 50° C. to yield 6-methylbenzofuran-2-carboxylic acid (11.2 g). LCMS retention time=1.00 minutes (LC method 3); MS (m−1)=175.0. $^1$H NMR (400 MHz, DMSO-d$_6$) δ 2.45 (s, 3H), 7.13-7.18 (m, 1H), 7.47 (s, 2H), 7.62 (d, J=8.0 Hz, 1H).

Step 3: Synthesis of methyl 6-methylbenzofuran-2-carboxylate

To a solution of 6-methylbenzofuran-2-carboxylic acid (11 g, 62.4 mmol) in 468 mL of toluene and 156 mL of MeOH was added 2N TMS-CHN$_2$ (46.8 mL, 94 mmol) dropwise at room temperature. The reaction was stirred at room temperature for 6 hr. The reaction was then quenched by addition of acetic acid dropwise at 0° C. until the yellow color vanished, and gas evolution ceased. The reaction was concentrated under reduced pressure, and the residue was purified by silica gel flash chromatography, 100% Heptane-10% Ethyl Acetate/90% Heptane, to give methyl 6-methylbenzofuran-2-carboxylate (7.96 g). $^1$H NMR (400 MHz, DMSO-d$_6$) δ 2.46 (s, 3H), 3.88 (s, 3H), 7.20 (dd, J=8.3, 1.0 Hz, 1H), 7.53 (s, 1H), 7.67 (d, J=8.1 Hz, 1H), 7.71 (d, J=1.0 Hz, 1H).

Step 4: methyl 6-(bromomethyl)benzofuran-2-carboxylate

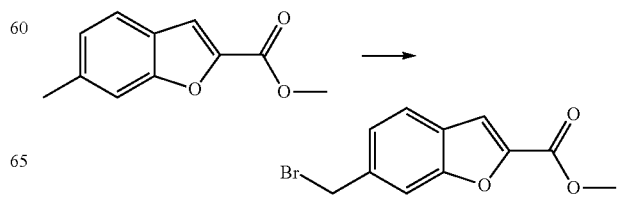

Methyl 6-(bromomethyl)benzofuran-2-carboxylate was prepared as described in general bromination procedure, example 37, Step 5, starting from methyl 6-methylbenzofuran-2-carboxylate. LCMS retention time=1.24 minutes (LC method 1); MS (m+1)=269.2. 1H NMR (400 MHz, DMSO-d$_6$) δ 3.90 (s, 3H), 4.87 (s, 2H), 7.46 (dd, J=8.2, 1.4 Hz, 1H), 7.77 (d, J=1.0 Hz, 1H), 7.80 (dd, J=8.1, 0.7 Hz, 1H), 7.84 (dt, J=1.6, 0.8 Hz, 1H).

Step 5: 6-(((3-bromo-4-(trifluoromethoxy)phenyl)amino)methyl)benzofuran-2-carboxylic acid

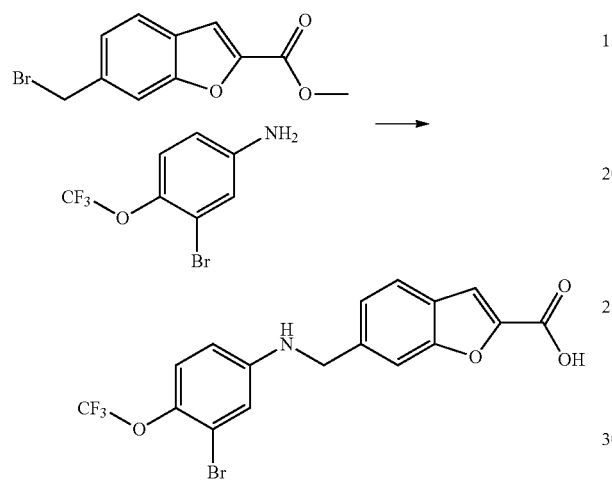

Methyl 6-(bromomethyl)benzofuran-2-carboxylate (150 mg, 0.56 mmol) was dissolved in DMF (5.57 mL). K$_2$CO$_3$ (116 mg, 0.84 mmol) was added, followed by 3-bromo-4-(trifluoromethoxy)aniline (143 mg, 0.56 mmol), and the mixture was stirred at RT for 18 hr. At this point LiOH H$_2$O (117 mg, 2.79 mmol) was added to the reaction followed by 4 mL of THF and 1 mL of water and the reaction was stirred for an additional 18 hr at RT. The reaction was concentrated under reduced pressure to remove THF. The crude mixture was diluted with EtOAc and water and acidifed to pH=1. The water layer was extracted×3 with EtOAc. The combined organic layers were washed with water, brine, dried over Na$_2$SO$_4$, filtered, and concentrated under reduced pressure. The crude mixture was purified on basic HPLC (ammonium hydroxide modifier) 15-40% MeCN/Water to give N-((2-(2H-tetrazol-5-yl)benzofuran-6-yl)methyl)-3-bromo-4-(trifluoromethoxy)aniline (413 mg). LCMS retention time=1.38 minutes (LC method 1); MS (m+1)=431.2. ¹H NMR (400 MHz, DMSO-d$_6$) δ 4.38 (d, J=5.4 Hz, 2H), 6.65 (dd, J=9.1, 2.8 Hz, 1H), 6.87 (t, J=5.9 Hz, 1H), 6.91 (d, J=2.7 Hz, 1H), 7.02 (d, J=4.2 Hz, 1H), 7.14-7.20 (m, 1H), 7.22 (dd, J=8.0, 1.4 Hz, 1H), 7.52 (s, 1H), 7.58 (d, J=8.0 Hz, 1H).

N-((5-fluoro-2-(1H-tetrazol-5-yl)benzofuran-6-yl)methyl)-4-(trifluoromethoxy)-3-(trifluoromethyl)aniline

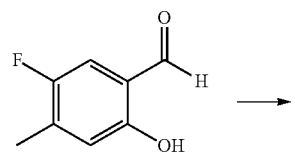

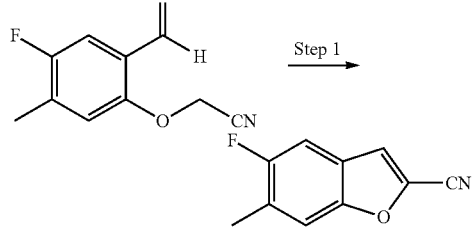

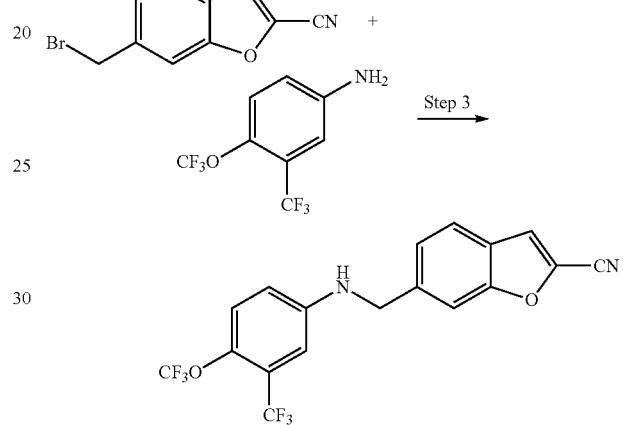

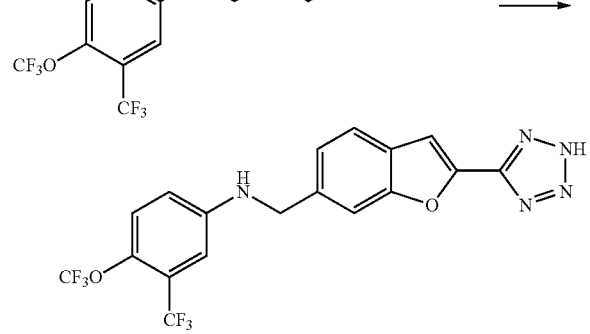

Step 1: Synthesis of 5-fluoro-6-methylbenzofuran-2-carbonitrile

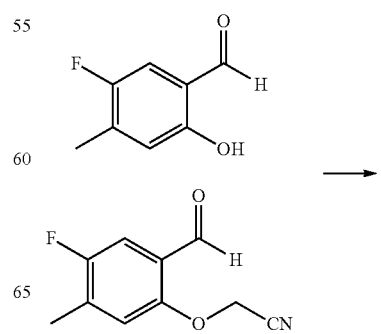

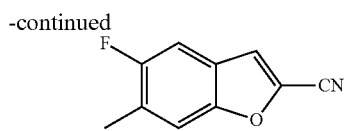

To the solution of 5-fluoro-2-hydroxy-4-methylbenzaldehyde (500 mg, 3.24 mmol) in 10.5 ml acetonitrile in a microwave vial was added $Cs_2CO_3$ (1.268 g, 3.885 mmol), followed by 2-bromoacetonitrile (271 ul, 3.885 mmol). The reaction mixture was stirred at room temperature for 1 hr. LC/MS showed that all the starting material was converted to ring opened intermediate, 2-(4-fluoro-2-formyl-5-methylphenoxy)acetonitrile. LCMS retention time=1.19 minutes (RxNMON-Acidic:ZQ12); MS (m+1)=194.1. Then, the reaction vial was sealed, and the mixture was heated to 150° C. on microwave for 20 min. This reaction was repeated 20 times. The combined reaction mixture was filtered, washed with acetonitrile, the filtrate was concentrated. The residue was purified by silica gel flash chromatography (100% heptane-10% ethyl acetate/heptane) to give 5-fluoro-6-methylbenzofuran-2-carbonitrile (5.55 g). $^1$H NMR (400 MHz, DMSO-$d_6$) δ 2.38 (d, J=2.2 Hz, 3H), 7.62 (d, J=9.3 Hz, 1H), 7.72 (d, J=6.0 Hz, 1H), 8.04 (d, J=1.0 Hz, 1H).

Step 2: Synthesis of 6-(bromomethyl)-5-fluorobenzofuran-2-carbonitrile

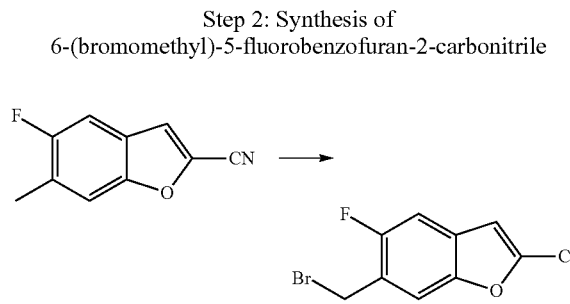

To the solution of 5-fluoro-6-methylbenzofuran-2-carbonitrile (1.44 g, 8.22 mmol) in 82 mL of $CCl_4$ was added NBS (1.536 g, 8.63 mmol) and AIBN (0.067 g, 0.411 mmol). After the reaction mixture was refluxed overnight, the solvent was removed. The residue was purified by silica gel flash chromatography (100% heptane-7% ethyl acetate/heptane) to give 6-(bromomethyl)-5-fluorobenzofuran-2-carbonitrile (1.6 g). $^1$H NMR (400 MHz, DMSO-$d_6$) δ 4.82 (d, J=1.1 Hz, 2H), 7.75 (d, J=9.5 Hz, 1H), 8.02 (d, J=5.9 Hz, 1H), 8.10 (d, J=0.86 Hz, 1H).

Step 3: Synthesis of 5-fluoro-6-(((4-(trifluoromethoxy)-3-(trifluoromethyl)phenyl)amino)-methyl)benzofuran-2-carbonitrile

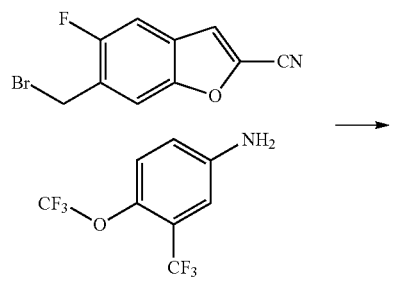

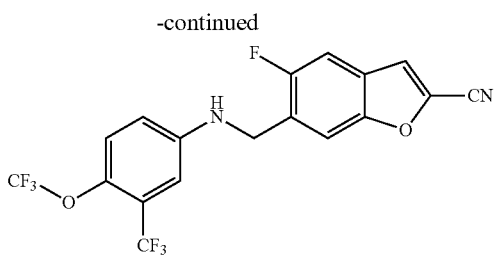

The mixture of 4-(2,2,2-trifluoroethoxy)-3-(trifluoromethyl)aniline (448 mg, 1.828 mmol), $K_2CO_3$ (49.0 mg, 0.354 mmol) and 6-(bromomethyl)-5-fluorobenzofuran-2-carbonitrile (387 mg, 1.523 mmol) in 2.3 ml DMF was stirred at room temperature overnight. After cooled to room temperature, the mixture was diluted with DCM, the organic layer was washed with $H_2O$, brine and dried over $Na_2SO_4$, and concentrated. The resulting crude product was directly carried over for next step reaction without purification.

Step 4: Synthesis of N-((5-fluoro-2-(1H-tetrazol-5-yl)benzofuran-6-yl)methyl)-4-(trifluoromethoxy)-3-(trifluoromethyl)aniline

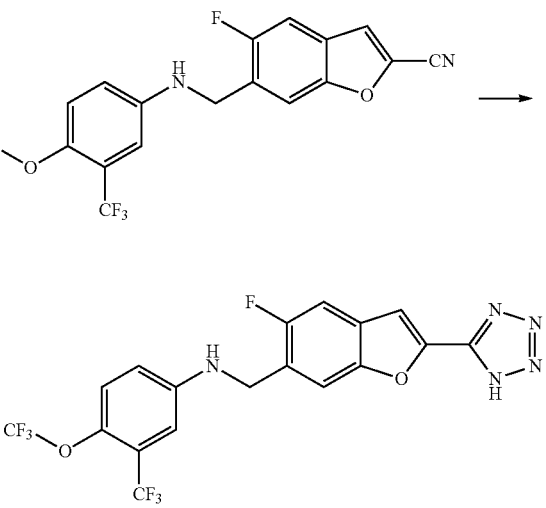

To the solution of 5-fluoro-6-(((4-(trifluoromethoxy)-3-(trifluoromethyl)phenyl)amino)methyl)-benzofuran-2-carbonitrile (637 mg, 1.523 mmol) in 15 mL DMF was added $NH_4Cl$ (326 mg, 6.09 mmol) and $NaN_3$ (198 mg, 3.05 mmol). After the reaction mixture was stirred at room temperature overnight, the mixture was adjusted to pH=1 by addition of 1N HCl aqueous solution. The mixture was then diluted with AcOEt and washed with water, brine, dried over $Na_2SO_4$, and concentrated. The crude product was purified on basic HPLC (ammonium hydroxide modifier) 15-45% MeCN/Water to give N-((5-fluoro-2-(1H-tetrazol-5-yl)benzofuran-6-yl)methyl)-4-(trifluoromethoxy)-3-(trifluoromethyl)aniline (194 mg). LCMS retention time=1.41 minutes (LC method 1); MS (m+1)=462.1. $^1$H NMR (400 MHz, DMSO-$d_6$) δ 4.50 (d, J=5.2 Hz, 2H), 6.93 (dd, J=9.2, 3.0 Hz, 1H), 7.00 (br. s., 1H), 7.05 (d, J=2.8 Hz, 1H), 7.33 (d, J=9.0 Hz, 1H), 7.61-7.69 (m, 2H), 7.75 (d, J=5.7 Hz, 1H).

Intermediate 1: 5-(((4-propyl-3-(trifluoromethylyl)phenyl)amino)methyl)benzofuran-2-carbonitrile

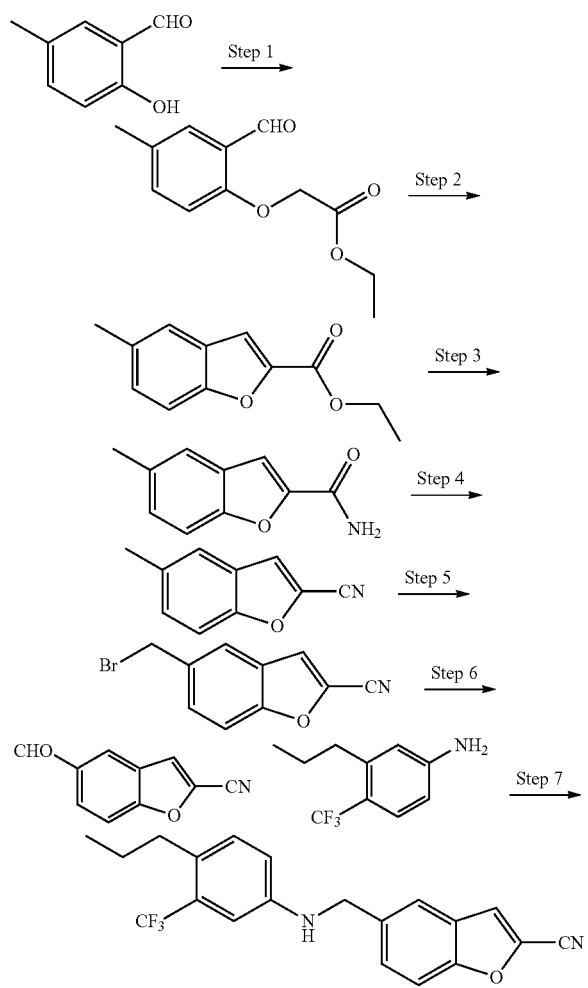

Step 1: Synthesis of ethyl 2-(2-formyl-4-methylphenoxy)acetate

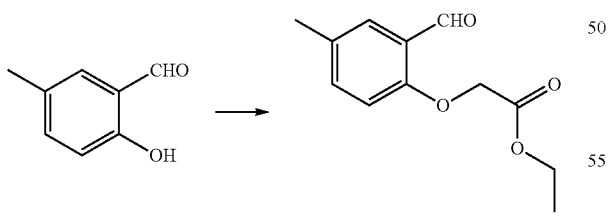

To a solution of 2-hydroxy-5-methylbenzaldehyde (2 g, 14.69 mmol) in 22 mL of DMF was added K$_2$CO$_3$ (4.06 g, 29.4 mmol) under N$_2$ at room temperature. After the mixture was stirred for 10 min, ethyl 2-bromoacetate (1.625 mL, 14.69 mmol) was added. The reaction mixture was stirred at room temperature overnight, and filtered through Celite to remove solids. The filtrate was concentrated under reduced pressure, and the resulting residue was purified by silica gel flash chromatography, 100% Heptane-20% Ethyl Acetate/80% Heptane, to give a white solid, ethyl 2-(2-formyl-4-methylphenoxy)acetate (2.5 g). LCMS retention time=1.19 minutes (LC method 3); MS (m+1)=222.9. $^1$H NMR (400 MHz, DMSO-d$_6$) δ 1.20 (t, J=7.1 Hz, 3H), 2.28 (s, 3H), 4.17 (q, J=7.2 Hz, 2H), 4.95 (s, 2H), 7.08 (d, J=8.6 Hz, 1H), 7.45 (ddd, J=8.6, 2.5, 0.6 Hz, 1H), 7.51 (d, J=2.2 Hz, 1H), 10.41 (s, 1H).

Step 2: Synthesis of Ethyl 5-methylbenzofuran-2-carboxylate

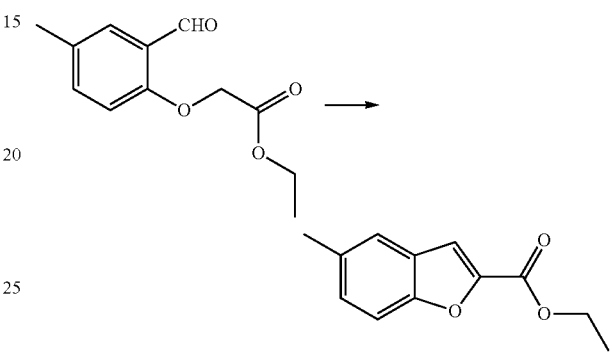

To a solution of ethyl 2-(2-formyl-4-methylphenoxy)acetate (2.24 g, 10.08 mmol) in 15 mL of DMF was added K$_2$CO$_3$ (2.79 g, 20.16 mmol), the mixture was stirred under nitrogen at 90° C. for 3 hr. After cooling to room temperature, the mixture was filtered through Celite, and washed with DCM. The combined filtrate was concentrated, and the resulting residue was purified by silica gel flash chromatography, 100% Heptane-20% Ethyl Acetate/80% Heptane, to give a white solid, ethyl 5-methylbenzofuran-2-carboxylate (1.2 g). LCMS retention time=1.54 minutes (LC method 3); MS (m+1)=204.8. $^1$H NMR (400 MHz, DMSO-d$_6$) δ 1.33 (t, J=7.1 Hz, 3H), 2.41 (s, 3H), 4.35 (q, J=7.1 Hz, 2H), 7.34 (dd, J=8.5, 1.4 Hz, 1H), 7.55-7.63 (m, 2H), 7.68 (d, J=0.9 Hz, 1H).

Step 3: Synthesis of 5-methylbenzofuran-2-carboxamide

Ethyl 5-methylbenzofuran-2-carboxylate, (1.19 g, 5.83 mmol) was suspended in 20 ml of 7M NH$_3$ in MeOH. The mixture was stirred at 50° C. in a sealed tube overnight. After cooling to room temperature, the solvent was evaporated under reduced pressure to give pure 5-methylbenzofuran-2-carboxamide, as a white solid (1.02 g). LCMS retention time=1.00 minutes (LC method 3); $^1$H NMR (400 MHz, DMSO-$d_6$) δ 2.40 (s, 3H), 7.45 (d, J=0.9 Hz, 1H), 7.51 (d, J=8.4 Hz, 1H), 7.53 (t, J=0.7 Hz, 1H), 7.63 (br. s., 1H), 8.05 (br. s., 1H).

Step 4: Synthesis of 5-methylbenzofuran-2-carbonitrile

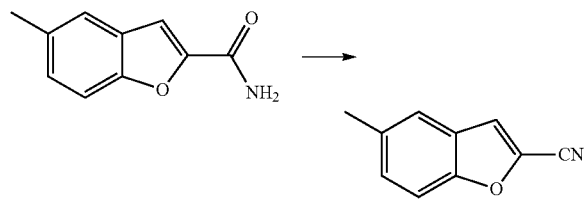

To the suspension of 5-methylbenzofuran-2-carboxamide (5.17 g, 29.5 mmol) in 66 mL of anhydrous THF was added TEA (8.23 mL, 59.0 mmol). TFAA (6.25 mL, 44.3 mmol) was added dropwise to the above mixture at 0° C. (internal temperature did not exceed 15° C.). After stirring at 0° C. for 1 hr, the reaction was complete by TLC. The reaction mixture was poured into 610 mL of $H_2O$, and extracted with EtOAc 3 times. The organic layer was washed with sat. $NaHCO_3$, brine and dried over $Na_2SO_4$, filtered and concentrated under reduced pressure, and the resulting residue was purified by silica gel flash chromatography, 100% Heptane-8% Ethyl Acetate/92% Heptane, to yield 5-methylbenzofuran-2-carbonitrile (3.65 g). $^1$H NMR (400 MHz, DMSO-$d_6$) δ 2.42 (s, 3H), 7.42 (dd, J=8.6, 1.8 Hz, 1H), 7.59-7.67 (m, 2H), 8.03 (d, J=0.9 Hz, 1H).

Step 5: Synthesis of 5-(bromomethyl)benzofuran-2-carbonitrile

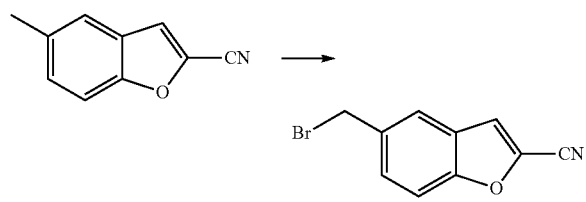

5-(Bromomethyl)benzofuran-2-carbonitrile was prepared as described in general bromination procedure, example 37, Step 5, starting from 5-methylbenzofuran-2-carbonitrile. $^1$H NMR (400 MHz, DMSO-$d_6$) δ 4.86 (s, 2H), 7.66-7.70 (m, 1H), 7.73-7.77 (m, 1H), 7.93 (d, J=1.6 Hz, 1H), 8.12 (d, J=0.7 Hz, 1H).

Step 6: Synthesis of 5-formylbenzofuran-2-carbonitrile

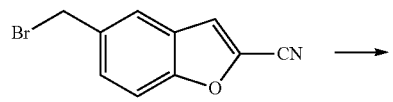

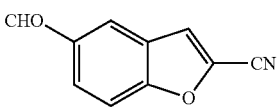

Trimethlamine-N-oxide (6.75 g, 90 mmol) was added to a solution of 5-(bromomethyl)benzofuran-2-carbonitrile (4.46 g, 18.89 mmol) in 57 mL of DMSO and 6 mL of $H_2O$. The mixture was stirred at 70° C. for 3 hr. After the reaction was cooled to room temperature, the mixture was diluted with 72 mL of brine, and extracted with EtOAc (3×100 mL). The combined organic layers were washed with $H_2O$ (2×20 mL), brine, dried over $Na_2SO_4$, filtered, and concentrated under reduced pressure. The resulting residue was purified by silica gel flash chromatography, 100% Heptane-30% Ethyl Acetate/70% Heptane, to give 5-formylbenzofuran-2-carbonitrile (1.5 g). $^1$H NMR (400 MHz, DMSO-$d_6$) δ 7.96 (d, J=8.7 Hz, 1H), 8.12 (dd, J=8.7, 1.7 Hz, 1H), 8.30 (d, J=0.9 Hz, 1H), 8.46 (dd, J=1.6, 0.6 Hz, 1H), 10.11 (s, 1H).

Step 7: Synthesis of 5-(((4-propyl-3-(trifluoromethyl)phenyl)amino)methyl)benzofuran-2-carbonitrile

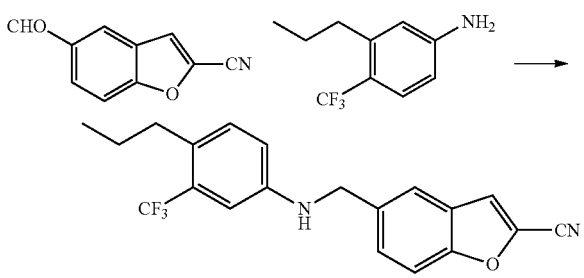

5-Formylbenzofuran-2-carbonitrile (168 mg, 0.98 mmol) was added to 2 mL of TFE and stirred at 35-40° C. After 5 min, the solution became clear, 4-propyl-3-(trifluoromethyl) aniline (199 mg, 0.982 mmol) was added, and a yellow precipitate formed. The mixture was vigorously stirred at the same temperature for 0.5 hr, $NaBH_4$ (44.6 mg, 1.18 mmol) was added and the reaction was stirred at this temperature for another 0.5 hr. LCMS indicated the reaction was complete, the mixture was filtered, and the residue was washed with TFE (2 mL). The solvent was concentrated under reduced pressure and the crude product was purified by silica gel flash chromatography, 100% Heptane-10% Ethyl Acetate/90% Heptane, to give 5-(((4-propyl-3 (trifluoromethyl)phenyl) amino)-methyl)benzofuran-2-carbonitrile (243 mg). LCMS retention time=1.76 minutes (LC method 3); MS (m+1)= 358.8. $^1$H NMR (400 MHz, DMSO-$d_6$) δ 0.88 (t, J=7.3 Hz, 3H), 1.48 (sxt, J=7.5 Hz, 2H), 2.47 (br. s., 2H) 4.41 (d, J=6.0 Hz, 2H), 6.64 (t, J=6.1 Hz, 1H), 6.74 (dd, J=8.4, 2.4 Hz, 1H), 6.86 (d, J=2.5 Hz, 1H), 7.10 (d, J=8.4 Hz, 1H), 7.59 (dd, J=8.7, 1.7 Hz, 1H), 7.71 (d, J=8.7 Hz, 1H), 7.78 (d, J=1.0 Hz, 1H), 8.09 (d, J=0.9 Hz, 1H).

Intermediate 2: 6-(((3-bromo-4-(trifluoromethoxy)phenyl)amino)methyl)-3-methylbenzofuran-2-carbonitrile

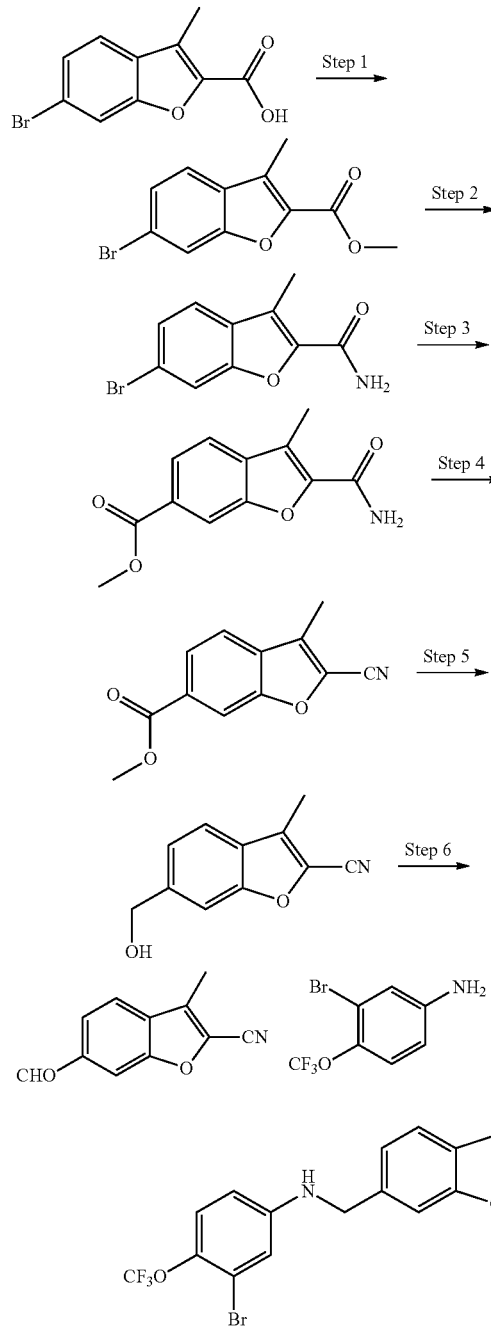

Step 1: Synthesis of methyl 6-bromo-3-methylbenzofuran-2-carboxylate

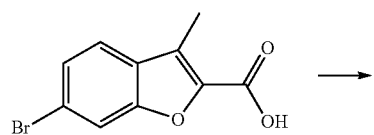

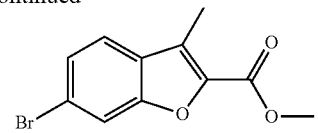

To a suspension of 6-bromo-3-methylbenzofuran-2-carboxylic acid (5 g, 19.6 mmol) in 196 mL of MeOH was added SOCl$_2$ (2.9 mL, 39.2 mmol). After the mixture was heated to reflux for 1 hr, the reaction solution became clear, and the color changed to green. The mixture was concentrated to remove part of solvent, and the color of the solution changed to yellow. After cooling to room temperature a white PPT formed, and the suspension was filtered, and the solid was washed with small amounts of EtOAc. The solid was dried under vacuum at 50° C. to give pure methyl 6-bromo-3-methylbenzofuran-2-carboxylate (3.56 g). LCMS retention time=1.58 minutes (LC method 3); MS (m+1)=270.9. $^1$H NMR (400 MHz, CHLOROFORM-d) δ 2.59 (s, 3H), 3.99 (s, 3H), 7.41-7.47 (m, 1H), 7.48-7.53 (m, 1H), 7.72 (d, J=1.5 Hz, 1H).

Step 2 and 3: Synthesis of methyl 2-carbamoyl-3-methylbenzofuran-6-carboxylate

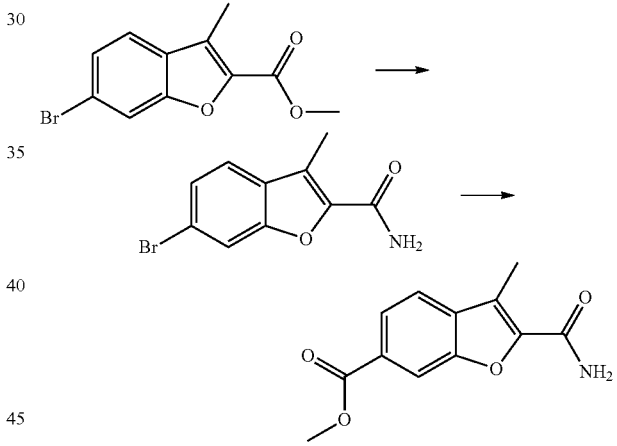

Methyl 6-bromo-3-methylbenzofuran-2-carboxylate (3.65 g, 13.56 mmol) was converted to 6-bromo-3-methylbenzofuran-2-carboxamide (2.99 g) by the method as described in preparation of Intermediate 1, Step 3. LCMS retention time=1.05 minutes (RxNMON-Acidic:SQ4); MS (m+1)= 256.2.

To a mixture of 6-bromo-3-methylbenzofuran-2-carboxamide (2.99 g, 11.77 mmol) in 238 mL of DMSO and 119 mL of MeOH was added TEA (8.20 mL, 58.8 mmol) followed by Pd(OAc)$_2$ (264 mg, 1.18 mmol) and DPPF (6.52 g, 11.77 mmol). The resulting mixture was purged with CO gas and heated at 85° C. under 1 atm of CO gas for 3 hr. The reaction was monitored by LCMS. After the solution was cooled to room temperature, the reaction was diluted with 600 mL of EtOAc and 600 mL of water. The organic layer was separated and the aqueous layer was further extracted with EtOAc. The combined organic layers were washed with brine, dried over Na$_2$SO$_4$, filtered and concentrated under reduced pressure. The resulting residue was purified by silica gel flash chromatography, 100% Heptane-50% Ethyl Acetate/50% Heptane to give methyl 2-carbamoyl-3-methylbenzofuran-6-carboxylate (2.19 g). LCMS retention time=1.26 minutes (LC method 3); MS (m+1)=234.0. $^1$H NMR (400 MHz, DMSO-d$_6$) δ 2.54 (s, 3H), 3.90 (s, 3H), 7.75 (br. s., 1H), 7.85-7.90 (m, 1H), 7.90-7.96 (m, 1H), 8.01 (br. s., 1H), 8.06 (s, 1H).

Step 4: Synthesis of methyl 2-cyano-3-methylbenzofuran-6-carboxylate

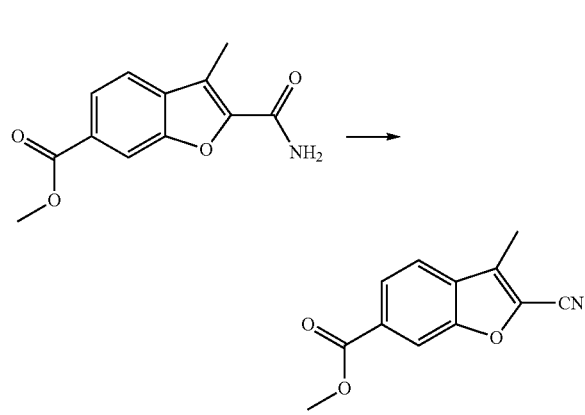

2-Cyano-3-methylbenzofuran-6-carboxylate was prepared as described in Intermediate 1, Step 4, starting from methyl 2-carbamoyl-3-methylbenzofuran-6-carboxylate. LCMS retention time=1.52 minutes (LC method 3); MS (m+1)=216.0. $^1$H NMR (400 MHz, DMSO-d$_6$) δ 2.48 (s, 3H), 3.90-3.92 (m, 3H), 7.96-8.03 (m, 2H), 8.22-8.25 (m, 1H).

Step 5: Synthesis of 6-(hydroxymethyl)-3-methyl-benzofuran-2-carbonitrile

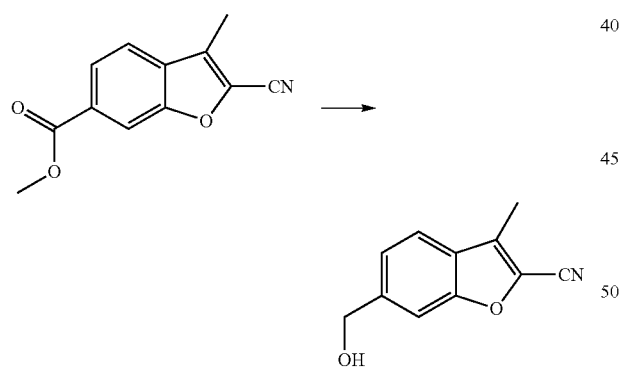

2-Cyano-3-methylbenzofuran-6-carboxylate (540 mg, 2.51 mmol) was dissolved in 17 mL of EtOH, and CaCl$_2$ (557 mg, 5.02 mmol) was added and the mixture was briefly stirred in the ultrasound bath. Then the mixture was cooled to 0° C. and a solution of NaBH$_4$ (380 mg, 10.04 mmol) in 17 mL of THF was added. The mixture was stirred at 0° C. for 1.5 hr, and then 1N HCl was carefully added. The organic layer was separated, and the aqueous phase was extracted with DCM (4×7 mL), the combined organic phases were dried over Na$_2$SO$_4$, filtered off and evaporated under reduced pressure. The crude product was purified by silica gel flash chromatography 100% DCM-7% MeOH/93% DCM to give 6-(hydroxymethyl)-3-methylbenzofuran-2-carbonitrile (233 mg).

$^1$H NMR (400 MHz, DMSO-d$_6$) δ 2.44 (s, 3H), 4.65 (d, J=5.8 Hz, 2H), 5.42 (t, J=5.8 Hz, 1H), 7.35-7.42 (m, 1H), 7.60 (s, 1H), 7.77 (d, J=8.2 Hz, 1H).

Step 6: Synthesis of 6-formyl-3-methylbenzofuran-2-carbonitrile

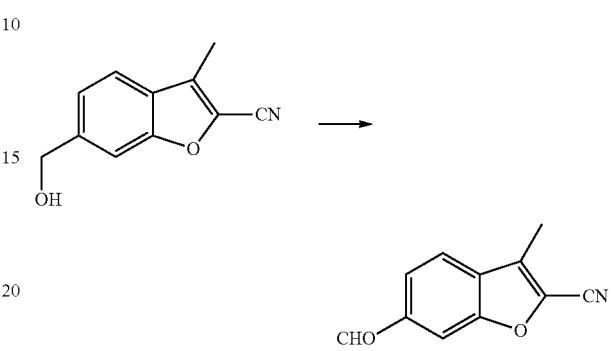

To a solution of 6-(hydroxymethyl)-3-methylbenzofuran-2-carbonitrile (116 mg, 0.62 mmol) in 6 mL of DCM was added NaHCO$_3$ (125 mg, 1.49 mmol), followed by Dess-Martin periodinane (315 mg, 0.74 mmol). The reaction was stirred at room temperature for 1 hr. The reaction was quenched by addition of 2 mL of sat. NaHCO$_3$ and 2 mL of sat. Na$_2$S$_2$O$_3$ and stirred for 30 min. The reaction mixture was extracted with DCM (3×50 mL), the organic layer was washed with H$_2$O, brine, dried over Na$_2$SO$_4$, filtered and concentrated under reduced pressure. The crude product was purified by silica gel flash chromatography 100% Heptane-50% Ethyl Acetate/50% Heptane) to give 6-formyl-3-methylbenzofuran-2-carbonitrile (96 mg). $^1$H NMR (400 MHz, DMSO-d$_6$) δ 2.51 (br. s., 3H), 7.97 (dd, J=8.1, 1.2 Hz, 1H), 8.04-8.09 (m, 1H), 8.27 (s, 1H), 10.14 (s, 1H).

Step 7: Synthesis of 6-(((3-bromo-4-(trifluoromethoxy)phenyl)amino)methyl)-3-methylbenzofuran-2-carbonitrile

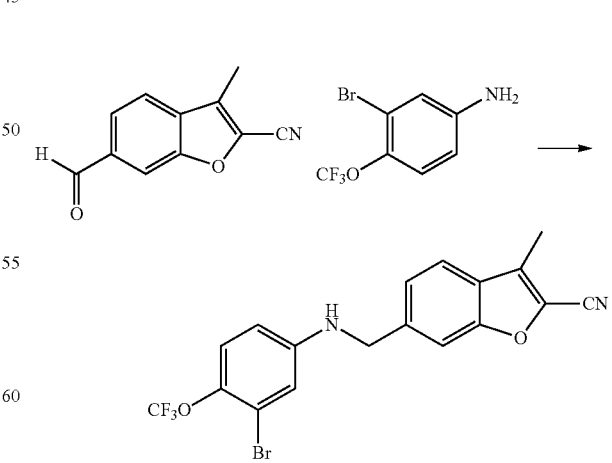

The title compound was prepared as described in general reductive amination procedure, starting from 3-bromo-4-(trifluoromethoxy)aniline and 6-formyl-3-methylbenzofuran-2- carbonitrile, Intermediate 4. LCMS retention time=1.64 minutes (LC method 3); MS (m+1)=426.0.

General Reductive Amination Procedure

Synthesis of 5-(((4-propyl-3-(trifluoromethyl)phenyl)amino)methyl)benzofuran-2-carbonitrile

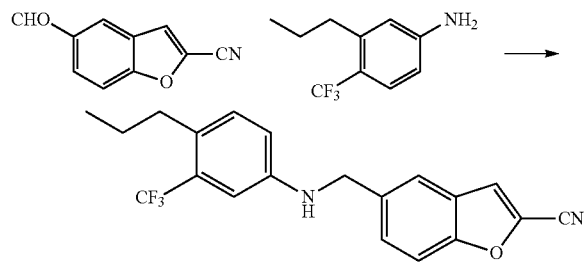

5-Formylbenzofuran-2-carbonitrile (168 mg, 0.98 mmol) was added to 2 mL of TFE and stirred at 35-40° C. After 5 min, the solution became clear, 4-propyl-3-(trifluoromethyl) aniline (199 mg, 0.982 mmol) was added, and a yellow precipitate formed. The mixture was vigorously stirred at the same temperature for 0.5 hr, NaBH$_4$ (44.6 mg, 1.18 mmol) was added and the reaction was stirred at this temperature for another 0.5 hr. The mixture was then filtered, and the residue was washed with TFE (2 mL). The solvent was concentrated under reduced pressure and the crude product was purified by silica gel flash chromatography, 100% Heptane-10% Ethyl Acetate/90% Heptane, to give 5-(((4-propyl-3 (trifluoromethyl)phenyl)amino)-methyl)benzofuran-2-carbonitrile (243 mg). LCMS retention time=1.76 minutes (LC method 3); MS (m+1)=358.8. $^1$H NMR (400 MHz, DMSO-d$_6$) δ 0.88 (t, J=7.3 Hz, 3H), 1.48 (sxt, J=7.5 Hz, 2H), 2.47 (br. s., 2H) 4.41 (d, J=6.0 Hz, 2H), 6.64 (t, J=6.1 Hz, 1H), 6.74 (dd, J=8.4, 2.4 Hz, 1H), 6.86 (d, J=2.5 Hz, 1H), 7.10 (d, J=8.4 Hz, 1H), 7.59 (dd, J=8.7, 1.7 Hz, 1H), 7.71 (d, J=8.7 Hz, 1H), 7.78 (d, J=1.0 Hz, 1H), 8.09 (d, J=0.9 Hz, 1H).

General Bromomethylbenzofuran Aniline Coupling Reaction

Synthesis of 6-(((3-bromo-4-(trifluoromethoxy)phenyl)amino)methyl)benzofuran-2-carbonitrile

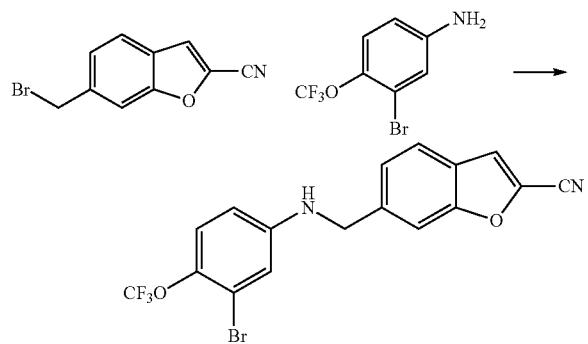

6-(bromomethyl)benzofuran-2-carbonitrile (0.5 g, 2.12 mmol) was dissolved in DMF (21.2 ml). K$_2$CO$_3$ (0.44 g, 3.18 mmol) was added, followed by 3-bromo-4-(trifluoromethoxy)aniline (314 μL, 2.12 mmol), and the mixture was stirred at RT for 18 hr. The reaction was diluted with EtOAc and water. The organic layer was washed with water×6, brine, dried over Na$_2$SO$_4$, filtered, and concentrated under reduced pressure. The crude mixture was diluted with DCM and silica gel was added. The mixture was concentrated under reduced pressure to dry-load material for purification. The crude mixture was purified via silica gel FCC, 100% Heptane-50% EtOAc/50% Heptane to give 6-(((3-bromo-4-(trifluoromethoxy)phenyl)amino)methyl)benzofuran-2-carbonitrile (651 mg). LCMS retention time=1.57 minutes (LC method 1); MS (m+1)=412.1. $^1$H NMR (400 MHz, DMSO-d$_6$) δ 4.46 (d, J=6.0 Hz, 2H), 6.62 (dd, J=9.0, 2.8 Hz, 1H), 6.88-6.95 (m, 2H), 7.17 (dq, J=9.0, 1.3 Hz, 1H), 7.44 (dd, J=8.2, 1.4 Hz, 1H), 7.70 (s, 1H), 7.80 (dd, J=8.1, 0.7 Hz, 1H), 8.08 (d, J=1.0 Hz, 1H).

Intermediate 3: Ethyl 2-(5-methyl-2-(2,2,2-trifluoroacetyl)phenoxy)acetate

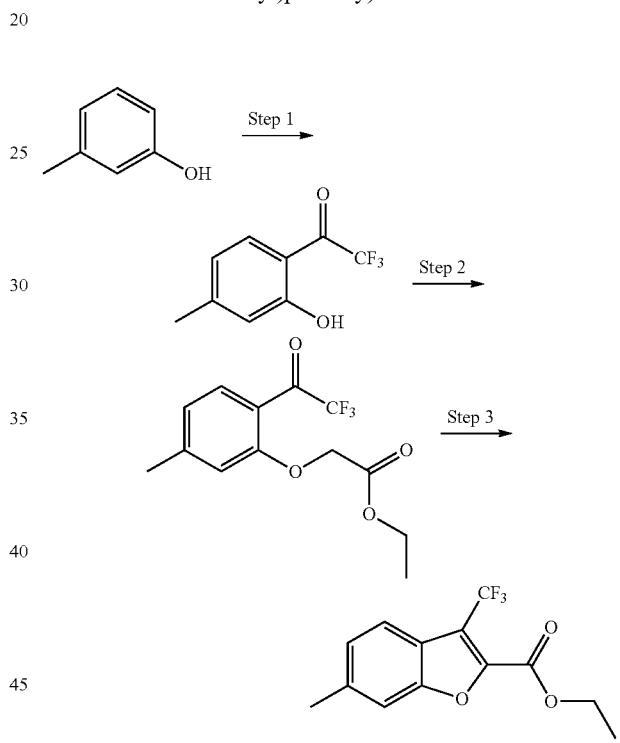

Step 1: Synthesis of 2,2,2-trifluoro-1-(2-hydroxy-4-methylphenyl)ethanone

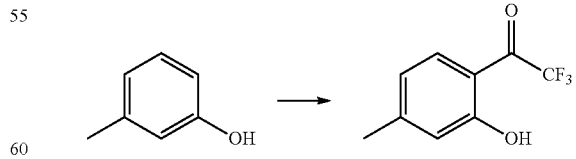

To a pre-cooled (0° C.) solution of m-cresol (5.84 mL, 83 mmol) in 333 mL of DCE was added TFAA (16.75 mL, 119 mmol) over 20 min. Aluminum trichloride (36.2 g, 271 mmol) was then added portion-wise over 30 min. The reaction mixture was gradually warmed to room temperature over 2 hr and then heated at 40° C. for 19 hr. The reaction mixture was cooled to room temperature and poured over ice water. The resulting mixture was extracted with DCM (2×50 mL), the combined organic layers were washed with a sat. NaHCO$_3$ solution (1500 mL), followed by a brine solution (1500 mL), dried over Na$_2$SO$_4$, filtered, and concentrated under reduced pressure. The resulting residue was purified by silica gel flash chromatography, 100% Heptane-5% Ethyl Acetate/95% Heptane) to give 2,2,2-trifluoro-1-(2-hydroxy-4-methylphenyl) ethanone (6.77 g). $^1$H NMR (400 MHz, CHLOROFORM-d) δ 2.41 (s, 3H), 6.82 (dd, J=8.5, 1.1 Hz, 1H), 6.90 (s, 1H), 7.70 (dq, J=8.5, 2.2 Hz, 1H), 11.11 (s, 1H).

Step 2: Synthesis of ethyl 2-(5-methyl-2-(2,2,2-trifluoroacetyl)phenoxy)acetate

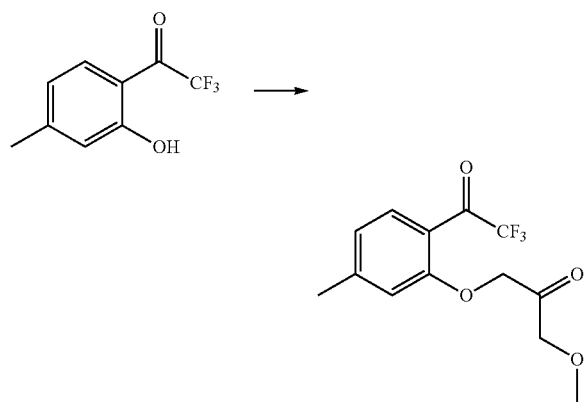

The title compound was prepared as described in Intermediate 1, Step 1, starting from 2,2,2-trifluoro-1-(2-hydroxy-4-methylphenyl) ethanone. LCMS retention time=1.33 minutes (LC method 1); MS (m+1)=291.3. $^1$H NMR (400 MHz, CHLOROFORM-d) δ 1.30 (t, J=7.1 Hz, 3H), 2.41 (s, 3H), 4.28 (d, J=7.2 Hz, 2H), 4.72 (s, 2H), 6.71 (s, 1H), 6.93 (dd, J=8.0, 0.6 Hz, 1H), 7.64 (d, J=8.0 Hz, 1H).

Step 3: Synthesis of ethyl 6-methyl-3-(trifluoromethyl)benzofuran-2-carboxylate

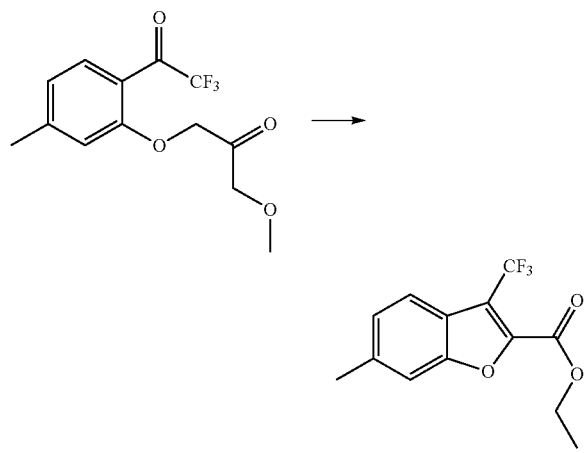

The mixture of ethyl 2-(5-methyl-2-(2,2,2-trifluoroacetyl) phenoxy)acetate (7.3 g, 25.2 mmol) and pre-oven dried K$_2$CO$_3$ (5.21 g, 37.7 mmol) in 25 mL of CH$_3$CN in sealed tube was heated and stirred at 90° C. for two days. After cooling to room temperature, the reaction was filtered, and the solid was washed with anhydrous CH$_3$CN. The combined filtrate was concentrated to dryness under reduced pressure. The resulting residue was purified by silica gel flash chromatography, 100% Heptane-2% Ethyl Acetate/98% Heptane, to give ethyl 6-methyl-3-(trifluoromethyl)benzofuran-2-carboxylate (2.35 g). LCMS retention time=1.52 minutes (LC method 1); MS (m+1)=273.3. $^1$H NMR (400 MHz, CHLOROFORM-d) δ 1.45 (t, J=7.1 Hz, 3H), 2.53 (s, 3H), 4.50 (q, J=7.2 Hz, 2H), 7.24 (dd, J=8.3, 0.9 Hz, 1H), 7.43 (d, J=0.6 Hz, 1H), 7.69-7.77 (m, 1H).

Intermediate 4: 5-(1-((3-chloro-4-propylphenyl) amino)ethyl)benzofuran-2-carbonitrile

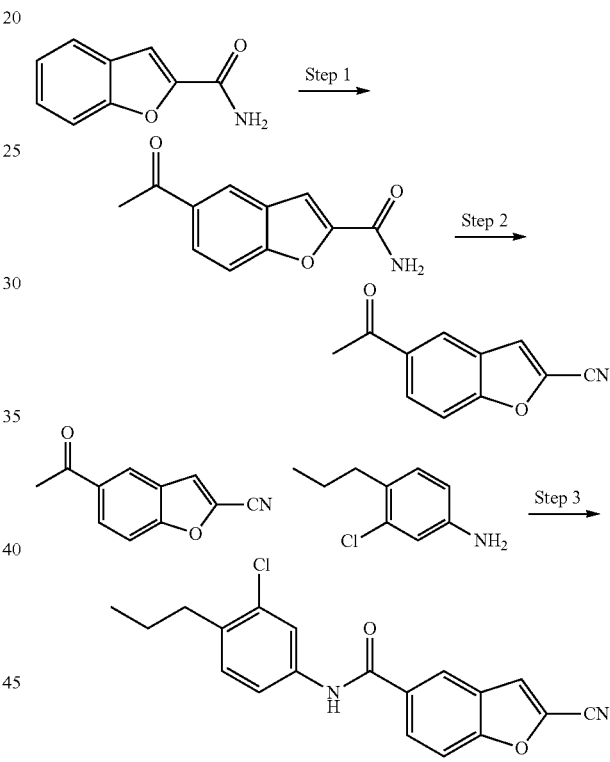

Step 1: Synthesis of 5-acetylbenzofuran-2-carboxamide
To a suspension of benzofuran-2-carboxamide (4.07 g, 25.3 mmol) in 200 mL of DCM was added acetyl chloride (5.34 mL, 75 mmol). AlCl$_3$ (13.5 g, 101 mmol) was added to above mixture while stirring in small portions, and the solution became clear. The reaction was stirred at room temperature for 19 hr. The reaction mixture was added to 200 mL 0.1N HCl, then extracted with DCM (3×150 mL), the organic layer was washed with H$_2$O, brine and dried over Na$_2$SO$_4$, filtered, and concentrated under reduced pressure. The residue was purified by silica gel flash chromatography, 50% Ethyl Acetate/50% Heptane-75% Ethyl Acetate/25% Heptane, to give 5-acetylbenzofuran-2-carboxamide (2.69 g). LCMS retention time=0.81 minutes (LC method 3); MS (m+1)=203.9. $^1$H NMR (400 MHz, DMSO-d$_6$) δ 2.65 (s, 3H), 7.67 (d, J=0.9 Hz, 1H), 7.72-7.78 (m, 2H), 8.02-8.07 (m, 1H), 8.20 (br. s., 1H), 8.46 (d, J=1.7 Hz, 1H).

Step 2: Synthesis of 5-acetylbenzofuran-2-carbonitrile

5-Acetylbenzofuran-2-carbonitrile was prepared as described in Intermediate 1, Step 4, starting from 5-acetyl-benzofuran-2-carboxamide. LCMS retention time=1.05 minutes (LC method 1); MS (m+1)=186.1. $^1$H NMR (400 MHz, DMSO-d$_6$) δ 2.66 (s, 3H), 7.87 (d, J=8.9 Hz, 1H), 8.17 (dd, J=8.8, 1.8 Hz, 1H), 8.24 (d, J=0.9 Hz, 1H), 8.51 (d, J=1.8 Hz, 1H).

Step 3: Synthesis of (±) 5-(1-((3-chloro-4-propylphenyl)amino)ethyl)benzofuran-2-carbonitrile A mixture of 5-acetylbenzofuran-2-carbonitrile (64 mg, 0.35 mmol), 3-chloro-4-propylaniline (140 mg, 0.82 mmol) and Ti(OiPr)$_4$ (205 μL, 0.69 mmol) was heated to 50° C. for 3 hr, then 60° C. for 2 hr. The reaction mixture was diluted with 10 mL of DCM, and celite was added to the solution (enough to equal the volume of the mixture). The reaction was quenched with 5 mL of sat. NaHCO$_3$:H$_2$O=1:1, and filtered. The separated organic layer was washed with H$_2$O, brine and dried over Na$_2$SO$_4$, filtered, and concentrated under reduced pressure. The residue was dissolved in 1.4 mL of TFE and NaBH$_4$ (15.69 mg, 0.415 mmol) was added. The reaction was stirred at 40° C. for 2 hr. After cooling to room temperature, the reaction mixture was diluted with 50 mL of DCM, which was then washed with H$_2$O, brine, dried over Na$_2$SO$_4$, filtered, and concentrated under reduced pressure. The residue was purified by silica gel flash chromatography, 100% Heptane-30% Ethyl Acetate/70% Heptane, to give (±) 5-(1-((3-chloro-4-propylphenyl)amino)ethyl)benzofuran-2-carbonitrile (113 mg). LCMS retention time=1.66 minutes (LC method 1); MS (m+1)=339.3.

Intermediate 5: 5-formyl-3-methylbenzofuran-2-carboxamide

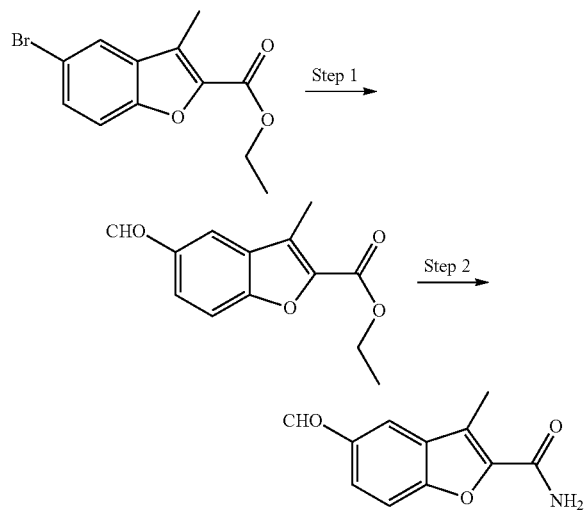

Step 1: Synthesis of ethyl 5-formyl-3-methylbenzofuran-2-carboxylate

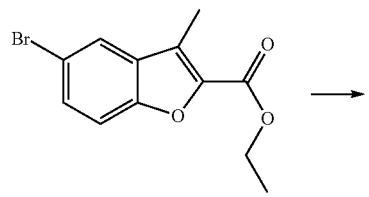

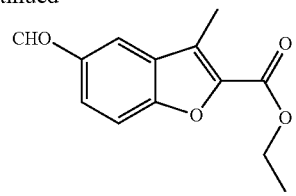

To a 10 mL flask, fitted with a inlet needle, was placed PdCl$_2$(PPh$_3$)$_2$ (179 mg, 0.25 mmol), ethyl 5-bromo-3-methylbenzofuran-2-carboxylate (3.6 g, 12.72 mmol) and sodium formate (1.30 g, 19.07 mmol). After the mixture was degassed by CO gas, 13 mL of DMF was added by syringe, and a slow stream of CO was passed into the suspension. The mixture was vigorously stirred at 110° C. for 5 hr. After the reaction mixture was cooled to room temperature 2 mL of 1N NaOH was added to the reaction mixture and the mixture was diluted with EtOAc. The separated organic layer was washed with H$_2$O and brine, dried over Na$_2$SO$_4$, filtered and concentrated under reduced pressure. The residue was purified by silica gel flash chromatography, 100% Heptane-15% Ethyl Acetate/85% Heptane, to yield 5-formyl-3-methylbenzofuran-2-carboxylate (1.33 g). LCMS retention time=1.15 minutes (LC method 1); MS (m+1)=233.2. $^1$H NMR (400 MHz, DMSO-d6) δ 1.36 (t, J=7.1 Hz, 3H), 2.62 (s, 3H), 4.38 (q, J=7.1 Hz, 2H), 7.88 (d, J=8.7 Hz, 1H), 8.06 (dd, J=8.7, 1.71 Hz, 1H), 8.45 (dd, J=1.6, 0.6 Hz, 1H), 10.11 (s, 1H).

Step 2: Synthesis of 5-formyl-3-methylbenzofuran-2-carboxamide

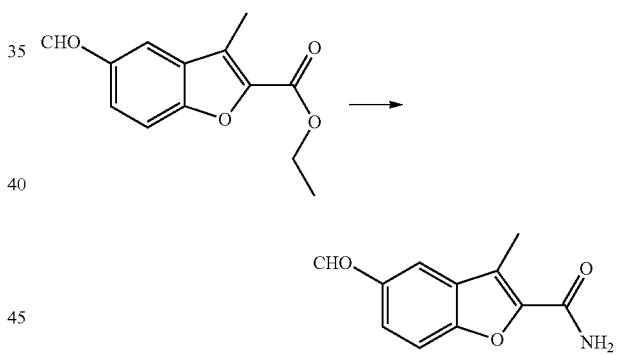

5-Formyl-3-methylbenzofuran-2-carboxamide was prepared as described in Intermediate 1, Step 3, starting from 5-formyl-3-methylbenzofuran-2-carboxylate. LCMS retention time=1.17 minutes (LC method 1); MS (m+1)=203.9. $^1$H NMR (400 MHz, DMSO-d$_6$) δ 2.58 (s, 3H), 7.72 (br. s., 1H), 7.76 (d, J=8.6 Hz, 1H), 8.01 (dd, J=8.6, 1.7 Hz, 2H), 8.37 (d, J=1.2 Hz, 1H), 10.10 (s, 1H).

Intermediate 6

4-Propyl-3-(trifluoromethyl)aniline

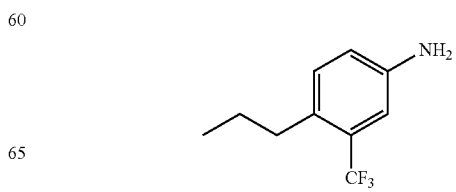

Step 1: Synthesis of 4-propyl-3-(trifluoromethyl)aniline

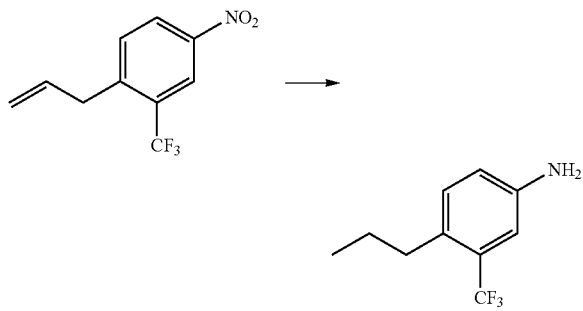

To a solution of 1-allyl-4-nitro-2-(trifluoromethyl)benzene (750 mg, 3.24 mmol) in 18 mL of THF and 3.6 mL of H$_2$O was added 10% Pd/C (250 mg, 3.24 mmol). The reaction was stirred at room temperature under an H$_2$ balloon for 24 hr. After filtering to remove Pd/C, the reaction solution was concentrated under reduced pressure. The residue was purified by silica gel flash chromatography, 100% Heptane-10% Ethyl Acetate/90% Heptane, to give 4-propyl-3-(trifluoromethyl)aniline (440 mg). LCMS retention time=1.53 minutes (LC method 3); MS (m+1)=203.8. $^1$H NMR (400 MHz, DMSO-d$_6$) δ 0.93 (t, J=7.4 Hz, 3H), 1.54 (sxt, J=7.6 Hz, 2H), 2.51-2.56 (m, 2H), 5.66 (s, 2H), 6.44 (dd, J=8.5, 1.9 Hz, 1H), 6.52 (d, J=2.1 Hz, 1H), 7.24 (d, J=8.6 Hz, 1H).

Intermediate 7

3-Fluoro-4-propylaniline

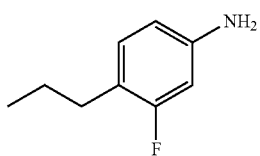

Step 1: Synthesis of 1-allyl-2-fluoro-4-nitrobenzene

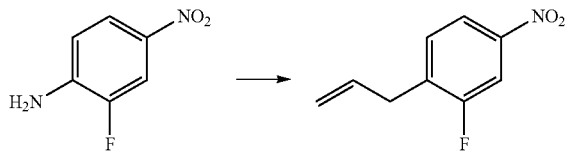

2-Fluoro-4-nitroaniline (5 g, 32.0 mmol) was added to a solution of 3-bromoprop-1-ene (41.5 mL, 480 mmol) and tert-butyl nitrite (5.76 mL, 48.0 mmol) in 32 mL of degassed anhydrous CH$_3$CN at 18-19° C. under nitrogen. At the end of the addition of the arylamine, another half-equivalent of tert-butyl nitrite (1.180 mL, 16.01 mmol) was added; the reaction was stirred at room temperature for 1 hr. The reaction was concentrated under reduced pressure to remove the volatile material. The residue was purified by silica gel flash chromatography, 100% Heptane-5% Ethyl Acetate/95% Heptane, to give 1-allyl-2-fluoro-4-nitrobenzene (2.98 g). $^1$H NMR (400 MHz, DMSO-d$_6$) δ 3.51 (dd, J=6.4, 1.1 Hz, 2H), 5.05-5.16 (m, 2H), 5.96 (ddt, J=16.8, 10.2, 6.6, 6.6 Hz, 1H), 7.56-7.62 (m, 1H), 8.03-8.11 (m, 2H).

Step 2: Synthesis of 3-fluoro-4-propylaniline

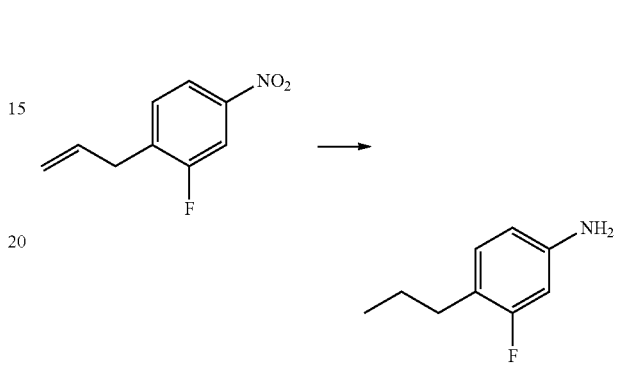

3-fluoro-4-propylaniline was prepared as described in Intermediate 6, step 1, starting from 1-allyl-2-fluoro-4-nitrobenzene. LCMS retention time=1.21 minutes (LC method 1); MS (m+1)=154.1. $^1$H NMR (400 MHz, DMSO-d$_6$) δ 0.85 (t, J=7.3 Hz, 3H), 1.47 (sxt, J=7.4 Hz, 2H), 2.37 (t, J=7.6 Hz, 2H), 5.15 (s, 2H), 6.24-6.32 (m, 2H), 6.81-6.88 (m, 1H).

Intermediate 8

3-Methoxy-4-propylaniline

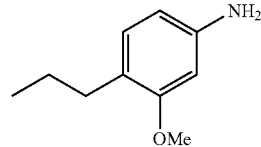

Step 1: Synthesis of 1-allyl-2-methoxy-4-nitrobenzene

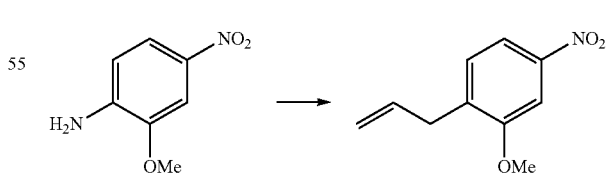

1-Allyl-2-methoxy-4-nitrobenzene was prepared as described in Intermediate 7, step 1, starting from 2-methoxy-4-nitroaniline. $^1$H NMR (400 MHz, DMSO-d$_6$) δ 3.41 (d, J=6.8 Hz, 2H), 3.92 (s, 3H), 5.04-5.07 (m, 1H), 5.08-5.11 (m, 1H), 5.89-6.00 (m, 1H), 7.40 (d, J=8.3 Hz, 1H), 7.74 (d, J=2.3 Hz, 1H), 7.81 (dd, J=8.3, 2.3 Hz, 1H).

Step 2: Synthesis of 3-methoxy-4-propylaniline

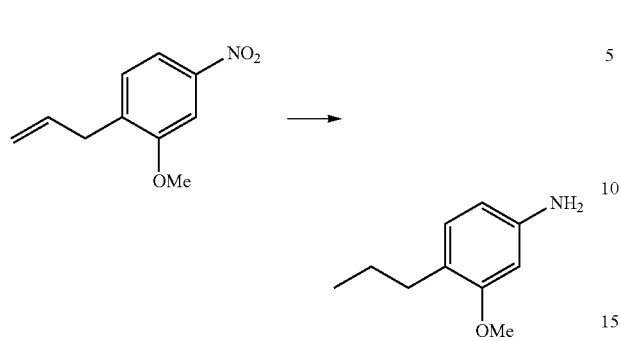

3-Methoxy-4-propylaniline was prepared as described in Intermediate 6, step 1, starting from 1-allyl-2-methoxy-4-nitrobenzene. LCMS retention time=1.08 minutes (LC method 3); MS (m+1)=165.8. $^1$H NMR (400 MHz, DMSO-$d_6$) δ 0.84 (t, J=7.5 Hz, 3H), 1.43 (sxt, J=7.4 Hz, 2H), 2.30-2.36 (m, 2H), 3.66 (s, 3H), 4.85 (br. s., 2H), 6.05 (dd, J=7.8, 2.0 Hz, 1H), 6.18 (d, J=2.0 Hz, 1H), 6.71 (d, J=7.8 Hz, 1H).

Intermediate 9

4-Propyl-3-(trifluoromethoxy)aniline

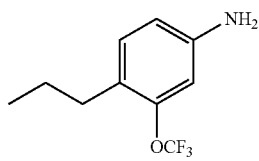

Step 1: Synthesis of 4-propyl-3-(trifluoromethoxy)aniline

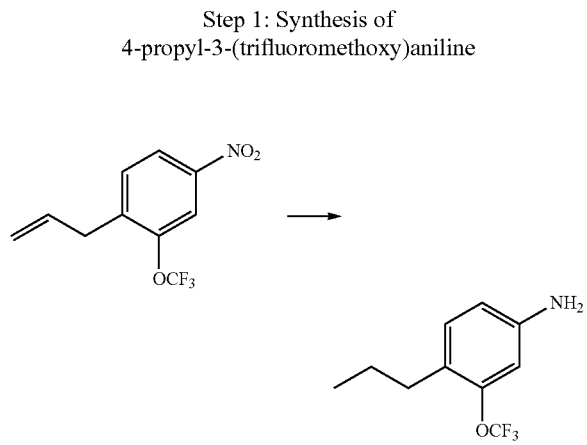

4-Propyl-3-(trifluoromethoxy)aniline was prepared as described in Intermediate 6, step 1, starting from 1-allyl-4-nitro-2-(trifluoromethoxy)benzene. LCMS retention time=1.50 minutes (LC method 3); MS (m+1)=219.8. $^1$H NMR (400 MHz, DMSO-$d_6$) δ 0.86 (t, J=7.3 Hz, 3H), 1.47 (sxt, J=7.4 Hz, 2H), 2.36-2.43 (m, 2H), 5.29 (br. s., 2H), 6.45-6.50 (m, 2H), 6.96 (d, J=8.8 Hz, 1H).

Intermediate 10

3-Chloro-5-methyl-4-propylaniline

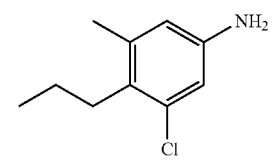

Step 1: Synthesis of 2-allyl-1-chloro-3-methyl-5-nitrobenzene

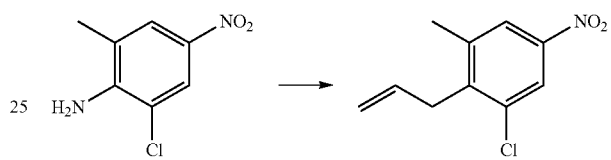

2-Allyl-1-chloro-3-methyl-5-nitrobenzene was prepared as described in Intermediate 7, step 1, starting from 2-chloro-6-methyl-4-nitroaniline. $^1$H NMR (400 MHz, DMSO-$d_6$) δ 2.44 (s, 3H), 3.61 (d, J=4.0 Hz, 2H), 4.90 (dd, J=17.2, 1.7 Hz, 1H), 5.07 (dq, J=10.2, 1.6 Hz, 1H), 5.83-5.94 (m, 1H), 8.08 (d, J=2.2 Hz, 1H), 8.12 (d, J=2.3 Hz, 1H).

Step 2: Synthesis of 3-chloro-5-methyl-4-propylaniline

A solution of 2-allyl-1-chloro-3-methyl-5-nitrobenzene (450 mg, 2.13 mmol) in 43 mL of MeOH was put on an H-cube with a Ra—Ni cartridge, the reaction was at room temperature and under 2 atm of $H_2$ for 3 hr. The reaction was concentrated under reduced pressure. The residue was purified by silica gel flash chromatography, 100% Heptane-15% Ethyl Acetate/85% Heptane, to give 3-chloro-5-methyl-4-propylaniline (212 mg). LCMS retention time=1.34 minutes (LC method 1); MS (m+1)=184.1. $^1$H NMR (400 MHz, DMSO-$d_6$) δ 0.92 (t, J=7.3 Hz, 3H), 1.34-1.48 (m, 2H), 2.16 (s, 3H), 2.48-2.52 (m, 2H), 5.03 (s, 2H), 6.32 (d, J=1.8 Hz, 1H), 6.43 (d, J=2.2 Hz, 1H).

Intermediate 11

3-(prop-1-en-2-yl)-4-(trifluoromethoxy)aniline

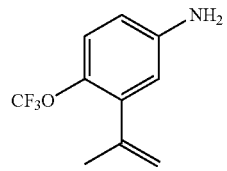

Step 1: Synthesis of 4-nitro-2-(prop-1-en-2-yl)-1-(trifluoromethoxy)benzene

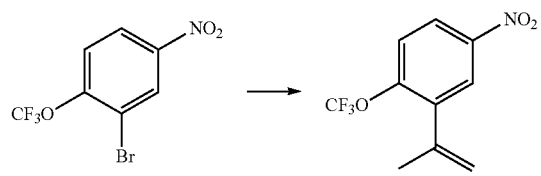

2-bromo-4-nitro-1-(trifluoromethoxy)benzene (0.56 g, 1.97 mmol), 4,4,5,5-tetramethyl-2-(prop-1-en-2-yl)-1,3,2-dioxaborolane (0.50 g, 2.96 mmol), PdCl2(dppf).CH2Cl2 adduct (0.16 g, 0.20 mmol), and $Na_2CO_3$ (0.63 g, 5.92 mmol) were combined in a 20 mL microwave vial and DME (15.78 mL) and Water (3.94 mL) were added. The mixture was stirred at RT for 6 s and then heated to 120° C. in the microwave for 30 min. The crude mixture was diluted with EtOAc and Water. The organic layer was washed with water and brine, dried over $Na_2SO_4$, filtered and concentrated under reduced pressure. The crude was diluted with DCM and silica gel was added. The mixture was concentrated under reduced pressure to dry-load material for purification. The crude was purified via silica gel FCC, 100% Heptane-100% EtOAc to give 4-nitro-2-(prop-1-en-2-yl)-1-(trifluoromethoxy)benzene (456 mg). $^1$H NMR (400 MHz, DMSO-$d_6$) δ 2.08-2.13 (m, 3H), 5.21 (p, J=1.0 Hz, 1H), 5.43 (p, J=1.5 Hz, 1H), 7.68 (dq, J=9.0, 1.6 Hz, 1H), 8.21 (d, J=2.9 Hz, 1H), 8.28 (dd, J=9.0, 2.9 Hz, 1H).

Step 2: Synthesis of 3-(prop-1-en-2-yl)-4-(trifluoromethoxy)aniline

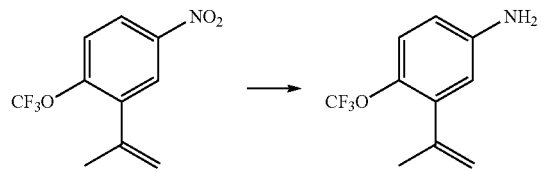

To a solution of 4-nitro-2-(prop-1-en-2-yl)-1-(trifluoromethoxy)benzene (275 mg, 1.11 mmol) in toluene (9.85 mL) was added iron (1.24 g, 22.25 mmol) and concentrated HCl (3.38 µL, 0.11 mmol) (3 drops). The mixture was stirred vigorously under reflux and water (0.20 mL, 11.13 mmol) was added and the rxn was stirred at reflux for 2 hr. The crude mixture was filtered through celite and concentrated under reduced pressure. The crude was diluted with EtOAc and dried with $Na_2SO_4$, filtered and concentrated under reduced pressure to give 3-(prop-1-en-2-yl)-4-(trifluoromethoxy) aniline (230 mg). LCMS retention time=1.46 minutes (LC method 5); MS (m+1)=218.2.

Intermediate 12

5-fluoro-6-methylbenzofuran-2-carbonitrile

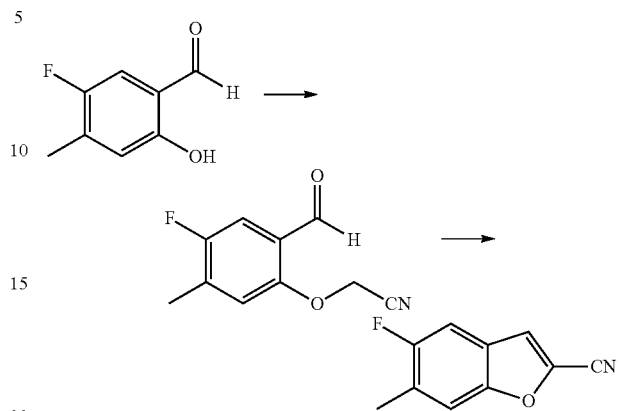

To a solution of 5-fluoro-2-hydroxy-4-methylbenzaldehyde (500 mg, 3.24 mmol) in 10.5 ml of acetonitrile in a microwave vial was added $Cs_2CO_3$ (1.268 g, 3.885 mmol), followed by 2-bromoacetonitrile (271 ul, 3.885 mmol). The reaction mixture was stirred at room temperature for 1 hr. LC/MS showed that all the starting material was converted to ring opened intermediate, 2-(4-fluoro-2-formyl-5-methylphenoxy)acetonitrile. LCMS retention time=1.19 minutes (RxNMON-Acidic:ZQ12); MS (m+1)=194.1. Then, the reaction vial was sealed, and the mixture was heated to 150° C. on microwave for 20 min. This reaction was repeated 20 times. The combined reaction mixture was filtered, washed with acetonitrile, the filtrate was concentrated. The residue was purified by silica gel flash chromatography (100% heptane-10% ethyl acetate/heptane) to give 5-fluoro-6-methylbenzofuran-2-carbonitrile (5.55 g). $^1$H NMR (400 MHz, DMSO-$d_6$) δ 2.38 (d, J=2.2 Hz, 3H) 7.62 (d, J=9.3 Hz, 1H) 7.72 (d, J=6.0 Hz, 1H) 8.04 (d, J=1.0 Hz, 1H).

Intermediate 13

Synthesis of 6-fluoro-5-methyl benzofuran-2-carbonitrile

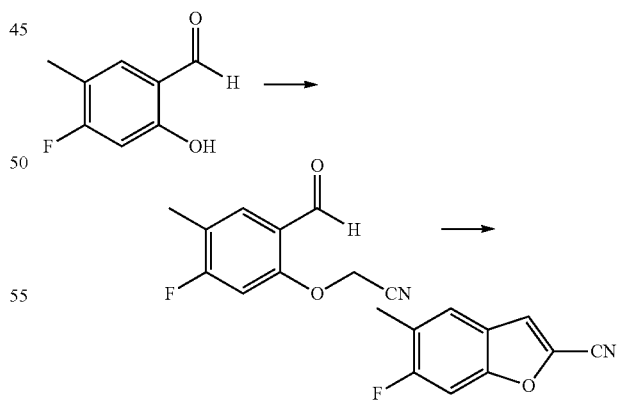

6-Fluoro-5-methylbenzofuran-2-carbonitrile was prepared as described in Intermediate 12 starting from 4-fluoro-2-hydroxy-5-methylbenzaldehyde, $^1$H NMR (400 MHz, DMSO-$d_6$) δ 2.31-2.36 (m, 3H) 7.67-7.77 (m, 2H) 8.07 (d, J=1.0 Hz, 1H).

Compounds of the present invention are made with the preceding procedures and intermediates and are exemplified below in Table 1.

TABLE 1

| Example | Compound | Characterization | LCMS RT (min) | LCMS Method |
|---|---|---|---|---|
| 1 | | MS (m + 1) = 419.3; $^1$H NMR (400 MHz, DMSO-$d_6$) δ 3.67 (s, 3H), 4.30-4.40 (m, 2H), 6.51 (dd, J = 13.6, 2.7 Hz, 1H), 6.59-6.67 (m, 2H), 7.11 (d, J = 0.9 Hz, 1H), 7.25 (dd, J = 8.2, 1.3 Hz, 1H), 7.56-7.63 (m, 2H). | 1.23 | 1 |
| 2 | | MS (m + 1) = 432.4; $^1$H NMR (400 MHz, DMSO-$d_6$) δ 1.26 (t, J = 7.0 Hz, 3H), 3.88 (q, J = 7.0 Hz, 2H), 4.35 (d, J = 5.2 Hz, 2H), 6.50 (dd, J = 13.4, 2.6 Hz, 1H), 6.61 (t, J = 6.0 Hz, 1H), 6.66 (dd, J = 2.7, 1.6 Hz, 1H), 7.15 (d, J = 0.9 Hz, 1H), 7.25 (dd, J = 7.9, 1.4 Hz, 1H), 7.61 (d, J = 7.9 Hz, 2H). | 1.31 | 1 |
| 3 | | MS (m + 1) = 439.1; $^1$H NMR (400 MHz, DMSO-$d_6$) δ 4.45 (d, J = 5.8 Hz, 2H), 6.69 (dd, J = 8.8, 2.3 Hz, 1H), 7.02 (d, J = 2.2 Hz, 1H), 7.08 (d, J = 0.9 Hz, 1H), 7.24 (dd, J = 8.0, 1.3 Hz, 1H), 7.28 (t, J = 11.2, 5.8 Hz, 1H), 7.44 (d, J = 8.7 Hz, 1H), 7.57-7.62 (m, 2H). | 1.32 | 1 |
| 4 | | MS (m + 1) = 516.1; $^1$H NMR (400 MHz, DMSO-$d_6$) δ 4.41 (d, J = 5.9 Hz, 2H), 6.89 (t, J = 73.2 Hz, 1H), 7.16 (d, J =1.0 Hz, 1H), 7.26 (dd, J = 79.1, 1.4 Hz, 1H), 7.58-7.65 (m, 2H). | 1.31 | 1 |
| 5 | | MS (m + 1) = 440.2; $^1$H NMR (400 MHz, DMSO-$d_6$) δ 1.30 (t, J = 7.0 Hz, 3H), 3.88 (q, J = 7.1 Hz, 2H), 4.44 (d, J = 4.9 Hz, 2H), 6.61-6.70 (m, 3H), 7.65 (s, 1H), 7.74 (s, 1H), 7.96 (s, 1H). | 1.46 | 1 |
| 6 | | MS (m + 1) = 478.2; $^1$H NMR (400 MHz, DMSO-$d_6$) δ 4.52 (d, J = 5.1 Hz, 2H), 6.84-6.91 (m, 1H), 7.02-7.11 (m, 2H), 7.33 (d, J = 9.1 Hz, 1H), 7.67 (s, 1H), 7.76 (s, 1H), 7.98 (s, 1H). | 1.48 | 1 |

TABLE 1-continued

| Example | Compound | Characterization | LCMS RT (min) | LCMS Method |
|---|---|---|---|---|
| 7 | [structure: 5-chloro-6-{[(3-fluoro-4-(trifluoromethylthio)phenyl)amino]methyl}benzofuran-2-yl tetrazole] | MS (m + 1) = 444.0; $^1$H NMR (400 MHz, DMSO-d$_6$) δ 4.52 (d, J = 5.8 Hz, 2H), 6.54-6.64 (m, 2H), 7.35-7.44 (m, 2H), 7.65 (s, 1H), 7.75 (s, 1H), 7.97 (s, 1H). | 1.71 | 4 |
| 8 | [structure: 5-chloro-6-{[(3-chloro-4-(trifluoromethoxy)phenyl)amino]methyl}benzofuran-2-yl tetrazole] | MS (m + 1) = 458.2; $^1$H NMR (400 MHz, DMSO-d$_6$) δ 4.44 (s, 2H), 4.61 (q, J = 8.9 Hz, 2H), 6.42 (br. s., 1 H), 6.54 (dd, J = 8.9, 2.8 Hz, 1H), 6.71 (d, J = 2.8 Hz, 1H), 7.04 (d, J = 8.9 Hz, 1H), 7.66 (d, J = 0.9 Hz, 1H), 7.71 (s, 1H), 7.95 (s, 1H). | 1.38 | 1 |
| 9 | [structure: 5-chloro-6-{[(4-fluoro-3-(trifluoromethoxy)phenyl)amino]methyl}benzofuran-2-yl tetrazole] | MS (m + 1) = 428.1; $^1$H NMR (400 MHz, DMSO-d$_6$) δ 4.45 (br. s., 2H), 6.59 (dt, J = 9.1, 3.3 Hz, 1H), 6.62-6.74 (m, 2H), 7.19 (dd, J = 10.3, 9.1 Hz, 1H), 7.67 (d, J = 0.9 Hz, 1H), 7.74 (s, 1 H), 7.96 (s, 1H). | 1.53 | 3 |
| 10 | [structure: 5-chloro-6-{[(4-ethoxy-3-(trifluoromethyl)phenyl)amino]methyl}benzofuran-2-yl tetrazole] | MS (m + 1) = 438.1; $^1$H NMR (400 MHz, DMSO-d$_6$) δ 1.25 (t, J = 7.0 Hz, 3H), 3.98 (q, J = 7.0 Hz, 2H), 4.45 (s, 2H), 6.77 (dd, J = 8.9, 2.7 Hz, 1H), 6.89 (d, J = 2.9 Hz, 1H), 7.02 (d, J = 8.9 Hz, 1H), 7.66 (d, J = 0.9 Hz, 1H), 7.72 (s, 1H), 7.96 (s, 1H). | 1.10 | 5 |
| 11 | [structure: 6-{[(3-isopropenyl-4-(trifluoromethoxy)phenyl)amino]methyl}benzofuran-2-yl tetrazole] | MS (m + 1) = 416.3; $^1$H NMR (400 MHz, DMSO-d$_6$) δ 1.98 (dd, J = 1.5, 0.9 Hz, 3H), 4.38 (d, J = 5.4 Hz, 2H), 4.97 (dd, J = 2.0, 1.0 Hz, 1H), 5.17 (q, J = 1.7 Hz, 1H), 6.52-6.60 (m, 3H), 6.98-7.04 (m, 1H), 7.10 (d, J = 0.9 Hz, 1H), 7.27 (dd, J = 7.9, 1.4 Hz, 1H), 7.59 (d, J = 8.21 Hz, 2H). | 1.41 | 1 |
| 12 | [structure: 5-chloro-6-{[(3-chloro-4-propylphenyl)amino]methyl}benzofuran-2-yl tetrazole] | MS (m + 1) = 402.2; $^1$H NMR (400 MHz, DMSO-d$_6$) δ 0.87 (t, J = 7.3 Hz, 3H), 1.49 (sxt, J = 7.4 Hz, 2H), 2.47 (t, J = 7.9 Hz, 2H), 4.44 (s, 2H), 6.51 (dd, J = 8.3, 2.5 Hz, 2H), 6.62 (d, J = 2.3 Hz, 1H), 7.00 (d, J = 8.3 Hz, 1H), 7.66 (s, 1H), 7.69 (s, 1H), 7.95 (s, 1H). | 1.55 | 1 |

TABLE 1-continued

| Example | Compound | Characterization | LCMS RT (min) | LCMS Method |
|---|---|---|---|---|
| 13 | 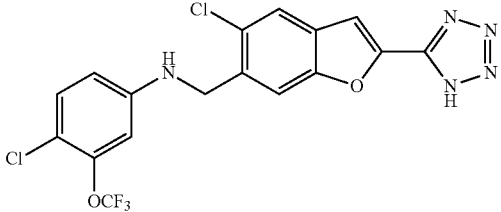 [SMILES: FC(F)(F)Oc1cc(NCc2cc3oc(-c4nnn[nH]4)cc3cc2Cl)ccc1Cl] | MS (m + 1) = 444.2; $^1$H NMR (400 MHz, DMSO-d$_6$) δ 4.48 (d, J = 3.3 Hz, 2H), 6.62 (dd, J = 8.7, 2.6 Hz, 1H), 6.75 (dd, J = 2.6, 1.3 Hz, 1H), 6.95 (br. s., 1H), 7.31 (d, J = 8.8 Hz, 1H), 7.68 (d, J = 0.9 Hz, 1H), 7.73 (s, 1H), 7.97 (s, 1H). | 1.45 | 1 |
| 14 | 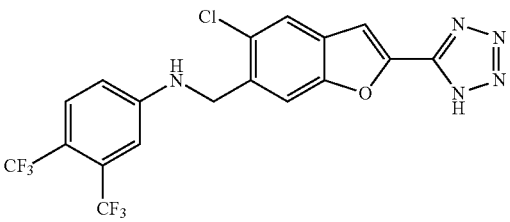 [SMILES: FC(F)(F)c1ccc(NCc2cc3oc(-c4nnn[nH]4)cc3cc2Cl)cc1C(F)(F)F] | MS (m + 1) = 462.1; $^1$H NMR (400 MHz, DMSO-d$_6$) δ 4.59 (d, J = 5.6 Hz, 2H), 6.88 (d, J = 8.7 Hz, 1H), 7.23 (d, J = 1.8 Hz, 1H), 7.55 (t, J = 5.8 Hz, 1H), 7.63-7.68 (m, 2H), 7.77 (s, 1H), 7.99 (s, 1H). | 1.71 | 3 |
| 15 | 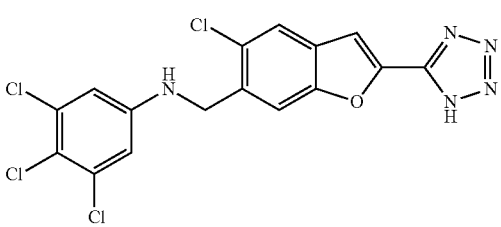 [SMILES: Clc1cc2cc(-c3nnn[nH]3)oc2cc1CNc1cc(Cl)c(Cl)c(Cl)c1] | MS (m + 1) = 430.0; $^1$H NMR (400 MHz, DMSO-d$_6$) δ 4.49 (d, J = 5.3 Hz, 2H), 6.86 (s, 2H), 7.00 (t, J = 5.8 Hz, 1H), 7.68 (d, J = 0.9 Hz, 1H), 7.76 (s, 1H), 7.98 (s, 1H). | 1.76 | 3 |
| 16 | 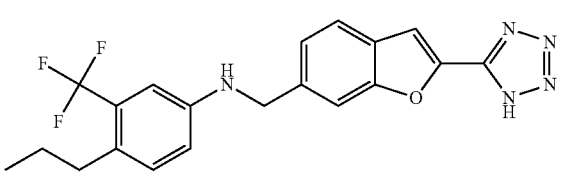 [SMILES: CCCc1ccc(NCc2ccc3cc(-c4nnn[nH]4)oc3c2)cc1C(F)(F)F] | MS (m + 1) = 402.1; $^1$H NMR (400 MHz, DMSO-d$_6$) δ 0.88 (t, J = 7.3 Hz, 3H), 1.43-1.56 (m, 2H), 2.47-2.49 (m, 2H), 4.40 (d, J = 5.2 Hz, 2H), 6.59 (t, J = 6.1 Hz, 1H), 6.79 (dd, J = 8.4, 2.5 Hz, 1H), 6.90 (d, J = 2.5 Hz, 1H), 7.08 (d, J = 0.9 Hz, 1H), 7.11 (d, J = 8.5 Hz, 1H), 7.26 (dd, J = 8.0, 1.4 Hz, 1H), 7.55-7.62 (m, 2H). | 1.38 | 1 |
| 17 | 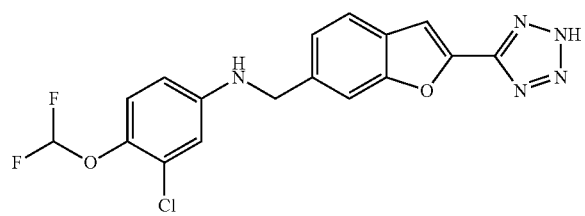 [SMILES: FC(F)Oc1ccc(NCc2ccc3cc(-c4nn[nH]n4)oc3c2)cc1Cl] | MS (m + 1) = 392.3; $^1$H NMR (400 MHz, DMSO-d$_6$) δ 4.39 (dd, J = 4.2, 1.8 Hz, 2H), 6.60 (dd, J = 8.9, 2.8 Hz, 1H), 6.63-6.71 (m, 1H), 6.74 (d, J = 2.7 Hz, 1H), 6.94 (t, J = 74.3 Hz, 1H), 7.05 (dt, J = 9.0, 0.9 Hz, 1H), 7.14 (d, J = 0.9 Hz, 1H), 7.26 (dd, J = 8.1, 1.3 Hz, 1H), 7.58-7.63 (m, 2H). | 1.24 | 1 |
| 18 | 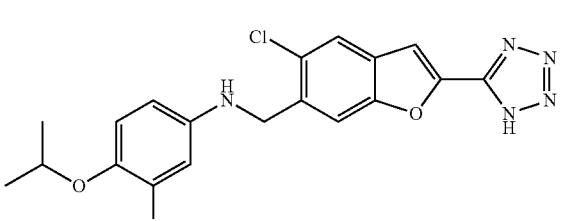 | MS (m + 1) = 452.3; $^1$H NMR (400 MHz, DMSO-d$_6$) δ 1.20 (d, J = 6.1 Hz, 6H), 4.45 (s, 2H), 4.50 (quin, J = 6.1 Hz, 1H), 6.37 (br. s., 1 H), 6.77 (dd, J = 8.9, 2.7 Hz, 1H), 6.87 (d, J = 2.8 Hz, 1H), 7.05 (d, J = 8.9 Hz, 1H), 7.65 (s, 1H), 7.73 (s, 1H), 7.95 (s, 1H). | 1.45 | 1 |

TABLE 1-continued

| Example | Compound | Characterization | LCMS RT (min) | LCMS Method |
|---|---|---|---|---|
| 19 | 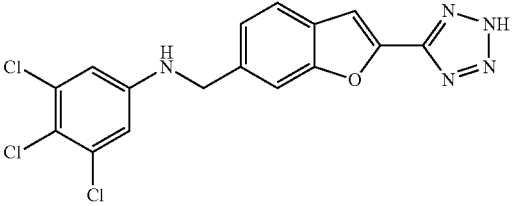 [SMILES: Clc1cc(NCc2ccc3cc(-c4nn[nH]n4)oc3c2)cc(Cl)c1Cl] | MS (m + 1) = 394.3; ¹H NMR (400 MHz, DMSO-d₆) δ 4.41 (d, J = 5.7 Hz, 2H), 6.81-6.87 (m, 2H), 7.00 (dt, J = 6.3, 3.1 Hz, 1H), 7.11 (s, 2H), 7.24 (d, J = 8.0 Hz, 1H), 7.57-7.63 (m, 2H). | 1.41 | 1 |
| 20 | 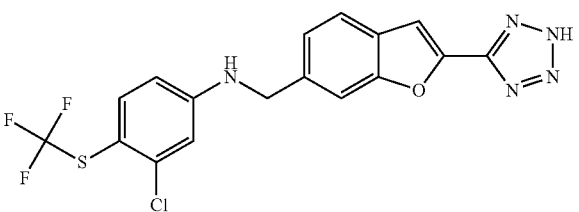 [SMILES: FC(F)(F)Sc1ccc(NCc2ccc3cc(-c4nn[nH]n4)oc3c2)cc1Cl] | MS (m + 1) = 426.0; ¹H NMR (400 MHz, DMSO-d₆) δ 4.47 (d, J = 5.8 Hz, 2H), 6.68 (dd, J = 8.7, 2.6 Hz, 1H), 6.89 (d, J = 2.5 Hz, 1H), 7.27-7.32 (m, 2H), 7.38 (t, J = 5.9 Hz, 1H), 7.48 (d, J = 8.7 Hz, 1H), 7.64 (s, 1H), 7.67 (d, J = 8.0 Hz, 1H). | 1.32 | 1 |
| 21 | 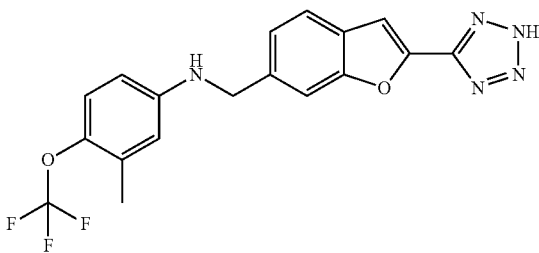 [SMILES: Cc1cc(NCc2ccc3cc(-c4nn[nH]n4)oc3c2)ccc1OC(F)(F)F] | MS (m + 1) = 390.4; ¹H NMR (400 MHz, DMSO-d₆) δ 2.13 (s, 3H), 4.30-4.44 (m, 2H), 6.40-6.52 (m, 2H), 6.56 (d, J = 2.8 Hz, 1H), 6.96 (d, J = 8.6 Hz, 1H), 7.08 (s, 1H), 7.25 (d, J = 8.3 Hz, 1H), 7.55-7.62 (m, 2H). | 1.34 | 1 |
| 22 | 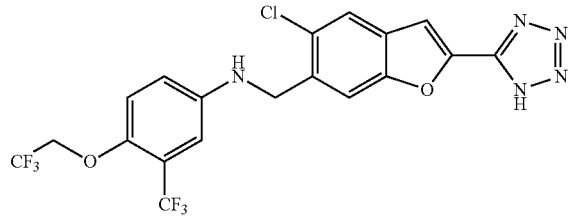 [SMILES: FC(F)(F)COc1ccc(NCc2cc3oc(-c4nnn[nH]4)cc3cc2Cl)cc1C(F)(F)F] | MS (m + 1) = 492.2; ¹H NMR (400 MHz, DMSO-d₆) δ 4.48 (br. s., 2H), 4.69 (q, J = 8.9 Hz, 2H), 6.55 (br. s., 1H), 6.80 (dd, J = 8.9, 2.8 Hz, 1H), 6.93 (d, J = 2.8 Hz, 1H), 7.14 (d, J = 9.1 Hz, 1H), 7.65 (s, 1H), 7.73 (s, 1H), 7.96 (s, 1H). | 1.40 | 1 |
| 23 | 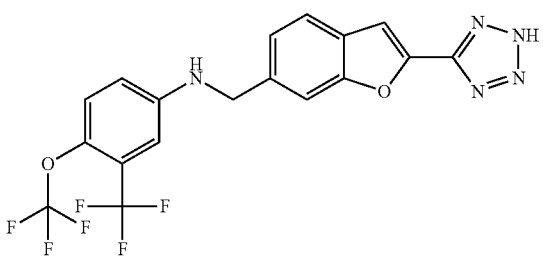 [SMILES: FC(F)(F)Oc1ccc(NCc2ccc3cc(-c4nn[nH]n4)oc3c2)cc1C(F)(F)F] | MS (m + 1) = 444.4; ¹H NMR (400 MHz, DMSO-d₆) δ 4.45 (d, J = 5.6 Hz, 2H), 6.90 (dd, J = 9.1, 2.9 Hz, 1H), 7.01 (d, J = 2.9 Hz, 1H), 7.05 (t, J = 5.9 Hz, 1H), 7.17 (d, J = 0.9 Hz, 1H), 7.26-7.33 (m, 2H), 7.60-7.65 (m, 2H). | 1.40 | 1 |
| 24 | 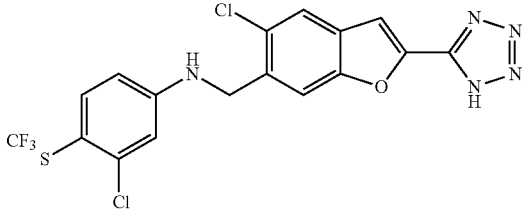 [SMILES: "CF3" ; Sc1ccc(NCc2cc3oc(-c4nnn[nH]4)cc3cc2Cl)cc1Cl] | MS (m + 1) = 460.1; ¹H NMR (400 MHz, DMSO-d₆) δ 4.53 (d, J = 5.8 Hz, 2H), 6.68 (dd, J = 8.7, 2.5 Hz, 1H), 6.91 (d, J = 2.6 Hz, 1H), 7.34 (t, J = 5.8 Hz, 1H), 7.52 (d, J = 8.7 Hz, 1H), 7.66 (s, 1H), 7.75 (s, 1H), 7.98 (s, 1H). | 1.76 | 4 |

TABLE 1-continued

| Example | Compound | Characterization | LCMS RT (min) | LCMS Method |
|---|---|---|---|---|
| 25 | | MS (m + 1) = 460.2; $^1$H NMR (400 MHz, DMSO-$d_6$) δ 4.50 (br. s., 2H), 6.79-6.91 (m, 2H), 6.99 (d, J = 2.9 Hz, 1H), 7.14 (d, J = 73.8 Hz, 1H), 7.18 (d, J = 8.9 Hz, 1H), 7.67 (d, J = 0.7 Hz, 1H), 7.73 (s, 1H), 7.97 (s, 1H). | 1.36 | 1 |
| 26 | | MS (m + 1) = 406.4; $^1$H NMR (400 MHz, DMSO-$d_6$) δ 2.34 (s, 3H), 4.43 (d, J = 5.5 Hz, 2H), 6.83 (dd, J = 8.6, 2.6 Hz, 1H), 6.90 (t, J = 6.0 Hz, 1H), 7.00 (d, J = 2.6 Hz, 1H), 7.08 (d, J = 0.9 Hz, 1H), 7.25 (dd, J = 7.9, 1.4 Hz, 1H), 7.36 (d, J = 8.6 Hz, 1H), 7.56-7.62 (m, 2H). | 1.30 | 1 |
| 27 | | MS (m + 1) = 458.4; $^1$H NMR (400 MHz, DMSO-$d_6$) δ 4.40 (d, J = 4.8 Hz, 2H), 4.66 (q, J = 8.9 Hz, 2H), 6.49 (t, J = 5.9 Hz, 1H), 6.83 (dd, J = 9.0, 2.9 Hz, 1H), 6.91 (d, J = 2.8 Hz, 1H), 7.08-7.14 (m, 2H), 7.26 (dd, J = 7.9, 1.4 Hz, 1H), 7.56-7.61 (m, 2H). | 1.32 | 1 |
| 28 | | MS (m + 1) = 338.2; $^1$H NMR (400 MHz, DMSO-$d_6$) δ 2.36 (s, 3H), 4.37 (d, J = 5.5 Hz, 2H), 6.34-6.43 (m, 3H), 6.51 (t, J = 2.0 Hz, 1H), 6.97 (t, J = 7.9 Hz, 1H), 7.07 (d, J = 21.0 Hz, 1H), 7.25 (dd, J = 8.0, 1.4 Hz, 1H), 7.55-7.62 (m, 2H). | 1.14 | 1 |
| 29 | | MS (m + 1) = 449.2; $^1$H NMR (400 MHz, DMSO-$d_6$) δ 4.48 (br. s., 2H), 5.13 (s, 2H), 6.61 (br. s., 1H), 6.84 (dd, J = 9.1, 2.8 Hz, 1H), 6.95 (d, J = 2.9 Hz, 1H), 7.20 (d, J = 8.9 Hz, 1H), 7.65 (d, J = 0.7 Hz, 1H), 7.74 (s, 1H), 7.96 (s, 1H). | 1.24 | 1 |
| 30 | | MS (m + 1) = 388.1; $^1$H NMR (400 MHz, DMSO-$d_6$) d ppm 4.61 (d, J = 5.87 Hz, 2H) 6.80 (d, J = 9.29 Hz, 2H) 7.38 (dd, J = 8.07, 1.22 Hz, 1H) 7.71 (s, 2H) 7.79 (dd, J = 7.95, 2.32 Hz, 3H) 8.04 (t, J = 6.11 Hz, 1H). | 1.17 | 1 |

TABLE 1-continued

| Example | Compound | Characterization | LCMS RT (min) | LCMS Method |
|---|---|---|---|---|
| 31 | | MS (m + 1) = 436.1; $^1$H NMR (400 MHz, DMSO-$d_6$) δ 0.89 (t, J = 7.3 Hz, 3H), 1.50 (sxt, J = 7.5 Hz, 2H), 2.53 (br. s., 2H), 4.48 (s, 2 H), 6.67 (br. s., 1H), 6.75 (dd, J = 8.5, 2.3 Hz, 1H), 7.15 (d, J = 8.5 Hz, 1H), 7.67 (d, J = 0.9 Hz, 1H), 7.72 (s, 1H), 7.96 (s, 1H). | 1.59 | 3 |
| 32 | | MS (m + 1) = 428.1; $^1$H NMR (400 MHz, DMSO-$d_6$) δ 4.48 (d, J = 5.3 Hz, 2H), 6.62 (dd, J = 9.0, 2.8 Hz, 1 H), 6.80 (d, J = 2.8 Hz, 1 H), 6.89 (t, J = 6.0 Hz, 1H), 7.24 (dd, J = 9.1, 2.1 Hz, 1 H), 7.65 (s, 1H), 7.73 (s, 1 H), 7.97 (s, 1H). | 1.66 | 4 |
| 33 | | MS (m + 1) = 326.1; $^1$H NMR (400 MHz, DMSO-$d_6$) δ 4.43 (s, 2H), 6.61 (d, J = 8.9 Hz, 2H), 7.06 (d, J = 8.9 Hz, 2H), 7.38 (dd, J = 8.1, 1.3 Hz, 1H), 7.66-7.71 (m, 2H), 7.76 (d, J = 8.0 Hz, 1H). | 1.16 | 1 |
| 34 | | MS (m + 1) = 448.2; $^1$H NMR (400 MHz, DMSO-$d_6$) δ 0.87 (t, J = 7.3 Hz, 3H), 1.48 (sxt, J = 7.5 Hz, 2H), 2.47 (m, 2H), 4.43 (br. s., 2 H), 6.49 (br. s., 1H), 6.55 (dd, J = 8.4, 2.4 Hz, 1H), 6.81 (d, J = 2.5 Hz, 1H), 7.00 (d, J = 8.4 Hz, 1H), 7.65 (s, 1H), 7.69 (s, 1H), 7.95 (s, 1H). | 1.57 | 1 |
| 35 | | MS (m + 1) = 407.3; $^1$H NMR (400 MHz, DMSO-$d_6$) δ 4.36 (d, J = 5.9 Hz, 2H), 6.63 (ddd, J = 13.2, 6.3, 2.8 Hz, 1H), 6.67-6.75 (m, 2H), 7.07 (d, J = 0.9 Hz, 1H), 7.24 (dd, J = 8.1, 1.3 Hz, 1H), 7.56-7.62 (m, 2H). | 1.29 | 1 |
| 36 | | MS (m + 1) = 489.9; $^1$H NMR (400 MHz, DMSO-$d_6$) δ 4.47 (d, J = 3.9 Hz, 2H), 6.65 (dd, J = 9.0, 2.8 Hz, 1 H), 6.82-6.91 (m, 1H), 6.95 (d, J = 2.8 Hz, 1H), 7.22 (dd, J = 9.0, 1.3 Hz, 1 H), 7.67 (d, J = 0.8 Hz, 1 H), 7.73 (s, 1H), 7.97 (s, 1 H). | 1.54 | 3 |

TABLE 1-continued

| Example | Compound | Characterization | LCMS RT (min) | LCMS Method |
|---|---|---|---|---|
| 37 | | MS (m + 1) = 454.2; ¹H NMR (400 MHz, DMSO-d₆) δ 4.39 (d, J = 5.8 Hz, 2H), 6.66 (d, J = 9.0, 2.8 Hz, 1H), 6.83 (t, J = 5.9 Hz, 1H), 6.93 (d, J = 2.7 Hz, 1H), 7.08 (d, J = 0.9 Hz, 1H), 7.17 (dd, J = 9.2, 1.1 Hz, 1H), 7.25 (dd, J = 8.0, 1.3 Hz, 1H), 7.54-7.64 (m, 2H). | 1.35 | 1 |
| 38 | | MS (m + 1) = 512.0; ¹H NMR (400 MHz, DMSO-d₆) δ 4.51 (s, 2H), 6.88 (dd, J = 9.1, 2.8 Hz, 1H), 7.02 (d, J = 2.9 Hz, 1H), 7.30 (d, J = 8.9 Hz, 1H), 7.46 (dd, J = 8.2, 1.0 Hz, 1H), 7.74 (d, J = 7.5 Hz, 1H), 7.79 (s, 1 H). | 1.57 | 3 |
| 39 | | MS (m + 1) = 439.2; ¹H NMR (400 MHz, DMSO-d₆) δ 4.42 (d, J = 5.8 Hz, 2H), 6.76 (dd, J = 8.8, 2.8 Hz, 1H), 6.99 (t, J = 5.9 Hz, 1H), 7.06-7.07 (m, 2H), 7.24 (dd, J = 7.9, 1.4 Hz, 1H), 7.45 (d, J = 8.8 Hz, 1H), 7.56-7.62 (m, 2H). | 1.35 | 1 |
| 40 | | MS (m + 1) = 372.2; ¹H NMR (400 MHz, DMSO-d₆) δ 4.43 (s, 2H), 6.36 (dd, J = 8.8, 2.3 Hz, 1H), 6.64 (d, J = 2.3 Hz, 1H), 7.06 (d, J = 8.7, Hz, 1H), 7.40 (dd, J = 8.0, 1.3 Hz, 1H), 7.69-7.73 (m, 2H), 7.77 (d, J = 8.1 Hz, 1H). | 1.19 | 1 |
| 41 | | MS (m + 1) = 460.4; ¹H NMR (400 MHz, DMSO-d₆) δ 4.40 (d, J = 5.7 Hz, 2H), 6.65 (dd, J = 9.1, 2.7 Hz, 1H), 6.73 (dq, J = 2.8, 1.4 Hz, 1H), 6.97 (t, J = 5.8 Hz, 1H), 7.06 (d, J = 0.9 Hz, 1H), 7.22-7.28 (m, 2H), 7.56-7.62 (m, 2H). | 1.41 | 1 |

TABLE 1-continued

| Example | Compound | Characterization | LCMS RT (min) | LCMS Method |
|---|---|---|---|---|
| 42 |  | MS (m + 1) = 414.1; ¹H NMR (400 MHz, DMSO-d₆) δ 0.86 (t, J = 7.3 Hz, 3H), 1.46 (sxt, J = 7.4 Hz, 2H), 2.43-2.47 (m, 2H), 4.41 (s, 2H), 6.51 (br. s, 1H), 6.56 (dd, J = 8.3, 2.3 Hz, 1H), 6.79 (d, J = 2.4 Hz, 1H), 6.97 (d, J = 8.3 Hz, 1H), 7.38 (dd, J = 8.1, 1.3 Hz, 1H), 7.68 (d, J = 4.4 Hz, 2H), 7.76 (d, J = 7.8 Hz, 1H). | 1.67 | 4 |
| 43 | 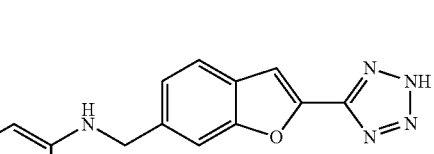 | MS (m + 1) = 394.4; ¹H NMR (400 MHz, DMSO-d₆) δ 4.40 (d, J = 5.5 Hz, 2H), 6.48 (ddd, J = 9.1, 2.7, 1.1 Hz, 1H), 6.58 (dd, J =13.6, 2.7 Hz, 1H), 6.90 (t, J = 5.9 Hz, 1H), 7.17 (td, J = 9.1, 1.2 Hz, 1H), 7.21 (d, J = 0.9 Hz, 1H), 7.28 (dd, J = 8.1, 1.3 Hz, 1H), 7.59-7.67 (m, 2H). | 1.32 | 1 |
| 44 |  | MS (m + 1) = 424.4; ¹H NMR (400 MHz, DMSO-d₆) δ 4.36 (s, 2H), 4.58 (q, J = 9.0 Hz, 2H), 6.37 (s, 1H), 6.56 (dd, J = 8.9, 2.8 Hz, 1H), 6.70 (d, J = 2.7 Hz, 1H), 7.00 (d, J = 8.9 Hz, 1H), 7.13 (d, J = 0.9 Hz, 1H), 7.26 (dd, J = 8.0, 1.3 Hz, 1H), 7.57-7.62 (m, 2H). | 1.29 | 1 |
| 45 | 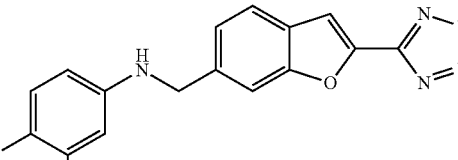 | MS (m + 1) = 410.2; ¹H NMR (400 MHz, DMSO-d₆) δ 4.83 (s, 2H), 7.20 (s, 2H), 7.23 (dd, J = 8.01, 1.3 Hz, 1H), 7.36 (s, 1H), 7.57 (s, 1H), 7.68 (d, J = 8.1 Hz, 1H). | 1.35 | 1 |
| 46 | 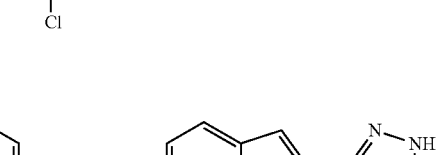 | MS (m + 1) = 410.3; ¹H NMR (400 MHz, DMSO-d₆) δ 4.42 (d, J = 5.2 Hz, 2H), 6.63 (dd, J = 9.0, 2.8 Hz, 1H), 6.78 (d, J = 2.8 Hz, 1H), 6.89 (t, J = 6.0 Hz, 1H), 7.20 (dd, J = 9.0, 1.3 Hz, 1H), 7.27-7.33 (m, 2H), 7.64 (s, 1H), 7.66 (d, J = 8.0 Hz, 1H). | 1.38 | 1 |
| 47 | 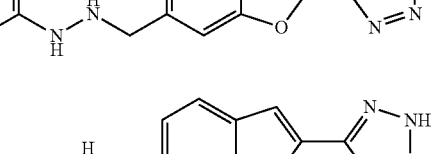 | MS (m + 1) = 524.3; ¹H NMR (400 MHz, DMSO-d₆) δ 4.50 (s, 2H), 6.62-6.68 (m, 1H), 6.92 (d, J = 2.8 Hz, 1H), 7.18 (dd, J = 9.0, 1.3 Hz, 1H), 7.50-7.56 (m, 1H), 7.79-7.85 (m, 2H). | 1.47 | 1 |

TABLE 1-continued

| Example | Compound | Characterization | LCMS RT (min) | LCMS Method |
|---|---|---|---|---|
| 48 | | MS (m + 1) = 455.3; ¹H NMR (400 MHz, DMSO-d$_6$) δ 4.40 (d, J = 5.5 Hz, 2H), 6.59 (dd, J = 8.9, 2.7 Hz, 1H), 6.72 (dq, J = 2.8, 1.5 Hz, 1H), 6.94 (t, J = 5.9 Hz, 1H), 7.15 (d, J = 0.9 Hz, 1H), 7.26 (dd, J = 8.0, 1.3 Hz, 1H), 7.37 (d, J = 8.8 Hz, 1H), 7.58-7.63 (m, 2H). | 1.38 | 1 |
| 49 | | MS (m + 1) = 472.3; ¹H NMR (400 MHz, DMSO-d$_6$) δ 1.29 (t, J = 7.0 Hz, 3H), 3.87 (q, J = 7.0 Hz, 2H), 4.41 (d, J = 5.6 Hz, 2H), 6.65-6.71 (m, 3H), 7.41 (dd, J = 8.1, 1.2 Hz, 1H), 7.69 (d, J = 7.5 Hz, 1H), 7.74 (s, 1H). | 1.47 | 1 |
| 50 | | MS (m + 1) = 428.2; ¹H NMR (400 MHz, DMSO-d$_6$) δ 4.47 (d, J = 5.3 Hz, 2H), 6.47 (dt, J = 9.0, 1.4 Hz, 1H), 6.60 (dd, J = 13.5, 2.7 Hz, 1H), 6.91 (t, J = 5.7 Hz, 1H), 7.18-7.25 (m, 1H), 7.65 (s, 1H), 7.73 (s, 1H), 7.96 (s, 1H). | 1.41 | 1 |
| 51 | | MS (m + 1) = 416.0; ¹H NMR (400 MHz, DMSO-d$_6$) δ 0.88 (t, J = 7.3 Hz, 3H), 1.48 (sxt, J = 7.5 Hz, 2H), 2.47-2.49 (m, 2H), 2.59 (s, 3H), 4.44 (s, 2H), 6.60-6.72 (m, 1H), 6.77 (dd, J = 8.4, 2.2 Hz, 1H), 6.88 (d, J = 2.3 Hz, 1H), 7.10 (d, J = 8.4 Hz, 1H), 7.36 (d, J = 8.1 Hz, 1H), 7.60 (s, 1H), 7.68 (d, J = 8.1 Hz, 1H). | 1.22 | 5 |
| 52 | | MS (m + 1) = 428.4; ¹H NMR (400 MHz, DMSO-d$_6$) δ 4.52 (d, J = 5.8 Hz, 2H), 6.90 (dd, J = 8.3, 1.8 Hz, 1H), 7.19 (d, J = 2.4 Hz, 1H), 7.20 (s, 1H), 7.28 (dd, J = 8.1, 1.3 Hz, 1H), 7.56 (t, J = 5.9 Hz, 1H), 7.60-7.67 (m, 3H). | 1.36 | 1 |
| 53 | | MS (m + 1) = 468.9; ¹H NMR (400 MHz, DMSO-d$_6$) δ 2.57 (s, 3H), 4.43 (d, J = 5.5 Hz, 2H), 6.65 (dd, J = 9.1, 2.8 Hz, 1H), 6.88 (t, J = 5.8 Hz, 1H), 6.91 (d, J = 2.8 Hz, 1H), 7.17 (dd, J = 9.0, 1.3 Hz, 1H), 7.33 (dd, J = 8.0, 1.0 Hz, 1H), 7.59 (s, 1H), 7.65 (d, J = 8.0 Hz, 1H). | 1.19 | 5 |

TABLE 1-continued

| Example | Compound | Characterization | LCMS RT (min) | LCMS Method |
|---|---|---|---|---|
| 54 | | MS (m + 1) = 478.4; $^1$H NMR (400 MHz, DMSO-d$_6$) δ 4.45 (d, J = 5.8 Hz, 2H), 6.62 (dd, J = 9.1, 2.8 Hz, 1 H), 6.78 (d, J = 2.8 Hz, 1 H), 6.92 (t, J = 5.9 Hz, 1H), 7.20 (dd, J = 9.0, 1.2 Hz, 1 H), 7.41 (dd, J = 8.1, 1.2 Hz, 1H), 7.69 (d, J = 7.3 Hz, 1H), 7.74 (s, 1H). | 1.44 | 1 |
| 55 | | MS (m + 1) = 471.4; $^1$H NMR (400 MHz, DMSO-d$_6$) δ 0.87 (t, J = 1.0 Hz, 3H), 1.23 (s, 2H), 1.49 (sxt, J = 7.5 Hz, 2H), 4.46 (s, 2H), 6.77 (dd, J = 8.4, 2.3 Hz, 1 H), 6.89 (d, J = 2.5 Hz, 1 H), 7.11 (d, J = 8.4 Hz, 1 H), 7.46 (d, J = 8.2 Hz, 1 H), 7.71 (d, J = 7.54 Hz, 1 H), 7.76 (s, 1H). | 1.56 | 1 |
| 56 | | MS (m + 1) = 472.0; $^1$H NMR (400 MHz, DMSO-d$_6$) δ 1.22-1.25 (m, 3H), 3.97 (q, J = 7.0 Hz, 2H), 4.43 (s, 2H), 6.79 (dd, J = 8.9, 2.8 Hz, 1H), 6.88 (d, J = 2.8 Hz, 1H), 6.99 (d, J = 8.9 Hz, 1H), 7.45 (dd, J = 8.3, 1.2 Hz, 1H), 7.70 (d, J = 7.3 Hz, 1H), 7.75 (s, 1H). | 1.52 | 3 |
| 57 | | MS (m + 1) = 486.0; $^1$H NMR (400 MHz, DMSO-d$_6$) δ 1.19 (d, J = 6.0 Hz, 6H), 4.41 (s, 2H), 4.49 (spt, J = 6.1 Hz, 1H), 6.35 (br. s., 1 H), 6.80 (dd, J = 8.9, 2.8 Hz, 1H), 6.85 (d, J = 2.9 Hz, 1H), 7.02 (d, J = 8.9 Hz, 1H), 7.42 (dd, J = 8.2, 1.2 Hz, 1H), 7.67 (d, J = 7.3 Hz, 1H), 7.74 (s, 1H). | 1.55 | 3 |
| 58 | | MS (m + 1) = 392.3; $^1$H NMR (400 MHz, DMSO-d$_6$) δ 3.52 (q, J = 11.4 Hz, 2H), 4.35 (s, 2H), 6.59 (ddd, J = 8.9, 4.2, 3.0 Hz, 1H), 6.66 (dd, J = 6.3, 2.9 Hz, 1H), 6.94 (t, J = 9.1 Hz, 1H), 7.13 (d, J = 0.9 Hz, 1H), 7.27 (dd, J = 7.9, 1.4 Hz, 1H), 7.55-7.62 (m, 2H). | 1.23 | 1 |

TABLE 1-continued

| Example | Compound | Characterization | LCMS RT (min) | LCMS Method |
|---|---|---|---|---|
| 59 | | MS (m + 1) = 371.2; $^1$H NMR (400 MHz, DMSO-$d_6$) δ 4.38 (d, J = 5.8 Hz, 2H), 6.58-6.66 (m, 3H), 6.78 (t, J = 2.0 Hz, 1H), 6.98 (t, J = 8.0 Hz, 1H), 7.08 (d, J = 1.0 Hz, 1H), 7.25 (dd, J = 8.1, 1.2 Hz, 1H), 7.54-7.62 (m, 2H). | 1.22 | 1 |
| 60 | | MS (m + 1) = 494.4; $^1$H NMR (400 MHz, DMSO-$d_6$) δ 4.52 (s, 2H), 6.81-6.88 (m, 1H), 6.96 (d, J = 2.91 Hz, 1H), 7.12 (d, J = 74.0 Hz, 1H), 7.14 (d, J = 8.84 Hz, 1H), 7.53 (dd, J = 8.27, 1.20 Hz, 1H), 7.78-7.85 (m, 2H). | 1.35 | 1 |
| 61 | | MS (m + 1) = 461.9; $^1$H NMR (400 MHz, DMSO-$d_6$) δ 4.53 (d, J = 4.8 Hz, 2H), 6.65 (dd, J = 8.8, 1.8 Hz, 1H), 6.83 (d, J = 2.1 Hz, 1H), 7.36-7.42 (m, 1H), 7.45 (d, J = 8.8 Hz, 2H), 7.75 (d, J = 6.5 Hz, 1H), 7.78 (s, 1H). | 1.53 | 1 |
| 62 | | MS (m + 1) = 382.4; $^1$H NMR (400 MHz, DMSO-$d_6$) δ 3.51 (s, 3H), 3.66 (s, 6H), 4.44 (s, 2H), 6.00 (s, 2H), 7.42 (dd, J = 8.1, 1.3 Hz, 1H), 7.71 (d, J = 1.0 Hz, 1H), 7.74 (s, 1H), 7.77 (d, J = 8.1 Hz, 1H). | 0.92 | 1 |
| 63 | | MS (m + 1) = 376.3; $^1$H NMR (400 MHz, DMSO-$d_6$) δ 4.39 (s, 2H), 6.59 (br. s., 1H), 6.62-6.68 (m, 2H), 7.03 (d, J = 8.3 Hz, 2H), 7.14 (d, J = 0.7 Hz, 1H), 7.27 (dd, J = 8.1, 1.1 Hz, 1H), 7.56-7.63 (m, 2H). | 1.27 | 1 |
| 64 | | MS (m + 1) = 425.1; $^1$H NMR (400 MHz, DMSO-$d_6$) δ 4.47 (d, J = 5.6 Hz, 2H), 6.67 (dd, J = 8.7, 2.6 Hz, 1H), 6.87 (d, J = 2.5 Hz, 1H), 7.39 (t, J = 5.8 Hz, 1H), 7.45-7.50 (m, 2H), 7.72 (s, 1H), 7.75 (s, 1H), 7.78 (d, J = 1.1 Hz, 1H). | 1.11 | 5 |

TABLE 1-continued

| Example | Compound | Characterization | LCMS RT (min) | LCMS Method |
|---|---|---|---|---|
| 65 | | MS (m + 1) = 409.9; ¹H NMR (400 MHz, DMSO-$d_6$) δ 4.41 (d, J = 3.8 Hz, 2H), 6.61 (dd, J = 9.1, 2.8 Hz, 1 H), 6.76 (d, J = 2.8 Hz, 1 H), 6.90 (br. s., 1H), 7.16-7.23 (m, 1H), 7.47 (dd, J = 8.6, 1.7 Hz, 1H), 7.74 (s, 2 H), 7.78 (d, J = 1.2 Hz, 1 H). | 1.07 | 5 |
| 66 | | MS (m + 1) = 402.1; ¹H NMR (400 MHz, DMSO-$d_6$) δ 0.88 (t, J = 7.3 Hz, 3H), 1.49 (sxt, J = 7.5 Hz, 2H), 2.53 (m, 2H), 4.41 (s, 2H), 6.63 (br. s., 1H), 6.77 (dd, J = 8.4, 2.3 Hz, 1H), 6.88 (d, J = 2.6 Hz, 1H), 7.11 (d, J = 8.4 Hz, 1H), 7.48 (dd, J = 8.7, 1.7 Hz, 1H), 7.69-7.74 (m, 2H), 7.78 (d, J = 1.1 Hz, 1H). | 1.11 | 5 |
| 67 | | MS (m + 1) = 372.0; ¹H NMR (400 MHz, DMSO-$d_6$) δ 4.37 (s, 2H) 6.35 (dd, J = 8.8, 2.3 Hz, 1H), 6.62 (d, J = 2.3 Hz, 1H), 7.06 (d, J = 8.8 Hz, 1H), 7.48 (dd, J = 8.7, 1.7 Hz, 1H), 7.67-7.74 (m, 2H), 7.78 (d, J = 1.0 Hz, 1H). | 1.00 | 5 |
| 68 | | MS (m + 1) = 368.0; ¹H NMR (400 MHz, METHANOL-$d_4$) δ 0.90 (t, J = 7.4 Hz, 3H) 1.50-1.63 (m, 2H) 2.56 (dd, J = 8.3, 6.9 Hz, 2H) 4.39 (s, 2H) 6.47 (dd, J = 8.6, 2.9 Hz, 1H) 6.55 (d, J = 2.8 Hz, 1H) 7.01 (d, J = 8.7 Hz, 1H) 7.26 (d, J = 1.0 Hz, 1H) 7.35 (dd, J = 8.5, 1.8 Hz, 1H) 7.53 (d, J = 8.6 Hz, 1H) 7.64 (d, J = 1.1 Hz, 1H). | 1.09 | 5 |
| 69 | | MS (m + 1) = 382.0; ¹H NMR (400 MHz, DMSO-$d_6$) δ 0.91 (t, J = 7.3 Hz, 3H), 1.33-1.46 (m, 2H), 2.17 (s, 3H), 2.46-2.48 (m, 2 H), 4.35 (s, 2H), 6.41-6.47 (m, 2H), 7.46 (dd, J = 8.7, 1.7 Hz, 1H), 7.69-7.73 (m, 2H), 7.76 (d, J = 1.1 Hz, 1 H). | 1.13 | 5 |
| 70 | | MS (m + 1) = 440.1; ¹H NMR (400 MHz, DMSO-$d_6$) δ 2.63 (s, 3H), 4.47 (d, J = 5.6 Hz, 2H), 6.68 (dd, J = 8.7, 2.5 Hz, 1H), 6.89 (d, J = 2.6 Hz, 1H), 7.35 (t, J = 5.8 Hz, 1H), 7.45-7.51 (m, 2H), 7.67 (d, J = 8.6 Hz, 1 H), 7.79 (d, J = 1.0 Hz, 1 H). | 1.11 | 5 |

TABLE 1-continued

| Example | Compound | Characterization | LCMS RT (min) | LCMS Method |
|---|---|---|---|---|
| 71 | (3-chloro-4-propylphenyl)aminomethyl-benzofuran-tetrazole | MS (m + 1) = 368.0; $^1$H NMR (400 MHz, DMSO-d$_6$) δ 0.86 (t, J = 7.3 Hz, 3H), 1.48 (sxt, J = 7.4 Hz, 2H), 2.45 (t, J = 7.8 Hz, 2H), 4.37 (s, 2H), 6.52 (dd, J = 8.3, 2.5 Hz, 1H), 6.60 (d, J = 2.5 Hz, 1H), 6.97 (d, J = 8.4 Hz, 1H), 7.47 (dd, J = 8.7, 1.7 Hz, 1H), 7.71 (t, J = 4.2 Hz, 2H), 7.77 (d, J = 1.0 Hz, 1H). | 1.07 | 5 |
| 72 | (4-fluoro-3-trifluoromethoxyphenyl)aminomethyl-benzofuran-tetrazole | MS (m + 1) = 394.0; $^1$H NMR (400 MHz, DMSO-d$_6$) δ 4.38 (s, 2H), 6.56-6.69 (m, 3H), 7.16 (dd, J = 10.4, 9.1 Hz, 1H), 7.47 (dd, J = 8.5, 1.5 Hz, 1H), 7.69-7.74 (m, 2H), 7.78 (d, J = 1.2 Hz, 1H). | 1.03 | 5 |
| 73 | 1-(3,4,5-trichlorophenyl)aminoethyl-benzofuran-tetrazole | MS (m + 1) = 410.2; $^1$H NMR (400 MHz, DMSO-d$_6$) δ 1.46 (d, J = 6.6 Hz, 3H), 4.65 (quin, J = 6.8 Hz, 1H), 6.73 (s, 2H), 6.99 (d, J = 7.0 Hz, 1H) 7.33-7.39 (m, 2H) 7.62 (d, J = 8.6 Hz, 1 H) 7.68 (d, J = 1.5 Hz, 1H). | 1.40 | 1 |
| 74 | 1-(3-chloro-4-trifluoromethylthiophenyl)aminoethyl-benzofuran-tetrazole | MS (m + 1) = 439.9; $^1$H NMR (400 MHz, DMSO-d$_6$) δ 1.49 (d, J = 6.7 Hz, 3H), 4.71 (quin, J = 6.8 Hz, 1H), 6.57 (dd, J = 8.7, 2.3 Hz, 1 H), 6.79 (d, J = 2.2 Hz, 1 H), 7.32 (d, J = 6.9 Hz, 1 H), 7.39-7.45 (m, 2H), 7.49 (s, 1H), 7.66 (d, J = 8.6 Hz, 1H), 7.73 (d, J = 1.5 Hz, 1H). | 1.11 | 5 |
| 75 | (3-chloro-5-trifluoromethoxyphenyl)aminomethyl-benzofuran-tetrazole | MS (m + 1) = 409.9; $^1$H NMR (400 MHz, DMSO-d$_6$) δ 4.39 (d, J = 5.6 Hz, 2H), 6.52 (d, J = 8.2 Hz, 2H), 6.65 (t, J = 1.9 Hz, 1H), 7.04 (t, J = 5.8 Hz, 1H), 7.33-7.37 (m, 2H), 7.64 (d, J = 8.4 Hz, 1H), 7.68 (s, 1H). | 1.19 | 5 |
| 76 | (3-trifluoromethoxy-4-propylphenyl)aminomethyl-benzofuran-tetrazole | MS (m + 1) = 418.0; $^1$H NMR (400 MHz, DMSO-d$_6$) δ 0.85 (t, J = 7.3 Hz, 3H), 1.46 (sxt, J = 7.4 Hz, 2H), 2.36-2.43 (m, 2H), 4.37 (s, 2H), 6.48-6.57 (m, 2 H), 7.02 (d, J = 8.3 Hz, 1 H), 7.47 (dd, J = 8.6, 1.5 Hz, 1H), 7.68-7.74 (m, 2 H), 7.77 (s, 1H). | 1.18 | 5 |

TABLE 1-continued

| Example | Compound | Characterization | LCMS RT (min) | LCMS Method |
|---|---|---|---|---|
| 77 | (structure) | MS (m + 1) = 425.0; $^1$H NMR (400 MHz, DMSO-$d_6$) δ 1.47 (d, J = 6.7 Hz, 3H), 4.64 (quin, J = 6.7 Hz, 1H), 6.52 (dd, J = 9.1, 2.8 Hz, 1 H), 6.67 (d, J = 2.7 Hz, 1 H), 6.85 (d, J = 6.9 Hz, 1 H), 7.14 (dd, J = 9.1, 1.2 Hz, 1H), 7.48 (dd, J = 8.7, 1.7 Hz, 1H), 7.64 (s, 1H), 7.69 (d, J = 8.6 Hz, 1H), 7.77 (d, J = 1.5 Hz, 1H). | 1.09 | 5 |
| 78 | (structure) | MS (m + 1) = 388.0; $^1$H NMR (400 MHz, DMSO-$d_6$) δ 1.17 (t, J = 7.5 Hz, 3H), 2.74 (q, J = 7.5 Hz, 2H), 5.08 (br. s., 2H), 7.30 (dd, J = 8.4, 1.6 Hz, 1 H,) 7.39 (d, J = 7.8 Hz, 1H), 7.51 (d, J = 8.2 Hz, 1H), 7.58 (s, 1 H), 7.66 (s, 1H), 7.68-7.74 (m, 2H). | 1.10 | 5 |
| 79 | (structure) | MS (m + 1) = 352.1; $^1$H NMR (400 MHz, DMSO-$d_6$) δ 0.84 (t, J = 7.3 Hz, 3H), 1.46 (sxt, J = 7.4 Hz, 2H), 2.37 (t, J = 7.5 Hz, 2H), 4.36 (s, 2H), 6.31 (dd, J = 13.1, 2.3 Hz, 1H), 6.37 (dd, J = 8.3, 2.3 Hz, 1H), 6.90 (t, J = 8.7 Hz, 1H), 7.47 (dd, J = 8.7, 1.7 Hz, 1H), 7.67-7.74 (m, 2H), 7.77 (d, J = 1.0 Hz, 1H). | 1.07 | 5 |
| 80 | (structure) | MS (m + 1) = 348.1; $^1$H NMR (400 MHz, DMSO-$d_6$) δ 0.87 (t, J = 7.3 Hz, 3H), 1.43 (sxt, J = 7.5 Hz, 2H), 2.11 (s, 3H), 2.32-2.39 (m, 2H), 4.34 (s, 2H), 6.35 (dd, J = 8.2, 2.5 Hz, 1H), 6.43 (d, J = 2.2 Hz, 1H), 6.78 (d, J = 8.2 Hz, 1H), 7.46 (dd, J = 8.7, 1.7 Hz, 1 H), 7.66-7.71 (m, 2H), 7.76 (d, J = 1.0 Hz, 1H). | 1.06 | 5 |
| 81 | (structure) | MS (m + 1) = 416.4; $^1$H NMR (400 MHz, DMSO-$d_6$) δ 0.85 (t, J = 7.3 Hz, 3H), 1.39-1.51 (m, 5H), 2.41-2.48 (m, 2H), 4.57 (quin, J = 6.6 Hz, 1H), 6.52 (d, J = 6.7 Hz, 1H), 6.65 (dd, J = 8.5, 2.1 Hz, 1H), 6.86 (d, J = 2.5 Hz, 1H), 7.03 (d, J = 8.3 Hz, 1H), 7.05 (d, J = 0.9 Hz, 1H), 7.29 (dd, J = 8.4, 1.7 Hz, 1H), 7.53 (d, J = 8.4 Hz, 1H), 7.61 (d, J = 1.5 Hz, 1H). | 1.46 | 1 |
| 82 | (structure) | MS (m + 1) = 416.0; $^1$H NMR (400 MHz, DMSO-$d_6$) δ 0.87 (t, J = 7.3 Hz, 3H), 1.44-1.62 (m, 2H), 2.56 (s, 3H), 2.68 (br. s., 2H), 5.09 (s, 2H), 7.27-7.34 (m, 1H), 7.39 (d, J = 8.4 Hz, 1H), 7.47 (s, 1H), 7.56 (d, J = 4.0 Hz, 2H), 7.64 (d, J = 8.6 Hz, 1H). | 1.13 | 5 |

TABLE 1-continued

| Example | Compound | Characterization | LCMS RT (min) | LCMS Method |
|---|---|---|---|---|
| 83 | | MS (m + 1) = 385.9; ¹H NMR (400 MHz, DMSO-$d_6$) δ 1.46 (d, J = 6.7 Hz, 3H), 4.60 br. s., 1H), 6.26 (dd, J = 8.8, 2.3 Hz, 1H), 6.52 (d, J = 2.2 Hz, 2H), 6.99 (d, J = 8.8 Hz, 1H), 7.49 (dd, J = 8.8, 1.7 Hz, 1H), 7.69 (t, J = 4.2 Hz, 2H), 7.78 (d, J = 1.5 Hz, 1H). | 1.01 | 5 |
| 84 | | MS (m + 1) = 382.3; ¹H NMR (400 MHz, DMSO-$d_6$) δ 0.83 (t, J = 7.3 Hz, 3H), 1.37-1.48 (m, 5H), 2.38-2.44 (m, 2H), 4.58 (br. s., 1 H), 6.35-6.45 (m, 2H), 6.52 (d, J = 2.3 Hz, 1H), 6.89 (d, J = 8.4 Hz, 1H), 7.49 (dd, J = 8.7, 1.7 Hz, 1 H), 7.66-7.71 (m, 2H), 7.78 (d, J = 1.5 Hz, 1H). | 1.44 | 1 |
| 85 | | MS (m + 1) = 504.5; ¹H NMR (400 MHz, DMSO-$d_6$) δ 4.43 (d, J = 5.9 Hz, 2H), 6.98 (s, 2H), 6.98-7.02 (m, 1H), 7.34 (dd, J = 8.2, 1.3 Hz, 1H), 7.63-7.64 (m, 1H), 7.64-7.66 (m, 1H), 7.75 (d, J = 8.1 Hz, 1H), 13.51 (br. s., 1H). | 1.21 | 8 |
| 86 | | MS (m + 1) = 371.6; ¹H NMR (400 MHz, DMSO-$d_6$) δ 4.45 (d, J = 6.0 Hz, 2H), 6.82 (s, 2H), 7.05 (t, J = 6.1 Hz, 1H), 7.34 (dd, J = 8.1, 1.4 Hz, 1H), 7.62-7.65 (m, 1H), 7.65 (s, 1H), 7.75 (d, J = 8.1 Hz, 1H), 13.51 (br. s, 1H). | 1.19 | 8 |
| 87 | | MS (m + 1) = 402.1; ¹H NMR (400 MHz, DMSO-$d_6$) δ 4.44 (d, J = 5.8 Hz, 2H), 6.66 (dd, J = 8.7, 2.5 Hz, 1H), 6.86 (d, J = 2.5 Hz, 1H), 7.08 (s, 1H), 7.23 (dd, J = 7.9, 1.4 Hz, 1H), 7.35 (t, J = 5.9 Hz, 1H), 7.47 (d, J = 8.6 Hz, 1H), 7.53 (s, 1H), 7.60 (d, J = 8.0 Hz, 1H). | 1.36 | 1 |
| 88 | | MS (m + 1) = 386.0; ¹H NMR (400 MHz, DMSO-$d_6$) δ 4.38 (d, J = 5.9 Hz, 2H), 6.61 (dd, J = 9.0, 2.8 Hz, 1H), 6.75 (d, J = 2.8 Hz, 1H), 6.85 (t, J = 5.9 Hz, 1H), 7.02 (s, 1H), 7.19 (dq, J = 9.0, 1.3 Hz, 1H), 7.22 (dd, J = 8.0, 1.4 Hz, 1H), 7.51 (s, 1H), 7.58 (d, J = 8.0 Hz, 1H). | 1.17 | 6 |

TABLE 1-continued

| Example | Compound | Characterization | LCMS RT (min) | LCMS Method |
|---|---|---|---|---|
| 89 | (2,2-difluorobenzo[d][1,3]dioxol-5-yl)aminomethyl-benzofuran-2-carboxylic acid | MS (m + 1) = 348.0; $^1$H NMR (400 MHz, DMSO-$d_6$) δ 4.33 (d, J = 5.9 Hz, 2H), 6.34 (dd, J = 8.8, 2.3 Hz, 1H), 6.50 (t, J = 6.0 Hz, 1H), 6.62 (d, J = 2.3 Hz, 1H), 6.88 (d, J = 1.0 Hz, 1H), 7.04 (d, J = 8.7 Hz, 1H), 7.20 (dd, J = 7.9, 1.4 Hz, 1H), 7.48 (s, 1H), 7.53 (d, J = 8.0 Hz, 1H). | 1.22 | 1 |
| 90 | 3-bromo-4-(trifluoromethoxy)phenylaminomethyl-benzofuran-2-carboxylic acid | MS (m + 1) = 431.2; $^1$H NMR (400 MHz, DMSO-$d_6$) δ 4.38 (d, J = 5.4 Hz, 2H), 6.65 (dd, J = 9.1, 2.8 Hz, 1H), 6.87 (t, J = 5.9 Hz, 1H), 6.91 (d, J = 2.7 Hz, 1H), 7.02 (d, J = 4.2 Hz, 1H), 7.14-7.20 (m, 1H), 7.22 (dd, J = 8.0, 1.4 Hz, 1H), 7.52 (s, 1H), 7.58 (d, J = 8.0 Hz, 1H). | 1.38 | 1 |
| 91 | 3-(trifluoromethyl)-4-(trifluoromethylthio)phenylaminomethyl-benzofuran-2-carboxylic acid | MS (m + 1) = 436.2; $^1$H NMR (400 MHz, DMSO-$d_6$) δ 4.49 (d, J = 5.8 Hz, 2H), 6.88 (dd, J = 8.8, 2.6 Hz, 1H), 7.14 (s, 1H), 7.16 (d, J = 2.7 Hz, 1H), 7.26 (dd, J = 8.0, 1.4 Hz, 1H), 7.54-7.60 (m, 3H), 7.62 (d, J = 8.0 Hz, 1H). | 1.39 | 1 |
| 92 | 3-(trifluoromethyl)-4-(trifluoromethoxy)phenylaminomethyl-benzofuran-2-carboxylic acid | MS (m + 1) = 420.4; $^1$H NMR (400 MHz, DMSO-$d_6$) δ 4.42 (d, J = 5.6 Hz, 2H), 6.87 (dd, J = 9.0, 3.1 Hz, 1H), 6.93 (d, J = 3.4 Hz, 1H), 6.99 (d, J = 3.0 Hz, 1H), 7.03 (t, J = 5.9 Hz, 1H), 7.18-7.25 (m, 1H), 7.29 (d, J = 9.0 Hz, 1H), 7.50 (d, J = 3.2 Hz, 1H), 7.56 (dd, J = 8.0, 3.7 Hz, 1H). | 1.38 | 1 |
| 93 | 3-chloro-4-propylphenylaminomethyl-benzofuran-2-carboxylic acid | MS (m + 1) = 344.2; $^1$H NMR (400 MHz, DMSO-$d_6$) δ 0.86 (t, J = 7.3 Hz, 3H), 1.42-1.53 (m, 2H), 2.43-2.46 (m, 2H), 4.37 (d, J = 5.7 Hz, 2H), 6.45 (t, J = 6.2 Hz, 1H), 6.51 (dd, J = 8.3, 2.4 Hz, 1H), 6.59 (d, J = 2.4 Hz, 1H), 6.96 (d, J = 8.3 Hz, 1H), 7.31 (dd, J = 7.9, 1.4 Hz, 1H), 7.42 (s, 1H), 7.59 (s, 1H), 7.67 (d, J = 8.1 Hz, 1H). | 1.41 | 1 |
| 94 | (2,2,3,3-tetrafluoro-2,3-dihydrobenzo[b][1,4]dioxin-6-yl)aminomethyl-benzofuran-2-carboxylic acid | MS (m + 1) = 398.3; $^1$H NMR (400 MHz, DMSO-$d_6$) δ 4.40 (d, J = 5.9 Hz, 2H), 6.50 (d, J = 2.6 Hz, 1H), 6.54 (dd, J = 9.0, 2.6 Hz, 1H), 6.76 (t, J = 6.1 Hz, 1H), 7.11 (d, J = 9.0 Hz, 1H), 7.32 (dd, J = 8.1, 1.3 Hz, 1H), 7.48 (s, 1H), 7.62 (s, 1H), 7.70 (d, J = 8.1 Hz, 1H). | 1.35 | 1 |

TABLE 1-continued

| Example | Compound | Characterization | LCMS RT (min) | LCMS Method |
|---|---|---|---|---|
| 95 | | MS (m + 1) = 378.2; $^1$H NMR (400 MHz, DMSO-d$_6$) δ 0.88 (t, J = 7.3 Hz, 3H), 1.42-1.56 (m, 2H), 2.46-2.49 (m, 2H), 4.37 (d, J = 5.9 Hz, 2H), 6.57 (t, J = 6.0 Hz, 1H), 6.77 (dd, J = 8.4, 2.5 Hz, 1H), 6.88 (d, J = 2.6 Hz, 1H), 6.89 (d, J = 1.0 Hz, 1H), 7.10 (d, J = 8.4 Hz, 1H), 7.21 (dd, J = 8.0, 1.4 Hz, 1H), 7.47 (s, 1H), 7.53 (d, J = 8.0 Hz, 1H). | 1.49 | 1 |
| 96 | | MS (m + 1) = 382.4; $^1$H NMR (600 MHz, DMSO-d$_6$) δ 2.34 (s, 3H), 4.42 (d, J = 5.4 Hz, 2H), 6.81 (dd, J = 8.7, 2.6 Hz, 1H), 6.92 (t, J = 6.0 Hz, 1H), 6.98 (d, J = 2.6 Hz, 1H), 7.04 (s, 1H), 7.23 (dd, J = 8.0, 1.4 Hz, 1H), 7.35 (d, J = 8.6 Hz, 1H), 7.52 (s, 1H), 7.58 (d, J = 8.0 Hz, 1H). | 1.31 | 1 |
| 97 | | MS (m + 1) = 314.1; $^1$H NMR (400 MHz, DMSO-d$_6$) δ 2.35 (s, 3H), 4.34 (d, J = 5.9 Hz, 2H), 6.34 (t, J = 6.1 Hz, 1H), 6.37-6.39 (m, 1H), 6.39-6.41 (m, 1H), 6.48 (t, J = 2.0 Hz, 1H), 6.86 (s, 1H), 6.96 (t, J = 7.9 Hz, 1H), 7.19 (dd, J = 8.1, 1.4 Hz, 1H), 7.46 (d, 1H), 7.51 (d, J = 8.0 Hz, 1H). | 1.15 | 1 |
| 98 | | MS (m + 1) = 432.2; $^1$H NMR (400 MHz, DMSO-d$_6$) δ 2.73-2.80 (m, 4H), 3.63-3.71 (m, 4H), 4.34 (d, J = 5.4 Hz, 2H), 6.36 (t, J = 5.7 Hz, 1H), 6.58 (dd, J = 8.7, 2.6 Hz, 1H), 6.85 (d, J = 2.6 Hz, 1H), 6.93 (d, J = 8.7 Hz, 1H), 7.18 (s, 1H), 7.25 (dd, J = 8.1, 1.4 Hz, 1H), 7.53 (s, 1H), 7.60 (d, J = 8.0 Hz, 1H). | 1.14 | 1 |
| 99 | | MS (m + 1) = 393.7; $^1$H NMR (400 MHz, DMSO-d$_6$) δ 4.43 (d, J = 5.9 Hz, 2H), 6.65 (d, J = 8.8 Hz, 2H), 7.02 (br. s, 1H), 7.19-7.21 (m, 1H), 7.47-7.54 (m, 3H), 7.57 (d, J = 8.0 Hz, 1H), 7.63-7.68 (m, 1H), 7.79-7.86 (m, 1H). | 1.27 | 1 |
| 100 | | MS (m + 1) = 364.1; $^1$H NMR (400 MHz, DMSO-d$_6$) δ 1.09 (t, J = 7.4 Hz, 3H), 2.55 (q, J = 7.5 Hz, 2H), 4.38 (d, J = 5.6 Hz, 2H), 6.59 (t, J = 6.1 Hz, 1H), 6.78 (dd, J = 8.4, 2.5 Hz, 1H), 6.88 (d, J = 2.5 Hz, 1H), 6.97 (s, 1H), 7.11 (d, J = 8.4 Hz, 1H), 7.22 (dd, J = 8.0, 1.4 Hz, 1H), 7.50 (s, 1H), 7.55 (d, J = 8.0 Hz, 1H). | 1.34 | 1 |

TABLE 1-continued

| Example | Compound | Characterization | LCMS RT (min) | LCMS Method |
|---|---|---|---|---|
| 101 | | MS (m + 1) = 404.4; 1H NMR (400 MHz, DMSO-$d_6$) δ 4.50 (d, J = 5.7 Hz, 2H), 6.87 (d, J = 8.5 Hz, 1H), 7.04 (s, 1H), 7.17 (d, J = 2.5 Hz, 1H), 7.23 (dd, J = 8.1, 1.4 Hz, 1H), 7.54 (s, 1H), 7.56-7.64 (m, 3H). | 1.38 | 1 |
| 102 | | MS (m + 1) = 366.3; 1H NMR (400 MHz, DMSO-$d_6$) δ 2.12 (s, 3H), 4.35 (d, J = 5.8 Hz, 2H), 6.42-6.51 (m, 2H), 6.54 (d, J = 2.8 Hz, 1H), 6.91-6.99 (m, 2H), 7.21 (dd, J = 7.9, 1.4 Hz, 1H), 7.49 (s, 1H), 7.54 (d, J = 8.0 Hz, 1H). | 1.36 | 1 |
| 103 | | MS (m + 1) = 364.2; 1H NMR (400 MHz, DMSO-$d_6$) δ ppm 4.53 (d, J = 5.99 Hz, 2 H) 6.78 (d, J = 9.05 Hz, 2H) 6.86 (d, J = 0.86 Hz, 1H) 7.18 (dd, J = 8.07, 1.34 Hz, 1 H) 7.49 (s, 1H) 7.54 (d, J = 8.07 Hz, 1H) 7.77 (d, J = 8.19 Hz, 2H) 8.02 (t, J = 5.99 Hz, 1H). | 1.25 | 1 |
| 104 | | MS (m + 1) = 436.4; 1H NMR (600 MHz, DMSO-$d_6$) δ 4.39 (d, J = 5.6 Hz, 2H), 6.62 (dd, J = 9.1, 2.7 Hz, 1H), 6.71 (dq, J = 2.8, 1.4 Hz, 1H), 6.97 (t, J = 5.9 Hz, 1H), 7.08 (s, 1H), 7.24 (ddd, J = 8.8, 2.9, 1.5 Hz, 2H), 7.53 (s, 1H), 7.60 (d, J = 8.0 Hz, 1H). | 1.42 | 1 |
| 105 | | MS (m + 1) = 326.2; 1H NMR (400 MHz, DMSO-$d_6$) δ 4.03-4.08 (m, 2H), 4.08-4.14 (m, 2H), 4.29 (s, 2H), 6.06 (d, J = 2.6 Hz, 1H), 6.12 (dd, J = 8.7, 2.6 Hz, 1H), 6.54 (d, J = 8.7 Hz, 1H), 7.22-7.32 (m, 2H), 7.54 (s, 1H), 7.61 (d, J = 8.0 Hz, 1H). | 0.95 | 1 |
| 106 | | MS (m + 1) = 383.3; 1H NMR (400 MHz, DMSO-$d_6$) δ 4.34 (d, J = 5.9 Hz, 2H), 6.60 (ddd, J = 13.2, 6.3, 2.7 Hz, 1H), 6.64-6.68 (m, 1H), 6.71 (t, J = 5.9 Hz, 1H), 6.95 (s, 1H), 7.20 (dd, J = 8.0, 1.4 Hz, 1H), 7.50 (s, 1H), 7.56 (d, J = 8.0 Hz, 1H). | 1.30 | 1 |

TABLE 1-continued

| Example | Compound | Characterization | LCMS RT (min) | LCMS Method |
|---|---|---|---|---|
| 107 | 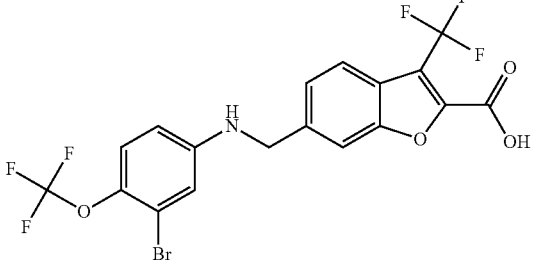 | MS (m + 1) = 500.3; $^1$H NMR (400 MHz, DMSO-$d_6$) δ 4.42 (d, J = 5.9 Hz, 2H), 6.63 (dd, J = 9.0, 2.8 Hz, 1H), 6.87 (t, J = 5.9 Hz, 1H), 6.90 (d, J = 2.7 Hz, 1H), 7.17 (dd, J = 9.0, 1.2 Hz, 1H), 7.37 (d, J = 8.4 Hz, 1H), 7.61-7.67 (m, 2H). | 1.50 | 1 |
| 108 | 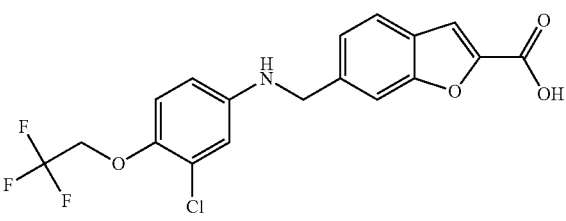 [SMILES: O=C(O)c1cc2ccc(CNc3ccc(OCC(F)(F)F)c(Cl)c3)cc2o1] | MS (m + 1) = 400.3; $^1$H NMR (400 MHz, DMSO-$d_6$) δ 4.33 (d, J = 5.7 Hz, 2H), 4.58 (q, J = 8.9 Hz, 2H), 6.35 (t, J = 6.1 Hz, 1H), 6.54 (dd, J = 8.9, 2.8 Hz, 1H), 6.68 (d, J = 2.7 Hz, 1H), 6.88 (d, J = 1.0 Hz, 1H), 6.99 (d, J = 8.9 Hz, 1H), 7.19 (dd, J = 8.1, 1.4 Hz, 1H), 7.47 (s, 1H), 7.52 (d, J = 8.0 Hz, 1H). | 1.30 | 1 |
| 109 | 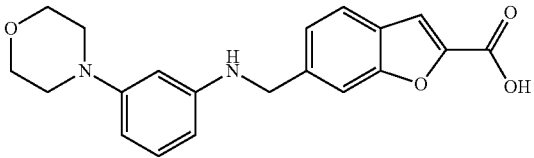 [SMILES: O=C(O)c1cc2ccc(CNc3cccc(N4CCOCC4)c3)cc2o1] | MS (m + 1) = 353.1; $^1$H NMR (400 MHz, DMSO-$d_6$) δ 2.94-3.02 (m, 4H), 3.64-3.73 (m, 4H), 4.32 (d, J = 6.0 Hz, 2H), 6.07 (t, J = 6.6 Hz, 1H), 6.08-6.15 (m, 2H), 6.20 (t, J = 2.3 Hz, 1H), 6.82 (d, J = 1.0 Hz, 1H), 6.87 (t, J = 8.0 Hz, 1H), 7.18 (dd, J = 8.0, 1.4 Hz, 1H), 7.45 (s, 1H), 7.49 (d, J = 8.0 Hz, 1H). | 0.95 | 1 |
| 110 | 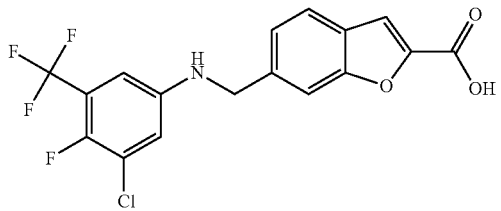 [SMILES: O=C(O)c1cc2ccc(CNc3cc(Cl)c(F)c(C(F)(F)F)c3)cc2o1] | MS (m + 1) = 388.1; $^1$H NMR (400 MHz, DMSO-$d_6$) δ 4.42 (d, J = 5.8 Hz, 2H), 6.89 (dd, J = 5.3, 2.9 Hz, 1H), 6.95 (t, J = 6.0 Hz, 1H), 6.98 (dd, J = 5.9, 2.9 Hz, 1H), 7.09 (s, 1H), 7.24 (dd, J = 8.0, 1.4 Hz, 1H), 7.55 (s, 1H), 7.61 (d, J = 8.0 Hz, 1H). | 1.32 | 1 |
| 111 | 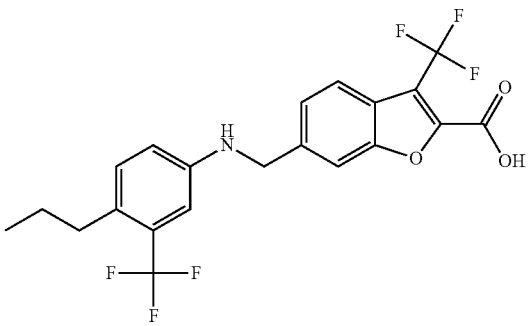 [SMILES: CCCc1ccc(NCc2ccc3c(C(F)(F)F)c(C(=O)O)oc3c2)cc1C(F)(F)F] | MS (m + 1) = 445.9; $^1$H NMR (400 MHz, DMSO-$d_6$) δ 0.88 (t, J = 7.3 Hz, 3H), 1.48 (sxt, J = 7.5 Hz, 2H), 2.48 (br. s., 2H), 4.42 (d, J = 4.7 Hz, 2H), 6.64 (t, J = 5.4 Hz, 1H), 6.75 (dd, J = 8.4, 2.3 Hz, 1H), 6.87 (d, J = 2.5 Hz, 1H), 7.10 (d, J = 8.4 Hz, 1H), 7.38 (d, J = 8.8 Hz, 1H), 7.60-7.66 (m, 2H). | 1.78 | 4 |
| 112 | 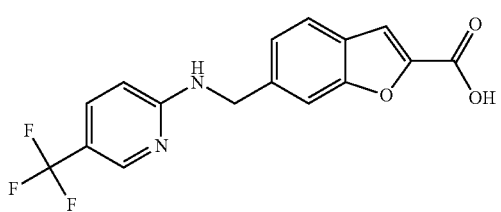 [SMILES: O=C(O)c1cc2ccc(CNc3ccc(C(F)(F)F)cn3)cc2o1] | MS (m + 1) = 337.1; $^1$H NMR (400 MHz, DMSO-$d_6$) δ 4.62 (d, J = 5.9 Hz, 2H), 6.65 (d, J = 8.9 Hz, 1H), 6.88 (s, 1H), 7.17 (dd, J = 7.9, 1.4 Hz, 1H), 7.45 (s, 1H), 7.52 (d, J = 8.0 Hz, 1H), 7.64 (dd, J = 8.9, 2.5 Hz, 1H), 7.87 (t, J = 5.9 Hz, 1H), 8.30 (s, 1H). | 0.87 | 6 |

TABLE 1-continued

| Example | Compound | Characterization | LCMS RT (min) | LCMS Method |
|---|---|---|---|---|
| 113 | (structure) | MS (m − 1) = 366.2; $^1$H NMR (400 MHz, DMSO-d$_6$) δ 4.40 (d, J = 5.9 Hz, 2H), 6.68 (d, J = 9.0 Hz, 2H), 6.94 (s, 1H), 7.04 (t, J = 6.0 Hz, 1H), 7.20 (dd, J = 8.0, 1.4 Hz, 1H), 7.33 (d, J = 8.6 Hz, 2H), 7.49 (s, 1H), 7.55 (d, J = 8.0 Hz, 1H). | 1.40 | 1 |
| 114 | (structure) | MS (m + 1) = 339.3; $^1$H NMR (400 MHz, DMSO-d$_6$) δ 2.67 (s, 3H), 4.42 (d, J = 5.7 Hz, 2H), 6.49 (t, J = 6.1 Hz, 1H), 6.81 (dd, J = 8.7, 2.3 Hz, 1H), 6.94 (s, 1H), 6.97 (d, J = 2.2 Hz, 1H), 7.25 (dd, J = 7.9, 1.4 Hz, 1H), 7.50-7.57 (m, 2H), 7.60 (d, J = 8.6 Hz, 1H). | 1.01 | 1 |
| 115 | (structure) | MS (m + 1) = 332.1; H NMR (400 MHz, DMSO-d$_6$) δ 3.68 (s, 3H), 4.30 (d, J = 5.8 Hz, 2H), 6.12 (t, J = 6.2 Hz, 1H), 6.53 (dd, J = 8.9, 2.8 Hz, 1H), 6.67 (d, J = 2.7 Hz, 1H), 6.87 (d, J = 8.9 Hz, 2H), 7.18 (dd, J = 8.0, 1.4 Hz, 1H), 7.46 (s, 1H), 7.51 (d, J = 8.0 Hz, 1H). | 1.09 | 1 |
| 116 | (structure) | MS (m − 1) = 402.0; $^1$H NMR (400 MHz, DMSO-d$_6$) δ 4.50 (d, J = 5.8 Hz, 2H), 7.04 (s, 1H), 7.07 (s, 1H), 7.16 (s, 2H), 7.25 (dd, J = 8.1, 1.4 Hz, 1H), 7.31 (t, J = 5.8 Hz, 1H), 7.56 (s, 1H), 7.60 (d, J = 8.0 Hz, 1H). | 1.36 | 1 |
| 117 | (structure) | MS (m + 1) = 366.1; $^1$H NMR (400 MHz, DMSO-d$_6$) δ 3.71 (s, 3H), 4.34 (d, J = 6.0 Hz, 2H), 6.28 (t, J = 6.1 Hz, 1H), 6.81 (dd, J = 8.9, 2.9 Hz, 1H), 6.84 (d, J = 1.0 Hz, 1H), 6.87 (d, J = 2.8 Hz, 1H), 6.99 (d, J = 8.9 Hz, 1H), 7.19 (dd, J = 8.0, 1.4 Hz, 1H), 7.46 (s, 1H), 7.51 (d, J = 7.9 Hz, 1H). | 1.17 | 1 |
| 118 | (structure) | MS (m + 1) = 434.4; $^1$H NMR (400 MHz, DMSO-d$_6$) δ 4.39 (s, 2H), 4.66 (q, J = 8.9 Hz, 2H), 6.46-6.57 (m, 1H), 6.81 (dd, J = 9.0, 2.8 Hz, 1H), 6.89 (d, J = 2.8 Hz, 1H), 7.11 (d, J = 9.0 Hz, 1H), 7.20 (s, 1H), 7.27 (dd, J = 8.0, 1.4 Hz, 1H), 7.55 (s, 1H), 7.61 (d, J = 8.0 Hz, 1H). | 1.32 | 1 |

TABLE 1-continued

| Example | Compound | Characterization | LCMS RT (min) | LCMS Method |
|---|---|---|---|---|
| 119 | (2,6-dichloropyridin-4-yl)aminomethyl-benzofuran-2-carboxylic acid structure | MS (m + 1) = 338.1; $^1$H NMR (400 MHz, DMSO-d$_6$) δ 4.61 (d, J = 5.7 Hz, 2H), 6.63 (s, 2H), 7.20 (d, J = 7.3 Hz, 1H), 7.27-7.36 (m, 2H), 7.48 (d, J = 8.2 Hz, 1H), 7.90 (t, J = 5.8 Hz, 1H). | 1.08 | 1 |
| 120 | (3,4,5-trichlorophenyl)aminomethyl-benzofuran-2-carboxylic acid structure | MS (m − 1) = 369.9; $^1$H NMR (400 MHz, METHANOL-d$_4$) δ 4.39 (s, 2H), 6.71 (s, 2H), 7.39-7.49 (m, 2H), 7.51-7.61 (m, 1H), 7.68 (d, J = 1.0 Hz, 1H). | 1.14 | 7 |
| 121 | (3-chloro-4-propylphenyl)aminomethyl-benzofuran-2-carboxylic acid structure | MS (m + 1) = 343.8; $^1$H NMR (400 MHz, DMSO-d$_6$) δ 0.86 (t, J = 7.3 Hz, 3H), 1.48 (sxt, J = 7.5 Hz, 2H), 2.43-2.48 (m, 2H), 4.29 (d, J = 5.6 Hz, 2H), 6.35 (t, J = 5.8 Hz, 1H), 6.51 (dd, J = 8.4, 2.4 Hz, 1H), 6.59 (d, J = 2.3 Hz, 1H), 6.95 (d, J = 8.3 Hz, 2H), 7.28 (dd, J = 8.4, 1.7 Hz, 1H), 7.47 (d, J = 8.4 Hz, 1H), 7.56 (d, J = 1.1 Hz, 1H). | 1.50 | 1 |
| 122 | (4-propyl-3-trifluoromethylphenyl)aminomethyl-benzofuran-2-carboxylic acid structure | MS (m + 1) = 377.9; $^1$H NMR (400 MHz, DMSO-d$_6$) δ 0.88 (t, J = 7.3 Hz, 3H), 1.49 (sxt, J = 7.5 Hz, 2H), 2.45 (m, 2H), 4.35 (d, J = 5.5 Hz, 2H), 6.56 (t, J = 5.7 Hz, 1H), 6.76 (dd, J = 8.4, 2.20 Hz, 1H), 6.87 (d, J = 2.3 Hz, 1H), 7.10 (d, J = 8.4 Hz, 1H), 7.23 (br. s., 1 H), 7.37 (d, J = 8.4 Hz, 1 H), 7.51-7.57 (m, 1H), 7.64 (s, 1H). | 1.49 | 3 |
| 123 | (3,4-dichlorophenyl)aminomethyl-benzofuran-2-carboxylic acid structure | MS (m + 1) = 337.1; $^1$H NMR (400 MHz, DMSO-d$_6$) δ 4.31 (d, J = 5.8 Hz, 2H), 6.59 (dd, J = 8.9, 2.7 Hz, 1H), 6.70 (t, J = 5.9 Hz, 1H), 6.77 (d, J = 2.7 Hz, 1H), 6.89 (d, J = 0.8 Hz, 1H), 7.19-7.28 (m, 2H), 7.46 (d, J = 8.5 Hz, 1H), 7.55 (d, J = 1.1 Hz, 1H). | 1.03 | 7 |
| 124 | (4-ethyl-3-trifluoromethylphenyl)aminomethyl-benzofuran-2-carboxylic acid structure | MS (m + 1) = 363.8; $^1$H NMR (400 MHz, DMSO-d$_6$) δ 1.10 (t, J = 7.5 Hz, 3H), 2.55 (q, J = 7.4 Hz, 2H), 4.33 (d, J = 5.8 Hz, 2H), 6.55 (t, J = 5.9 Hz, 1H), 6.77 (dd, J = 8.4, 2.2 Hz, 1 H), 6.87 (d, J = 2.3 Hz, 1 H), 6.94 (d, J = 0.6 Hz, 1 H), 7.11 (d, J = 8.4 Hz, 1 H), 7.28 (dd, J = 8.4, 1.7 Hz, 1H), 7.46 (d, J = 8.4 Hz, 1H), 7.57 (d, J = 0.9 Hz, 1H). | 1.43 | 4 |

TABLE 1-continued

| Example | Compound | Characterization | LCMS RT (min) | LCMS Method |
|---------|----------|------------------|---------------|-------------|
| 125 | (4-trifluoromethyl-3-propylphenyl)aminomethyl benzofuran-2-carboxylic acid | MS (m + 1) = 377.9; $^1$H NMR (400 MHz, DMSO-d$_6$) δ 0.87 (t, J = 7.3 Hz, 3H), 1.50 (sxt, J = 7.5 Hz, 2H), 2.51-2.56 (m, 2H), 4.42 (br. s., 2H), 6.48 (dd, J = 8.6, 2.0 Hz, 1H), 6.59 (d, J = 1.8 Hz, 1H), 6.92 (br. s., 1H), 7.28 (d, J = 8.7 Hz, 1H), 7.49 (dd, J = 8.7, 1.5 Hz, 1H), 7.63-7.69 (m, 2H), 7.73 (d, J = 1.0 Hz, 1H). | 1.49 | 3 |
| 126 | (4-chloro-3-propylphenyl)aminomethyl benzofuran-2-carboxylic acid | MS (m + 1) = 343.7; $^1$H NMR (400 MHz, DMSO-d$_6$) δ 0.86 (t, J = 7.3 Hz, 3H), 1.50 (sxt, J = 7.5 Hz, 2H), 2.47-2.54 (m, 2H), 4.29 (d, J = 5.7 Hz, 2H), 6.31 (t, J = 5.8 Hz, 1H), 6.43 (dd, J = 8.7, 2.8 Hz, 1H), 6.54 (d, J = 2.7 Hz, 1H), 6.92 (s, 1H), 7.00 (d, J = 8.6 Hz, 1H), 7.27 (dd, J = 8.4, 1.5 Hz, 1H), 7.45 (d, J = 8.4 Hz, 1H), 7.55 (s, 1H). | 1.46 | 3 |
| 127 | (4-trifluoromethoxy-3-trifluoromethylphenyl)aminomethyl 6-fluorobenzofuran-2-tetrazole | MS (m + 1) = 476.2; 1H NMR (400 MHz, DMSO-d6) δ 4.42 (s, 2H), 4.69 (q, J = 8.9 Hz, 2H), 6.46 (br. s., 1H), 6.83 (dd, J = 8.9, 2.8 Hz, 1H), 6.93 (d, J = 2.8 Hz, 1H), 7.14 (d, J = 9.1 Hz, 1H), 7.72 (d, J = 0.6 Hz, 1H), 7.75-7.84 (m, 2H). | 1.32 | 1 |
| 128 | (4-propyl-3-trifluoromethylphenyl)aminomethyl 6-fluorobenzofuran-2-tetrazole | MS (m + 1) = 420.1; 1H NMR (400 MHz, DMSO-d6) δ 0.89 (t, J = 7.3 Hz, 3H), 1.50 (sxt, J = 7.5 Hz, 2H), 4.42 (s, 2H), 6.58 (br. s., 1H), 6.78 (dd, J = 8.4, 2.3 Hz, 1H), 6.91 (d, J = 2.5 Hz, 1H), 7.14 (d, J = 8.4 Hz, 1H), 7.73 (s, 1H), 7.75-7.84 (m, 2H). | 1.67 | 3 |
| 129 | (3,4-dichlorophenyl)aminomethyl 6-fluorobenzofuran-2-tetrazole | MS (m + 1) = 378; 1H NMR (400 MHz, DMSO-d6) δ 4.41 (br. s., 2H), 6.61 (dd, J = 8.8, 2.7 Hz, 1H), 6.74 (br. s., 1H), 6.82 (d, J = 2.7 Hz, 1H), 7.26 (d, J = 8.8 Hz, 1H), 7.73 (d, J = 0.6 Hz, 1H), 7.75-7.81 (m, 2H). | 1.53 | 3 |
| 130 | (4-trifluoromethoxy-3-trifluoromethylphenyl)aminomethyl 6-fluorobenzofuran-2-tetrazole | MS (m + 1) = 462.1; 1H NMR (400 MHz, DMSO-d6) δ 4.47 (d, J = 2.9 Hz, 2H), 6.90 (dd, J = 9.1, 2.8 Hz, 1H), 6.98-7.05 (m, 2H), 7.33 (d, J = 8.9 Hz, 1H), 7.74 (d, J = 0.6 Hz, 1H), 7.77-7.84 (m, 2H). | 1.61 | 3 |
| 131 | (3-bromo-4-trifluoromethoxyphenyl)aminomethyl 6-fluorobenzofuran-2-tetrazole | MS (m + 1) = ; 1H NMR (400 MHz, DMSO-d6) δ 4.42 (br. s., 2H), 6.66 (dd, J = 8.9, 2.8 Hz, 1H), 6.80 (br. s., 1H), 6.95 (d, J = 2.8 Hz, 1H), 7.21 (dd, J = 9.0, 1.2 Hz, 1H), 7.75 (d, J = 0.6 Hz, 1H), 7.76-7.83 (m, 2H). | 1.38 | 1 |

TABLE 1-continued

| Example | Compound | Characterization | LCMS RT (min) | LCMS Method |
|---|---|---|---|---|
| 132 | (structure) | MS (m + 1) = 444.1; 1H NMR (400 MHz, DMSO-d6) δ 4.45 (br. s., 2H), 6.79 (br. s., 1H), 6.84-6.89 (m, 1 H), 6.99 (d, J = 2.9 Hz, 1 H), 7.05 (t, J = 72 Hz, 1H), 7.17 (d, J = 8.8 Hz, 1H), 7.73 (d, J = 0.9 Hz, 1H), 7.75-7.84 (m, 2H). | 1.51 | 3 |
| 133 | (structure) | MS (m + 1) = 526.1; 1H NMR (400 MHz, DMSO-d6) δ 4.55 (d, J = 5.5 Hz, 2H), 7.29 (s, 2H), 7.40 (t, J = 5.7 Hz, 1H), 7.73 (s, 1H), 7.78-7.85 (m, 2H). | 1.45 | 1 |
| 134 | (structure) | MS (m + 1) = 460.2; 1H NMR (400 MHz, DMSO-d6) δ 4.47 (s, 2H), 6.81 (dd, J = 9.0, 2.8 Hz, 1H), 6.97 (d, J = 2.8 Hz, 1H), 7.05 (t, J = 72.0 Hz, 1H), 7.18 (d, J = 8.9 Hz, 1H), 7.76 (s, 1H), 7.83 (s, 1H), 8.02 (d, J = 0.6 Hz, 1H). | 1.34 | 1 |
| 135 | (structure) | MS (m + 1) = 492.1; 1H NMR (400 MHz, DMSO-d6) δ 4.44 (s, 2H), 4.69 (q, J = 8.9 Hz, 2H), 6.55 (br. s., 1 H), 6.77 (dd, J = 8.9, 2.8 Hz, 1H), 6.92 (d, J = 2.8 Hz, 1H), 7.14 (d, J = 9.1 Hz, 1H), 7.75 (d, J = 1.0 Hz, 1H), 7.83 (s, 1H), 8.01 (d, J = 0.6 Hz, 1H). | 1.38 | 1 |
| 136 | (structure) | MS (m + 1) = 490; 1H NMR (400 MHz, DMSO-d6) δ 4.44 (br. s., 2H), 6.62 (dd, J = 9.0, 2.8 Hz, 1H), 6.86 (br. s., 1H), 6.93 (d, J = 2.7 Hz, 1H), 7.21 (dd, J = 8.9, 1.2 Hz, 1H), 7.75 (d, J = 0.9 Hz, 1H), 7.82 (s, 1H), 8.02 (s, 1H). | 1.66 | 3 |
| 137 | (structure) | MS (m + 1) = 542; 1H NMR (400 MHz, DMSO-d6) δ 4.56 (d, J = 5.4 Hz, 2H), 7.26 (s, 2H), 7.44 (t, J = 5.6 Hz, 1H), 7.74 (d, J = 0.7 Hz, 1H), 7.86 (s, 1H), 8.04 (s, 1H). | 1.73 | 3 |
| 138 | (structure) | MS (m + 1) = 428.1; 1H NMR (400 MHz, DMSO-d6) δ 4.50 (d, J = 5.6 Hz, 2H), 6.62 (dd, J = 8.8, 1.8 Hz, 1 H), 6.84 (d, J = 2.1 Hz, 1 H), 7.32 (t, J = 5.8 Hz, 1H), 7.48 (d, J = 8.8 Hz, 1H), 7.72 (s, 1H), 7.80 (s, 1H), 8.03 (s, 1H). | 1.4 | 1 |

TABLE 1-continued

| Example | Compound | Characterization | LCMS RT (min) | LCMS Method |
|---|---|---|---|---|
| 139 | (3,4-dichlorophenyl-NH-CH2-[6-chlorobenzofuran-2-yl]-tetrazole) | MS (m + 1) = 396; 1H NMR (400 MHz, DMSO-d6) δ 4.43 (d, J = 4.3 Hz, 2H), 6.57 (dd, J = 8.9, 2.8 Hz, 1H), 6.74-6.85 (m, 2H), 7.27 (d, J = 8.8 Hz, 1H), 7.73 (s, 1H), 7.79 (s, 1H), 8.01 (s, 1H). | 1.6 | 3 |
| 140 | (3-bromo-4-trifluoromethoxyphenyl-NH-CH2-[4-fluorobenzofuran-2-yl]-tetrazole) | MS (m + 1) = 474; 1H NMR (400 MHz, DMSO-d6) δ 4.44 (s, 2H), 6.67 (dd, J = 9.1, 2.8 Hz, 1H), 6.78 (br. s., 1H), 6.95 (d, J = 2.8 Hz, 1H), 7.20 (dd, J = 8.9, 1.2 Hz, 1H), 7.45-7.54 (m, 1H), 7.63 (dd, J = 8.6, 0.7 Hz, 1H), 7.80 (d, J = 0.9 Hz, 1H). | 1.00 | 4 |
| 141 | (4-difluoromethoxy-3-trifluoromethylphenyl-NH-CH2-[4-fluorobenzofuran-2-yl]-tetrazole) | MS (m + 1) = 442.2; 1H NMR (400 MHz, DMSO-d6) δ 4.46 (s, 2H), 6.78 (br. s., 1H), 6.88 (dd, J = 9.0, 2.9 Hz, 1H), 6.98 (d, J = 2.8 Hz, 1H), 7.04 (t, J = 72.0 Hz, 1H), 7.17 (d, J = 8.8 Hz, 1H), 7.47-7.54 (m, 1H), 7.62 (dd, J = 8.6, 0.86 Hz, 1H), 7.80 (d, J = 0.9 Hz, 1H). | 1.51 | 3 |
| 142 | (4-(trifluoromethoxymethoxy)-3-trifluoromethylphenyl-NH-CH2-[4-fluorobenzofuran-2-yl]-tetrazole) | MS (m + 1) = 476.1; 1H NMR (400 MHz, DMSO-d6) δ 4.43 (s, 2H), 4.68 (q, J = 8.8 Hz, 2H), 6.85 (dd, J = 8.9, 2.8 Hz, 1H), 6.92 (d, J = 2.8 Hz, 1H), 7.14 (d, J = 9.1 Hz, 1H), 7.46-7.54 (m, 1H), 7.61 (dd, J = 8.6, 0.9 Hz, 1H), 7.79 (d, J = 0.7 Hz, 1H). | 1.55 | 3 |
| 143 | (4-bromo-3,5-bis(trifluoromethyl)phenyl-NH-CH2-[4-fluorobenzofuran-2-yl]-tetrazole) | MS (m + 1) = 524.1; 1H NMR (400 MHz, DMSO-d6) δ 4.55 (d, J = 5.1 Hz, 2H), 7.30 (s, 2H), 7.39 (t, J = 5.6 Hz, 1H), 7.47-7.56 (m, 1H), 7.61-7.67 (m, 1H), 7.80 (s, 1H). | 1.05 | 4 |
| 144 | (4-trifluoromethoxy-3-trifluoromethylphenyl-NH-CH2-[4-fluorobenzofuran-2-yl]-tetrazole) | MS (m + 1) = 462.1; 1H NMR (400 MHz, DMSO-d6) δ 4.48 (br. s., 2H), 6.91 (dd, J = 9.1, 2.8 Hz, 1H), 7.00 (br. s., 1H), 7.02 (d, J = 2.9 Hz, 1H), 7.33 (d, J = 8.9 Hz, 1H), 7.48-7.55 (m, 1H), 7.63 (dd, J = 8.6, 0.9 Hz, 1H), 7.80 (d, J = 0.9 Hz, 1H). | 1.02 | 4 |

TABLE 1-continued

| Example | Compound | Characterization | LCMS RT (min) | LCMS Method |
|---|---|---|---|---|
| 145 | (structure) | MS (m + 1) = 444.1; 1H NMR (400 MHz, DMSO-d6) δ 4.44 (br. s., 2H), 6.81-6.85 (m, 1H), 6.88 (br. s., 1H), 6.95 (d, J = 2.8 Hz, 1H), 7.03 (t, J = 76.0 Hz, 1H), 7.15 (d, J = 8.9 Hz, 1H), 7.39 (d, J = 11.9 Hz, 1H), 7.62 (s, 1H), 7.79 (d, J = 2.7 Hz, 1H). | 0.94 | 4 |
| 146 | (structure) | MS (m + 1) = 462; 1H NMR (400 MHz, DMSO-d6) δ 4.46 (br. s., 2H), 6.87 (dd, J = 9.1, 2.9 Hz, 1H), 7.00 (d, J = 2.9 Hz, 1H), 7.10 (br. s., 1H), 7.31 (d, J = 9.1 Hz, 1H), 7.41 (dd, J = 11.9, 1.2 Hz, 1H), 7.63 (d, J = 1.1 Hz, 1H), 7.82 (d, J = 2.8 Hz, 1H). | 1.01 | 4 |
| 147 | (structure) | MS (m + 1) = 476.1; 1H NMR (400 MHz, DMSO-d6) δ 4.41 (s, 2H), 4.67 (q, J = 8.9 Hz, 2H), 6.81 (dd, J = 9.0, 2.8 Hz, 1H), 6.90 (d, J = 2.9 Hz, 1H), 7.12 (d, J = 8.9 Hz, 1H), 7.40 (dd, J = 11.9, 1.2 Hz, 1H), 7.62 (d, J = 1.1 Hz, 1H), 7.81 (d, J = 2.8 Hz, 1H). | 0.98 | 4 |
| 148 | (structure) | MS (m + 1) = 472; 1H NMR (400 MHz, DMSO-d6) δ 4.41 (br. s., 2H), 6.64 (dd, J = 9.1, 2.8 Hz, 1H), 6.92 (d, J = 2.7 Hz, 2H), 7.15-7.23 (m, 1H), 7.39 (dd, J = 11.9, 1.2 Hz, 1H), 7.62 (d, J = 1.2 Hz, 1H), 7.81 (d, J = 2.8 Hz, 1H). | 0.98 | 4 |
| 149 | (structure) | MS (m + 1) = 456.3; 1H NMR (400 MHz, DMSO-d6) δ 4.35 (d, J = 5.7 Hz, 2H), 6.65 (dd, J = 9.0, 2.8 Hz, 1H), 6.80 (t, J = 5.8 Hz, 1H), 6.92 (d, J = 2.8 Hz, 1H), 7.14 (s, 1H), 7.18 (dq, J = 9.0, 1.3 Hz, 1H), 7.28 (dd, J = 8.4, 1.8 Hz, 1H), 7.59 (d, J = 8.5 Hz, 1H), 7.62 (d, J = 1.1 Hz, 1H). | 1.35 | 1 |
| 150 | (structure) | MS (m + 1) = 412.1; 1H NMR (400 MHz, DMSO-d6) δ 4.49 (br. s., 2H), 6.86 (dd, J = 8.8, 2.8 Hz, 1H), 6.94 (br. s., 1H), 7.09 (d, J = 2.81 Hz, 1H), 7.35 (d, J = 8.68 Hz, 1H), 7.63-7.70 (m, 2H), 7.73 (d, J = 5.75 Hz, 1H). | 1.35 | 1 |

TABLE 1-continued

| Example | Compound | Characterization | LCMS RT (min) | LCMS Method |
|---|---|---|---|---|
| 151 | (structure) | MS (m + 1) = 526.1; 1H NMR (400 MHz, DMSO-d6) δ 4.61 (d, J = 5.5 Hz, 2H), 7.30 (s, 2H), 7.39 (dd, J = 8.0, 6.17 Hz, 1H), 7.43 (t, J = 5.9 Hz, 1H), 7.62 (d, J = 8.1 Hz, 1H), 7.78 (d, J = 2.7 Hz, 1H). | 1.05 | 5 |
| 152 | (structure) | MS (m + 1) = 444.3; 1H NMR (400 MHz, DMSO-d6) δ 4.43 (d, J = 4.9 Hz, 2H), 6.75 (t, J = 5.3 Hz, 1H), 6.89 (dd, J = 8.9, 2.7 Hz, 1H), 7.00 (d, J = 2.8 Hz, 1H), 7.04 (t, J = 76 Hz, 1H), 7.13-7.19 (m, 2H), 7.47 (d, J = 10.0 Hz, 1H), 7.62 (d, J = 5.8 Hz, 1H). | 1.27 | 1 |
| 153 | (structure) | MS (m + 1) = 488.3; 1H NMR (400 MHz, DMSO-d6) δ 3.92 (s, 3H), 4.36 (s, 2H), 4.67 (q, J = 8.9 Hz, 2H), 6.40 (br. s., 1H), 6.79 (dd, J = 9.0, 2.63 Hz, 1H), 6.91 (d, J = 2.8 Hz, 1H), 7.12 (d, J = 9.1 Hz, 1H), 7.37 (s, 1H), 7.55 (s, 1H), 7.65 (s, 1H). | 1.02 | 9 |
| 154 | (structure) | MS (m + 1) = 476.2; 1H NMR (400 MHz, DMSO-d6) δ 4.46 (br. s., 2H), 4.68 (q, J = 8.9 Hz, 2H), 6.45 (br. s., 1H), 6.85 (dd, J = 9.0, 2.75 Hz, 1H), 6.94 (d, J = 2.1 Hz, 1H), 7.07 (t, J = 56.0 Hz, 1H), 7.14 (d, J = 8.9 Hz, 1H), 7.31 (dd, J = 8.1 6.2 Hz, 1H), 7.43 (d, J = 2.8 Hz, 1H), 7.48 (d, J = 8.1 Hz, 1H). | 1.29 | 1 |
| 155 | (structure) | MS (m + 1) = 495.2; 1H NMR (400 MHz, DMSO-d6) δ 4.42 (d, J = 5.4 Hz, 2H), 5.13 (s, 2H), 6.59 (t, J = 5.9 Hz, 1H), 6.83 (dd, J = 8.9, 2.8 Hz, 1H), 6.91-6.97 (m, 1H), 7.07 (s, 1H), 7.18-7.23 (m, 1H), 7.30 (s, 1H), 7.68 (s, 1H), 8.01 (s, 1H). | 1.25 | 1 |
| 156 | (structure) | MS (m + 1) = 505.2; 1H NMR (400 MHz, DMSO-d6) δ 4.44 (d, J = 5.8 Hz, 2H), 6.78-6.89 (m, 2H), 6.93-7.00 (m, 2H), 7.03-7.09 (m, 1H), 7.14-7.25 (m, 2H), 7.26 (s, 1H), 7.66 (S, 1H), 8.00 (s, 1H). | 1.35 | 1 |

TABLE 1-continued

| Example | Compound | Characterization | LCMS RT (min) | LCMS Method |
|---|---|---|---|---|
| 157 | (structure: 5-chloro-benzofuran-tetrazole with CH2-NH linker to 4-(OCHF2)-3-(CF3)phenyl) | MS (m + 1) = 474.1; 1H NMR (400 MHz, DMSO-d6) δ 4.25 (td, J = 14.6, 3.67 Hz, 2H), 4.44 (br. s., 2H), 6.29 (tt, J = 52.0, 4.0 Hz, 1H), 6.47 (br. s., 1H), 6.79 (dd, J = 8.9, 2.8 Hz, 1H), 6.92 (d, J = 2.8 Hz, 1H), 7.11 (d, J = 9.1 Hz, 1H), 7.38 (s, 1 H), 7.68 (s, 1H), 7.85 (s, 1 H). | 1.33 | 1 |
| 158 | (structure: 5-fluoro-benzofuran-tetrazole with CH2-NH linker to 3,4-bis(CF3)phenyl) | MS (m + 1) = 446; 1H NMR (400 MHz, DMSO-d6) δ 4.53 (d, J = 5.8 Hz, 2H), 6.90-7.12 (m, 2H), 7.22 (d, J = 2.2 Hz, 2H), 7.37 (d, J = 0.7 Hz, 1H), 7.48 (t, J = 5.8 Hz, 1H), 7.57 (d, J = 9.9 Hz, 1H), 7.65 (d, J = 8.8 Hz, 1H), 7.71 (d, J = 5.8 Hz, 1H). | 1.04 | 10 |
| 159 | (structure: 5-fluoro-benzofuran-tetrazole with CH2-NH linker to 4-bromo-3,5-bis(CF3)phenyl) | MS (m + 1) = 526.2; 1H NMR (400 MHz, DMSO-d6) δ 4.51 (d, J = 5.6 Hz, 2H), 7.15 (d, J = 0.6 Hz, 1H), 7.31 (s, 2H), 7.37 (t, J = 5.8 Hz, 1H), 7.49 (d, J = 10.0 Hz, 1H), 7.68 (d, J = 5.9 Hz, 1H). | 1.45 | 1 |
| 160 | (structure: 5-fluoro-benzofuran-tetrazole with CH2-NH linker to 3-bromo-4-isopropylphenyl) | MS (m + 1) = 430.1; 1H NMR (400 MHz, DMSO-d6) δ 1.11 (d, J = 6.9 Hz, 6H), 4.41 (s, 2H), 6.41 (br. s., 1 H), 6.64 (dd, J = 8.5, 2.4 Hz, 1H), 6.83 (d, J = 2.5 Hz, 1H), 7.06 (d, J = 8.4 Hz, 1H), 7.60-7.72 (m, 3 H). | 1.04 | 5 |
| 161 | (structure: 5-fluoro-benzofuran-tetrazole with CH2-NH linker to 4-ethoxy-3-(CF3)phenyl) | MS (m + 1) = 422.2; 1H NMR (400 MHz, DMSO-d6) δ 1.25 (t, J = 7.0 Hz, 3H), 3.98 (q, J = 7.0 Hz, 2H), 4.43 (s, 2H), 6.83 (dd, J = 8.9, 2.8 Hz, 1H), 6.91 (d, J = 2.8 Hz, 1H), 7.02 (d, J = 8.9 Hz, 1H), 7.62-7.69 (m, 2H), 7.71 (d, J = 5.8 Hz, 1 H). | 0.97 | 5 |
| 162 | (structure: 5-fluoro-benzofuran-tetrazole with CH2-NH linker to 4-(OCHF2)-3-(CF3)phenyl) | MS (m + 1) = 458; 1H NMR (400 MHz, DMSO-d6) δ 4.25 (td, J = 14.6, 3.67 Hz, 2H), 4.40 (s, 2H), 6.85 (dd, J = 8.9, 2.8 Hz, 1H), 6.89-7.00 (m, 2H), 7.10 (d, J = 8.9 Hz, 1H), 7.21 (d, J = 0.7 Hz, 2H), 7.48 (d, J = 10.0 Hz, 1H), 7.63 (d, J = 5.9 Hz, 1H). | 0.98 | 10 |
| 163 | (structure: 5-fluoro-benzofuran-tetrazole with CH2-NH linker to 4-isopropoxy-3-(CF3)phenyl) | MS (m + 1) = 436.2; 1H NMR (400 MHz, DMSO-d6) δ 1.19 (d, J = 6.0 Hz, 6H), 4.42 (s, 2H), 4.50 (dt, J = 12.1, 6.1 Hz, 1H), 6.83 (dd, J = 8.8, 2.8 Hz, 1H), 6.88 (d, J = 2.8 Hz, 1H), 7.04 (d, J = 8.9 Hz, 1H), 7.62-7.69 (m, 2H), 7.72 (d, J = 5.8 Hz, 1H). | 1.36 | 1 |

TABLE 1-continued

| Example | Compound | Characterization | LCMS RT (min) | LCMS Method |
|---|---|---|---|---|
| 164 | 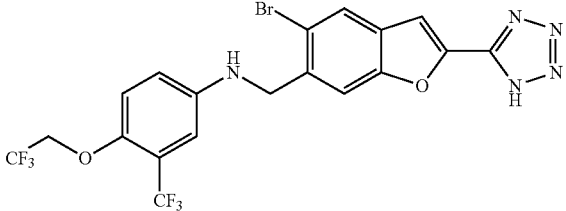 | MS (m + 1) = 538.2; 1H NMR (400 MHz, DMSO-d6) δ 4.40 (d, J = 5.8 Hz, 2H), 4.68 (q, J = 8.9 Hz, 2H), 6.51 (t, J = 5.9 Hz, 1H), 6.79 (dd, J = 8.9, 2.8 Hz, 1 H), 6.93 (d, J = 2.8 Hz, 1 H), 7.07-7.17 (m, 3H), 7.63 (s, 1H), 7.93 (s, 1H). | 1.47 | 1 |
| 165 | 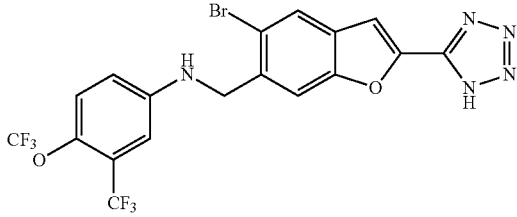 [SMILES: "CF3" ; Oc1ccc(NCc2cc3oc(-c4nnn[nH]4)cc3cc2Br)cc1C(F)(F)F] | MS (m + 1) = 524.2; 1H NMR (400 MHz, DMSO-d6) δ 4.45 (d, J = 5.6 Hz, 2H), 6.86 (dd, J = 9.1, 2.8 Hz, 1 H), 6.99-7.05 (m, 2H), 7.21 (d, J = 0.89 Hz, 2H), 7.33 (d, J = 8.9 Hz, 1H), 7.69 (s, 1H), 7.98 (s, 1H). | 1.48 | 1 |
| 166 | 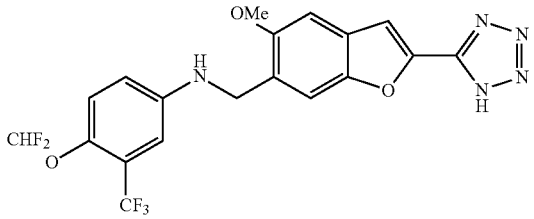 | MS (m + 1) = 456.2; 1H NMR (400 MHz, DMSO-d6) δ 3.92 (s, 3H), 4.38 (br. s., 2 H), 6.72 (br. s., 1H), 6.82 (dd, J = 8.9, 2.8 Hz, 1H), 6.97 (d, J = 2.8 Hz, 1H), 7.03 (t, J = 72.0 Hz, 1H), 7.15 (d, J = 8.9 Hz, 1H), 7.38 (s, 1H), 7.55 (s, 1H), 7.65 (d, J = 0.7 Hz, 1H). | 1.31 | 1 |
| 167 | 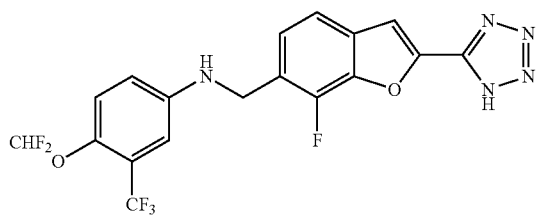 | MS (m + 1) = 444.1; 1H NMR (400 MHz, DMSO-d6) δ 4.52 (br. s., 2H), 6.82 (br. s., 1H), 6.88 (dd, J = 9.0, 2.9 Hz, 1H), 6.98 (d, J = 2.8 Hz, 1H), 7.04 (t, J = 76.0 Hz, 1H), 7.17 (d, J = 8.9 Hz, 1H), 7.38 (dd, J = 8.1, 6.1 Hz, 1H), 7.60 (d, J = 8.1 Hz, 1H), 7.77 (d, J = 2.8 Hz, 1H). | 1.25 | 1 |
| 168 | 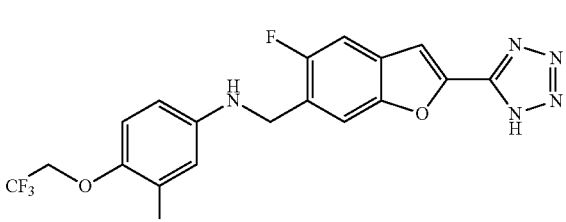 | MS (m + 1) = 476.1; 1H NMR (400 MHz, DMSO-d6) δ 4.41 (br. s., 2H), 4.68 (q, J = 8.9 Hz, 2H), 6.42 (br. s., 1H), 6.87 (dd, J = 9.0, 2.8 Hz, 1H), 6.95 (d, J = 2.7 Hz, 1H), 7.14 (d, J = 8.9 Hz, 1H), 7.24 (s, 1H), 7.49 (d, J = 10.0 Hz, 1H), 7.64 (d, J = 5.9 Hz, 1H). | 1.03 | 5 |
| 169 | 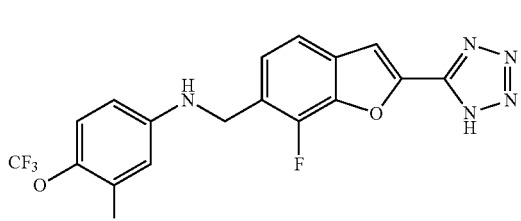 | MS (m + 1) = 462.1; 1H NMR (400 MHz, DMSO-d6) δ 4.53 (br. s., 2H), 6.91 (dd, J = 9.1, 2.9 Hz, 1H), 7.03 (d, J = 2.9 Hz, 2H), 7.33 (d, J = 8.9 Hz, 1H), 7.39 (dd, J = 8.1, 6.1 Hz, 1H), 7.61 (d, J = 8.1 Hz, 1H), 7.78 (d, J = 2.8 Hz, 1H). | 1.37 | 1 |

TABLE 1-continued

| Example | Compound | Characterization | LCMS RT (min) | LCMS Method |
|---|---|---|---|---|
| 170 | 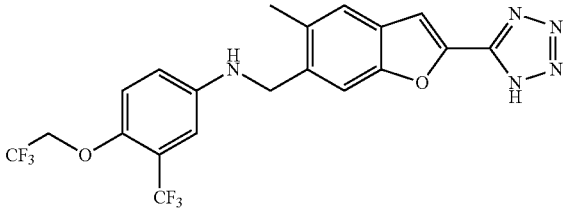 [SMILES: Cc1cc2cc(-c3nnn[nH]3)oc2cc1CNc1ccc(OCC(F)(F)F)c(C(F)(F)F)c1] | MS (m + 1) = 472.2; 1H NMR (400 MHz, DMSO-d6) δ 2.40 (s, 3H), 4.31 (d, J = 5.6 Hz, 2H), 4.68 (q, J = 8.9 Hz, 2H), 6.30 (t, J = 5.6 Hz, 1H), 6.83 (dd, J = 8.9, 2.7 Hz, 1H), 6.94 (d, J = 2.8 Hz, 1H), 7.01 (d, J = 1.0 Hz, 1H), 7.14 (d, J = 8.9 Hz, 1H), 7.44 (s, 1H), 7.48 (s, 1H). | 1.05 | 5 |
| 171 | 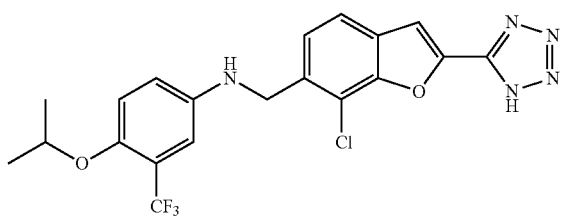 [SMILES: CC(C)Oc1ccc(NCc2ccc3cc(-c4nnn[nH]4)oc3c2Cl)cc1C(F)(F)F] | MS (m + 1) = 452; 1H NMR (400 MHz, DMSO-d6) δ 1.19 (d, J = 6.0 Hz, 6H), 4.45 (s, 2H), 4.47-4.55 (m, 1H), 6.32 (br. s., 1H), 6.77 (dd, J = 8.9, 2.8 Hz, 1H), 6.85 (d, J = 2.9 Hz, 1H), 7.04 (d, J = 8.9 Hz, 1H), 7.32-7.40 (m, 2H), 7.61 (d, J = 8.0 Hz, 1H). | 1.57 | 3 |
| 172 | 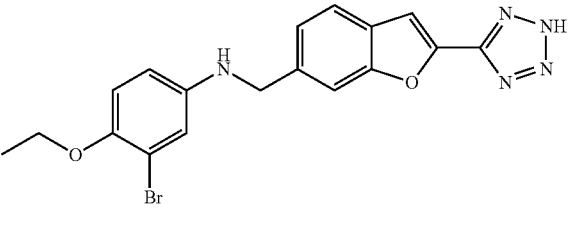 [SMILES: CCOc1ccc(NCc2ccc3cc(-c4nn[nH]n4)oc3c2)cc1Br] | MS (m + 1) = 414.2; 1H NMR (400 MHz, DMSO-d6) d ppm 1.20-1.30 (m, 3H) 3.85-3.95 (m, 2H) 4.25-4.35 (m, 2H) 6.06-6.23 (m, 1H) 6.49-6.62 (m, 1 H) 6.81-6.89 (m, 2H) 7.00-7.08 (m, 1H) 7.19-7.27 (m, 1H) 7.49-7.64 (m, 2 H) | 1.35 | 11 |
| 173 | 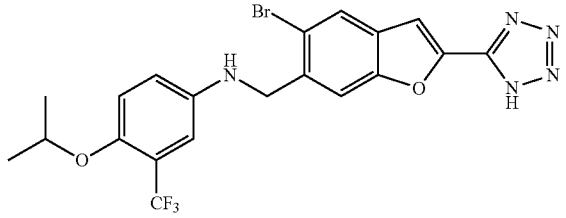 | MS (m + 1) = 498.3; 1H NMR (400 MHz, DMSO-d6) δ 1.20 (d, J = 6.0 Hz, 6H), 4.39 (s, 2H), 4.50 (dt, J = 12.1, 6.1 Hz, 1H), 6.36 (br. s., 1H), 6.76 (dd, J = 9.0, 2.8 Hz, 1H), 6.86 (d, J = 2.8 Hz, 1H), 7.02 (t, J = 40 Hz, 1H), 7.07 (d, J = 3.7 Hz, 1H), 7.34 (s, 1H), 7.68 (s, 1H), 8.01 (s, 1H). | 1.45 | 1 |
| 174 | 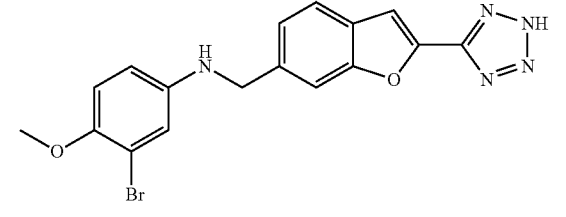 [SMILES: COc1ccc(NCc2ccc3cc(-c4nn[nH]n4)oc3c2)cc1Br] | MS (m + 1) = 401.2; 1H NMR (400 MHz, DMSO-d6) δ 3.67 (s, 3H), 4.33 (s, 2H), 6.60 (dd, J = 8.8, 2.7 Hz, 1H), 6.83-6.89 (m, 2H), 7.09 (s, 1H), 7.25 (dd, J = 8.0, 1.4 Hz, 1H), 7.52-7.62 (m, 2H). | 1.1 | 1 |
| 175 | 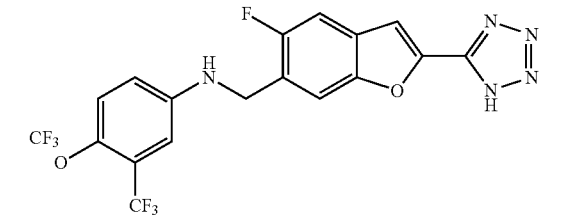 [SMILES: "CF3" ; Oc1ccc(NCc2cc3oc(-c4nnn[nH]4)cc3cc2F)cc1C(F)(F)F] | MS (m + 1) = 462.3; 1H NMR (400 MHz, DMSO-d6) δ 4.49 (d, J = 5.6 Hz, 2H), 6.89-6.95 (m, 1H), 7.00 (t, J = 5.8 Hz, 1H), 7.05 (d, J = 2.9 Hz, 1H), 7.33 (d, J = 9.1 Hz, 1H), 7.60 (s, 1H), 7.64 (d, J = 9.8 Hz, 1H), 7.74 (d, J = 5.8 Hz, 1H). | 1.39 | 1 |

TABLE 1-continued

| Example | Compound | Characterization | LCMS RT (min) | LCMS Method |
|---|---|---|---|---|
| 176 | | MS (m + 1) = 396.1; 1H NMR (400 MHz, DMSO-d6) δ 4.40 (d, J = 5.9 Hz, 2H), 6.60 (t, J = 6.0 Hz, 1H), 6.86-6.96 (m, 2H), 7.07 (d, J = 0.9 Hz, 1H), 7.15-7.23 (m, 1H), 7.44 (d, J = 10.0 Hz, 1H), 7.62 (d, J = 5.9 Hz, 1H). | 1.29 | 1 |
| 177 | | MS (m + 1) = 458.1; 1H NMR (400 MHz, DMSO-d6) δ 4.51 (d, J = 5.6 Hz, 2H), 6.71 (dd, J = 8.7, 2.1 Hz, 1 H), 7.25 (t, J = 5.8 Hz, 1H), 7.46 (d, J = 8.8 Hz, 1H), 7.65-7.70 (m, 2H), 7.73 (d, J = 5.8 Hz, 1H). | 1.35 | 1 |
| 178 | | MS (m + 1) = 484.2; 1H NMR (400 MHz, DMSO-d6) δ 1.25 (t, J = 7.0 Hz, 3H), 3.98 (q, J = 7.0 Hz, 2H), 4.38 (d, J = 3.8 Hz, 2H), 6.33 (br. s., 1H), 6.76 (dd, J = 8.9, 2.8 Hz, 1H), 6.89 (d, J = 2.8 Hz, 1H), 7.02 (d, J = 9.1 Hz, 1H), 7.12 (s, 1 H), 7.64 (s, 1H), 7.93 (s, 1H). | 1.4 | 1 |
| 179 | | MS (m + 1) = 429; 1H NMR (400 MHz, DMSO-d6) δ 4.58 (d, J = 5.8 Hz, 2H), 7.19 (t, J = 5.9 Hz, 1H), 7.47 (d, J = 2.8 Hz, 1H), 7.65 (s, 1H), 7.83 (s, 1H), 7.98 (s, 1H), 8.03 (d, J = 2.8 Hz, 1H). | 1.28 | 1 |
| 180 | | MS (m + 1) = 424; 1H NMR (400 MHz, DMSO-d6) δ 4.37 (d, J = 5.8 Hz, 2H), 6.63-6.70 (m, 2H), 6.99 (d, J = 2.7 Hz, 1H), 7.07 (d, J = 0.9 Hz, 1H), 7.25 (d, J = 8.7 Hz, 1H), 7.44 (d, J = 10.2 Hz, 1H), 7.61 (d, J = 5.9 Hz, 1H). | 1.35 | 1 |
| 181 | | MS (m + 1) = 416; 1H NMR (400 MHz, DMSO-d6) δ 1.07 (t, J = 7.5 Hz, 3H), 2.52 (m, 2H), 4.42 (s, 2H), 6.41 (br. s., 1H), 6.60 (dd, J = 8.3, 2.5 Hz, 1H), 6.84 (d, J = 2.5 Hz, 1H), 7.02 (d, J = 8.3 Hz, 1H), 7.59-7.71 (m, 3H). | 1 | 5 |
| 182 | | MS (m + 1) = 406; 1H NMR (400 MHz, DMSO-d6) δ 4.37 (d, J = 5.9 Hz, 2H), 6.64 (dd, J = 8.8, 2.7 Hz, 1H), 6.74 (t, J = 6.0 Hz, 1H), 6.95 (d, J = 2.7 Hz, 1H), 7.05 (d, J = 0.9 Hz, 1H), 7.23 (dd, J = 8.8, 2.5 Hz, 2H), 7.54-7.61 (m, 2H). | 1.31 | 1 |

TABLE 1-continued

| Example | Compound | Characterization | LCMS RT (min) | LCMS Method |
|---|---|---|---|---|
| 183 | | MS (m + 1) = 472.1; 1H NMR (400 MHz, DMSO-d6) δ 4.45 (br. s., 2H), 6.69 (dd, J = 8.9, 2.81 Hz, 1H), 6.80 (br. s., 1H), 6.98 (d, J = 2.8 Hz, 1H), 7.21 (dd, J = 8.9, 1.2 Hz, 1H), 7.62-7.71 (m, 2H), 7.73 (d, J = 5.8 Hz, 1 H). | 1.04 | 5 |
| 184 | | MS (m + 1) = 477.9; 1H NMR (400 MHz, DMSO-d6) δ 4.54 (d, J = 5.8 Hz, 2H), 6.86 (dd, J = 9.1, 2.8, 1 H), 7.00-7.06 (m, 2H), 7.07 (t, J = 52 Hz, 1H), 7.33 (d, J = 9.3 Hz, 1H), 7.51 (s, 1H), 7.68 (d, J = 8.1 Hz, 1H). | 1.62 | 3 |
| 185 | | MS (m + 1) = 534; 1H NMR (400 MHz, DMSO-d6) δ 4.46 (d, J = 4.5 Hz, 2H), 6.84 (t, J = 5.3 Hz, 1H), 6.90 (t, J = 72.0 Hz, 1H), 6.97 (s, 2H), 7.64-7.69 (m, 2H), 7.74 (d, J = 5.8 Hz, 1H). | 1.52 | 1 |
| 186 | | MS (m + 1) = 428; 1H NMR (400 MHz, DMSO-d6) δ 4.46 (br. s., 2H), 6.66 (dd, J = 9.1, 2.8 Hz, 1H), 6.83 (d, J = 2.7 Hz, 2H), 7.23 (dd, J = 9.1, 1.2 Hz, 1H), 7.63-7.70 (m, 2H), 7.73 (d, J = 5.8 Hz, 1H). | 1.61 | 3 |
| 187 | | MS (m + 1) = 492; 1H NMR (400 MHz, DMSO-d6) δ 4.50 (d, J = 2.9 Hz, 2H), 4.68 (q, J = 8.8 Hz, 2H), 6.53 (br. s., 1H), 6.79 (dd, J = 9.1, 2.8 Hz, 1H), 6.91 (d, J = 2.8 Hz, 1H), 7.07 (t, J = 52 Hz, 1H), 7.14 (d, J = 9.1 Hz, 1H), 7.39 (d, J = 8.1 Hz, 1H), 7.52 (s, 1H), 7.66 (d, J = 8.1 Hz, 1H). | 1.56 | 3 |
| 188 | | MS (m + 1) = 414.1; 1H NMR (400 MHz, DMSO-d6) δ 2.37 (d, J = 0.9 Hz, 3H), 4.47 (s, 2H), 6.44 (d, J = 1.1 Hz, 1H), 6.55 (d, J = 2.1 Hz, 1H), 6.70 (d, J = 2.1 Hz, 1H), 7.66 (s, 1H), 7.72 (s, 1H), 7.96 (s, 1H). | 1.39 | 1 |
| 189 | | MS (m + 1) = 542.3; 1H NMR (400 MHz, DMSO-d6) δ 4.59 (d, J = 5.6 Hz, 2H), 7.28 (s, 2H), 7.44 (t, J = 5.8 Hz, 1H), 7.67 (s, 1H), 7.82 (s, 1H), 7.99 (s, 1H). | 1.52 | 1 |

TABLE 1-continued

| Example | Compound | Characterization | LCMS RT (min) | LCMS Method |
|---|---|---|---|---|
| 190 | | MS (m + 1) = 370.2; 1H NMR (400 MHz, DMSO-d6) δ 0.85 (t, J = 7.3 Hz, 3H), 1.47 (sxt, J = 7.4 Hz, 2H), 2.38 (t, J = 7.5 Hz, 2H), 4.41 (s, 2H), 6.31-6.45 (m, 3 H), 6.93 (t, J = 8.6 Hz, 1H), 7.62-7.72 (m, 3H). | 1.59 | 4 |
| 191 | | MS (m + 1) = 463.2; 1H NMR (400 MHz, DMSO-d6) δ 4.43 (d, J = 5.8 Hz, 2H), 6.85 (t, J = 5.9 Hz, 1H), 6.92-6.98 (m, 2H), 7.00 (d, J = 2.9 Hz, 1H), 7.14 (t, J = 76, 1H), 7.20 (s, 1H), 7.35 (s, 1H), 7.67 (s, 1H), 8.03 (s, 1H). | 1.16 | 1 |
| 192 | | MS (m + 1) = 412.1; 1H NMR (400 MHz, DMSO-d6) δ 4.45 (d, J = 3.2 Hz, 2H), 6.50 (dt, J = 9.1, 1.4 Hz, 1 H), 6.63 (dd, J = 13.6, 2.7 Hz, 1H), 6.85 (br. s., 1H), 7.20 (td, J = 9.0, 0.9 Hz, 1 H), 7.62-7.70 (m, 2H), 7.73 (d, J = 5.8 Hz, 1H). | 1 | 4 |
| 193 | | MS (m + 1) = 474; 1H NMR (400 MHz, DMSO-d6) δ 4.49 (br. s., 2H), 6.67 (dd, J = 8.9, 2.8 Hz, 1H), 6.93 (br. s., 1H), 6.95 (d, J = 2.8 Hz, 1H), 7.20 (dd, J = 9.1, 1.2 Hz, 1H), 7.37 (dd, J = 8.0, 6.2 Hz, 1H), 7.60 (d, J = 8.1 Hz, 1H), 7.78 (d, J = 2.8 Hz, 1H). | 1.35 | 1 |
| 194 | | MS (m + 1) = 380.1; 1H NMR (400 MHz, DMSO-d6) δ 2.37 (d, J = 1.1 Hz, 3H), 4.38 (s, 2H), 6.26 (s, 1H), 6.42 (d, J = 1.2 Hz, 1H), 6.60 (d, J = 2.1 Hz, 1H), 6.67 (d, J = 2.1 Hz, 1H), 7.08 (d, J = 0.9 Hz, 1H), 7.27 (dd, J = 8.0, 1.4 Hz, 1H), 7.57 (d, J = 8.0 Hz, 1H), 7.61 (s, 1H). | 1.24 | 1 |
| 195 | | MS (m + 1) = 392.1; 1H NMR (400 MHz, DMSO-d6) δ 2.24 (s, 3H), 4.48 (br. s., 2 H), 6.67 (s, 2H), 6.73 (d, J = 8.0 Hz, 2H), 7.62-7.70 (m, 2H), 7.72 (d, J = 5.8 Hz, 1H). | 1.55 | 3 |
| 196 | | MS (m + 1) = 412.1; 1H NMR (400 MHz, DMSO-d6) δ 4.52 (d, J = 5.4 Hz, 2H), 6.69 (dd, J = 8.7, 2.0 Hz, 1 H), 6.88 (d, J = 2.2 Hz, 1 H), 7.28 (t, J = 5.8 Hz, 1H), 7.47 (d, J = 8.8 Hz, 1H), 7.64-7.71 (m, 2H), 7.74 (d, J = 5.8 Hz, 1H). | 1.35 | 1 |

TABLE 1-continued

| Example | Compound | Characterization | LCMS RT (min) | LCMS Method |
|---|---|---|---|---|
| 197 |  | MS (m + 1) = 401.1; 1H NMR (400 MHz, DMSO-d6) δ 4.44 (d, J = 5.8 Hz, 2H), 6.78 (t, J = 6.1 Hz, 1H), 6.95 (d, J = 1.6 Hz, 1H), 6.97-7.02 (m, 1H), 7.06 (d, J = 12.5 Hz, 1H), 7.13 (t, J = 76.0 Hz, 1H), 7.19 (d, J = 8.1 Hz, 2H), 7.35 (s, 1H), 7.55 (d, J = 9.9 Hz, 1 H), 7.67 (d, J = 5.9 Hz, 1H). | 0.87 | 5 |
| 198 | 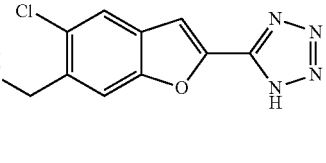 | MS (m + 1) = 428.2; 1H NMR (400 MHz, DMSO-d6) δ 4.59 (d, J = 5.6 Hz, 2H), 7.28 (s, 2H), 7.43 (t, J = 5.8 Hz, 1H), 7.64 (s, 1H), 7.82 (s, 1H), 7.98 (s, 1H). | 1.43 | 1 |
| 199 | 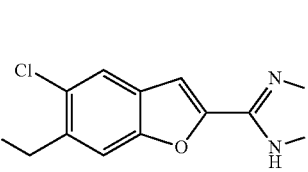 | MS (m + 1) = 426.1; 1H NMR (400 MHz, DMSO-d6) δ 4.46 (br. s., 2H), 6.58 (dd, J = 8.9, 2.8 Hz, 1H), 6.71 (br. s., 1H), 6.75 (d, J = 2.8 Hz, 1H), 6.97 (7, J = 72.0 Hz, 1 H), 7.09 (d, J = 8.9 Hz, 1 H), 7.66 (d, J = 0.7 Hz, 1 H), 7.71 (s, 1H), 7.96 (s, 1 H). | 1.49 | 3 |
| 200 | 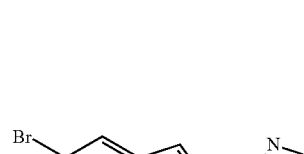 | MS (m + 1) = 463.2; 1H NMR (400 MHz, DMSO-d6) δ 4.43 (d, J = 5.8 Hz, 2H), 6.85 (t, J = 5.9 Hz, 1H), 6.92-6.98 (m, 2H), 7.00 (d, J = 2.9 Hz, 1H), 7.14 (t, J = 76, 1H), 7.20 (s, 1H), 7.35 (s, 1H), 7.67 (s, 1H), 8.03 (s, 1H). | 1.21 | 1 |
| 201 | 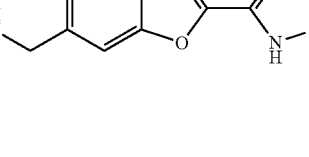 | MS (m + 1) = 446.1; 1H NMR (400 MHz, DMSO-d6) δ 4.51 (d, J = 5.3 Hz, 2H), 6.94 (dd, J = 5.0, 2.9 Hz, 2 H), 7.02 (dd, J = 5.8, 2.9 Hz, 1H), 7.67 (d, J = 0.7 Hz, 1H), 7.79 (s, 1H), 7.98 (s, 1H). | 1.47 | 1 |
| 202 | 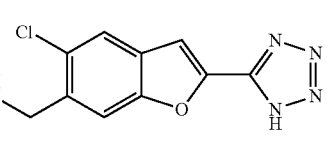 | MS (m + 1) = 417.3; 1H NMR (400 MHz, DMSO-d6) δ 4.48 (d, J = 5.6 Hz, 2H), 6.79 (t, J = 5.7 Hz, 1H), 6.92-6.97 (m, 1H), 7.01 (d, J = 2.9 Hz, 1H), 7.16 (s, 1H), 7.19 (d, J = 8.9 Hz, 1 H), 7.23 (d, J = 72.0 Hz, 1 H), 7.30 (d, J = 8.1 Hz, 1 H), 7.57 (d, J = 8.0 Hz, 1H). | 1.15 | 1 |
| 203 | 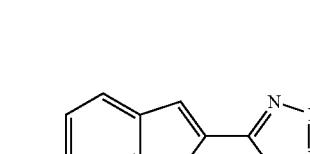 | MS (m + 1) = 396.1; 1H NMR (400 MHz, DMSO-d6) δ 4.51 (d, J = 5.6 Hz, 2H), 6.54-6.66 (m, 2H), 7.32 (t, J = 5.7 Hz, 1H), 7.38 (t, J = 8.7 Hz, 1H), 7.64-7.69 (m, 2H), 7.74 (d, J = 5.8 Hz, 1 H). | 1.51 | 3 |

TABLE 1-continued

| Example | Compound | Characterization | LCMS RT (min) | LCMS Method |
|---|---|---|---|---|
| 204 | | MS (m + 1) = 395.1; 1H NMR (400 MHz, DMSO-d6) δ 4.52 (d, J = 5.9 Hz, 2H), 7.23 (t, J = 6.0 Hz, 1H), 7.29-7.37 (m, 2H), 7.44 (d, J = 2.9 Hz, 1H), 7.65-7.72 (m, 2H), 8.02 (d, J = 2.9 Hz, 1H). | 1.17 | 1 |
| 205 | | MS (m + 1) = 442.1; 1H NMR (400 MHz, DMSO-d6) δ 4.36 (br. s., 2H), 4.60 (q, J = 8.9 Hz, 2H), 6.28 (br s., 1H), 6.59 (dd, J = 8.9, 2.8 Hz, 1H), 6.74 (d, J = 2.7 Hz, 1H), 7.03 (d, J = 8.9 Hz, 1H), 7.16 (s, 1H), 7.46 (d, J = 10.0 Hz, 1H), 7.61 (d, J = 5.9 Hz, 1H). | 1.31 | 1 |
| 206 | | MS (m + 1) = 438; 1H NMR (400 MHz, DMSO-d6) δ 1.25 (t, J = 7.0 Hz, 3H) 3.98 (q, J = 7.0 Hz, 2H), 4.46 (s, 2H), 6.33 (br. s., 1H), 6.74-6.79 (m, 1H), 6.88 (s, 1H), 7.02 (s, 1H), 7.37 (d, J = 8.1 Hz, 1H), 7.40 (s, 1H), 7.62 (d, J = 8.1 Hz, 1H). | 1.51 | 3 |
| 207 | | MS (m + 1) = 436.2; 1H NMR (400 MHz, DMSO-d6) δ 1.14 (d, J = 6.9 Hz, 6H), 3.01-3.14 (m, 2H), 4.44 (d, J = 3.7 Hz, 2H), 6.62 (br. s., 1H), 6.81 (dd, J = 8.6, 2.32 Hz, 1H), 6.88 (s, 1H), 7.21 (s, 1H), 7.31 (d, J = 8.6 Hz, 1H), 7.66 (s, 1H), 7.79 (s, 1H). | 1.6 | 3 |
| 208 | | MS (m + 1) = 378.1; 1H NMR (400 MHz, DMSO-d6) δ 4.44 (d, J = 4.4 Hz, 2H), 6.64 (dd, J = 8.8, 2.7 Hz, 1H), 6.74 (br. s., 1H), 6.84 (d, J = 2.7 Hz, 1H), 7.26 (d, J = 8.8 Hz, 1H), 7.61-7.67 (m, 2H), 7.71 (d, J = 5.9 Hz, 1H). | 1.33 | 1 |
| 209 | | MS (m + 1) = 363.3; 1H NMR (400 MHz, DMSO-d6) δ 2.52 (s, 3H), 4.55 (s, 2H), 7.05 (d, J = 2.1 Hz, 1H), 7.10 (dd, J = 8.8, 2.2 Hz, 1H), 7.47 (dd, J = 8.2, 1.3 Hz, 1H), 7.69 (d, J = 0.9 Hz, 1H), 7.74-7.82 (m, 3H). | 1.07 | 1 |
| 210 | | MS (m + 1) = 449.3; 1H NMR (400 MHz, DMSO-d6) δ 4.49 (d, J = 5.3 Hz, 2H), 5.13 (s, 2H), 6.56 (t, J = 5.8 Hz, 1H), 6.83 (dd, J = 8.9, 2.8 Hz, 1H), 6.94 (d, J = 3.1 Hz, 1H), 7.13 (d, J = 44.0 Hz, 1H), 7.20 (d, J = 2.8 Hz, 1H), 7.32 (s, 1H), 7.35 (d, J = 8.1 Hz, 1H), 7.61 (d, J = 8.1 Hz, 1H). | 1.18 | 1 |

TABLE 1-continued

| Example | Compound | Characterization | LCMS RT (min) | LCMS Method |
|---|---|---|---|---|
| 211 | (structure) | MS (m + 1) = 388.1; 1H NMR (400 MHz, DMSO-d6) δ 1.26 (t, J = 7.0 Hz, 3H), 3.92 (q, J = 7.0 Hz, 2H), 4.39 (s, 2H), 6.56 (dd, J = 8.8, 2.8 Hz, 1H), 6.72 (d, J = 2.8 Hz, 1H), 6.90 (d, J = 8.9 Hz, 1H), 7.64 (d, J = 9.8 Hz, 1H), 7.67-7.73 (m, 2H). | 0.92 | 5 |
| 212 | (structure) | MS (m + 1) = 444.2; 1H NMR (400 MHz, DMSO-d6) δ 4.49 (d, J = 5.4 Hz, 2H), 6.53-6.60 (m, 2H), 6.68 (t, J = 19.1 Hz, 1H), 7.07 (t, J = 5.8 Hz, 1H), 7.67 (s, 1H), 7.76 (s, 1H), 7.97 (s, 1H). | 1.5 | 1 |
| 213 | (structure) | MS (m + 1) = 408.2; 1H NMR (400 MHz, DMSO-d6) δ 2.24 (s, 3H), 4.50 (br. s., 2H), 6.68 (s, 2H), 6.70-6.79 (m, 2H), 7.67 (d, J = 0.7 Hz, 1H), 7.72 (s, 1H), 7.97 (s, 1H). | 1.43 | 1 |
| 214 | (structure) | MS (m + 1) = 362.1; 1H NMR (400 MHz, DMSO-d6) δ 4.44 (br. s., 2H), 6.51 (dt, J = 8.8, 13.9 Hz, 1H), 6.61 (dd, J = 12.5, 2.7 Hz, 1H), 6.77 (br. s., 1H), 7.20 (t, J = 8.7 Hz, 1H), 7.62-7.69 (m, 2H), 7.71 (d, J = 5.9 Hz, 1H). | 1.26 | 1 |
| 215 | (structure) | MS (m + 1) = 362.1; 1H NMR (400 MHz, DMSO-d6) δ 4.42 (s, 2H), 6.47 (br. s., 1H), 6.57-6.63 (m, 1H), 6.76 (dd, J = 6.3, 2.9 Hz, 1H), 7.11 (t, J = 9.2 Hz, 1H), 7.65 (d, J = 9.8 Hz, 1H), 7.68 (d, J = 0.9 Hz, 1H), 7.71 (d, J = 5.8 Hz, 1H). | 1.46 | 1 |
| 216 | (structure) | MS (m + 1) = 444.2; 1H NMR (400 MHz, DMSO-d6) δ ppm 0.90-1.00 (m, 6H) 1.88-2.01 (m, 1H) 3.58-3.67 (m, 2H) 4.28-4.40 (m, 2H) 6.53-6.63 (m, 1H) 6.80-6.88 (m, 2H) 6.93-7.13 (m, 1H) 7.16-7.21 (m, 1H) 7.23-7.31 (m, 1H) 7.55-7.66 (m, 2H) | 1.52 | 11 |
| 217 | (structure) | MS (m + 1) = 404.1; 1H NMR (400 MHz, DMSO-d6) δ 1.27 (t, J = 7.0 Hz, 3H), 3.92 (q, J = 7.0 Hz, 2H), 4.42 (s, 2H), 6.51 (dd, J = 8.8, 2.8 Hz, 1H), 6.69 (d, J = 2.7 Hz, 1H), 6.91 (d, J = 8.8 Hz, 1H), 7.67 (d, J = 0.9 Hz, 1H), 7.70 (s, 1H), 7.95 (s, 1H). | 1.5 | 3 |

TABLE 1-continued

| Example | Compound | Characterization | LCMS RT (min) | LCMS Method |
|---|---|---|---|---|
| 218 | | MS (m + 1) = 394.3; 1H NMR (400 MHz, DMSO-d6) δ 4.50 (d, J = 5.8 Hz, 2H), 6.53-6.62 (m, 1H), 6.67 (t, J = 9.8 Hz, 1H), 6.92 (d, J = 9.0 Hz, 1H), 7.20 (dd, J = 11.9, 2.1 Hz, 1H), 7.30 (d, J = 0.9 Hz, 1H), 7.32 (dd, J = 8.2, 1.3 Hz, 1H), 7.60-7.70 (m, 2H). | 1.3 | 1 |
| 219 | | MS (m + 1) = 422.3; 1H NMR (400 MHz, DMSO-d6) δ 4.42 (d, J = 5.8 Hz, 2H), 6.80 (t, J = 5.9 Hz, 1H), 6.90 (d, J = 2.8 Hz, 1H), 7.00 (dd, J = 9.2, 2.8 Hz, 1H), 7.06 (d, J = 1.0 Hz, 1H), 7.17 (dt, J = 9.1, 1.1 Hz, 1H), 7.26 (dd, J = 8.0, 1.4 Hz, 1H), 7.59 (d, J = 8.0 Hz, 1H), 7.61 (s, 1H). | 1.32 | 1 |
| 220 | | MS (m + 1) = 416.3; 1H NMR (400 MHz, DMSO-d6) δ 0.91 (t, J = 7.3 Hz, 3H), 1.33-1.48 (m, 2H), 2.18 (s, 3H), 4.42 (s, 2H), 6.38 (br. s., 1H), 6.42-6.49 (m, 2H), 7.62 (s, 1H), 7.69 (s, 1H), 7.94 (s, 1H). | 1.59 | 1 |
| 221 | | MS (m + 1) = 426.2; 1H NMR (400 MHz, DMSO-d6) δ 3.54 (q, J = 11.4 Hz, 3H), 4.43 (s, 2H), 6.41 (br. s., 1H), 6.57 (dt, J = 8.9, 3.5 Hz, 1H), 6.65 (dd, J = 6.1, 2.9 Hz, 1H), 6.98 (t, J = 9.2 Hz, 1H), 7.65 (s, 1H), 7.69 (s, 1H), 7.95 (s, 1H). | 1.34 | 1 |
| 222 | | MS (m + 1) = 428.3; 1H NMR (400 MHz, DMSO-d6) δ 4.53 (d, J = 5.9 Hz, 2H), 6.45 (s, 1H), 6.60 (d, J = 2.3 Hz, 1H), 6.80 (dd, J = 9.0, 2.3 Hz, 1H), 7.10 (d, J = 0.9 Hz, 1H), 7.27 (dd, J = 7.9, 1.5 Hz, 1H), 7.36-7.44 (m, 1H), 7.58-7.63 (m, 2H), 7.71 (t, J = 6.1 Hz, 1H). | 1.19 | 1 |
| 223 | | MS (m + 1) = 436.1; 1H NMR (400 MHz, DMSO-d6) δ 4.43 (d, J = 5.9 Hz, 2H), 6.77-6.84 (m, 2H), 6.90 (s, 1H), 6.96 (d, J = 2.7 Hz, 1H), 7.04 (t, J = 76.0 Hz, 1H), 7.15 (d, J = 8.9 Hz, 1H), 7.53 (s, 1H), 7.72 (s, 1H). | 1.6 | 4 |

TABLE 1-continued

| Example | Compound | Characterization | LCMS RT (min) | LCMS Method |
|---|---|---|---|---|
| 224 | (5-chloro-6-{[(4-(trifluoromethoxy)-3-(trifluoromethyl)phenyl)amino]methyl}benzofuran-2-carboxylic acid) | MS (m + 1) = 468; 1H NMR (400 MHz, DMSO-d6) δ 4.42 (d, J = 5.8 Hz, 2H), 4.68 (q, J = 8.9 Hz, 2H), 6.50 (t, J = 6.0 Hz, 1H), 6.78 (dd, J = 9.0, 2.75 Hz, 1 H), 6.91 (d, J = 2.8 Hz, 1 H), 7.08-7.22 (m, 3H), 7.59 (s, 1H), 7.79 (s, 1H). | 1.4 | 1 |
| 225 | (5-fluoro-6-{[(3-chloro-4-(trifluoromethoxy)phenyl)amino]methyl}benzofuran-2-carboxylic acid) | MS (m + 1) = 418.3; 1H NMR (400 MHz, DMSO-d6) δ 4.34 (d, J = 5.9 Hz, 2H), 4.59 (q, J = 9.0 Hz, 2H), 6.27 (t, J = 6.1 Hz, 1H), 6.56 (dd, J = 8.9, 2.8 Hz, 1 H), 6.72 (d, J = 2.7 Hz, 1 H), 6.98-7.08 (m, 2H), 7.43 (d, J = 10.0 Hz, 1H), 7.52 (d, J = 5.9 Hz, 1H). | 0.93 | 9 |
| 226 | (5-fluoro-6-{[(3-chloro-4-(trifluoromethoxy)phenyl)amino]methyl}benzofuran-2-carboxylic acid) | MS (m + 1) = 404.3; 1H NMR (400 MHz, DMSO-d6) δ 4.39 (d, J = 5.9 Hz, 2H), 6.63 (dd, J = 9.1, 2.8 Hz, 1 H), 6.77 (t, J = 6.0 Hz, 1H), 6.80 (d, J = 2.8 Hz, 1H), 7.13 (br. s., 2H), 7.21 (dd, J = 8.9, 1.2 Hz, 1H), 7.47 (d, J = 10.0 Hz, 1H), 7.57 (d, J = 5.8 Hz, 1H). | 0.97 | 9 |
| 227 | (5-fluoro-6-{[(3-bromo-4-(trifluoromethoxy)phenyl)amino]methyl}benzofuran-2-carboxylic acid) | MS (m + 1) = 448.2; 1H NMR (400 MHz, DMSO-d6) δ 4.39 (d, J = 5.9 Hz, 2H), 6.67 (dd, J = 9.0, 2.8 Hz, 1 H), 6.75 (t, J = 5.9 Hz, 1H), 6.95 (d, J = 2.8 Hz, 1H), 7.13 (br. s., 1H), 7.19 (dd, J = 8.9, 1.2 Hz, 2H), 7.49 (d, J = 9.9 Hz, 1H), 7.58 (d, J = 5.8 Hz, 1H). | 0.98 | 9 |
| 228 | (5-fluoro-6-{[(3-chloro-4-(trifluoromethylthio)phenyl)amino]methyl}benzofuran-2-carboxylic acid) | MS (m + 1) = 420.3; 1H NMR (400 MHz, DMSO-d6) δ 4.44 (d, J = 5.8 Hz, 2H), 6.68 (dd, J = 8.7, 2.6 Hz, 1 H), 6.91 (d, J = 2.6 Hz, 1 H), 7.12 (br. s., 2H), 7.25 (t, J = 5.8 Hz, 1H), 7.44-7.52 (m, 2H), 7.58 (d, J = 5.8 Hz, 1H). | 1.01 | 9 |
| 229 | (5-fluoro-6-{[(4-bromo-3,5-bis(trifluoromethyl)phenyl)amino]methyl}benzofuran-2-carboxylic acid) | MS (m + 1) = 501.8; 1H NMR (400 MHz, DMSO-d6) δ 4.51 (d, J = 5.9 Hz, 2H), 7.23 (br. s., 1H), 7.29 (s, 2 H), 7.35 (t, J = 5.81 Hz, 1H), 7.52 (d, J = 9.9 Hz, 1H), 7.65 (d, J = 5.6 Hz, 1H). | 1.04 | 9 |
| 230 | (5-fluoro-6-{[(4-(difluoromethoxy)-3-(trifluoromethyl)phenyl)amino]methyl}benzofuran-2-carboxylic acid) | MS (m + 1) = 420.3; 1H NMR (400 MHz, DMSO-d6) δ 4.44 (d, J = 5.9 Hz, 2H), 6.76 (t, J = 6.1 Hz, 1H), 6.84-6.89 (m, 1H), 6.98 (d, J = 2.9 Hz, 1H), 7.04 (t, J = 72.0 Hz, 1H), 7.16 (d, J = 8.9 Hz, 1H), 7.29 (br. s., 1H), 7.52 (d, J = 9.9 Hz, 1 H), 7.60 (d, J = 5.8 Hz, 1H). | 0.94 | 9 |

TABLE 1-continued

| Example | Compound | Characterization | LCMS RT (min) | LCMS Method |
|---|---|---|---|---|
| 231 | (structure: 5-fluoro-6-[(3-trifluoromethyl-4-trifluoromethoxyphenylamino)methyl]benzofuran-2-carboxylic acid) | MS (m + 1) = 542.3; 1H NMR (400 MHz, DMSO-d6) δ 4.41 (d, J = 5.5 Hz, 2H), 4.68 (q, J = 8.8 Hz, 2H), 6.42 (t, J = 6.0 Hz, 1H), 6.84 (dd, J = 9.0, 2.75 Hz, 1H), 6.93 (d, J = 2.8 Hz, 1H), 7.13 (d, J = 9.1 Hz, 2H), 7.30 (br. s., 1H), 7.51 (d, J = 9.9 Hz, 1H), 7.60 (d, J = 5.8 Hz, 1H). | 0.97 | 9 |
| 232 | (structure: 5-fluoro-6-[(3,4,5-trichlorophenylamino)methyl]benzofuran-2-carboxylic acid) | MS (m + 1) = 388.3; 1H NMR (400 MHz, DMSO-d6) δ 4.40 (d, J = 5.9 Hz, 2H), 6.86 (s, 2H), 6.89 (t, J = 5.9 Hz, 1H), 7.12 (br. s., 1H), 7.48 (d, J = 9.9 Hz, 1H), 7.59 (d, J = 5.8 Hz, 1H). | 0.98 | 9 |
| 233 | (structure: 3-(tetrazol-5-yl)-6-[(3-bromo-4-trifluoromethoxyphenylamino)methyl]benzofuran) | MS (m + 2) = 456.2; $^1$H NMR (400 MHz, DMSO-d6) δ 4.40 (d, J = 5.6 Hz, 2H), 6.66 (dd, J = 9.0, 2.8 Hz, 1H), 6.84 (t, J = 5.9 Hz, 1H), 6.93 (d, J = 2.8 Hz, 1H), 7.15-7.20 (m, 2H), 7.27 (dd, J = 8.0, 1.4 Hz, 1H), 7.60-7.65 (m, 2H). | 1.35 | 1 |

Biological Example 1

A patch-clamp assay on the QPatch© automated patch clamp system was employed to assesses whether compounds functionally enhance the cardiac delayed rectifier hERG (human ether-a-go-go-related gene) potassium channel. The assay measures electric the current passing through hERG channels that are heterologously expressed in a stable Chinese hamster ovary (CHO) cell line. Channels are opened by a hERG-specific voltage protocol and the compound effect is directly characterized by the activation of the hERG current. $EC_{50}$ values are obtained from fitting 4-concentration dose response curves (1.1, 3.3, 10 & 30 uM) in triplicates at 4 different sections of the voltage protocol (steady state current amplitude at +10 mV, at +30 mV, peak tail current amplitude and tail current amplitude at 7 second). In the absence of a clear trend of saturation at 30 uM, only increased % current values for the 4 parameters are utilized.

Activity Table: hERG Activator EC - QPatch hERG activator 4-concentration EC50 assay % change@TL7@10 uM

| Ex | % change |
|---|---|
| 1 | 166* |
| 2 | 126* |
| 3 | 121* |
| 4 | 155* |
| 5 | 146 |
| 6 | 264 |
| 7 | 198 |
| 8 | 128 |
| 9 | 78 |
| 10 | 285 |
| 11 | 129 |
| 12 | 85 |
| 13 | 39 |
| 14 | 196 |
| 15 | 162 |
| 16 | 521 |
| 17 | 477 |
| 18 | 409 |
| 19 | 394 |
| 20 | 340 |
| 21 | 333 |
| 22 | 328 |
| 23 | 290 |
| 24 | 280 |
| 25 | 269 |
| 26 | 267 |
| 27 | 261 |
| 28 | 260 |
| 29 | 258 |
| 30 | 228 |
| 31 | 218 |
| 32 | 193 |
| 33 | 192 |
| 34 | 191 |

Activity Table: hERG Activator EC - QPatch hERG activator
4-concentration EC50 assay % change@TL7@10 uM

| Ex | % change |
|---|---|
| 35 | 180 |
| 36 | 174 |
| 37 | 170 |
| 38 | 164 |
| 39 | 164 |
| 40 | 161 |
| 41 | 160 |
| 42 | 159 |
| 43 | 148 |
| 44 | 146 |
| 45 | 145 |
| 46 | 139 |
| 47 | 131 |
| 48 | 123 |
| 49 | 106 |
| 50 | 100 |
| 51 | 99 |
| 52 | 95 |
| 53 | 95 |
| 54 | 94 |
| 55 | 90 |
| 56 | 88 |
| 57 | 76 |
| 58 | 71 |
| 59 | 61 |
| 60 | 58 |
| 61 | 47 |
| 62 | 43 |
| 63 | 34 |
| 64 | 348 |
| 65 | 284 |
| 66 | 261 |
| 67 | 247 |
| 68 | 224 |
| 69 | 221 |
| 70 | 200 |
| 71 | 193 |
| 72 | 176 |
| 73 | 132 |
| 74 | 124 |
| 75 | 123 |
| 76 | 120 |
| 77 | 118 |
| 78 | 108 |
| 79 | 101 |
| 80 | 83 |
| 81 | 74 |
| 82 | 39 |
| 83 | 36 |
| 84 | 29 |
| 85 | 397 |
| 86 | 381 |
| 87 | 326 |
| 88 | 274 |
| 89 | 270 |
| 90 | 247 |
| 91 | 226 |
| 92 | 215 |
| 93 | 212 |
| 94 | 194 |
| 95 | 193 |
| 96 | 185 |
| 97 | 159 |
| 98 | 158 |
| 99 | 157 |
| 100 | 156 |
| 101 | 156 |
| 102 | 153 |
| 103 | 112 |
| 104 | 111 |
| 105 | 105 |
| 106 | 90 |
| 107 | 85 |
| 108 | 82 |
| 109 | 81 |
| 110 | 76 |
| 111 | 65 |
| 112 | 53 |
| 113 | 53 |
| 114 | 45 |
| 115 | 41 |
| 116 | 31 |
| 117 | 28 |
| 118 | 27 |
| 119 | 22 |
| 120 | 282 |
| 121 | 210 |
| 122 | 184 |
| 123 | 183 |
| 124 | 167 |
| 125 | 138 |
| 126 | 64 |
| 127 | 268 |
| 128 | 142 |
| 129 | 154 |
| 130 | 220 |
| 131 | 209 |
| 132 | 371 |
| 133 | 326 |
| 134 | 217 |
| 135 | 181 |
| 136 | 143 |
| 137 | 166 |
| 138 | 196 |
| 139 | 112 |
| 140 | 290 |
| 141 | 144 |
| 142 | 188 |
| 143 | 193 |
| 144 | 236 |
| 145 | 103 |
| 146 | 171 |
| 147 | 151 |
| 148 | 201 |
| 149 | 335 |
| 150 | 218 |
| 151 | 308 |
| 152 | 333* |
| 153 | 381 |
| 154 | 325 |
| 155 | 370 |
| 156 | 356 |
| 157 | 350 |
| 158 | 277 |
| 159 | 388 |
| 160 | 347 |
| 161 | 288 |
| 162 | 372 |
| 163 | 250 |
| 164 | 308 |
| 165 | 307 |
| 166 | 318 |
| 167 | 303 |
| 168 | 240 |
| 169 | 246 |
| 170 | 299 |
| 171 | 291 |
| 172 | 284 |
| 173 | 278 |
| 174 | 273 |
| 175 | 384 |
| 176 | 120 |
| 177 | 215* |
| 178 | 262 |
| 179 | 249 |
| 180 | 231 |
| 181 | 322 |
| 182 | 249 |

-continued

Activity Table: hERG Activator EC - QPatch hERG activator
4-concentration EC50 assay % change@TL7@10 uM

| Ex | % change |
|---|---|
| 183 | 249 |
| 184 | 243 |
| 185 | 234*** |
| 186 | 255 |
| 187 | 230 |
| 188 | 108 |
| 189 | 350 |
| 190 | 167 |
| 191 | 216 |
| 192 | 167 |
| 193 | 243 |
| 194 | 205 |
| 195 | 249 |
| 196 | 169 |
| 197 | 244 |
| 198 | 187 |
| 199 | 228 |
| 200 | 180 |
| 201 | 225 |
| 202 | 174 |
| 203 | 136 |
| 204 | 165 |
| 205 | 222 |
| 206 | 160 |
| 207 | 297 |
| 208 | 285 |
| 209 | 137 |
| 210 | 134 |
| 211 | 248 |
| 212 | 116 |
| 213 | 144 |
| 214 | 138 |
| 215 | 132 |
| 216 | 88 |
| 217 | 116 |
| 218 | 73 |
| 219 | 71 |
| 220 | 148 |
| 221 | 81 |
| 222 | 41 |
| 223 | 176 |
| 224 | 222 |
| 225 | 138 |
| 226 | 182 |
| 227 | 188 |
| 228 | 140 |
| 229 | 424 |
| 230 | 244 |
| 231 | 239 |
| 232 | 247 |
| 233 | 202* |

*@3.3 uM
**@0.3 uM
***@30 uM

What is claimed is:

1. A compound, or salt thereof, of formula (I):

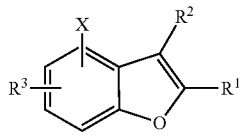

(I)

wherein
$R^1$ is selected from: $CO_2H$ or tetrazole and $R^2$ is selected from: H, halo, $(C_1-C_4)$alkyl or halo-substituted$(C_1-C_4)$alkyl, or $R^1$ is H and $R^2$ is $CO_2H$ or tetrazole;

X is selected from: H, halo, $(C_1-C_4)$alkyl, $(C_1-C_4)$alkoxy, $NR^8R^9$, halo-substituted$(C_1-C_4)$alkyl, phenyl or a 5 to 6 membered heteroaryl containing 1 to 3 heteroatoms each independently selected from O, N, or S, where said phenyl or heteroaryl are optionally substituted with 1 to 2 substituents each independently selected from halo, $(C_1-C_4)$alkyl, $(C_1-C_4)$alkoxy, halo-substituted$(C_1-C_4)$alkyl, hydroxy-substituted$(C_1-C_4)$alkyl, $(C_1-C_4)$alkylamino-substituted$(C_1-C_4)$alkyl, dimethylamino-substituted$(C_1-C_4)$alkyl;

$R^8$ is selected from: H, or $(C_1-C_4)$alkyl;
$R^9$ is selected from: H, or $(C_1-C_4)$alkyl;
$R^3$ is

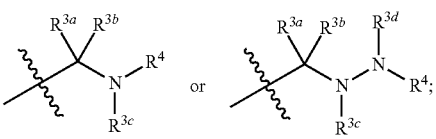

where $R^{3a}$ is selected from: H, $(C_1-C_4)$alkyl or halo-substituted$(C_1-C_4)$alkyl;
$R^{3b}$ is selected from: H, $(C_1-C_4)$alkyl or taken together with $R^{3a}$ forms a 3 to 7 membered saturated cycloalkyl or a 3 to 7 membered saturated heterocycle containing 1 to 2 heteroatoms selected from O, S or N;
$R^{3c}$ is selected from: H or $CH_3$;
$R^{3d}$ is selected from: H or $CH_3$;
$R^4$ is selected from:

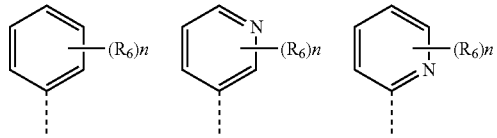

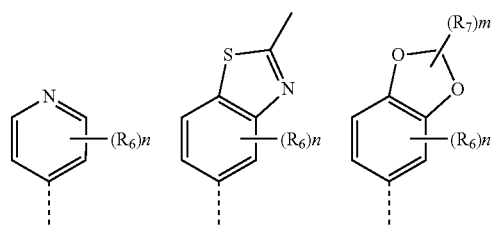

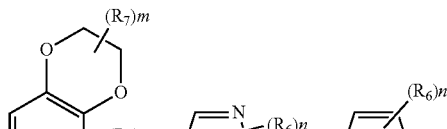

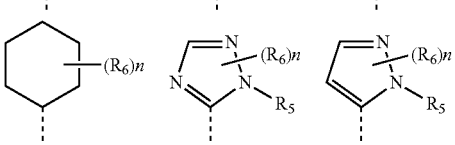

-continued

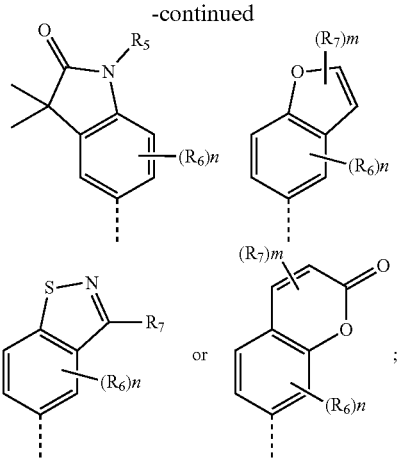

wherein the dotted line indicates the point of attachment;
$R^5$ is selected from: H or $CH_3$;
$R^6$ is independently selected from: halo, nitrile, $(C_1-C_4)$alkyl, halo-substituted$(C_1-C_4)$alkyl, nitrile-substituted $(C_1-C_4)$alkyl, $(C_1-C_4)$alkoxy, halo-substituted$(C_1-C_4)$alkoxy, nitrile-substituted$(C_1-C_4)$alkoxy, $(C_1-C_4)$alkylene, N-acetyl, trifluouroacetyl, $(C_1-C_4)$alkylthio, halo-substituted thio, halo-substituted $(C_1-C_4)$alkylthio, $(C_3-C_6)$cycloalkyl, methylamino-substituted$(C_1-C_4)$alkyl, dimethylamino-substituted$(C_1-C_4)$alkyl, halo-substituted$(C_1-C_4)$ hydroxyalkyl, a 4 to 6 membered saturated heterocycle containing 1 to 2 heteroatoms selected from O, S or N, or a 5 to 6 membered heteroaryl containing 1 to 3 heteroatoms each independently selected from O, N, or S, where said heterocycle or heteroaryl are optionally substituted with 1 to 2 substituents each independently selected from $(C_1-C_4)$alkyl, halo, hydroxyl, amino or $(C_1-C_4)$alkoxy;
$R^7$ is selected from: H or halo;
n is 1, 2 or 3;
m is 0, 1 or 2;
or $R^{3c}$ and $R^4$ taken together with the amine to which $R^{3c}$ and $R^4$ are attached forms a fully saturated 4 to 7 membered heterocycle, where 1 to 2 of the ring carbons are each independently optionally replaced with a N or O, and said heterocycle is optionally substituted with 1 to 2 substituents each independently selected from $(C_1-C_4)$alkoxy, $(C_1-C_4)$alkyl, halo-substituted$(C_1-C_4)$alkyl, hydroxy$(C_1-C_4)$alkyl, cyclopropyl or oxo or a pharmaceutically acceptable salt thereof.

2. A compound, or salt thereof, according to claim 1, wherein
$R^1$ is selected from: $CO_2H$, or tetrazole;
$R^2$ is selected from: H, halo, $(C_1-C_4)$alkyl or halo-substituted$(C_1-C_4)$alkyl;
X is selected from: H, halo, $(C_1-C_4)$alkyl, $(C_1-C_4)$alkoxy, $NR^8R^9$, halo-substituted$(C_1-C_4)$alkyl, phenyl or a 5 to 6 membered heteroaryl containing 1 to 3 heteroatoms each independently selected from O, N, or S, where said phenyl or heteroaryl are optionally substituted with 1 to 2 substituents each independently selected from halo, $(C_1-C_4)$alkyl, $(C_1-C_4)$alkoxy, halo-substituted$(C_1-C_4)$alkyl, hydroxy-substituted$(C_1-C_4)$alkyl, $(C_1-C_4)$alkylamino-substituted$(C_1-C_4)$alkyl, dimethylamino-substituted$(C_1-C_4)$alkyl;
$R^8$ is selected from: H, or $(C_1-C_4)$alkyl;
$R^9$ is selected from: H, or $(C_1-C_4)$alkyl;

$R^3$ is

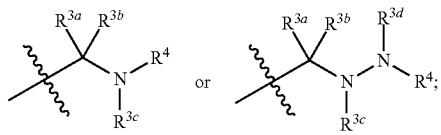

where $R^{3a}$ is selected from: H, $(C_1-C_4)$alkyl or halo-substituted$(C_1-C_4)$alkyl;
$R^{3b}$ is selected from: H, $(C_1-C_4)$alkyl or taken together with $R^{3a}$ forms a 3 to 7 membered saturated cycloalkyl or a 3 to 7 membered saturated heterocycle containing 1 to 2 heteroatoms selected from O, S or N;
$R^{3c}$ is selected from: H or $CH_3$;
$R^{3d}$ is selected from: H or $CH_3$;
$R^4$ is selected from:

wherein the dotted line indicates the point of attachment;
$R^5$ is selected from: H or $CH_3$;
$R^6$ is independently selected from: halo, $(C_1-C_4)$alkyl, halo-substituted$(C_1-C_4)$alkyl, $(C_1-C_4)$alkoxy, halo-substituted$(C_1-C_4)$alkoxy, nitrile-substituted$(C_1-C_4)$alkoxy, $(C_1-C_4)$alkylene, N-acetyl, trifluouroacetyl, $(C_1-C_4)$alkylthio, halo-substituted thio, halo-substituted $(C_1-C_4)$alkylthio, $(C_3-C_6)$cycloalkyl, methylamino-substituted$(C_1-C_4)$alkyl, dimethylamino-substituted ($C_1$-$C_4$)alkyl, halo-substituted($C_1$-$C_4$) hydroxyalkyl, a 4 to 6 membered saturated heterocycle containing 1 to 2 heteroatoms selected from O, S or N, or a 5 to 6 membered heteroaryl containing 1 to 3 heteroatoms each independently selected from O, N, or S, where said heterocycle or heteroaryl are optionally substituted with 1 to 2 substituents each independently selected from ($C_1$-$C_4$)alkyl, halo, hydroxyl, amino or ($C_1$-$C_4$)alkoxy;

$R^7$ is selected from: H or halo;

n is 1, 2 or 3;

m is 0, 1, 2, 3 or 4;

or $R^{3c}$ and $R^4$ taken together with the amine to which $R^{3c}$ and $R^4$ are attached forms a fully saturated 4 to 7 membered heterocycle, where 1 to 2 of the ring carbons are each independently optionally replaced with a N or O, and said heterocycle is optionally substituted with 1 to 2 substituents each independently selected from ($C_1$-$C_4$) alkoxy, ($C_1$-$C_4$)alkyl, halo-substituted($C_1$-$C_4$)alkyl, hydroxy($C_1$-$C_4$)alkyl, cyclopropyl or oxo or a pharmaceutically acceptable salt thereof.

3. The compound of claim 1, or a salt thereof, wherein the compound is of formula (II):

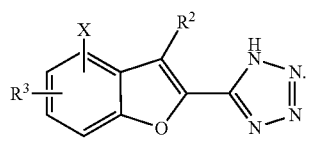

(II)

4. The compound of claim 1, or a salt thereof, wherein the compound is of formula (III):

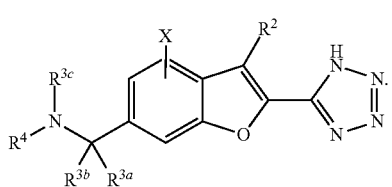

(III)

5. The compound of claim 1, or a salt thereof, wherein the compound is of formula (IV):

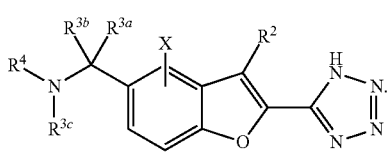

(IV)

6. The compound of claim 1, or a salt thereof, wherein the compound is of formula (V):

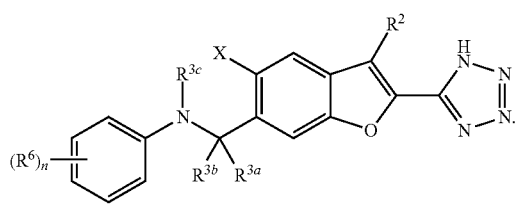

(V)

7. The compound of claim 1, or a salt thereof, wherein the compound is of formula (VI):

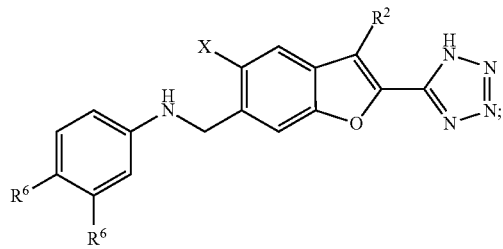

(VI)

wherein, $R^2$ is selected from: H, $CH_3$ or $CF_3$;

X is selected from: H, halo, ($C_1$-$C_4$)alkyl, ($C_1$-$C_4$)alkoxy, halo-substituted($C_1$-$C_4$)alkyl;

$R^6$ is independently selected from: halo, ($C_1$-$C_4$)alkyl, halo-substituted($C_1$-$C_4$)alkyl, ($C_1$-$C_4$)alkoxy, halo-substituted($C_1$-$C_4$)alkoxy; or a pharmaceutically acceptable salt thereof.

8. The compound of claim 1, or a salt thereof, wherein the compound is of formula (VII):

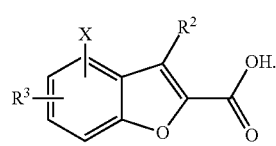

(VII)

9. The compound of claim 1, or a salt thereof, wherein the compound is of formula (VIII):

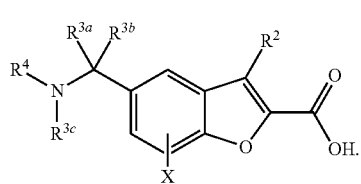

(VIII)

10. The compound of claim 1, or a salt thereof, wherein the compound is of formula (IX):

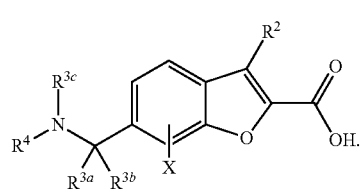

(IX)

11. The compound, or salt thereof, of claim 1, wherein X is selected from: H, halo, ($C_1$-$C_4$)alkyl, ($C_1$-$C_4$)alkoxy, halo-substituted($C_1$-$C_4$)alkyl;

$R^{3b}$ is H; or a pharmaceutically acceptable salt thereof.

12. The compound of claim 1, or a salt thereof, wherein the compound is selected from:

N-((2-(2H-tetrazol-5-yl)benzofuran-6-yl)methyl)-3-bromo-5-fluoro-4-methoxyaniline;

N-((2-(2H-tetrazol-5-yl)benzofuran-6-yl)methyl)-3-bromo-4-ethoxy-5-fluoroaniline;

N-((2-(2H-tetrazol-5-yl)benzofuran-6-yl)methyl)-3-bromo-4-(trifluoromethyl)aniline;
N-((2-(2H-tetrazol-5-yl)benzofuran-6-yl)methyl)-3,5-dibromo-4-(difluoromethoxy)aniline;
3,5-dichloro-N-((5-chloro-2-(1H-tetrazol-5-yl)benzofuran-6-yl)methyl)-4-ethoxyaniline;
N-((5-chloro-2-(1H-tetrazol-5-yl)benzofuran-6-yl)methyl)-4-(trifluoromethoxy)-3-(trifluoromethyl)aniline;
N-((5-chloro-2-(1H-tetrazol-5-yl)benzofuran-6-yl)methyl)-3-fluoro-4-((trifluoromethyl)thio)aniline;
3-chloro-N-((5-chloro-2-(1H-tetrazol-5-yl)benzofuran-6-yl)methyl)-4-(2,2,2-trifluoroethoxy)aniline;
N-((5-chloro-2-(1H-tetrazol-5-yl)benzofuran-6-yl)methyl)-4-fluoro-3-(trifluoromethoxy)aniline;
N-((5-chloro-2-(1H-tetrazol-5-yl)benzofuran-6-yl)methyl)-4-ethoxy-3-(trifluoromethyl)aniline;
N-((2-(2H-tetrazol-5-yl)benzofuran-6-yl)methyl)-3-(prop-1-en-2-yl)-4-(trifluoromethoxy)aniline;
3-chloro-N-((5-chloro-2-(1H-tetrazol-5-yl)benzofuran-6-yl)methyl)-4-propylaniline;
4-chloro-N-((5-chloro-2-(1H-tetrazol-5-yl)benzofuran-6-yl)methyl)-3-(trifluoromethoxy)aniline;
N-((5-chloro-2-(1H-tetrazol-5-yl)benzofuran-6-yl)methyl)-3,4-bis(trifluoromethyl)aniline;
3,4,5-trichloro-N-((5-chloro-2-(1H-tetrazol-5-yl)benzofuran-6-yl)methyl)aniline;
N-((2-(1H-tetrazol-5-yl)benzofuran-6-yl)methyl)-4-propyl-3-(trifluoromethyl)aniline;
N-((2-(2H-tetrazol-5-yl)benzofuran-6-yl)methyl)-3-chloro-4-(difluoromethoxy)aniline;
N-((5-chloro-2-(1H-tetrazol-5-yl)benzofuran-6-yl)methyl)-4-isopropoxy-3-(trifluoromethyl)aniline;
N-((2-(2H-tetrazol-5-yl)benzofuran-6-yl)methyl)-3,4,5-trichloroaniline;
N-((2-(2H-tetrazol-5-yl)benzofuran-6-yl)methyl)-3-chloro-4-((trifluoromethyl)thio)aniline;
N-((2-(2H-tetrazol-5-yl)benzofuran-6-yl)methyl)-3-methyl-4-(trifluoromethoxy)aniline;
N-((5-chloro-2-(1H-tetrazol-5-yl)benzofuran-6-yl)methyl)-4-(2,2,2-trifluoroethoxy)-3-(trifluoromethyl)aniline;
N-((2-(2H-tetrazol-5-yl)benzofuran-6-yl)methyl)-4-(trifluoromethoxy)-3-(trifluoromethyl)aniline;
3-chloro-N-((5-chloro-2-(1H-tetrazol-5-yl)benzofuran-6-yl)methyl)-4-((trifluoromethyl)thio)aniline;
N-((5-chloro-2-(1H-tetrazol-5-yl)benzofuran-6-yl)methyl)-4-(difluoromethoxy)-3-(trifluoromethyl)aniline;
N-((2-(2H-tetrazol-5-yl)benzofuran-6-yl)methyl)-4-(methylthio)-3-(trifluoromethyl)aniline;
N-((2-(2H-tetrazol-5-yl)benzofuran-6-yl)methyl)-4-(2,2,2-trifluoroethoxy)-3-(trifluoromethyl)aniline;
N-((2-(2H-tetrazol-5-yl)benzofuran-6-yl)methyl)-3-(methylthio)aniline;
2-(4-(((5-chloro-2-(1H-tetrazol-5-yl)benzofuran-6-yl)methyl)amino)-2-(trifluoromethyl)phenoxy)acetonitrile;
1-(4-(((2-(1H-tetrazol-5-yl)benzofuran-6-yl)methyl)amino)phenyl)-2,2,2-trifluoroethanone;
N-((5-chloro-2-(1H-tetrazol-5-yl)benzofuran-6-yl)methyl)-4-propyl-3-(trifluoromethyl)aniline;
3-chloro-N-((5-chloro-2-(1H-tetrazol-5-yl)benzofuran-6-yl)methyl)-4-(trifluoromethoxy)aniline;
N-((2-(2H-tetrazol-5-yl)benzofuran-6-yl)methyl)-4-chloroaniline;
3-bromo-N-((5-chloro-2-(1H-tetrazol-5-yl)benzofuran-6-yl)methyl)-4-propylaniline;
N-((2-(2H-tetrazol-5-yl)benzofuran-6-yl)methyl)-3-bromo-4,5-difluoroaniline;
3-bromo-N-((5-chloro-2-(1H-tetrazol-5-yl)benzofuran-6-yl)methyl)-4-(trifluoromethoxy)aniline;
N-((2-(2H-tetrazol-5-yl)benzofuran-6-yl)methyl)-3-bromo-4-(trifluoromethoxy)aniline;
N-((2-(1H-tetrazol-5-yl)-3-(trifluoromethyl)benzofuran-6-yl)methyl)-4-(trifluoromethoxy)-3-(trifluoromethyl)aniline;
N-((2-(2H-tetrazol-5-yl)benzofuran-6-yl)methyl)-4-bromo-3-(trifluoromethyl)aniline;
N-((2-(2H-tetrazol-5-yl)benzofuran-6-yl)methyl)-2,2-difluorobenzo[d][1,3]dioxol-5-amine;
N-((2-(2H-tetrazol-5-yl)benzofuran-6-yl)methyl)-3,4-bis(trifluoromethoxy)aniline;
N-((2-(1H-tetrazol-5-yl)benzofuran-6-yl)methyl)-3-bromo-4-propylaniline;
N-((2-(2H-tetrazol-5-yl)benzofuran-6-yl)methyl)-3-fluoro-4-(trifluoromethoxy)aniline;
N-((2-(2H-tetrazol-5-yl)benzofuran-6-yl)methyl)-3-chloro-4-(2,2,2-trifluoroethoxyl)aniline;
5-(6-((2-(3,4,5-trichlorophenyl)hydrazinyl)methyl)benzofuran-2-yl)-2H-tetrazole;
N-((2-(2H-tetrazol-5-yl)benzofuran-6-yl)methyl)-3-chloro-4-(trifluoromethoxy)aniline;
N-((2-(1H-tetrazol-5-yl)-3-(trifluoromethyl)benzofuran-6-yl)methyl)-3-bromo-4-(trifluoromethoxy)aniline;
N-((2-(2H-tetrazol-5-yl)benzofuran-6-yl)methyl)-4-bromo-3-(trifluoromethoxy)aniline;
N-((2-(1H-tetrazol-5-yl)-3-(trifluoromethyl)benzofuran-6-yl)methyl)-3,5-dichloro-4-ethoxyaniline;
N-((5-chloro-2-(1H-tetrazol-5-yl)benzofuran-6-yl)methyl)-3-fluoro-4-(trifluoromethoxy)aniline;
N-((3-methyl-2-(1H-tetrazol-5-yl)benzofuran-6-yl)methyl)-4-propyl-3-(trifluoromethyl)aniline;
N-((2-(2H-tetrazol-5-yl)benzofuran-6-yl)methyl)-3,4-bis(trifluoromethyl)aniline;
3-bromo-N-((3-methyl-2-(1H-tetrazol-5-yl)benzofuran-6-yl)methyl)-4-(trifluoromethoxy)aniline;
N-((2-(1H-tetrazol-5-yl)-3-(trifluoromethyl)benzofuran-6-yl)methyl)-3-chloro-4-(trifluoromethoxy)aniline;
N-((2-(1H-tetrazol-5-yl)-3-(trifluoromethyl)benzofuran-6-yl)methyl)-4-propyl-3-(trifluoromethyl)aniline;
N-((2-(1H-tetrazol-5-yl)-3-(trifluoromethyl)benzofuran-6-yl)methyl)-4-ethoxy-3-(trifluoromethyl)aniline;
N-((2-(1H-tetrazol-5-yl)-3-(trifluoromethyl)benzofuran-6-yl)methyl)-4-isopropoxy-3-(trifluoromethyl)aniline;
N-((2-(2H-tetrazol-5-yl)benzofuran-6-yl)methyl)-4-fluoro-3-(2,2,2-trifluoroethyl)aniline;
N-((2-(2H-tetrazol-5-yl)benzofuran-6-yl)methyl)-3-bromoaniline;
N-((2-(1H-tetrazol-5-yl)-3-(trifluoromethyl)benzofuran-6-yl)methyl)-4-(difluoromethoxy)-3-(trifluoromethyl)aniline;
N-((2-(1H-tetrazol-5-yl)-3-(trifluoromethyl)benzofuran-6-yl)methyl)-3-chloro-4-(trifluoromethyl)aniline;
N-((2-(2H-tetrazol-5-yl)benzofuran-6-yl)methyl)-3,4,5-trimethoxyaniline;
N-((2-(2H-tetrazol-5-yl)benzofuran-6-yl)methyl)-4-(trifluoromethoxy)aniline;
N-((2-(1H-tetrazol-5-yl)benzofuran-5-yl)methyl)-3-chloro-4-((trifluoromethyl)thio)aniline;
N-((2-(1H-tetrazol-5-yl)benzofuran-5-yl)methyl)-3-chloro-4-(trifluoromethoxy)aniline;
N-((2-(1H-tetrazol-5-yl)benzofuran-5-yl)methyl)-4-propyl-3-(trifluoromethyl)aniline;

N-((2-(1H-tetrazol-5-yl)benzofuran-5-yl)methyl)-2,2-difluorobenzo[d][1,3]dioxol-5-amine;
N-((2-(1H-tetrazol-5-yl)benzofuran-5-yl)methyl)-4-chloro-3-propylaniline;
N-((2-(1H-tetrazol-5-yl)benzofuran-5-yl)methyl)-3-chloro-5-methyl-4-propylaniline;
3-chloro-N-((3-methyl-2-(1H-tetrazol-5-yl)benzofuran-5-yl)methyl)-4-((trifluoromethyl)thio)aniline;
N-((2-(1H-tetrazol-5-yl)benzofuran-5-yl)methyl)-3-chloro-4-propylaniline;
N-((2-(1H-tetrazol-5-yl)benzofuran-5-yl)methyl)-4-fluoro-3-(trifluoromethoxy)aniline;
N-(1-(2-(1H-tetrazol-5-yl)benzofuran-5-yl)ethyl)-3,4,5-trichloroaniline;
N-(1-(2-(1H-tetrazol-5-yl)benzofuran-5-yl)ethyl)-3-chloro-4-((trifluoromethyl)thio)aniline;
N-((2-(1H-tetrazol-5-yl)benzofuran-5-yl)methyl)-3-chloro-5-(trifluoromethoxy)aniline;
N-((2-(1H-tetrazol-5-yl)benzofuran-5-yl)methyl)-4-propyl-3-(trifluoromethoxy)aniline;
N-(1-(2-(1H-tetrazol-5-yl)benzofuran-5-yl)ethyl)-3-chloro-4-(trifluoromethoxy)aniline;
N-((2-(1H-tetrazol-5-yl)benzofuran-5-yl)methyl)-4-ethyl-3-(trifluoromethyl)aniline;
N-((2-(1H-tetrazol-5-yl)benzofuran-5-yl)methyl)-3-fluoro-4-propylaniline;
N-((2-(1H-tetrazol-5-yl)benzofuran-5-yl)methyl)-3-methyl-4-propylaniline;
N-(1-(2-(1H-tetrazol-5-yl)benzofuran-5-yl)ethyl)-4-propyl-3-(trifluoromethyl)aniline;
N-((3-methyl-2-(1H-tetrazol-5-yl)benzofuran-5-yl)methyl)-4-propyl-3-(trifluoromethyl)aniline;
N-(1-(2-(1H-tetrazol-5-yl)benzofuran-5-yl)ethyl)-2,2-difluorobenzo[d][1,3]dioxol-5-amine;
N-(1-(2-(1H-tetrazol-5-yl)benzofuran-5-yl)ethyl)-3-chloro-4-propylaniline;
6-(((3,4,5-tribromophenyl)amino)methyl)benzofuran-2-carboxylic acid;
6-(((3,4,5-trichlorophenyl)amino)methyl)benzofuran-2-carboxylic acid;
6-(((3-chloro-4-((trifluoromethyl)thio)phenyl)amino)methyl)benzofuran-2-carboxylic acid;
6-(((3-chloro-4-(trifluoromethoxy)phenyl)amino)methyl)benzofuran-2-carboxylic acid;
6-(((2,2-difluorobenzo[d][1,3]dioxol-5-yl)amino)methyl)benzofuran-2-carboxylic acid;
6-(((3-bromo-4-(trifluoromethoxy)phenyl)amino)methyl)benzofuran-2-carboxylic acid;
6-(((3-(trifluoromethyl)-4-((trifluoromethyl)thio)phenyl)amino)methyl)benzofuran-2-carboxylic acid;
6-(((4-(trifluoromethoxy)-3-(trifluoromethyl)phenyl)amino)methyl)benzofuran-2-carboxylic acid;
6-(((3-chloro-4-propylphenyl)amino)methyl)benzofuran-2-carboxylic acid;
6-(((2,2,3,3-tetrafluoro-2,3-dihydrobenzo[b][1,4]dioxin-6-yl)amino)methyl)benzofuran-2-carboxylic acid;
6-(((4-propyl-3-(trifluoromethyl)phenyl)amino)methyl)benzofuran-2-carboxylic acid;
6-(((4-(methylthio)-3-(trifluoromethyl)phenyl)amino)methyl)benzofuran-2-carboxylic acid;
6-(((3-(methylthio)phenyl)amino)methyl)benzofuran-2-carboxylic acid;
6-(((3-bromo-4-morpholinophenyl)amino)methyl)benzofuran-2-carboxylic acid;
6-(((4-(pentafluorothio)phenyl)amino)methyl)benzofuran-2-carboxylic acid;
6-(((4-ethyl-3-(trifluoromethyl)phenyl)amino)methyl)benzofuran-2-carboxylic acid;
6-(((3,4-bis(trifluoromethyl)phenyl)amino)methyl)benzofuran-2-carboxylic acid;
6-(((3-methyl-4-(trifluoromethoxy)phenyl)amino)methyl)benzofuran-2-carboxylic acid;
6-(((4-(2,2,2-trifluoroacetyl)phenyl)amino)methyl)benzofuran-2-carboxylic acid;
6-(((3,4-bis(trifluoromethoxy)phenyl)amino)methyl)benzofuran-2-carboxylic acid;
6-(((2,3-dihydrobenzo[b][1,4]dioxin-6-yl)amino)methyl)benzofuran-2-carboxylic acid;
6-(((3-bromo-4,5-difluorophenyl)amino)methyl)benzofuran-2-carboxylic acid;
6-(((3-bromo-4-(trifluoromethoxy)phenyl)amino)methyl)-3-(trifluoromethyl)benzofuran-2-carboxylic acid;
6-(((3-chloro-4-(2,2,2-trifluoroethoxy)phenyl)amino)methyl)benzofuran-2-carboxylic acid;
6-(((3-morpholinophenyl)amino)methyl)benzofuran-2-carboxylic acid;
6-(((3-chloro-4-fluoro-5-(trifluoromethyl)phenyl)amino)methyl)benzofuran-2-carboxylic acid;
6-(((4-propyl-3-(trifluoromethyl)phenyl)amino)methyl)-3-(trifluoromethyl)benzofuran-2-carboxylic acid;
6-(((5-(trifluoromethyl)pyridin-2-yl)amino)methyl)benzofuran-2-carboxylic acid;
6-(((4-((trifluoromethyl)thio)phenyl)amino)methyl)benzofuran-2-carboxylic acid;
6-(((2-methylbenzo[d]thiazol-5-yl)amino)methyl)benzofuran-2-carboxylic acid;
6-(((3-chloro-4-methoxyphenyl)amino)methyl)benzofuran-2-carboxylic acid;
6-(((3,5-bis(trifluoromethyl)phenyl)amino)methyl)benzofuran-2-carboxylic acid;
6-(((4-methoxy-3-(trifluoromethyl)phenyl)amino)methyl)benzofuran-2-carboxylic acid;
6-(((4-(2,2,2-trifluoroethoxy)-3-(trifluoromethyl)phenyl)amino)methyl)benzofuran-2-carboxylic acid;
6-(((2,6-dichloropyridin-4-yl)amino)methyl)benzofuran-2-carboxylic acid;
5-(((3,4,5-trichlorophenyl)amino)methyl)benzofuran-2-carboxylic acid;
5-(((3-chloro-4-propylphenyl)amino)methyl)benzofuran-2-carboxylic acid;
5-(((4-propyl-3-(trifluoromethyl)phenyl)amino)methyl)benzofuran-2-carboxylic acid;
5-(((3,4-dichlorophenyl)amino)methyl)benzofuran-2-carboxylic acid;
5-(((4-ethyl-3-(trifluoromethyl)phenyl)amino)methyl)benzofuran-2-carboxylic acid;
5-(((3-propyl-4-(trifluoromethyl)phenyl)amino)methyl)benzofuran-2-carboxylic acid;
5-(((4-chloro-3-propylphenyl)amino)methyl)benzofuran-2-carboxylic acid;
N-((6-fluoro-2-(1H-tetrazol-5-yl)benzofuran-5-yl)methyl)-4-(2,2,2-trifluoroethoxy)-3-(trifluoromethyl)aniline;
N-((6-fluoro-2-(1H-tetrazol-5-yl)benzofuran-5-yl)methyl)-4-propyl-3-(trifluoromethyl)aniline;
3,4-dichloro-N-((6-fluoro-2-(1H-tetrazol-5-yl)benzofuran-5-yl)methyl)aniline;
N-((6-fluoro-2-(1H-tetrazol-5-yl)benzofuran-5-yl)methyl)-4-(trifluoromethoxy)-3-(trifluoromethyl)aniline;
3-bromo-N-((6-fluoro-2-(1H-tetrazol-5-yl)benzofuran-5-yl)methyl)-4-(trifluoromethoxy)aniline;
4-(difluoromethoxy)-N-((6-fluoro-2-(1H-tetrazol-5-yl)benzofuran-5-yl)methyl)-3-(trifluoromethyl)aniline;

4-bromo-N-((6-fluoro-2-(1H-tetrazol-5-yl)benzofuran-5-yl)methyl)-3,5-bis(trifluoromethyl)aniline;
N-((6-chloro-2-(1H-tetrazol-5-yl)benzofuran-5-yl)methyl)-4-(difluoromethoxy)-3-(trifluoromethyl)aniline;
N-((6-chloro-2-(1H-tetrazol-5-yl)benzofuran-5-yl)methyl)-4-(2,2,2-trifluoroethoxy)-3-(trifluoromethyl)aniline;
3-bromo-N-((6-chloro-2-(1H-tetrazol-5-yl)benzofuran-5-yl)methyl)-4-(trifluoromethoxy)aniline;
4-bromo-N-((6-chloro-2-(1H-tetrazol-5-yl)benzofuran-5-yl)methyl)-3,5-bis(trifluoromethyl)aniline;
3-chloro-N-((6-chloro-2-(1H-tetrazol-5-yl)benzofuran-5-yl)methyl)-4-(trifluoromethyl)aniline;
3,4-dichloro-N-((6-chloro-2-(1H-tetrazol-5-yl)benzofuran-5-yl)methyl)aniline;
3-bromo-N-((4-fluoro-2-(1H-tetrazol-5-yl)benzofuran-5-yl)methyl)-4-(trifluoromethoxy)aniline;
4-(difluoromethoxy)-N-((4-fluoro-2-(1H-tetrazol-5-yl)benzofuran-5-yl)methyl)-3-(trifluoromethyl)aniline
N-((4-fluoro-2-(1H-tetrazol-5-yl)benzofuran-5-yl)methyl)-4-(2,2,2-trifluoroethoxy)-3-(trifluoromethyl)aniline;
4-bromo-N-((4-fluoro-2-(1H-tetrazol-5-yl)benzofuran-5-yl)methyl)-3,5-bis(trifluoromethyl)aniline;
N-((4-fluoro-2-(1H-tetrazol-5-yl)benzofuran-5-yl)methyl)-4-(trifluoromethoxy)-3-(trifluoromethyl)aniline;
4-(difluoromethoxy)-N-((7-fluoro-2-(1H-tetrazol-5-yl)benzofuran-5-yl)methyl)-3-(trifluoromethyl)aniline;
N-((7-fluoro-2-(1H-tetrazol-5-yl)benzofuran-5-yl)methyl)-4-(trifluoromethoxy)-3-(trifluoromethyl)aniline;
N-((7-fluoro-2-(1H-tetrazol-5-yl)benzofuran-5-yl)methyl)-4-(2,2,2-trifluoroethoxy)-3-(trifluoromethyl)aniline;
3-bromo-N-((7-fluoro-2-(1H-tetrazol-5-yl)benzofuran-5-yl)methyl)-4-(trifluoromethoxy)aniline;
4-chloro-N-((5-fluoro-2-(1H-tetrazol-5-yl)benzofuran-6-yl)methyl)-3-(trifluoromethyl)aniline;
4-bromo-N-((7-fluoro-2-(1H-tetrazol-5-yl)benzofuran-6-yl)methyl)-3,5-bis(trifluoromethyl)aniline;
4-(difluoromethoxy)-N-((5-fluoro-2-(1H-tetrazol-5-yl)benzofuran-6-yl)methyl)-3-(trifluoromethyl)aniline;
N-((5-methoxy-2-(1H-tetrazol-5-yl)benzofuran-6-yl)methyl)-4-(2,2,2-trifluoroethoxy)-3-(trifluoromethyl)aniline;
N-((7-fluoro-2-(1H-tetrazol-5-yl)benzofuran-6-yl)methyl)-4-(2,2,2-trifluoroethoxy)-3-(trifluoromethyl)aniline;
2-(4-(((5-bromo-2-(1H-tetrazol-5-yl)benzofuran-6-yl)methyl)amino)-2-(trifluoromethyl)phenoxy)acetonitrile;
N-((5-bromo-2-(1H-tetrazol-5-yl)benzofuran-6-yl)methyl)-4-(difluoromethoxy)-3-(trifluoromethyl)aniline;
N-((5-chloro-2-(1H-tetrazol-5-yl)benzofuran-6-yl)methyl)-4-(2,2-difluoroethoxy)-3-(trifluoromethyl)aniline;
N-((5-fluoro-2-(1H-tetrazol-5-yl)benzofuran-6-yl)methyl)-3,4-bis(trifluoromethyl)aniline;
4-bromo-N-((5-fluoro-2-(1H-tetrazol-5-yl)benzofuran-6-yl)methyl)-3,5-bis(trifluoromethyl)aniline;
3-bromo-N-((5-fluoro-2-(1H-tetrazol-5-yl)benzofuran-6-yl)methyl)-4-isopropylaniline;
N-((2-(2H-tetrazol-5-yl)benzofuran-5-yl)methyl)-3-bromo-4-(trifluoromethoxy)aniline;
4-ethoxy-N-((5-fluoro-2-(1H-tetrazol-5-yl)benzofuran-6-yl)methyl)-3-(trifluoromethyl)aniline;
4-(2,2-difluoroethoxy)-N-((5-fluoro-2-(1H-tetrazol-5-yl)benzofuran-6-yl)methyl)-3-(trifluoromethyl)aniline;
N-((5-fluoro-2-(1H-tetrazol-5-yl)benzofuran-6-yl)methyl)-4-isopropoxy-3-(trifluoromethyl)aniline;
N-((5-bromo-2-(1H-tetrazol-5-yl)benzofuran-6-yl)methyl)-4-(2,2,2-trifluoroethoxy)-3-(trifluoromethyl)aniline;
N-((5-bromo-2-(1H-tetrazol-5-yl)benzofuran-6-yl)methyl)-4-(trifluoromethoxy)-3-(trifluoromethyl)aniline;
4-(difluoromethoxy)-N-((5-methoxy-2-(1H-tetrazol-5-yl)benzofuran-6-yl)methyl)-3-(trifluoromethyl)aniline;
4-(difluoromethoxy)-N-((7-fluoro-2-(1H-tetrazol-5-yl)benzofuran-6-yl)methyl)-3-(trifluoromethyl)aniline;
N-((5-fluoro-2-(1H-tetrazol-5-yl)benzofuran-6-yl)methyl)-4-(2,2,2-trifluoroethoxy)-3-(trifluoromethyl)aniline;
N-((7-fluoro-2-(1H-tetrazol-5-yl)benzofuran-6-yl)methyl)-4-(trifluoromethoxy)-3-(trifluoromethyl)aniline;
N-((5-methyl-2-(1H-tetrazol-5-yl)benzofuran-6-yl)methyl)-4-(2,2,2-trifluoroethoxy)-3-(trifluoromethyl)aniline;
N-((7-chloro-2-(1H-tetrazol-5-yl)benzofuran-6-yl)methyl)-4-isopropoxy-3-(trifluoromethyl)aniline;
N-((2-(2H-tetrazol-5-yl)benzofuran-6-yl)methyl)-3-bromo-4-ethoxyaniline;
N-((5-bromo-2-(1H-tetrazol-5-yl)benzofuran-6-yl)methyl)-4-isopropoxy-3-(trifluoromethyl)aniline;
N-((2-(2H-tetrazol-5-yl)benzofuran-6-yl)methyl)-3-bromo-4-methoxyaniline;
N-((5-fluoro-2-(1H-tetrazol-5-yl)benzofuran-6-yl)methyl)-4-(trifluoromethoxy)-3-(trifluoromethyl)aniline;
4-fluoro-N-((5-fluoro-2-(1H-tetrazol-5-yl)benzofuran-6-yl)methyl)-3-(trifluoromethyl)aniline;
3-bromo-N-((5-fluoro-2-(1H-tetrazol-5-yl)benzofuran-6-yl)methyl)-4-(trifluoromethyl)aniline;
N-((5-bromo-2-(1H-tetrazol-5-yl)benzofuran-6-yl)methyl)-4-ethoxy-3-(trifluoromethyl)aniline;
6-chloro-N-((5-chloro-2-(1H-tetrazol-5-yl)benzofuran-6-yl)methyl)-5-(trifluoromethyl)pyridin-3-amine;
3-bromo-4-chloro-N-((5-fluoro-2-(1H-tetrazol-5-yl)benzofuran-6-yl)methyl)aniline;
3-bromo-4-ethyl-N-((5-fluoro-2-(1H-tetrazol-5-yl)benzofuran-6-yl)methyl)aniline;
N-((2-(2H-tetrazol-5-yl)benzofuran-6-yl)methyl)-3-bromo-4-chloroaniline;
3-bromo-N-((5-fluoro-2-(1H-tetrazol-5-yl)benzofuran-6-yl)methyl)-4-(trifluoromethoxy)aniline;
N-((7-chloro-2-(1H-tetrazol-5-yl)benzofuran-6-yl)methyl)-4-(trifluoromethoxy)-3-(trifluoromethyl)aniline;
3,5-dibromo-4-(difluoromethoxy)-N-((5-fluoro-2-(1H-tetrazol-5-yl)benzofuran-6-yl)methyl)aniline;
3-chloro-N-((5-fluoro-2-(1H-tetrazol-5-yl)benzofuran-6-yl)methyl)-4-(trifluoromethoxy)aniline;
N-((7-chloro-2-(1H-tetrazol-5-yl)benzofuran-6-yl)methyl)-4-(2,2,2-trifluoroethoxy)-3-(trifluoromethyl)aniline;
7-chloro-N-((5-chloro-2-(1H-tetrazol-5-yl)benzofuran-6-yl)methyl)-2-methylbenzofuran-5-amine;
4-bromo-N-((5-chloro-2-(1H-tetrazol-5-yl)benzofuran-6-yl)methyl)-3,5-bis(trifluoromethyl)aniline;
3-fluoro-N-((5-fluoro-2-(1H-tetrazol-5-yl)benzofuran-6-yl)methyl)-4-propylaniline;
N-((7-chloro-2-(1H-tetrazol-5-yl)benzofuran-6-yl)methyl)-4-(difluoromethoxy)-3-(trifluoromethyl)aniline;
3-fluoro-N-((5-fluoro-2-(1H-tetrazol-5-yl)benzofuran-6-yl)methyl)-4-(trifluoromethoxy)aniline;
3-bromo-N-((7-fluoro-2-(1H-tetrazol-5-yl)benzofuran-6-yl)methyl)-4-(trifluoromethoxy)aniline;

N-((2-(2H-tetrazol-5-yl)benzofuran-6-yl)methyl)-7-chloro-2-methylbenzofuran-5-amine;
N-((5-fluoro-2-(1H-tetrazol-5-yl)benzofuran-6-yl)methyl)-3-methyl-5-(trifluoromethyl)aniline;
3-chloro-N-((5-fluoro-2-(1H-tetrazol-5-yl)benzofuran-6-yl)methyl)-4-(trifluoromethyl)aniline;
2-(difluoromethoxy)-5-(((5-fluoro-2-(1H-tetrazol-5-yl)benzofuran-6-yl)methyl)amino)benzonitrile;
3-chloro-N-((5-chloro-2-(1H-tetrazol-5-yl)benzofuran-6-yl)methyl)-4-(trifluoromethyl)aniline;
3-chloro-N-((5-chloro-2-(1H-tetrazol-5-yl)benzofuran-6-yl)methyl)-4-(difluoromethoxy)aniline;
5-(((5-bromo-2-(1H-tetrazol-5-yl)benzofuran-6-yl)methyl)amino)-2-(difluoromethoxy)benzonitrile;
3-chloro-N-((5-chloro-2-(1H-tetrazol-5-yl)benzofuran-6-yl)methyl)-4-fluoro-5-(trifluoromethyl)aniline;
5-(((7-chloro-2-(1H-tetrazol-5-yl)benzofuran-6-yl)methyl)amino)-2-(difluoromethoxy)benzonitrile;
3-fluoro-N-((5-fluoro-2-(1H-tetrazol-5-yl)benzofuran-6-yl)methyl)-4-(trifluoromethyl)aniline;
N-((2-(2H-tetrazol-5-yl)benzofuran-6-yl)methyl)-6-chloro-5-(trifluoromethyl)pyridin-3-amine;
3-chloro-N-((5-fluoro-2-(1H-tetrazol-5-yl)benzofuran-6-yl)methyl)-4-(2,2,2-trifluoroethoxy)aniline;
N-((7-chloro-2-(1H-tetrazol-5-yl)benzofuran-6-yl)methyl)-4-ethoxy-3-(trifluoromethyl)aniline;
N-((5-chloro-2-(1H-tetrazol-5-yl)benzofuran-6-yl)methyl)-4-isopropyl-3-(trifluoromethyl)aniline;
3,4-dichloro-N-((5-fluoro-2-(1H-tetrazol-5-yl)benzofuran-6-yl)methyl)aniline;
N-((2-(2H-tetrazol-5-yl)benzofuran-6-yl)methyl)-3-methylbenzo[d]isothiazol-5-amine;
2-(4-(((7-chloro-2-(1H-tetrazol-5-yl)benzofuran-6-yl)methyl)amino)-2-(trifluoromethyl)phenoxy)acetonitrile;
3-chloro-4-ethoxy-N-((5-fluoro-2-(1H-tetrazol-5-yl)benzofuran-6-yl)methyl)aniline;
3-chloro-N-((5-chloro-2-(1H-tetrazol-5-yl)benzofuran-6-yl)methyl)-5-(trifluoromethoxy)aniline;
N-((5-chloro-2-(1H-tetrazol-5-yl)benzofuran-6-yl)methyl)-3-methyl-5-(trifluoromethyl)aniline;
4-chloro-3-fluoro-N-((5-fluoro-2-(1H-tetrazol-5-yl)benzofuran-6-yl)methyl)aniline;
3-chloro-4-fluoro-N-((5-fluoro-2-(1H-tetrazol-5-yl)benzofuran-6-yl)methyl)aniline;
N-((2-(2H-tetrazol-5-yl)benzofuran-6-yl)methyl)-3-bromo-4-isobutoxyaniline;
3-chloro-N-((5-chloro-2-(1H-tetrazol-5-yl)benzofuran-6-yl)methyl)-4-ethoxyaniline;
N-((2-(2H-tetrazol-5-yl)benzofuran-6-yl)methyl)-2-fluoro-4-(trifluoromethoxy)aniline;
N-((2-(2H-tetrazol-5-yl)benzofuran-6-yl)methyl)-2,2,4,4-tetrafluoro-4H-benzo[d][1,3]dioxin-6-amine;
3-chloro-N-((5-chloro-2-(1H-tetrazol-5-yl)benzofuran-6-yl)methyl)-5-methyl-4-propylaniline;
N-((5-chloro-2-(1H-tetrazol-5-yl)benzofuran-6-yl)methyl)-4-fluoro-3-(2,2,2-trifluoroethyl)aniline;
N,N-bis((2-(2H-tetrazol-5-yl)benzofuran-6-yl)methyl)-3-bromo-4-isobutoxyaniline;
7-(((2-(2H-tetrazol-5-yl)benzofuran-6-yl)methyl)amino)-4-(trifluoromethyl)-2H-chromen-2-one;
5-chloro-6-(((4-(difluoromethoxy)-3-(trifluoromethyl)phenyl)amino)methyl)benzofuran-2-carboxylic acid;
5-chloro-6-(((4-(2,2,2-trifluoroethoxy)-3-(trifluoromethyl)phenyl)amino)methyl)benzofuran-2-carboxylic acid;
6-(((3-chloro-4-(2,2,2-trifluoroethoxyl)phenyl)amino)methyl)-5-fluorobenzofuran-2-carboxylic acid;
6-(((3-chloro-4-(trifluoromethoxy)phenyl)amino)methyl)-5-fluorobenzofuran-2-carboxylic acid;
6-(((3-bromo-4-(trifluoromethoxy)phenyl)amino)methyl)-5-fluorobenzofuran-2-carboxylic acid;
6-(((3-chloro-4-((trifluoromethyl)thio)phenyl)amino)methyl)-5-fluorobenzofuran-2-carboxylic acid;
6-(((4-bromo-3,5-bis(trifluoromethyl)phenyl)amino)methyl)-5-fluorobenzofuran-2-carboxylic acid;
6-(((4-(difluoromethoxy)-3-(trifluoromethyl)phenyl)amino)methyl)-5-fluorobenzofuran-2-carboxylic acid;
5-fluoro-6-(((4-(2,2,2-trifluoroethoxy)-3-(trifluoromethyl)phenyl)amino)methyl)benzofuran-2-carboxylic acid;
5-fluoro-6-(((3,4,5-trichlorophenyl)amino)methyl)benzofuran-2-carboxylic acid; and
N-((3-(2H-tetrazol-5-yl)benzofuran-6-yl)methyl)-3-bromo-4-(trifluoromethoxy)aniline.

13. A pharmaceutical composition comprising a therapeutically effective amount of a compound of claim 1, or a pharmaceutically acceptable salt thereof and one or more pharmaceutically acceptable carriers.

14. A combination comprising a therapeutically effective amount of a compound of claim 1 or a pharmaceutically acceptable salt thereof and one or more therapeutically active co-agents.

15. A method to treat, prevent or ameliorate a hERG related condition, comprising administering to a subject in need thereof an effective amount of a compound, or salt thereof, of claim 1.

16. The method of claim 15, wherein the hERG related condition is selected from LQT syndrome, GOF syndrome, Na syndrome, Jervell syndrome and Lange-Nielsen syndrome.

* * * * *